United States Patent
Shamji et al.

(10) Patent No.: US 10,265,321 B2
(45) Date of Patent: Apr. 23, 2019

(54) USES OF SALT-INDUCIBLE KINASE (SIK) INHIBITORS

(71) Applicants: Dana-Farber Cancer Institute, Inc., Boston, MA (US); The Broad Institute, Inc., Cambridge, MA (US); President and Fellows of Harvard College, Cambridge, MA (US); The General Hospital Corporation, Boston, MA (US)

(72) Inventors: Alykhan Shamji, Somerville, MA (US); Thomas Sundberg, Boston, MA (US); Nathanael S. Gray, Boston, MA (US); Ramnik Xavier, Brookline, MA (US); Stuart L. Schreiber, Boston, MA (US); Hwan Geun Choi, Chestnut Hill, MA (US); Yanke Liang, Brookline, MA (US)

(73) Assignees: Dana-Farber Cancer Institute, Inc., Boston, MA (US); The Broad Institute, Inc., Cambridge, MA (US); President and Fellows of Harvard College, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 15/847,856

(22) Filed: Dec. 19, 2017

(65) Prior Publication Data

US 2018/0221379 A1 Aug. 9, 2018

Related U.S. Application Data

(62) Division of application No. 15/502,287, filed as application No. PCT/US2015/044387 on Aug. 8, 2015, now abandoned.

(Continued)

(51) Int. Cl.
*A61K 31/5377* (2006.01)
*A61K 31/519* (2006.01)
(Continued)

(52) U.S. Cl.
CPC ........ *A61K 31/5377* (2013.01); *A61K 31/506* (2013.01); *A61K 31/519* (2013.01); *A61K 45/06* (2013.01)

(58) Field of Classification Search
None
See application file for complete search history.

(56) References Cited

U.S. PATENT DOCUMENTS 6,150,373 A 11/2000 Harris et al.
6,217,875 B1 4/2001 Murai et al.
(Continued)

FOREIGN PATENT DOCUMENTS

CN 104 482 860 A 4/2015
EP 1 544 295 A1 6/2005
(Continued)

OTHER PUBLICATIONS

U.S. Appl. No. 15/327,690, filed Jan. 20, 2017, Gray et al.
(Continued)

*Primary Examiner* — Karl J Puttlitz
(74) *Attorney, Agent, or Firm* — Wolf, Greenfield & Sacks, P.C.

(57) ABSTRACT

The present disclosure provides methods of treating and/or preventing inflammatory bowel disease (IBD) and graft-versus-host disease (GVHD) using salt-inducible kinase (SIK) inhibitors, such as macrocyclic SIK inhibitors of Formula (I), imidazolyl SIK inhibitors of Formula (II), and urea and carbamate SIK inhibitors of Formula (III-A) (e.g., urea and carbamate SIK inhibitors of Formula (III)).

(Continued)

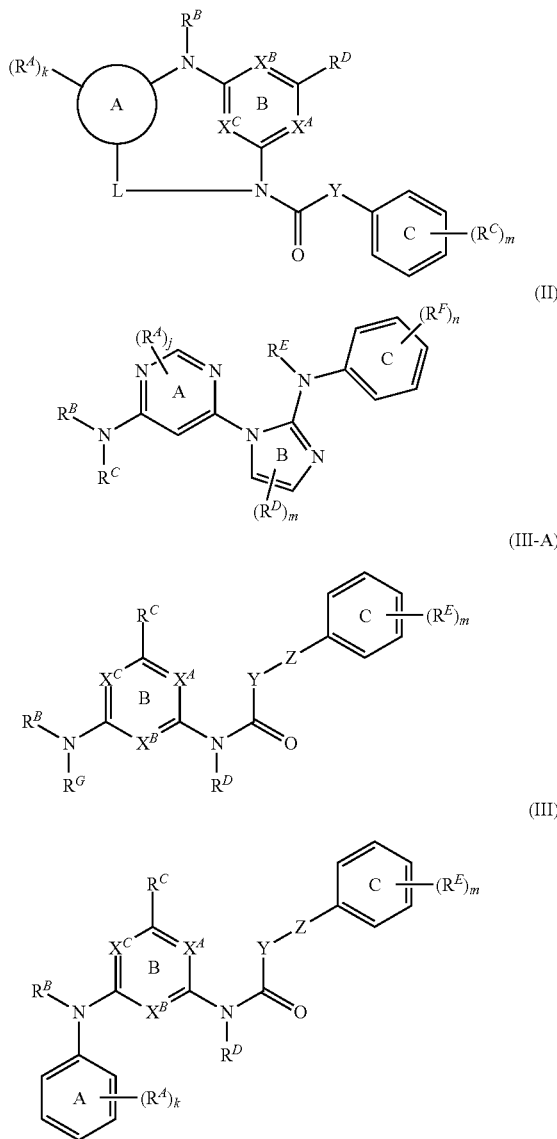

(51) Int. Cl.
*A61K 45/06* (2006.01)
*A61K 31/506* (2006.01)

(56) References Cited

U.S. PATENT DOCUMENTS

| | | |
|---|---|---|
| 7,084,270 B2 | 8/2006 | Chen et al. |
| 7,112,676 B2 | 9/2006 | Dermatakis et al. |
| 7,312,225 B2 | 12/2007 | Luecking et al. |
| 9,586,936 B2 | 3/2017 | Sim et al. |
| 9,670,165 B2 | 6/2017 | Cohen et al. |
| 9,783,504 B2 | 10/2017 | Gray et al. |
| 2004/0204427 A1 | 10/2004 | Chen et al. |
| 2005/0026914 A1 | 2/2005 | Buchanan et al. |
| 2005/0202001 A1 | 9/2005 | Shen et al. |
| 2006/0258687 A1 | 11/2006 | Boehm et al. |
| 2007/0225286 A1 | 9/2007 | Ren et al. |
| 2008/0249079 A1 | 10/2008 | Chen et al. |
| 2009/0137804 A1 | 5/2009 | Ding et al. |
| 2010/0056524 A1 | 3/2010 | McIver et al. |
| 2011/0086858 A1 | 4/2011 | Wang et al. |
| 2011/0207711 A1 | 8/2011 | Katz et al. |
| 2017/0204082 A1 | 7/2017 | Gray et al. |
| 2017/0204116 A1 | 7/2017 | Gray et al. |
| 2017/0224700 A1 | 8/2017 | Shamji et al. |
| 2017/0342036 A1 | 11/2017 | Cohen et al. |

FOREIGN PATENT DOCUMENTS

| | | |
|---|---|---|
| EP | 2 746 283 A1 | 6/2014 |
| EP | 15824907.8 | 1/2018 |
| WO | WO 2000/024744 A1 | 5/2000 |
| WO | WO 2004/041821 A1 | 5/2004 |
| WO | WO 2004/041822 A1 | 5/2004 |
| WO | WO 2004/048343 A1 | 6/2004 |
| WO | WO 2005/009443 A1 | 2/2005 |
| WO | WO 2005/009978 A1 | 2/2005 |
| WO | WO 2005/011597 A2 | 2/2005 |
| WO | WO 2005/123719 A1 | 12/2005 |
| WO | WO 2006/000420 A1 | 1/2006 |
| WO | WO 2006/024545 A1 | 3/2006 |
| WO | WO 2007/071752 A2 | 6/2007 |
| WO | WO 2007/136465 A2 | 11/2007 |
| WO | WO 2008/060248 A1 | 5/2008 |
| WO | WO 2009/122180 A1 | 10/2009 |
| WO | WO 2009/152027 A1 | 12/2009 |
| WO | WO 2013/045653 A1 | 4/2013 |
| WO | WO 2013/074986 A1 | 5/2013 |
| WO | WO 2013/136070 A1 | 9/2013 |
| WO | WO 2014/144737 A1 | 9/2014 |
| WO | WO 2015/006492 A1 | 1/2015 |
| WO | PCT/US2015/041360 | 9/2015 |
| WO | PCT/US2015/041360 | 12/2015 |
| WO | 2016/014551 * | 1/2016 |
| WO | WO 2016/014542 A1 | 1/2016 |
| WO | WO 2016/014551 A1 | 1/2016 |
| WO | WO 2016/023014 A1 | 2/2016 |

OTHER PUBLICATIONS

U.S. Appl. No. 15/327,705, filed Jan. 20, 2017, Gray et al.
U.S. Appl. No. 15/502,287, filed Feb. 7, 2017, Shamji et al.
U.S. Appl. No. 15/385,077, filed Sep. 12, 2014, Cohen et al.
U.S. Appl. No. 15/606,970, filed May 26, 2017, Cohen et al.

38 Claims, 29 Drawing Sheets

Specification includes a Sequence Listing.

Related U.S. Application Data

(60) Provisional application No. 62/035,332, filed on Aug. 8, 2014.

(56) References Cited

OTHER PUBLICATIONS

Invitation to Pay Additional Fees for PCT/US2015/041360 dated Sep. 24, 2015.
International Search Report and Written Opinion for PCT/US2015/041360 dated Dec. 15, 2015.
International Preliminary Report on Patentability for PCT/US2015/041360 dated Feb. 2, 2017.
International Search Report and Written Opinion for PCT/US2015/41348 dated Oct. 28, 2015.
International Preliminary Report on Patentability for PCT/US2015/41348 dated Feb. 2, 2017.
Invitation to Pay Additional Fees for PCT/US2015/044387, dated Jan. 28, 2016.
International Search Report and Written Opinion for PCT/US2015/044387, dated Mar. 25, 2016.
International Preliminary Report on Patentability for PCT/US2015/044387, dated Feb. 23, 2017.
International Preliminary Report on Patentability for PCT/GB2013/050618, dated Sep. 25, 2014.
International Search Report and Written Opinion for PCT/GB2013/050618, dated May 17, 2013.
Invitation to Pay Additional Fees for PCT/US2017/040722, dated Oct. 18, 2017.
International Search Report and Written Opinion for PCT/US2017/040722, dated Dec. 12, 2017.
Extended European Search Report for EP 15824907.8, dated Jan. 2, 2018.
Extended European Search Report for EP 15824975.5, dated Nov. 27, 2017.
Altarejos et al., CREB and the CRTC co-activators: sensors for hormonal and metabolic signals. Nat Rev Mol Cell Biol. Mar. 2011;12(3):141-51. doi: 10.1038/nrm3072.
Bain et al., The selectivity of protein kinase inhibitors: a further update. Biochem J. Dec. 15, 2007;408(3):297-315.
Benoit et al., Macrophage polarization in bacterial infections. J Immunol. Sep. 15, 2008;181(16):3733-9.
Berdesux et al., SIK1 is a class II HDAC kinase that promotes survival of skeletal myocytes. Nat Med. May 2007;13(5):597-603. Epub Apr. 29, 2007.
Bettencourt-Dias et al., Genome-wide survey of protein kinases required for cell cycle progression. Nature. Dec. 23, 2004;432(7020):980-7.
Clark et al., Phosphorylation of CRTC3 by the salt-inducible kinases controls the interconversion of classically activated and regulatory macrophages. Proc Natl Acad Sci U S A. Oct. 16, 2012;109(42):16986-91. doi: 10.1073/pnas.1215450109. Epub Oct. 2, 2012. With Supporting Information.
Eyers et al., Conversion of SB 203580-insensitive MAP kinase family members to drug-sensitive forms by a single amino-acid substitution. Chem Biol. Jun. 1998;5(6):321-8.
Fleming et al., Regulatory macrophages: setting the threshold for therapy. Eur J Immunol. Sep. 2011;41(9):2498-502. doi: 10.1002/eji.201141717.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fu et al., Parathyroid hormone controls receptor activator of NF-kappaB ligand gene expression via a distant transcriptional enhancer. Mol Cell Biol. Sep. 2006;26(17):6453-68.
Fu et al., Parathyroid hormone stimulates receptor activator of NFkappa B ligand and inhibits osteoprotegerin expression via protein kinase A activation of cAMP-response element-binding protein. J Biol Chem. Dec. 13, 2002;277(50):48868-75. Epub Oct. 2, 2002.
Hahn et al., Targeted therapies in systemic lupus erythematosus: successes, failures and future. Ann Rheum Dis. Mar. 2011;70 Suppl 1:i64-i66. doi: 10.1136/ard.2010.142208.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Henriksson et al., SIK2 regulates CRTCs, HDAC4 and glucose uptake in adipocytes. J Cell Sci. Feb. 1, 2015;128(3):472-86.
Henriksson et al., The AMPK-related kinase SIK2 is regulated by cAMP via phosphorylation at Ser358 in adipocytes. Biochem J. Jun. 15, 2012;444(3):503-14. doi: 10.1042/BJ20111932.
Heppner et al., Immune attack: the role of inflammation in Alzheimer disease. Nat Rev. Neurosci. Jun. 2015;16(6):358-72. doi: 10.1038/nrn3880.
Horike et al., Downregulation of SIK2 expression promotes the melanogenic program in mice. Pigment Cell Melanoma Res. Dec. 2010;23(6):809-19. doi: 10.1111/j.1755-148X.2010.00760.x. Epub Aug. 31, 2010.
Jansson et al., Glucose controls CREB activity in islet cells via regulated phosphorylation of TORC2. Proc Natl Acad Sci U S A. Jul. 22, 2008;105(29):10161-6. doi: 10.1073/pnas.0800796105. Epub Jul. 14, 2008.
Kantarjian et al., Dasatinib versus imatinib in newly diagnosed chronic-phase chronic myeloid leukemia. N Engl J Med. Jun. 17, 2010;362(24):2260-70.
Kopf et al., Averting inflammation by targeting the cytokine environment. Nat Rev Drug Discov. Sep. 2010;9(9):703-18. doi: 10.1038/nrd2805.
Kuhn et al., Interleukin-10-deficient mice develop chronic enterocolitis. Cell. Oct. 22, 1993;75(2):263-74.
Kumagai et al., A potent inhibitor of SIK2, 3, 3', 7-trihydroxy-4'-methoxyflavon (4'-O-methylfisetin), promotes melanogenesis in B16F10 melanoma cells. PLoS One. 2011;6(10):e26148. doi: 10.1371/journal.pone.0026148. Epub Oct. 13, 2011.
Liu et al., Engineering Src family protein kinases with unnatural nucleotide specificity. Chem Biol. Feb. 1998;5(2):91-101.
Liu et al., Salt-inducible kinase is involved in the regulation of corticotropin-releasing hormone transcription in hypothalamic neurons in rats. Endocrinology. Jan. 2012;153(1):223-33. doi: 10.1210/en.2011-1404. Epub Nov. 22, 2011.
Mair et al., Lifespan extension induced by AMPK and calcineurin is mediated by CRTC-1 and CREB. Nature. Feb. 17, 2011;470(7334):404-8. doi: 10.1038/nature09706.
Mallison et al., Macrocycles in new drug discovery. Future Med Chem. Jul. 2012;4(11):1409-38. doi: 10.4155/fmc.12.93.
Martin et al., Novel 2-aminopyrimidine carbamates as potent and orally active inhibitors of Lck: synthesis, SAR, and in vivo antiinflammatory activity. J Med Chem. Aug. 10, 2006;49(16):4981-91.
Mcwhirter et al., IFN-regulatory factor 3-dependent gene expression is defective in Tbk1-deficient mouse embryonic fibroblasts. Proc Natl Acad Sci U S A. Jan. 6, 2004;101(1):233-8. Epub Dec. 16, 2003.
Mosser et al., Interleukin-10: new perspectives on an old cytokine. Immunol Rev. Dec. 2008;226:205-18. doi: 10.1111/j.1600-065X.2008.00706.x.
O'Garra et al., Strategies for use of IL-10 or its antagonists in human disease. Immunol Rev. Jun. 2008;223:114-31. doi: 10.1111/j.1600-065X.2008.00635.x.
Park et al., SIK2 is critical in the regulation of lipid homeostasis and adipogenesis in vivo. Diabetes. Nov. 2014;63(11):3659-73. doi: 10.2337/db13-1423. Epub Jun. 4, 2014.
Patel et al., The LKB1-salt-inducible kinase pathway functions as a key gluconeogenic suppressor in the liver. Nat Commun. Aug. 4, 2014;5:4535. doi: 10.1038/ncomms5535.
Popov et al., Lack of salt-inducible kinase 2 (SIK2) prevents the development of cardiac hypertrophy in response to chronic high-salt intake. PLoS One. Apr. 21, 2014;9(4):e95771. doi: 10.1371/journal.pone.0095771. eCollection 2014.
Sakamaki et al., Role of the SIK2-p35-PJA2 complex in pancreatic β-cell functional compensation. Nat Cell Biol. Mar. 2014;16(3):234-44. doi: 10.1038/ncb2919.
Saraiva et al., The regulation of IL-10 production by immune cells. Nat Rev Immunol. Mar. 2010;10(3):170-81. doi: 10.1038/nri2711. Epub Feb. 15, 2010.

(56) References Cited

OTHER PUBLICATIONS

Sasagawa et al., SIK3 is essential for chondrocyte hypertrophy during skeletal development in mice. Development. Mar. 2012;139(6):1153-63. doi: 10.1242/dev.072652. Epub Feb. 8, 2012.

Sasaki et al., SIK2 is a key regulator for neuronal survival after ischemia via TORC1-CREB. Neuron. Jan. 13, 2011;69(1):106-19. doi: 10.1016/j.neuron.2010.12.004.

Screaton et al., The CREB coactivator TORC2 functions as a calcium- and cAMP-sensitive coincidence detector. Cell. Oct. 1, 2004;119(1):61-74.

Sundberg et al., Development of Chemical Probes for Investigation of Salt-Inducible Kinase Function in Vivo. ACS Chem Biol. Aug. 19, 2016;11(8):2105-11. doi: 10.1021/acschembio.6b00217. Epub Jun. 6, 2016.

Sundberg et al., Small-molecule screening identifies inhibition of salt-inducible kinases as a therapeutic strategy to enhance immunoregulatory functions of dendritic cells. Proc Natl Acad Sci U S A. Aug. 26, 2014;111(34):12468-73. doi: 10.1073/pnas.1412308111. Epub Aug. 11, 2014.

Takemori et al., Inactivation of HDAC5 by SIK1 in AICAR-treated C2C12 myoblasts. Endocr J. 2009;56(1):121-30. Epub Oct. 22, 2008.

Triantafillidis et al., Current and emerging drugs for the treatment of inflammatory bowel disease. Drug Des Devel Ther. Apr. 6, 2011;5:185-210. doi: 10.2147/DDDT.S11290.

Walkinshaw et al., The tumor suppressor kinase LKB1 activates the downstream kinases SIK2 and SIK3 to stimulate nuclear export of class IIa histone deacetylases. J Biol Chem. Mar. 29, 2013;288(13):9345-62. doi: 10.1074/jbc.M113.456996. Epub Feb. 7, 2013.

Wang et al. Cloning of a novel kinase (SIK) of the SNF1/AMPK family from high salt diet-treated rat adrenal. FEBS Lett. Jun. 18, 1999;453(1-2):135-9.

Yahara et al., Pterosin B prevents chondrocyte hypertrophy and osteoarthritis in mice by inhibiting Sik3. Nat Commun. Mar. 24, 2016;7:10959. doi: 10.1038/ncomms10959.

Partial Supplementary European Search Report for EP 15829427.2, dated Feb. 8, 2018.

Extended European Search Report for EP 15829427.2, dated May 15, 2018.

International Search Report and Written Opinion for PCT/US2018/020335, dated May 17, 2018.

Antiga et al., Serum levels of the regulatory cytokines transforming growth factor-β and interleukin-10 are reduced in patients with discoid lupus erythematosus. Lupus. May 2011;20(6):556-60. doi: 10.1177/0961203310392424. Epub Mar. 3, 2011.

Maier et al., Development of N-4,6-pyrimidine-N-alkyl-N'-phenyl ureas as orally active inhibitors of lymphocyte specific tyrosine kinase. Bioorg Med Chem Lett. Jul. 15, 2006;16(14):3646-50. Epub May 8, 2006.

Pethe et al., A chemical gentic screen in *Mycobacterium tuberculosis* identifies carbon-source-dependent growth inhibitors devoid of in vivo efficacy. Nature Communications 2010;1:57. doi:10.1038/ncomms1060.

Wu et al., Exploring the selectivity of PI3Kα and mTOR inhibitors by 3D-QSAR, molecular dynamics simulations and MM/GBSA binding free energy decomposition. Med. Chem. Commun., 2013;4:1482-1496. DOI: 10.1039/C3MD00157A.

\* cited by examiner

| Inhibitor | Reported Target | IL-10 Potentiation | |
|---|---|---|---|
| | | $EC_{50}$ (μM) | MAX Effect (%$PGE_2$) |
| Dasatinib | Bcr-Abl/cKit | 0.08 | 102 |
| GDC-0879 | BrafV600E | 0.25 | 88 |
| Bosutinib | Bcr-Abl/c-Src | 1.8 | 93 |
| Dabrafinib | BrafV600E | 2.1 | 63 |
| TAE-684 | Alk | 2.3 | 56 |
| MK 1775 | Wee1 | 4.8 | 50 |
| Vemurafinib | BrafV600E | 5.0 | 41 |
| Ruxolitinib | Jak1/Jak2 | 5.7 | 95 |
| CHIR-99021 | GSK3-a/GSK3-b | 7.4 | 68 |
| Saracatinib | c-Src/Bcr-Abl | >10 | 49 |

| Analog | IC$_{50}$ (nM) | | | IL-10 Potentiation | | Viability loss | |
| --- | --- | --- | --- | --- | --- | --- | --- |
| | SIK1 | SIK2 | SIK3 | EC$_{50}$ (µM) | Max Effect (%PGE$_2$) | EC$_{50}$ (µM) | Max Effect (%DMSO) |
| HG-10-11-01 | N.D. | 10.1 | 17.4 | 0.30 | 66 | >10 | -59 |
| HG-9-91-01 | 0.92 | 6.5 | 19.4 | 0.43 | 87 | >10 | -55 |
| HG-10-7-01 | 36.2 | 65.1 | 120 | 1.5 | 35 | 1.0 | -60 |
| HG-9-148-01 | 13.2 | 73.3 | 49.3 | 1.7 | 22 | >10 | -57 |
| HG-9-150-01 | 9.2 | 78.3 | 85.8 | 2.4 | 94 | 7.6 | -76 |
| HG-9-88-01 | 13.1 | 20.5 | 64.1 | 5.3 | 47 | >25 | No Change |

Figure 2A

| Analog | Core | R₁ | R₂ | X,Y | IC₅₀ (nM) | | | IL-10 potentiation | | Viability loss | |
|---|---|---|---|---|---|---|---|---|---|---|---|
| | | | | | SIK1 | SIK2 | SIK3 | EC₅₀ (μM) | Max Effect (%PGE₂) | EC₅₀ (μM) | Max Effect (%DMSO) |
| HG-10-11-01 | pyrimidine | piperazine-phenyl | dimethoxyphenyl | O,NH | N.D. | 10.1 | 17.4 | 0.30 | 66 | >10 | -59 |
| HG-9-91-01 | pyrimidine | piperazine-phenyl-ethyl | dimethoxyphenyl | O,NH | 0.92 | 6.5 | 19.4 | 0.43 | 87 | >10 | -55 |
| HG-10-7-01 | pyrimidine | piperazine-phenyl-ethyl | pyrazole | N,NH | 36.2 | 65.1 | 120 | 1.5 | 35 | 1.0 | -60 |
| HG-9-148-01 | pyrimidine | piperazine-phenyl | CH₃ | O,NH | 13.2 | 73.3 | 49.33 | 1.7 | 22 | >10 | -57 |
| HG-9-150-01 | pyrimidine | piperazine-phenyl | CH₃ | O,O | 9.2 | 78.3 | 85.8 | 2.4 | 94 | 7.6 | -76 |
| HG-9-88-01 | pyrimidine | trimethoxyphenyl | dimethoxyphenyl | O,NH | 13.1 | 20.5 | 64.1 | 5.3 | 47 | >25 | No change |

Figure 9B

SEQUENCE LISTING

<160> NUMBER OF SEQ ID NOS: 187

<210> SEQ ID NO 1
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 1
ttcaaaattt tatcgatcgc accagcgtgt ggatccgaga acagatctgg cctcgg    56

<210> SEQ ID NO 2
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 2
actaaccggt acgcgttcta gagtcgcggc cttagac    37

<210> SEQ ID NO 3
<211> LENGTH: 87
<212> TYPE: DNA
<213> ORGANISM: Artificial Sequence
<220> FEATURE:
<223> OTHER INFORMATION: Synthetic polynucleotide

<400> SEQUENCE: 3
acaccagaca ttgacgtaag ctgccagatc ccattcccgt catactctga cgtctttcag    60 acacccatt gacgtcaatg ggagaac    87

<210> SEQ ID NO 4
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 4
gcaccagcgt gtggatc    17

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
gccagatctg ttctcggatc    20

<210> SEQ ID NO 6
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 6
ggattggcaa ggtgatggaa    20

<210> SEQ ID NO 7
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 7
ctggtgcttg tctcactgac                                              20

<210> SEQ ID NO 8
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 8
tcagcgtgct gcagagaa                                                18

<210> SEQ ID NO 9
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 9
attgccgaga agaagggaga a                                            21

<210> SEQ ID NO 10
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 10
agccttggat ccaggagaac                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
tcggagacga gttcaacgaa                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 12
caggaagttg gtgagctggt a                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 13
```
ctgtggcctg cctcagatta                                              20

<210> SEQ ID NO 14
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 14
ccttcttgct gtggcaattc a                                            21

<210> SEQ ID NO 15
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 15
gtggtcctca tcacgtcctt a                                            21

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 16
cagtgtccag ggatgaggaa                                              20

<210> SEQ ID NO 17
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 17
atggcagtgt gcacgtcta                                               19

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 18
gccatccggg accttaagaa                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19
agccaagacg ttctcctacc                                              20

<210> SEQ ID NO 20
<211> LENGTH: 20
<212> TYPE: DNA
<213> ORGANISM: Artificial Sequence

```
<220> FEATURE:
<223> OTHER INFORMATION: Synthetic polynucleotide

<400> SEQUENCE: 20
cctgaagctc ccttggttca                                               20

<210> SEQ ID NO 21
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 21
atccggaatc taagaccatc aagaa                                         25

<210> SEQ ID NO 22
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 22
gaacaggaag gtcacagcca ta                                            22

<210> SEQ ID NO 23
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 23
ggacatgggc tccatcacat a                                             21

<210> SEQ ID NO 24
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 24
cccaactggg ataacgagtt ca                                            22

<210> SEQ ID NO 25
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 25
aagtaccgac tccgctacc                                                19

<210> SEQ ID NO 26
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 26 gccccttga ccagatgaac                                                20
```

<210> SEQ ID NO 27
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 27
cgactcggta gcccattaca a                                              21

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
gcggcaaagc ggacaataac                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 29
cgaggagtgt ggcccattta                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 30
atgggctctc ctgtcaacac                                                20

<210> SEQ ID NO 31
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 31
gacgagactt ggaagacagt ca                                             22

<210> SEQ ID NO 32
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 32
cctaccgggt tcggatgtaa                                                20

<210> SEQ ID NO 33
<211> LENGTH: 18
<212> TYPE: DNA
<213> ORGANISM: Artificial Sequence
<220> FEATURE:
<223> OTHER INFORMATION: Synthetic polynucleotide

```
<400> SEQUENCE: 33
tgagcctgga gcaacaca                                            18

<210> SEQ ID NO 34
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 34
tgaagcacct ccggaacc                                            18

<210> SEQ ID NO 35
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 35
tcgacacagc ctcgatatga a                                        21

<210> SEQ ID NO 36
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 36
agaaccagat ctacgccatt cc                                       22

<210> SEQ ID NO 37
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 37
tcaagcacag ggtgacagaa                                          20

<210> SEQ ID NO 38
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 38
gaacacggac atcagcatcc                                          20

<210> SEQ ID NO 39
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 39
tgctttgagc gctttgaca                                           19

<210> SEQ ID NO 40
```

```
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40
agctccaaga aaggacgaac a                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 41
ggcacagtca ttgaaagcct a                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 42
gcataaagag cgatgccaca a                                              21

<210> SEQ ID NO 43
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 43
aaaggaccag ctggacaaca                                                20

<210> SEQ ID NO 44
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 44
aaaccagcac attgaagacc                                                20

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 45
atcgttttgc tggtgtctcc                                                20

<210> SEQ ID NO 46
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 46
```

```
agcttattga ggagctgagc aa                                              22

<210> SEQ ID NO 47
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 47
cgtgctctac cttgcaaaca                                                 20

<210> SEQ ID NO 48
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 48
tgagtccagg gagagcttca                                                 20

<210> SEQ ID NO 49
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 49
aagcagccat tggagaaacc                                                 20

<210> SEQ ID NO 50
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 50
caaagaaagc cgcctcaaac                                                 20

<210> SEQ ID NO 51
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 51
tggcaactgt tcctgaactc a                                               21

<210> SEQ ID NO 52
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 52
cccaggatgc tcaccttcaa a                                               21

<210> SEQ ID NO 53
<211> LENGTH: 22
<212> TYPE: DNA
```

```
<213> ORGANISM: Artificial Sequence
<220> FEATURE:
<223> OTHER INFORMATION: Synthetic polynucleotide

<400> SEQUENCE: 53
gtggggaaga agcaatggag aa                                           22

<210> SEQ ID NO 54
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 54
gatcctgaac ttctatcagc tcca                                         24

<210> SEQ ID NO 55
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 55
tggtgccttt cctgaccaaa                                              20

<210> SEQ ID NO 56
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 56
ctgcatgcta gcctggaac                                               19

<210> SEQ ID NO 57
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 57
cccaatgttt ccctgacttt cc                                           22

<210> SEQ ID NO 58
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 58
tgcgttgctt aggaaactcc                                              20

<210> SEQ ID NO 59
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 59
actcaaaact gatgatgaag gac                                          23
```

<210> SEQ ID NO 60
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 60
ggtcccgcct tgcaaaata                                                    19

<210> SEQ ID NO 61
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 61
acggagatgg atgtgccaaa                                                   20

<210> SEQ ID NO 62
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 62
gatgaggctt cctgtcccta                                                   20

<210> SEQ ID NO 63
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 63
ccagaaaccg ctatgaagtt cc                                                22

<210> SEQ ID NO 64
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 64
cagctgcttg tgtctctcc                                                    19

<210> SEQ ID NO 65
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 65
tccccattga gccaagcata                                                   20

<210> SEQ ID NO 66
<211> LENGTH: 19
<212> TYPE: DNA
<213> ORGANISM: Artificial Sequence
<220> FEATURE:

```
<223> OTHER INFORMATION: Synthetic polynucleotide

<400> SEQUENCE: 66
tgccactggt gaccggata                                                19

<210> SEQ ID NO 67
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 67
ttccagggga cctagagcta                                               20

<210> SEQ ID NO 68
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 68
aggaagacgc atccagttac c                                             21

<210> SEQ ID NO 69
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 69
acacatcccg tcagatgtca                                               20

<210> SEQ ID NO 70
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 70
tgatccgcct gaagcagaa                                                19

<210> SEQ ID NO 71
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 71
aaacgggact ggcttgtca                                                19

<210> SEQ ID NO 72
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 72
agtgctgcat gaggagaca                                                19
```

```
<210> SEQ ID NO 73
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 73
gtgcccaaag atggcaagaa                                               20

<210> SEQ ID NO 74
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 74
tacagccgcc ctttcttttc c                                             21

<210> SEQ ID NO 75
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 75
gaggagcagg tggaagacta                                               20

<210> SEQ ID NO 76
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 76
ggacggcgtg aatacctaca                                               20

<210> SEQ ID NO 77
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 77
aagctgcaga cctggtgata                                               20

<210> SEQ ID NO 78
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 78
ttgactatga tggctccagg ac                                            22

<210> SEQ ID NO 79
<211> LENGTH: 20
<212> TYPE: DNA
<213> ORGANISM: Artificial Sequence
<220> FEATURE:
<223> OTHER INFORMATION: Synthetic polynucleotide
```

<400> SEQUENCE: 79
cttctccctg aagccgtaca 20

<210> SEQ ID NO 80
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 80
tggagctctg ccagaatgac 20

<210> SEQ ID NO 81
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 81
aaccaagtgg ccaggttcaa 20

<210> SEQ ID NO 82
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 82
aacagatgca cgtcctcgat a 21

<210> SEQ ID NO 83
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 83
gctgtgctgt gctcatgac 19

<210> SEQ ID NO 84
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 84
atccgcgtgc acttcca 17

<210> SEQ ID NO 85
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 85
gccggagatt tcgcttcg 18

<210> SEQ ID NO 86
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 86
aaggagcaag gtcgcttaca                                                    20

<210> SEQ ID NO 87
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 87
ctggatggcc cacacttaa                                                     19

<210> SEQ ID NO 88
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 88
gctgaaggaa gctgccctat a                                                  21

<210> SEQ ID NO 89
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 89
caagttcaac cagcaccaga c                                                  21

<210> SEQ ID NO 90
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 90
aagaggcggt caagggaaaa                                                    20

<210> SEQ ID NO 91
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 91
cagctgacgt agaccccaaa                                                    20

<210> SEQ ID NO 92
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 92
```
cagcaagtgg tggatttgga a                                              21

<210> SEQ ID NO 93
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 93
ctgaagcctg cagtggtcaa                                                20

<210> SEQ ID NO 94
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 94
gctctccagt accttcattc c                                              21

<210> SEQ ID NO 95
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 95
ggacgcgctt cttcctaca                                                 19

<210> SEQ ID NO 96
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 96
attctacggg agcatccaga c                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 97
cgacatcaaa gctcaggtga a                                              21

<210> SEQ ID NO 98
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 98
ggtgggtggc gtgagtata                                                 19

<210> SEQ ID NO 99
<211> LENGTH: 22
<212> TYPE: DNA
<213> ORGANISM: Artificial Sequence

```
<220> FEATURE:
<223> OTHER INFORMATION: Synthetic polynucleotide

<400> SEQUENCE: 99
tctccttcga actttcctgt ca                                              22

<210> SEQ ID NO 100
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 100
cggcggcaga tgaattacaa                                                 20

<210> SEQ ID NO 101
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 101
ggctgctgca ttgttccc                                                   18

<210> SEQ ID NO 102
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 102
accatttgag ggtggtcttc a                                               21

<210> SEQ ID NO 103
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 103
cttgccctgg acagtcagaa                                                 20

<210> SEQ ID NO 104
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 104
cagtcttccg catcattagc a                                               21

<210> SEQ ID NO 105
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 105
ggcagcagat actgtcttcc a                                               21
```

<210> SEQ ID NO 106
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 106
acaagcctgg gcaattgtac                                               20

<210> SEQ ID NO 107
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 107
ttcggggaac cgtctgaaa                                                19

<210> SEQ ID NO 108
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 108
tggcaagaat cagagcaaaa cc                                            22

<210> SEQ ID NO 109
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 109
atctttgcca gtgtggggaa                                               20

<210> SEQ ID NO 110
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 110
ccctccggca tcttctgta                                                19

<210> SEQ ID NO 111
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 111
ttctccgtta cttggggaca c                                             21

<210> SEQ ID NO 112
<211> LENGTH: 19
<212> TYPE: DNA
<213> ORGANISM: Artificial Sequence
<220> FEATURE:
<223> OTHER INFORMATION: Synthetic polynucleotide

```
<400> SEQUENCE: 112
gctctctgct gtccatcca                                                19

<210> SEQ ID NO 113
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 113 agcgccctg tttgaacata                                                20

<210> SEQ ID NO 114
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 114
tccctcgact gtagagcaga a                                             21

<210> SEQ ID NO 115
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 115
ttcagggcca cacaggaaaa                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 116
ggtgaaagtc gtggcttcaa                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 117
ggagcgaagc tactcggata                                               20

<210> SEQ ID NO 118
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 118
gtcagaccga tgtccatcac a                                             21

<210> SEQ ID NO 119
```

```
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 119
atccagtggg agccagtgtt a                                              21

<210> SEQ ID NO 120
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 120
agcggttcca tatgtgtctt cc                                             22

<210> SEQ ID NO 121
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 121
gctgtcaccg tggggataa                                                 19

<210> SEQ ID NO 122
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 122
tgggcattgg gttcttgtca                                                20

<210> SEQ ID NO 123
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 123
ccgcagttca cacactcc                                                  18

<210> SEQ ID NO 124
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 124
agcgtggatg acctcttgaa                                                20

<210> SEQ ID NO 125
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 125
```

```
cgcggtattt ccccaacac                                                19
```

<210> SEQ ID NO 126
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 126

```
ttccggctca taacccatca                                               20
```

<210> SEQ ID NO 127
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 127

```
gcattcggca atgtggtcaa                                               20
```

<210> SEQ ID NO 128
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 128

```
atcacctgca gctcctcaaa                                               20
```

<210> SEQ ID NO 129
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 129

```
agccacagag tactttgcta tca                                           23
```

<210> SEQ ID NO 130
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 130

```
gcagattgct ctccagtgac                                               20
```

<210> SEQ ID NO 131
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 131

```
tggatggcaa aggcagtgta                                               20
```

<210> SEQ ID NO 132
<211> LENGTH: 21
<212> TYPE: DNA

```
<213> ORGANISM: Artificial Sequence
<220> FEATURE:
<223> OTHER INFORMATION: Synthetic polynucleotide

<400> SEQUENCE: 132
gccagttcct ccagatatcc a                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 133
tctgccatct cgttgtggtt a                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 134
taaggcttgg caacccaagt a                                              21

<210> SEQ ID NO 135
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 135
ggaagaagtc tctctagtag cc                                             22

<210> SEQ ID NO 136
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 136
ggagtccagt ccacctctac                                                20

<210> SEQ ID NO 137
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 137
ccaggtccac actccatacc                                                20

<210> SEQ ID NO 138
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 138
tttctcctcc agctcctcac                                                20
```

<210> SEQ ID NO 139
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 139
cgctgctgcc ttcactgta                                              19

<210> SEQ ID NO 140
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 140
ggcaagtccc aacatcaaca                                             20

<210> SEQ ID NO 141
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 141
gacgcaagag tcttctgaca                                             20

<210> SEQ ID NO 142
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 142
gggtccgtca acttcaaaga ac                                          22

<210> SEQ ID NO 143
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 143
ccgcagaggt ccaagttca                                              19

<210> SEQ ID NO 144
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 144
ctttaccacc gctgcctgaa                                             20

<210> SEQ ID NO 145
<211> LENGTH: 21
<212> TYPE: DNA
<213> ORGANISM: Artificial Sequence
<220> FEATURE:

<223> OTHER INFORMATION: Synthetic polynucleotide

<400> SEQUENCE: 145
ggccttctga aacaggcaa a                                              21

<210> SEQ ID NO 146
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 146
tctggatgtt ctggtcgtca c                                             21

<210> SEQ ID NO 147
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 147
actggatacg gggcacatta                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 148
cgaagtgtgg tagcgaggaa                                               20

<210> SEQ ID NO 149
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 149
ctggtgttca agttgagctg ta                                            22

<210> SEQ ID NO 150
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 150
tctccttggc tttccacgaa                                               20

<210> SEQ ID NO 151
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 151
agaacggagt ctcatgcagt a                                             21

```
<210> SEQ ID NO 152
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 152
gcaccttgga agccctaca                                                       19

<210> SEQ ID NO 153
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 153
ttcagtatgt ctagcccctg aa                                                   22

<210> SEQ ID NO 154
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 154
gttgtcacca gcatcagtcc                                                      20

<210> SEQ ID NO 155
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 155
tggcattggt cagctgtaac                                                      20

<210> SEQ ID NO 156
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 156
cgaggatgtc ccggtaatac a                                                    21

<210> SEQ ID NO 157
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 157
agctgatgac catctgggag aa                                                   22

<210> SEQ ID NO 158
<211> LENGTH: 21
<212> TYPE: DNA
<213> ORGANISM: Artificial Sequence
<220> FEATURE:
<223> OTHER INFORMATION: Synthetic polynucleotide
```

<400> SEQUENCE: 158
gacaccagga aatcgttacc c    21

<210> SEQ ID NO 159
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 159
atacaaggca cgctgaggaa    20

<210> SEQ ID NO 160
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 160
gggtagaagg tggggatttc a    21

<210> SEQ ID NO 161
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 161
ctgctggacg cgtttatacc    20

<210> SEQ ID NO 162
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 162
ccgccttcta ggtcctgtac    20

<210> SEQ ID NO 163
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 163
tctccacaga caccacatca a    21

<210> SEQ ID NO 164
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 164
agtcagcaat ggcccgata    19

<210> SEQ ID NO 165
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 165
gttgtccggc acagggtaaa                                                  20

<210> SEQ ID NO 166
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 166
ggaaaagact gcaccgaaga ta                                               22

<210> SEQ ID NO 167
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 167
gacattcgtc cacatcctct gta                                              23

<210> SEQ ID NO 168
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 168
acgagcactc tctcaaacca                                                  20

<210> SEQ ID NO 169
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 169
caggtggagg tgtccaatca                                                  20

<210> SEQ ID NO 170
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 170
tgtcactgta gagggctttc aa                                               22

<210> SEQ ID NO 171
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 171
```
ggccctgcac attctgacta                                                  20

<210> SEQ ID NO 172
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 172
acggtgattg tgagcgtgaa                                                  20

<210> SEQ ID NO 173
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 173
catccggggc atgtaggaa                                                   19

<210> SEQ ID NO 174
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 174
gatggccacg atgctcagat a                                                21

<210> SEQ ID NO 175
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 175
agctcgaaaa ggcagtcgaa                                                  20

<210> SEQ ID NO 176
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 176
acttgctgtg ggtgaccat                                                   19

<210> SEQ ID NO 177
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 177
aatccccagc agcggaataa                                                  20

<210> SEQ ID NO 178
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 178
ccccatctga atctgggtaa c         21

<210> SEQ ID NO 179
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 179
tctgggagag ggactcaatc a         21

<210> SEQ ID NO 180
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 180
ccacggtgaa ggacaggaa         19

<210> SEQ ID NO 181
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 181
ggccttctcc gggtaagtac         20

<210> SEQ ID NO 182
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 182
gggcgacagc gggtaata         18

<210> SEQ ID NO 183
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 183
caaggccgtg agttttctcc         20

<210> SEQ ID NO 184
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 184
aagtgccagg catcaaacca         20

```
<210> SEQ ID NO 185
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 185
ctcagtgacc gtcaggtcta                                           20

<210> SEQ ID NO 186
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 186
tgggattcca atcaggtcat cc                                        22

<210> SEQ ID NO 187
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 187
catccaccat cagggtcaca                                           20
```

USES OF SALT-INDUCIBLE KINASE (SIK) INHIBITORS

RELATED APPLICATIONS

The present application is a divisional of and claims priority under 35 U.S.C. § 120 to U.S. application, U.S. Ser. No. 15/502,287, filed Feb. 7, 2017 and abandoned, which is a national stage filing under 35 U.S.C. § 371 of international PCT application, PCT/US2015/044387, filed Aug. 8, 2015, which claims priority under 35 U.S.C. § 119(e) to U.S. provisional application, U.S. Ser. No. 62/035,332, filed Aug. 8, 2014, each of which is incorporated herein by reference.

BACKGROUND OF THE INVENTION

Inflammatory bowel disease (IBD) is a group of inflammatory conditions of the colon and small intestine, principally including Crohn's disease and ulcerative colitis, with other forms of IBD representing far fewer cases (e.g., collagenous colitis, lymphocytic colitis, diversion colitis, Behçet's disease and indeterminate colitis). Pathologically, Crohn's disease affects the full thickness of the bowel wall (e.g., transmural lesions) and can affect any part of the gastrointestinal tract, while ulcerative colitis is restricted to the mucosa (epithelial lining) of the colon and rectum. Graft-versus-host disease (GVHD) is an immune-related disease that can occur following an allogeneic tissue transplant. It is commonly associated with stem cell or bone marrow transplants, but GVHD also applies to other forms of tissue graft. In GVHD immune cells of the tissue graft recognize the recipient host as foreign and attack the host's cells.

It has long been recognized that IBD and GVHD are diseases associated with increased immune activity. The causes of IBD, while not well understood, may be related to an aberrant immune response to the microbiota in genetically susceptible individuals. IBD affects over 1.4 million people in the United States and over 2.2 million in Europe and is on the increase. With both environmental and genetic factors playing a role in the development and progression of IBD, response to current treatments (e.g., anti-inflammatory drugs, immune system suppressors, antibiotics, surgery, and other symptom specific medications) are unpredictable.

Similarly, a fundamental feature of GVHD is increased immune activity. As yet, the pathophysiology underlying GVHD is not well understood. It is a significant cause of morbidity and mortality following allogenic haematopoietic stem-cell transplantation and thus the focus of much ongoing research. Despite the advances in understanding the pathophysiology (e.g., predisposing factors), a standardized therapeutic strategy is still lacking. Currently both acute and chronic forms of GVHD are treated using corticosteroids (e.g., anti-inflammatory treatments). There is a need for new approaches to treating IBD and GVHD.

SUMMARY OF THE INVENTION

In one aspect, described herein are novel uses of several compound classes as salt-inducible kinase (SIK) inhibitors. The described SIK inhibitors include macrocyclic compounds of Formula (I), imidazolyl compounds of Formula (II), urea and carbamate compounds of Formula (III-A) (e.g., urea and carbamate compounds of Formula (III)), and pharmaceutically acceptable salts, solvates, hydrates, polymorphs, co-crystals, tautomers, stereoisomers, isotopically labeled derivatives, and prodrugs thereof. The described SIK inhibitors are able to inhibit the activity of a SIK (e.g., SIK1, SIK2, SIK3), to enhance interleukin 10 (IL-10) production, and/or to treat and/or prevent inflammatory bowel disease (IBD) and/or graft-versus-host disease (GVHD) in a subject in need thereof.

In certain embodiments, the SIK inhibitor for use in the invention described herein is a compound of Formula (I):

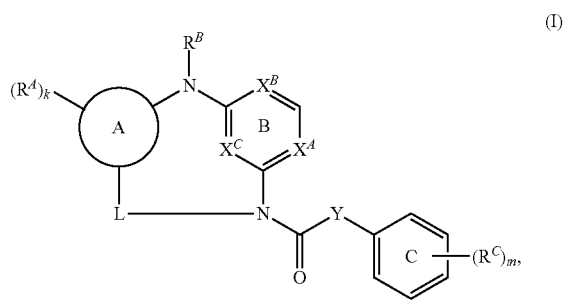

or a pharmaceutically acceptable salt, solvate, hydrate, polymorph, co-crystal, tautomer, stereoisomer, isotopically labeled derivative, or prodrug thereof.

Exemplary compounds of Formula (I) include, but are not limited to:

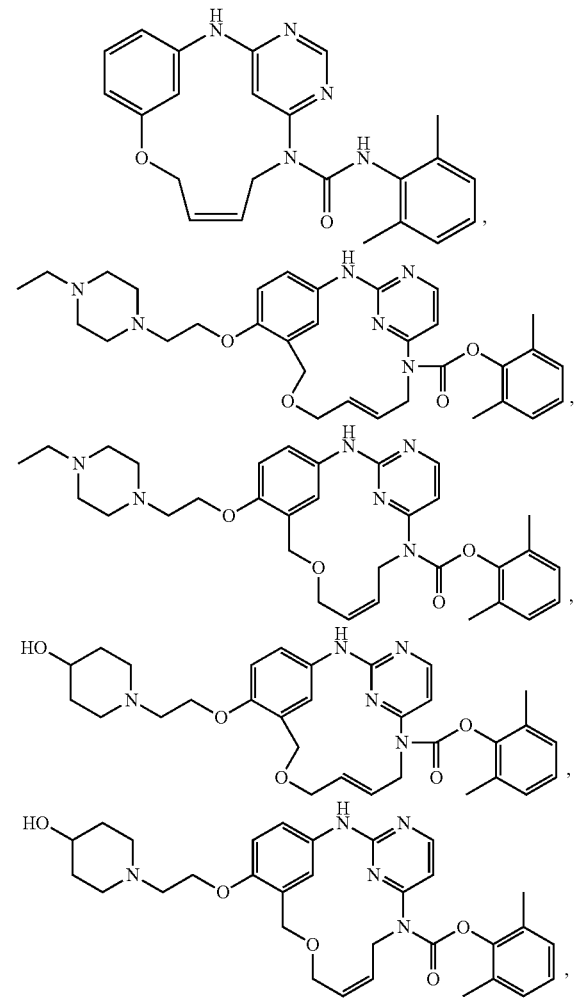

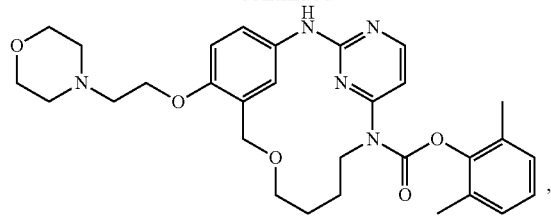
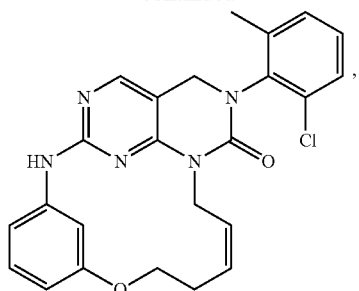
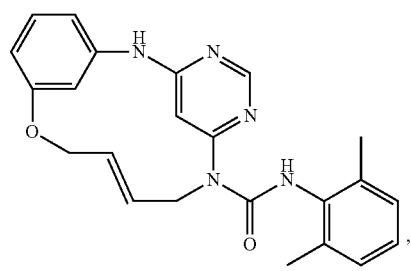
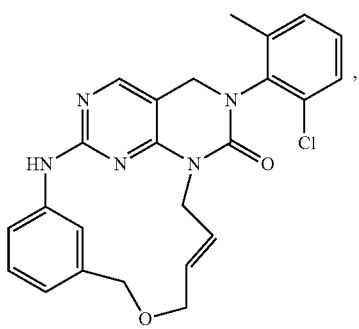
and pharmaceutically acceptable salts, solvates, hydrates, polymorphs, co-crystals, tautomers, stereoisomers, isotopically labeled derivatives, and prodrugs thereof.
Additional exemplary compounds of Formula (I) include, but are not limited to:
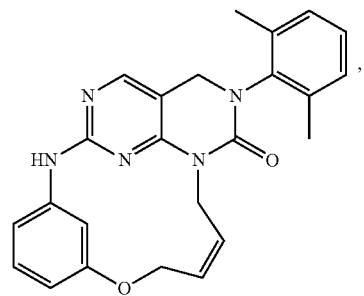
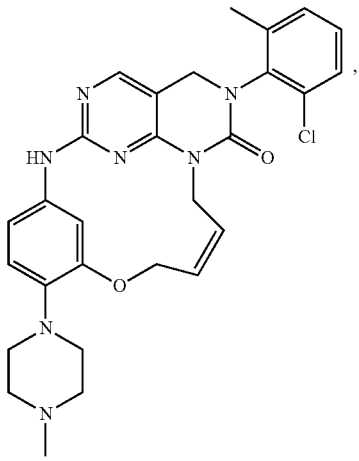
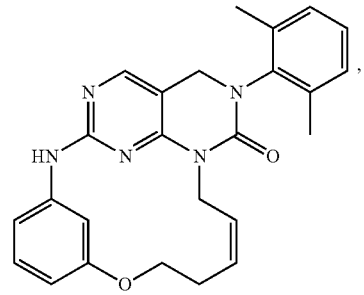
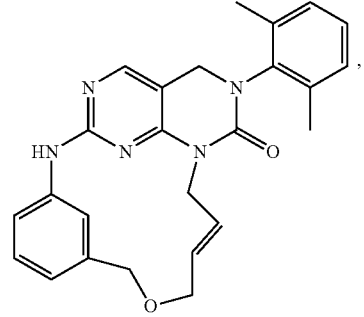
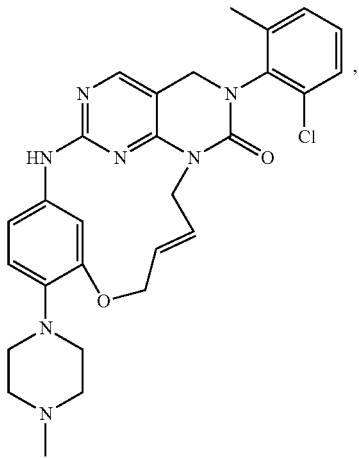

-continued

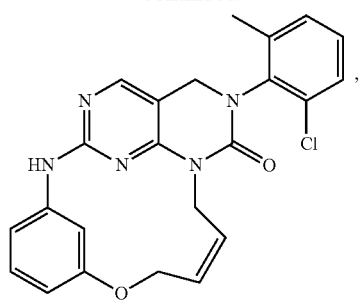

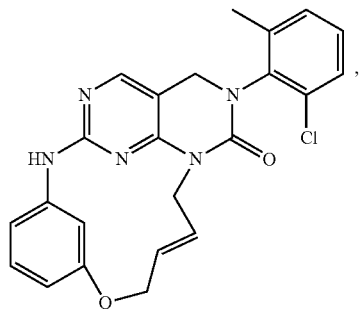

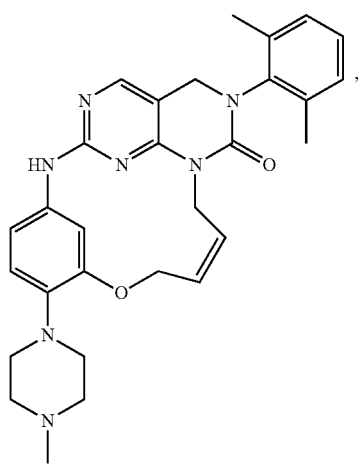

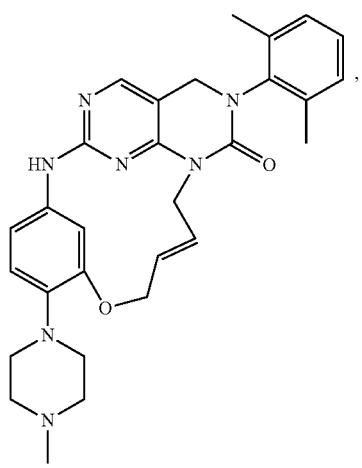

-continued

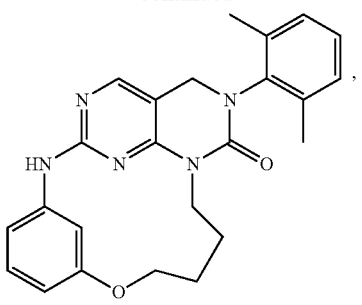

and pharmaceutically acceptable salts, solvates, hydrates, polymorphs, co-crystals, tautomers, stereoisomers, isotopically labeled derivatives, and prodrugs thereof.

In certain embodiments, the SIK inhibitor for use in the invention described herein is a compound of Formula (II):


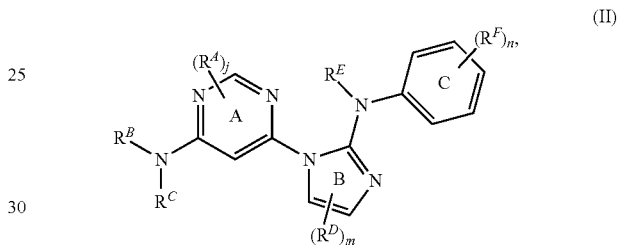

or a pharmaceutically acceptable salt, solvate, hydrate, polymorph, co-crystal, tautomer, stereoisomer, isotopically labeled derivative, or prodrug thereof.

Exemplary compounds of Formula (II) include, but are not limited to:

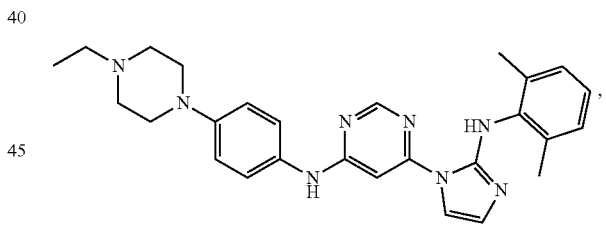

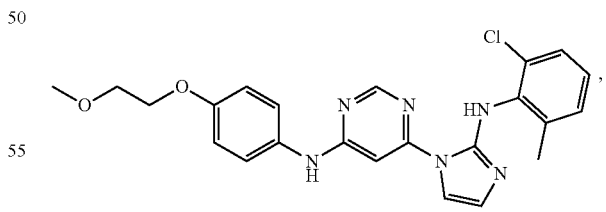

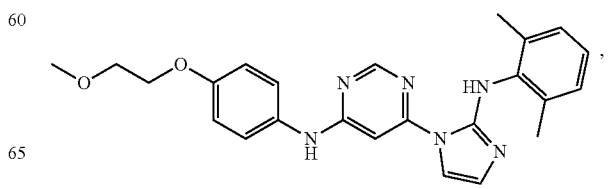

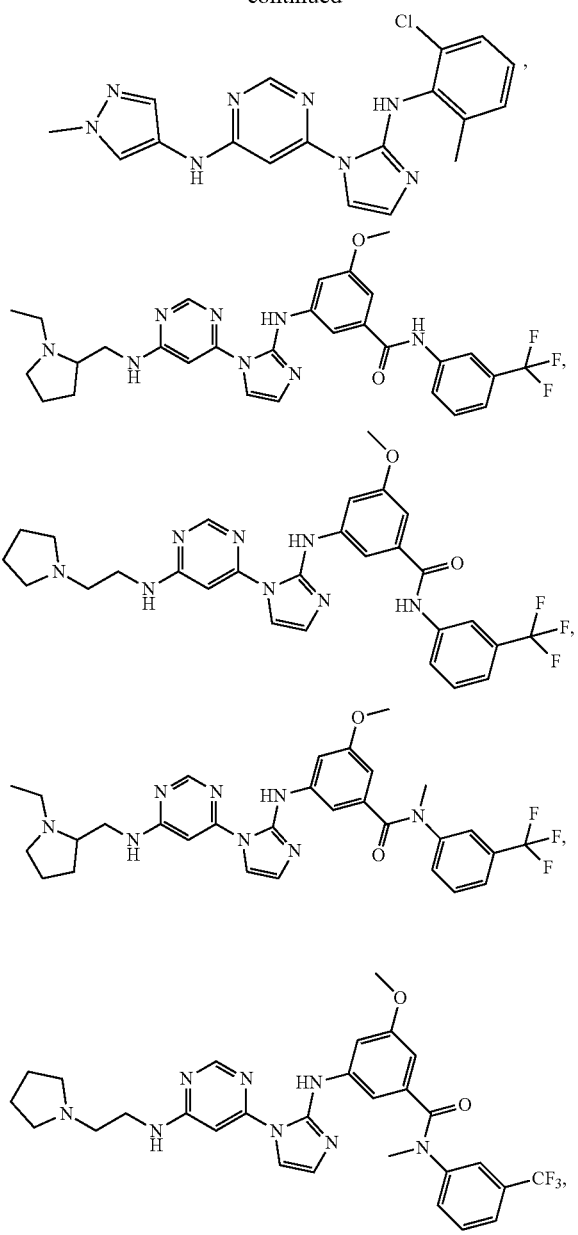

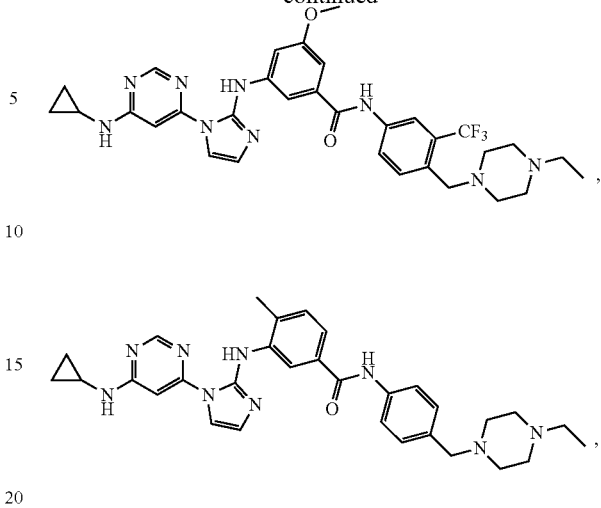

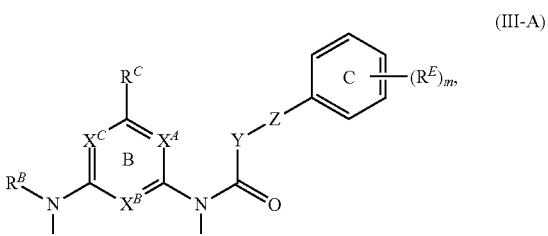

and pharmaceutically acceptable salts, solvates, hydrates, polymorphs, co-crystals, tautomers, stereoisomers, isotopically labeled derivatives, and prodrugs thereof.

In certain embodiments, the SIK inhibitor for use in the invention described herein is a compound of Formula (III-A):

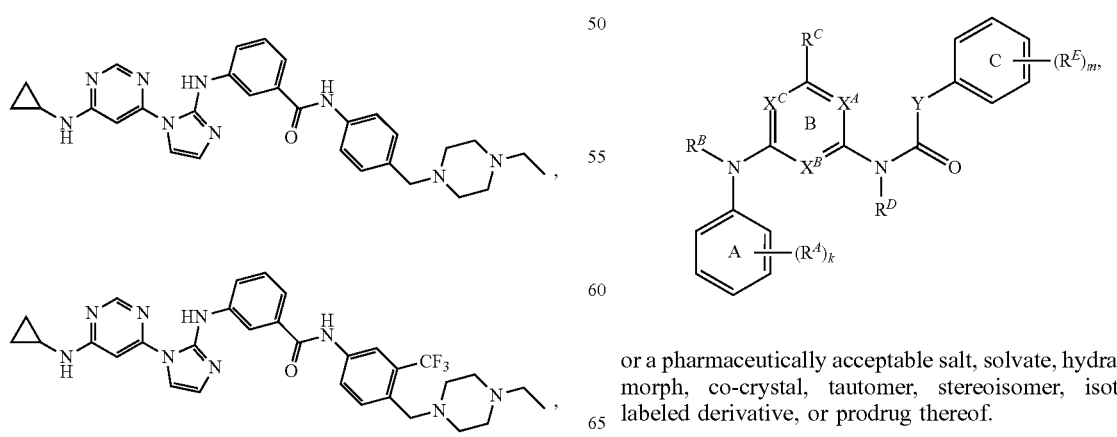

or a pharmaceutically acceptable salt, solvate, hydrate, polymorph, co-crystal, tautomer, stereoisomer, isotopically labeled derivative, or prodrug thereof.

In certain embodiments, the SIK inhibitor of Formula (III-A) is a compound of Formula (III):

or a pharmaceutically acceptable salt, solvate, hydrate, polymorph, co-crystal, tautomer, stereoisomer, isotopically labeled derivative, or prodrug thereof.

Exemplary compounds of Formula (III-A) include, but are not limited to:

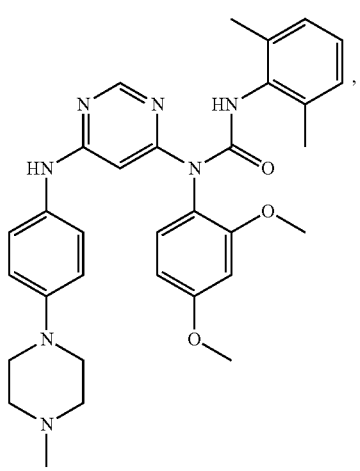
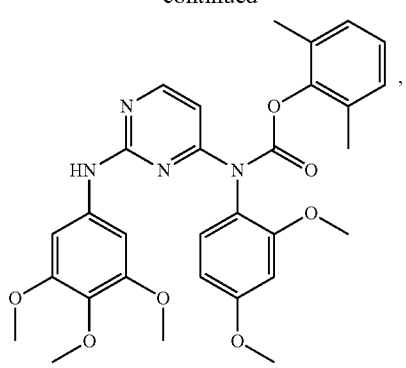
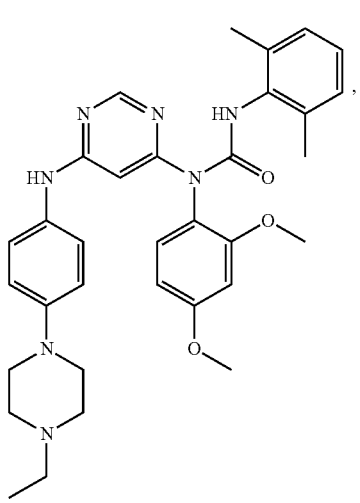
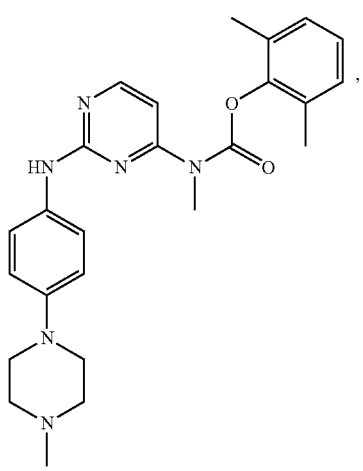
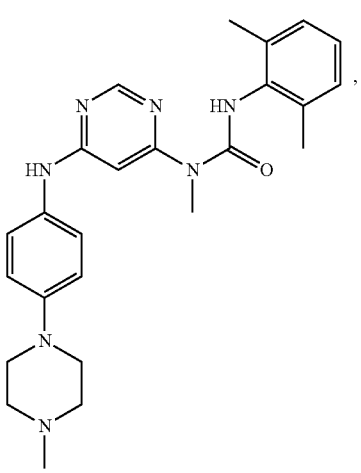
and pharmaceutically acceptable salts, solvates, hydrates, polymorphs, co-crystals, tautomers, stereoisomers, isotopically labeled derivatives, and prodrugs thereof.
Additional exemplary compounds of Formula (III-A) include, but are not limited to:
HG-9-96-01
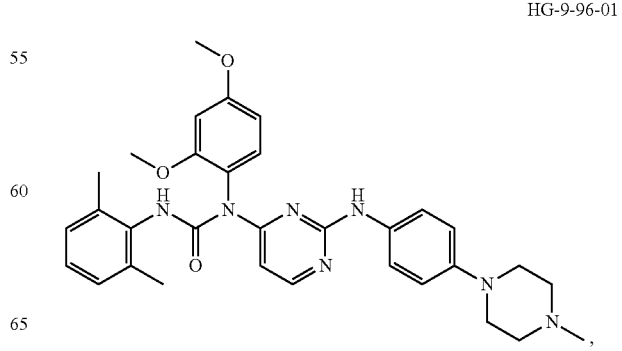

-continued
HG-9-148-02
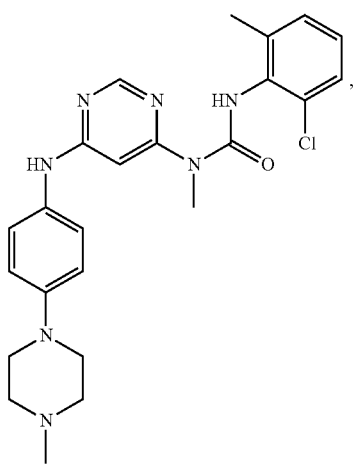
HG-10-8-01
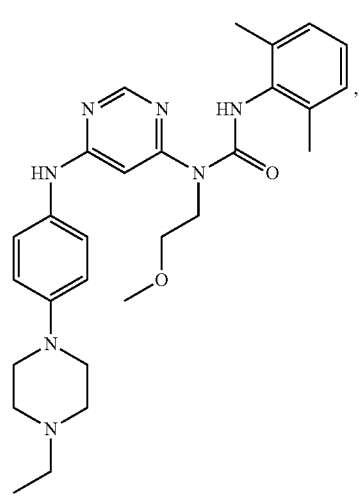
HG-10-8-02
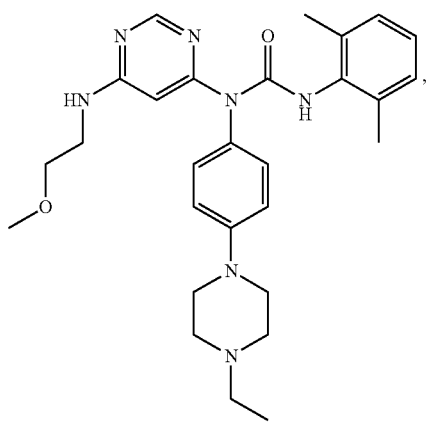
-continued
HG-10-9-01
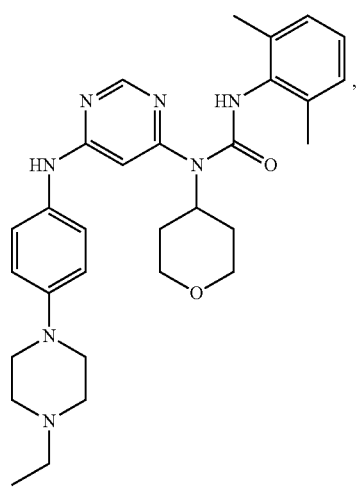
HG-10-15-02
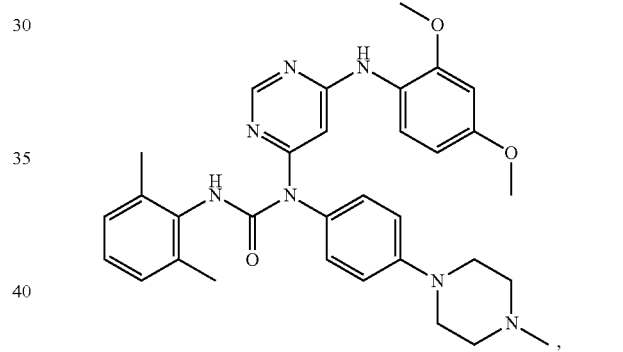
HG-10-15-03
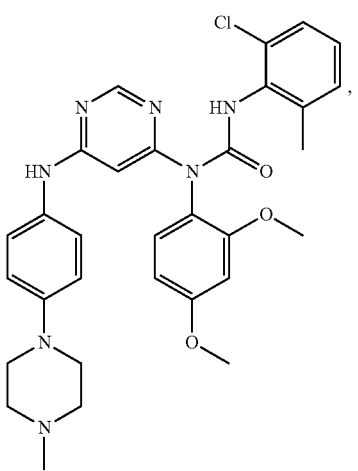

-continued
HG-10-15-04
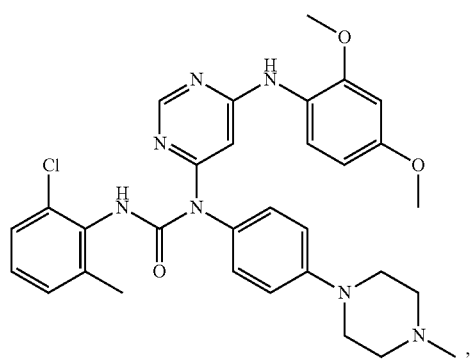
HG-10-27-01
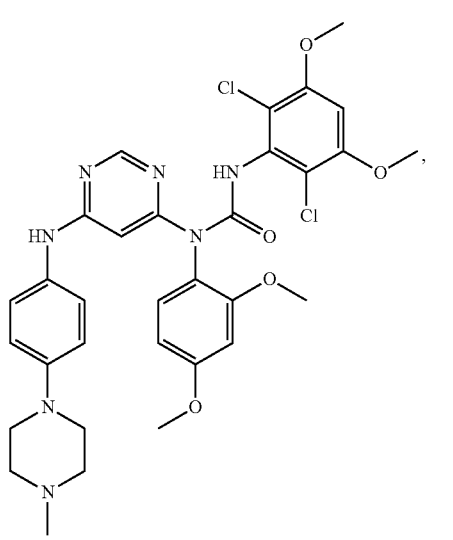
HG-10-27-02
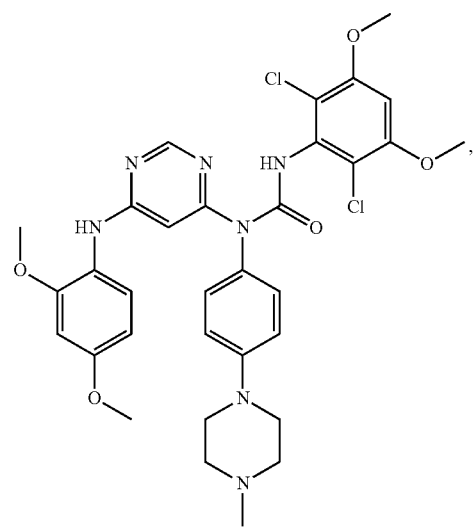
-continued
HG-10-28-01
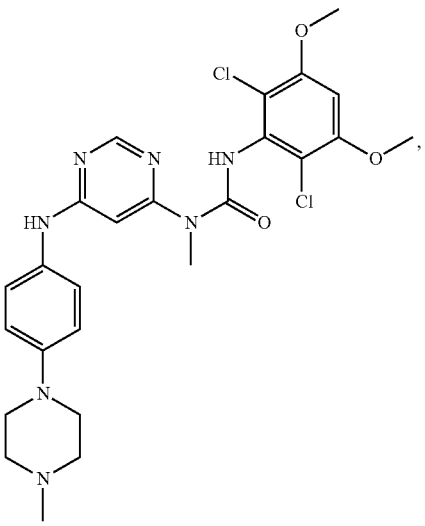
HG-10-31-01
HG-10-31-02
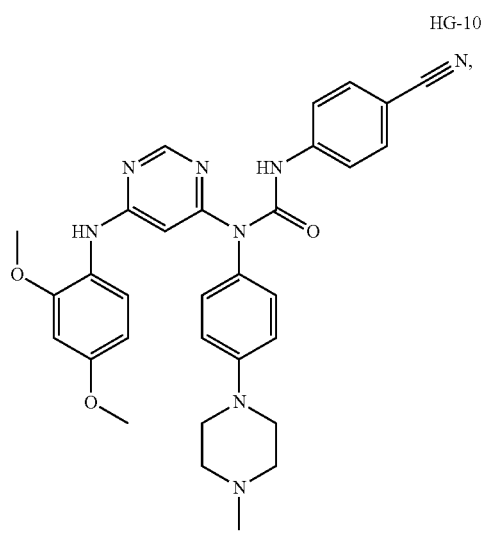

HG-10-36-01
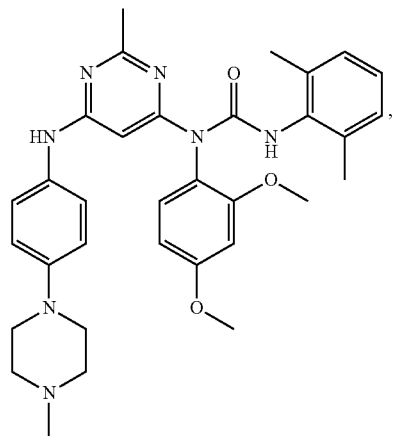
HG 10-60-01
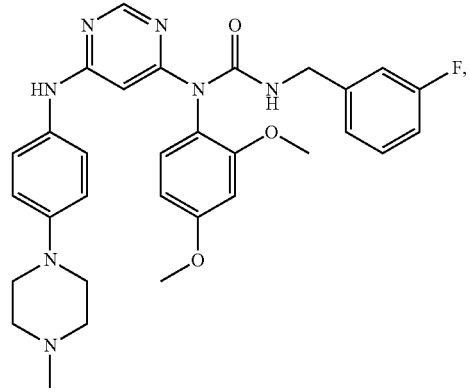
HG-10-36-02
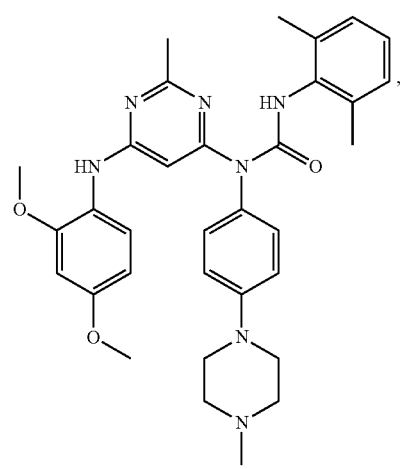
HG 10-60-02
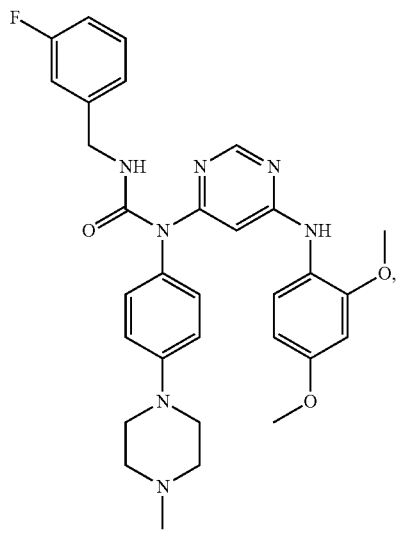
HG 10-59-02
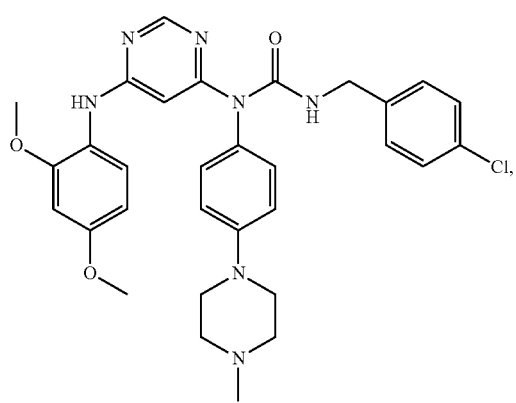
HG 10-61-01
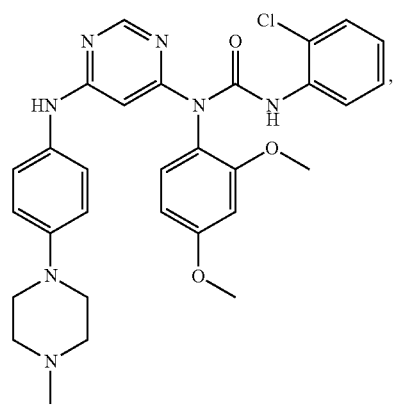

HG 10-61-02
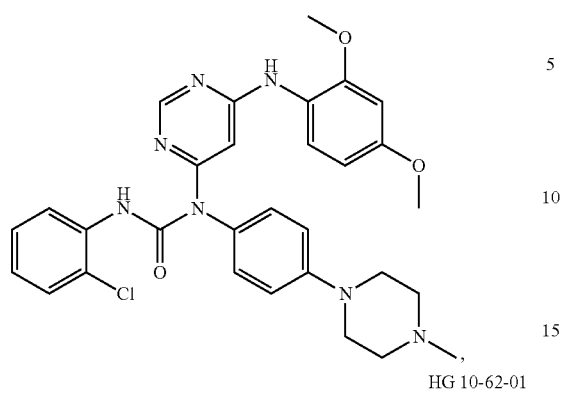
HG 10-62-01
HG 10-62-02
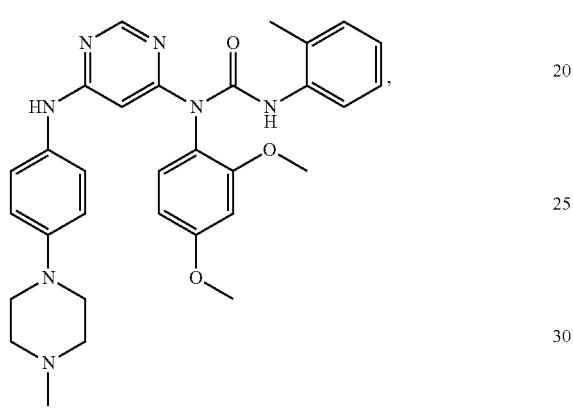
HG 10-63-01
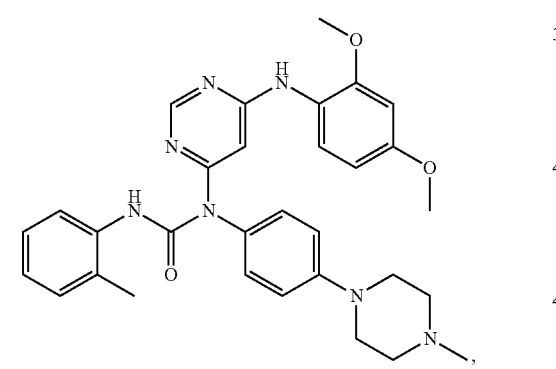
HG 10-63-02
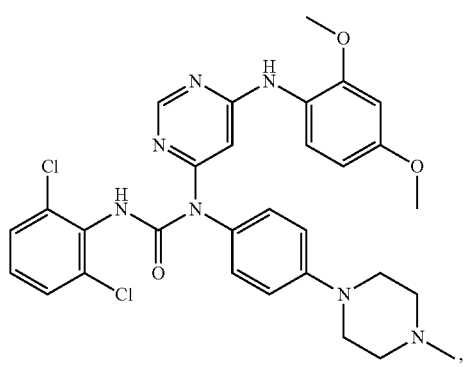
HG 10-64-01
HG 10-64-02
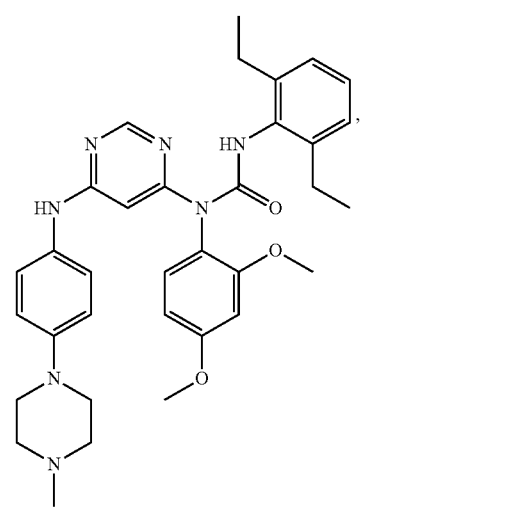

HG 10-65-01
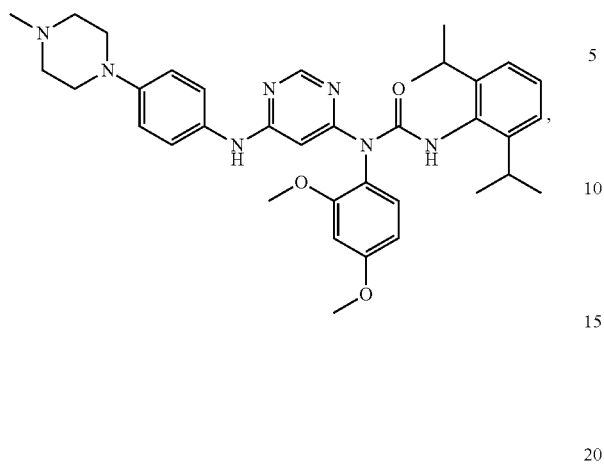
HG 10-65-02
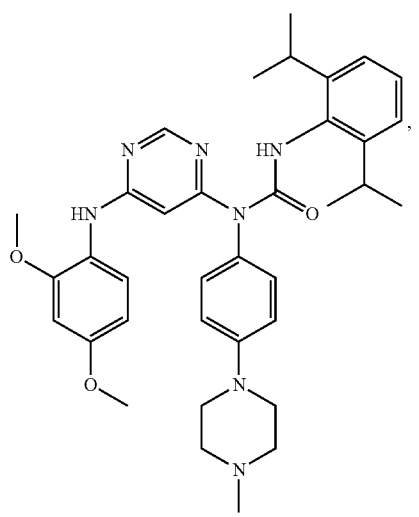
HG-10-149-01
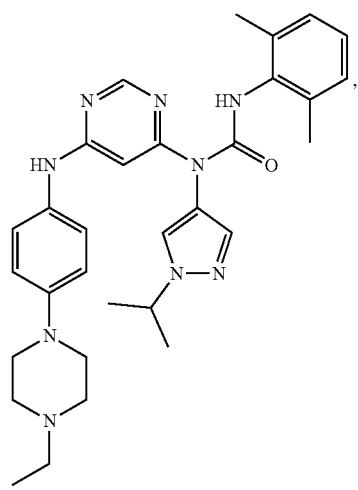
HG-10-149-02
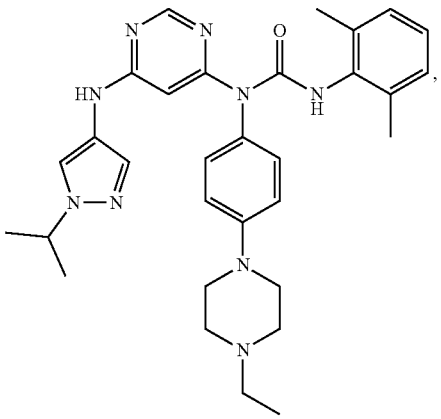
HG-10-150-01
HG-10-150-02
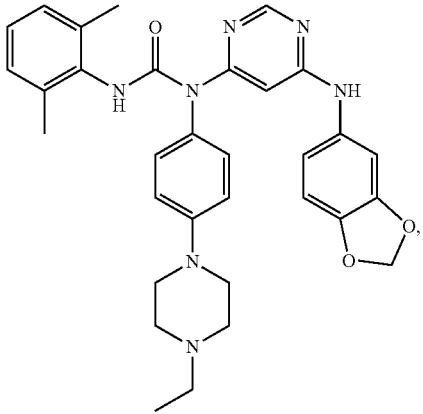

HG-11-18-01
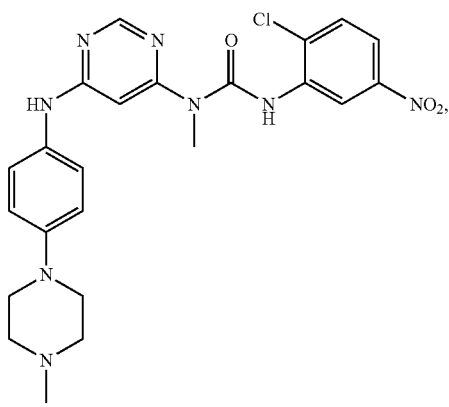
HG-11-21-01
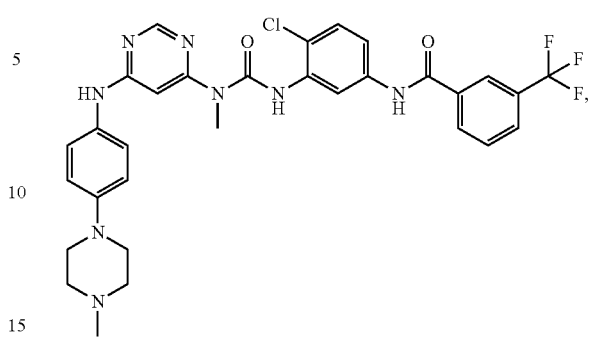
HG-11-18-02
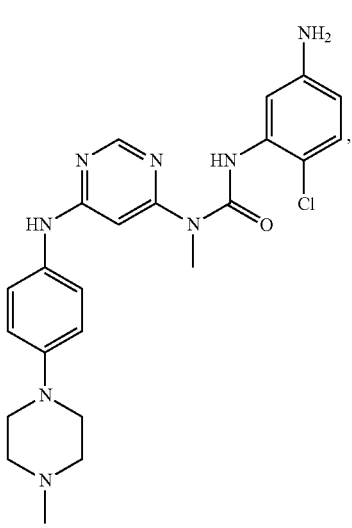
HG-11-22-01
and pharmaceutically acceptable salts, solvates, hydrates, polymorphs, co-crystals, tautomers, stereoisomers, isotopically labeled derivatives, and prodrugs thereof.
Additional exemplary compounds of Formula (III-A) also include, but are not limited to:
HG-3-09-01
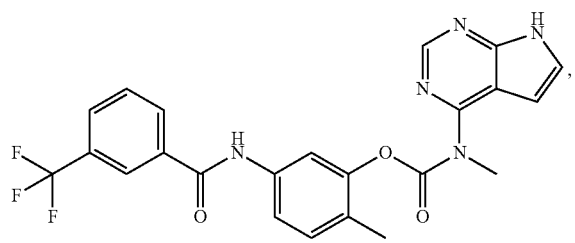
HG-9-87-02
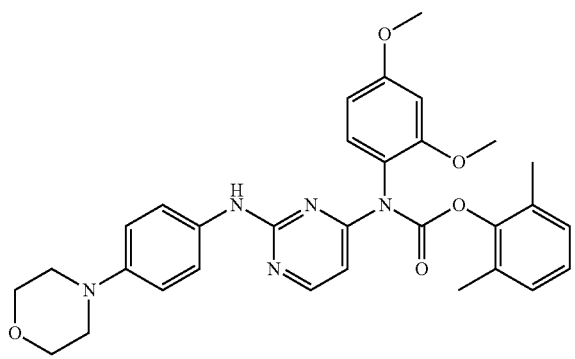

HG-9-87-03
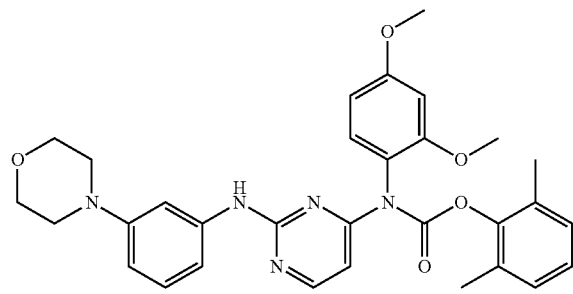
HG-9-87-04
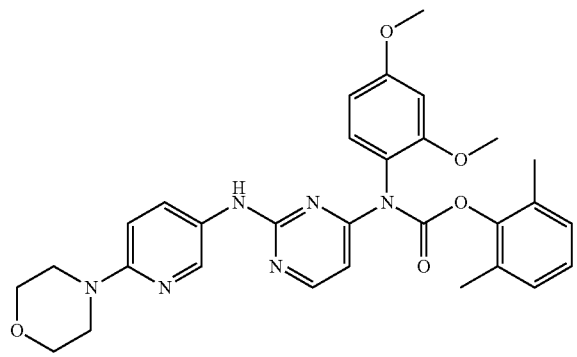
HG-9-88-02
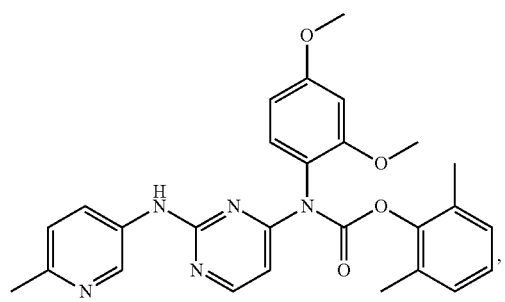
HG-9-88-03
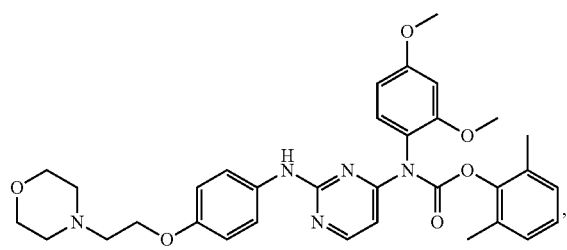
HG-9-88-04
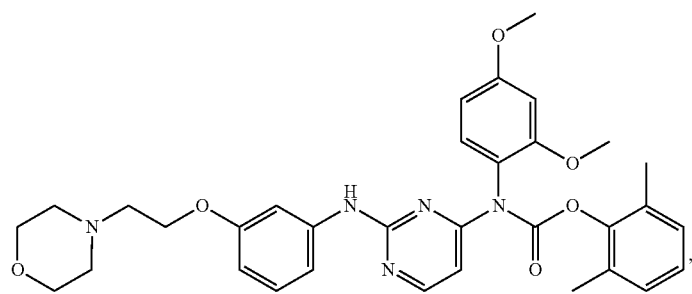
HG-9-88-05
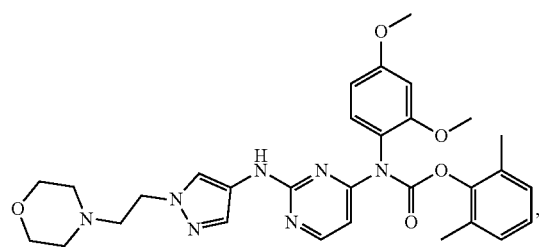
HG-9-90-01
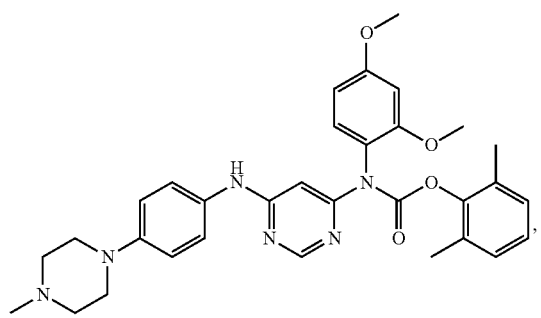

-continued
HG-9-90-02
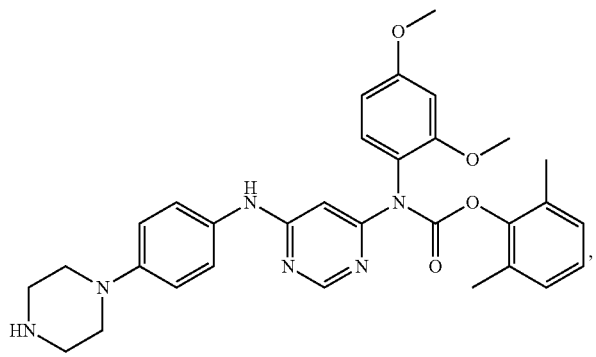
HG-9-139-02
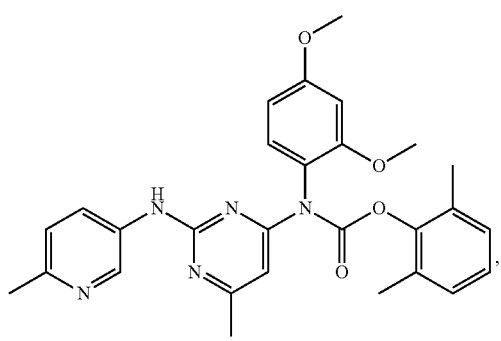
HG-9-139-04
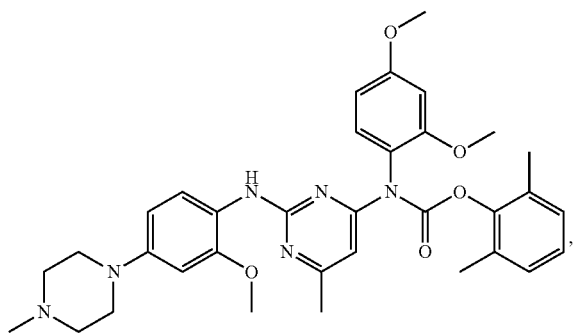
HG-9-140-01
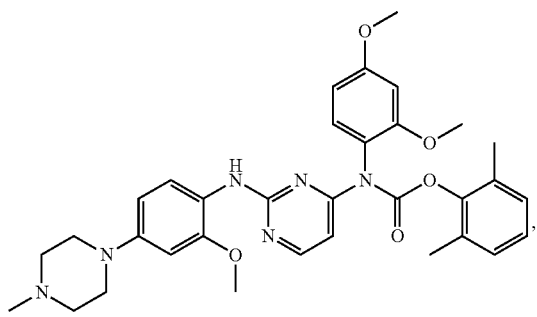
HG-9-90-03
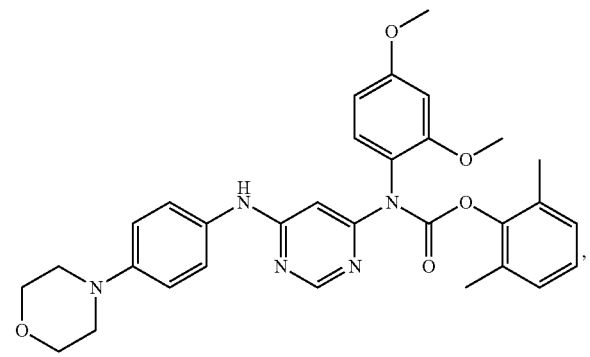
HG-9-139-03
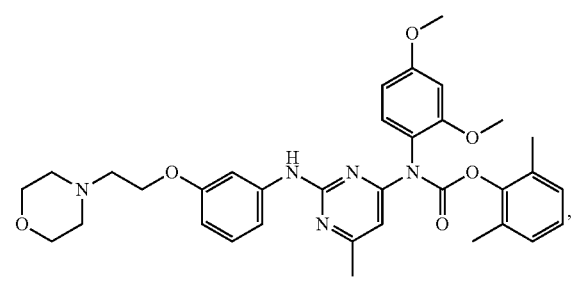
HG-9-139-05
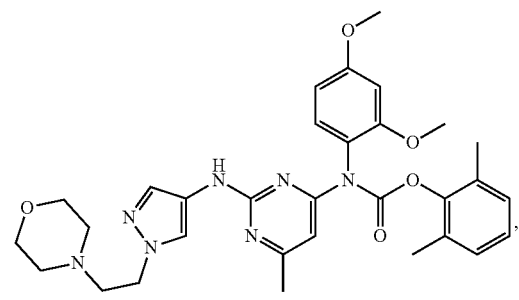
HG-9-144-01
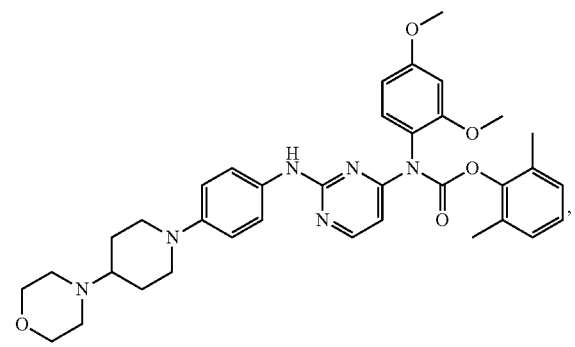

-continued
HG-9-144-02
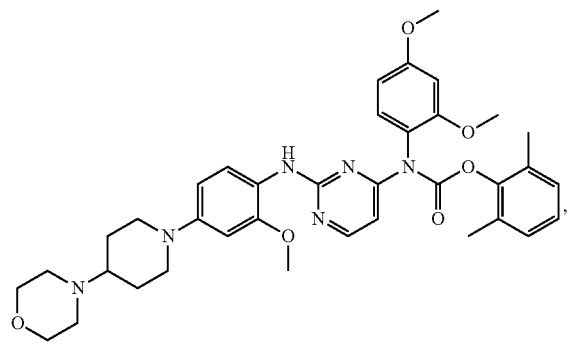
HG-9-144-03
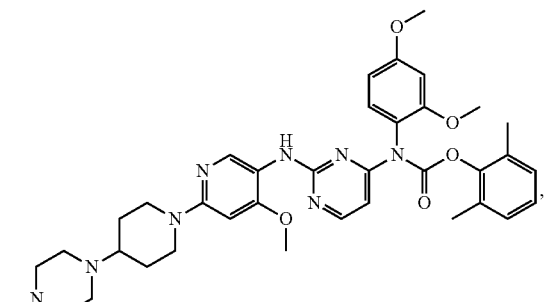
HG-9-144-04
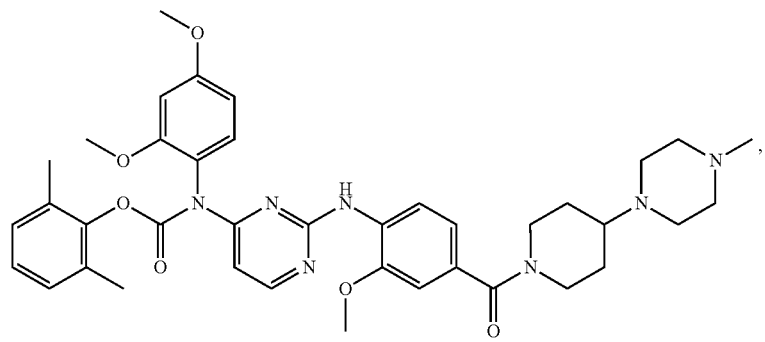
HG-9-144-05
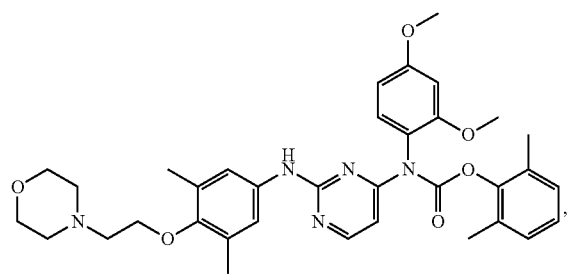
HG-9-150-02
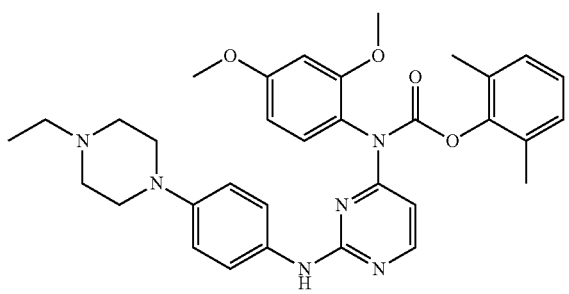
HG-11-6-01
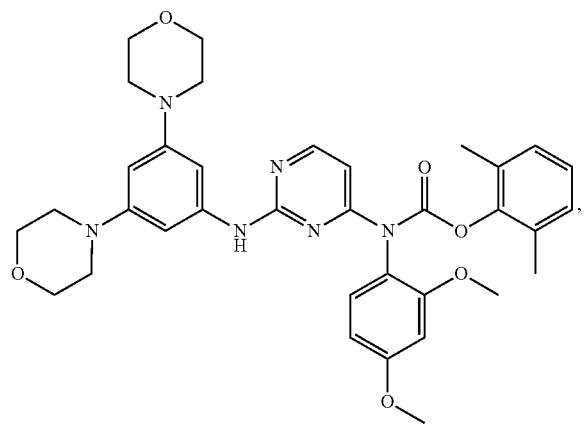
HG-11-6-02
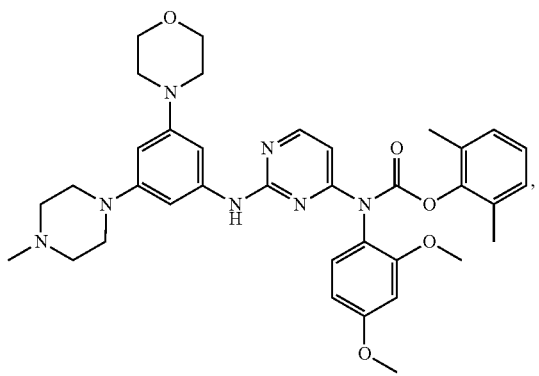

WH-4-023
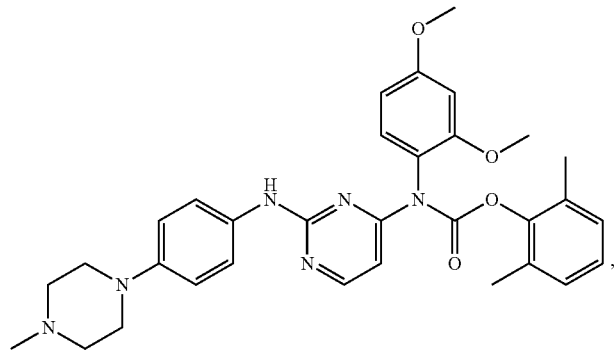
WH-4-025
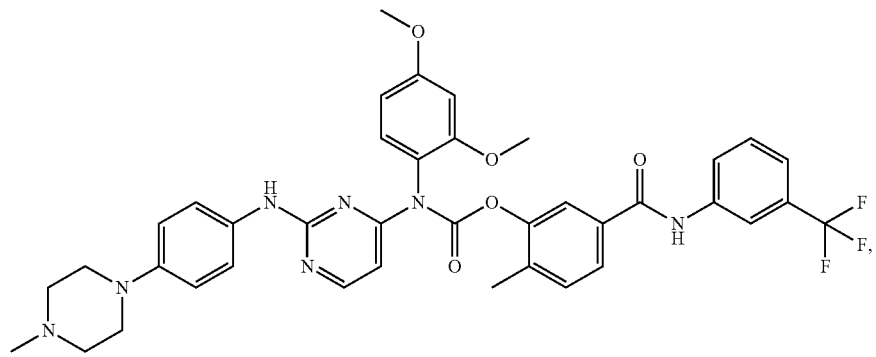
WH4-113
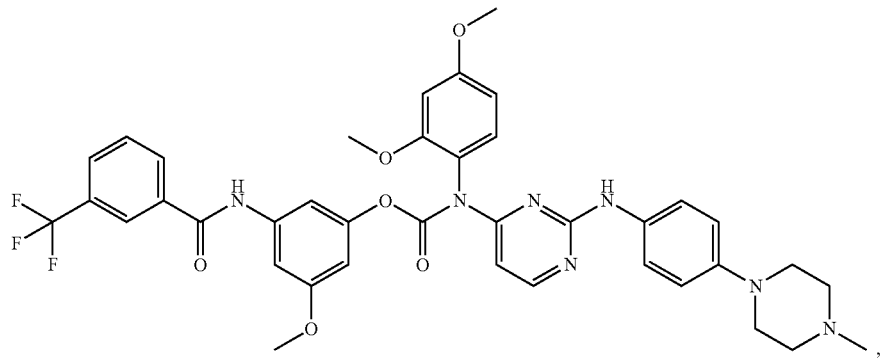
WH4-124-1
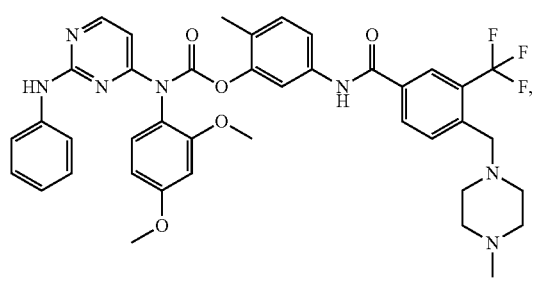
WH4-124-2
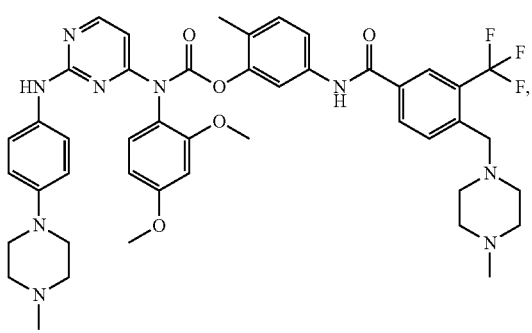

WH4-199-1

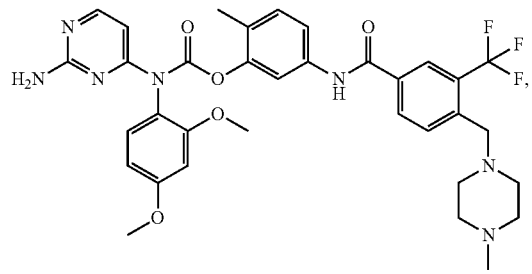

WH4-199-2

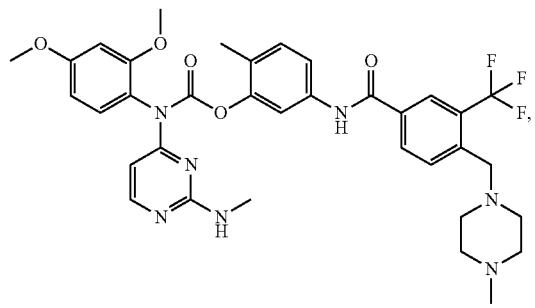

WH4-200-1

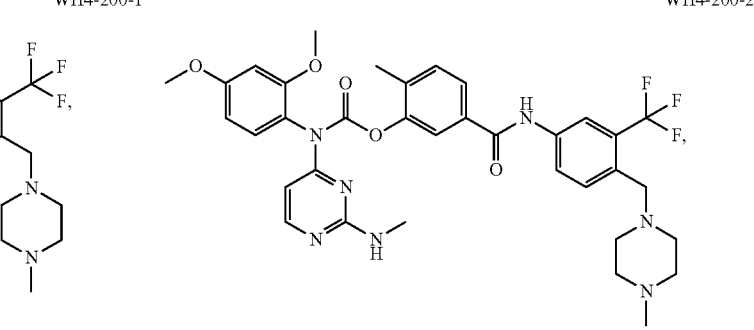

WH4-200-2

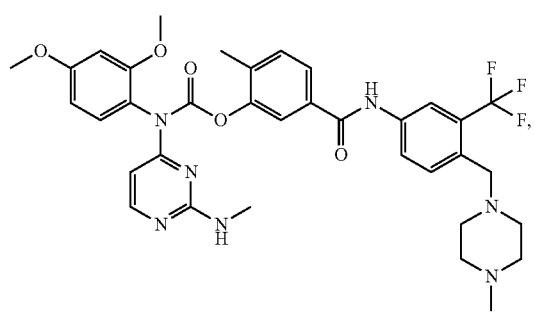

and pharmaceutically acceptable salts, solvates, hydrates, polymorphs, co-crystals, tautomers, stereoisomers, isotopically labeled derivatives, and prodrugs thereof.

In another aspect, the present disclosure provides methods of treating IBD in a subject in need thereof.

In another aspect, the present disclosure provides methods of preventing IBD in a subject in need thereof.

In another aspect, the present disclosure provides methods of treating GVHD in a subject in need thereof.

In another aspect, the present disclosure provides methods of preventing GVHD in a subject in need thereof.

Another aspect of the disclosure relates to methods of inhibiting the activity of a SIK in a subject.

Another aspect of the disclosure relates to methods of inhibiting the activity of a SIK in a cell.

Another aspect of the disclosure relates to methods of increasing the level of IL-10 in a subject.

Another aspect of the disclosure relates to methods of increasing the level of IL-10 in a cell.

In another aspect, the present disclosure provides methods of decreasing the level of a pro-inflammatory cytokine (e.g., IL-1β, IL-6, IL-12, or TNF-α) in a subject.

In another aspect, the present disclosure provides methods of decreasing the level of a pro-inflammatory cytokine (e.g., IL-1β, IL-6, IL-12, or TNF-α) in a cell.

In still another aspect, the present disclosure provides methods of converting bone marrow-derived dendritic cells (BMDCs) to an anti-inflammatory phenotype in a subject.

In certain embodiments, a method described herein includes administering to the subject an effective amount of a SIK inhibitor described herein. In certain embodiments, the subject is a human. In certain embodiments, a method described herein includes contacting the cell an effective amount of a SIK inhibitor described herein. In certain embodiments, the cell is in vitro.

In further another aspect, the present disclosure provides the SIK inhibitors for use in a method described herein.

The present disclosure refers to various issued patents, published patent applications, journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, --- is absent or a single bond, and ═══ or ≡≡≡ is a single or double bond. In a formula, ⌇⌇ is a single bond where the stereochemistry of the moieties immediately attached thereto is not specified. Such a ⌇⌇ bond may be ▬ or ⁞⁞⁞⁞.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is unspecified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents.

In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{aa}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3{}^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein X$^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of RU is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S) NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HCO$_3{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4{}^-$, PF$_4{}^-$, PF$_6{}^-$, AsF$_6{}^-$, SbF$_6{}^-$, B[3,5-(CF$_3$)$_2$C$_6$H$_3$]$_4{}^-$, B(C$_6$F$_5$)$_4{}^-$, BPh$_4{}^-$, Al(OC(CF$_3$)$_3$)$_4{}^-$, and carborane anions (e.g., CB$_{11}$H$_{12}{}^-$ or (HCB$_{11}$Me$_5$Br$_6$)$^-$). Exemplary counterions which may be multivalent include CO$_3{}^{2-}$, HPO$_4{}^{2-}$, PO$_4{}^{3-}$, B$_4$O$_7{}^{2-}$, SO$_4{}^{2-}$, S$_2$O$_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)N)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3{}^+$X$^-$, —OP(OR$^{cc}$)$_2$, —OP(OR$^{cc}$)$_3{}^+$X$^-$, —OP(=O)(R$^{aa}$)$_2$, —OP(=O)(OR$^{cc}$)$_2$, and —OP(=O)(N(R$^{bb}$))$_2$, wherein X$^-$, R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,1-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonoethyl carbamate (Peoc), 2-triphenylphosphinoisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, a-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2C^CH_3)$— includes one chain atom $C^A$, one hydrogen atom on $C^A$, and non-chain substituent —$(C^BH_2C^CH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

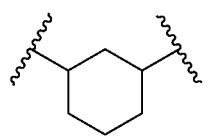 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$—, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

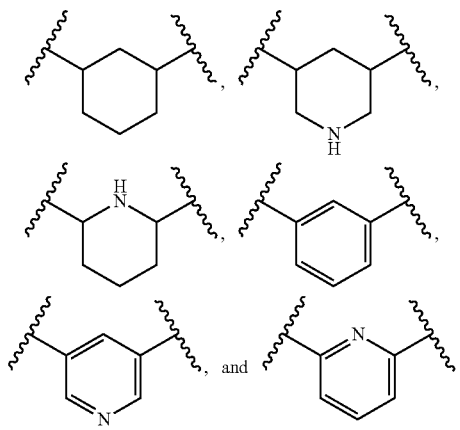

are all examples of a hydrocarbon chain. In contrast, in certain embodiments,

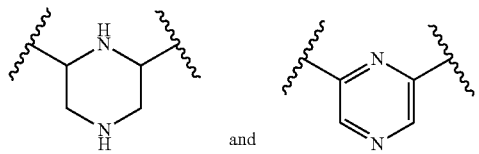 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

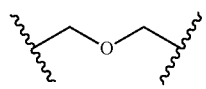 [SMILES: *COC*]

is a $C_3$ hydrocarbon chain wherein one chain atom is replaced with an oxygen atom.

The term "leaving group" is given its ordinary meaning in the art of synthetic organic chemistry and refers to an atom or a group capable of being displaced by a nucleophile.

Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. In certain embodiments, the leaving group is an activated substituted hydroxyl group (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O) R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, or —OP(=O)(NR$^{bb}$)$_2$, wherein R$^{aa}$, R$^{bb}$, and R$^{cc}$ are as defined herein).

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N$^+$(C$_{1-4}$ alkyl)$_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The "molecular weight" of a monovalent moiety —R is calculated by subtracting 1 from the molecular weight of the compound R—H. The "molecular weight" of a divalent moiety -L- is calculated by subtracting 2 from the molecular weight of the compound H-L-H.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile. A "patient" refers to a human subject in need of treatment of a disease described herein.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective treatment. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, salt-inducible kinase (SIK, e.g., salt-inducible kinase 1 (SIK1), salt-inducible kinase 2 (SIK2), salt-inducible kinase 3 (SIK3)).

The term "salt-inducible kinase" or "SIK" refers to a subfamily of serine/threonine protein kinases including SIK1, SIK2, and SIK3 that belong to an AMP-activated protein kinase family.

The term "inhibition", "inhibiting", "inhibit," or "inhibitor" refer to the ability of a compound to reduce, slow, halt, and/or prevent activity of a particular biological process (e.g., kinase activity) in a cell relative to vehicle.

When a compound, pharmaceutical composition, method, or use is referred to as "selectively" or "specifically" modulating (e.g., increasing or inhibiting) the activity of a first protein kinase, the compound, pharmaceutical composition, method, or use modulates the activity of the first protein kinase to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least a second protein kinase that is different from the first protein kinase.

BRIEF DESCRIPTION OF THE DRAWINGS

FIG. 2A. Activity of HG-9-91-01 analogs suggests specific role for SIK2 inhibition in IL-10 up-regulation. Inhibitory activity of HG-9-91-01 analogs on recombinant SIKs as well as their effects on IL-10 production and viability of zymosan-stimulated BMDCs. N.D. (not determined). Data are mean of two independent experiments.

FIG. 9B. Inhibitory activity of HG-9-91-01 analogs on recombinant SIKs as well as their effects on IL-10 production and viability of zymosan-stimulated BMDCs. N.D., not determined. Data are mean of two independent experiments.

DETAILED DESCRIPTION OF CERTAIN EMBODIMENTS OF THE INVENTION

Figures 1A, 1B:
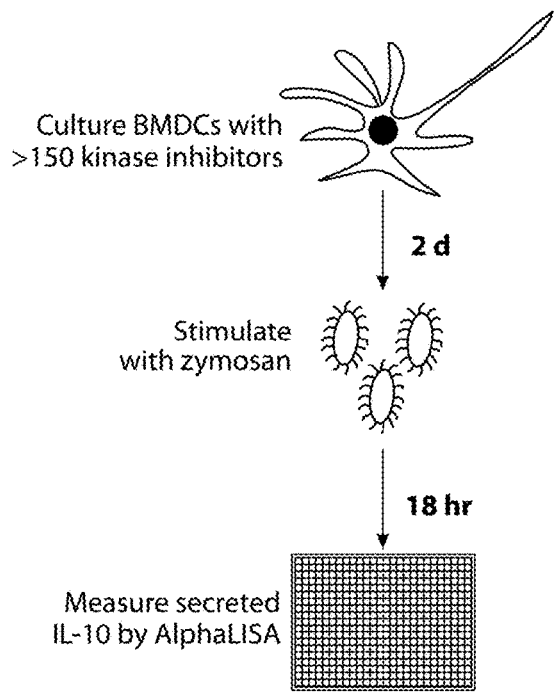
FIG. 1A. Targeted small-molecule screen identifies SIK inhibition as a common activity of multi-kinase inhibitors that up-regulate IL-10 production by inflammatory dendritic cells DCs. Screening strategy for identification of small-molecule enhancers of IL-10 production.
FIG. 1B. IL-10-potentiating activity and reported targets of hit compounds. Data are mean of two independent experiments.

Described herein are macrocyclic compounds of Formula (I), imidazolyl compounds of Formula (II), urea or carbamate compounds of Formula (III-A), and pharmaceutically acceptable salts, solvates, hydrates, polymorphs, co-crystals, tautomers, stereoisomers, isotopically labeled derivatives, and prodrugs thereof. The described compounds are able to inhibit the activity (e.g., increased activity) of a salt-inducible kinase (SIK, e.g., SIK1, SIK2, SIK3). The described compounds are also able to enhance interleukin 10 (IL-10) production by macrophages and dendritic cells of the gut, to decrease the level of a pro-inflammatory cytokine in a subject or cell, and/or to convert bone marrow-derived dendritic cells (BMDCs) to an anti-inflammatory phenotype. Also provided in the present disclosure are methods of treating and/or preventing inflammatory bowel disease (IBD) and/or graft-versus-host disease (GVHD) in a subject in need thereof using the described compounds.

Compounds for Use in the Invention
Compounds of Formula (I)

In one aspect, the present disclosure provides macrocyclic compounds of Formula (I) for use in the present invention:

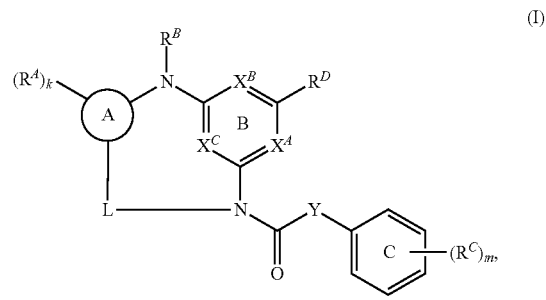

and pharmaceutically acceptable salts, solvates, hydrates, polymorphs, co-crystals, tautomers, stereoisomers, isotopically labeled derivatives, and prodrugs thereof, wherein:

Ring A is a substituted or unsubstituted phenyl ring or a substituted or unsubstituted, monocyclic, 5- to 6-membered heteroaryl ring, wherein one, two, three, or four atoms in the heteroaryl ring system are independently nitrogen, oxygen, or sulfur;

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

k is 0, 1, 2, 3, or 4;

L is a substituted or unsubstituted, saturated or unsaturated $C_{3-10}$ hydrocarbon chain, optionally wherein one or more chain atoms of the hydrocarbon chain are independently replaced with —O—, —S—, —NR$^N$—, —N=, or =N—, wherein each instance of $R^N$ is independently hydrogen, substituted or unsubstituted acyl, substituted or unsubstituted $C_{1-6}$ alkyl, or a nitrogen protecting group;

$R^B$ is hydrogen, substituted or unsubstituted acyl, substituted or unsubstituted $C_{1-6}$ alkyl, or a nitrogen protecting group;

each of $X^A$, $X^B$, and $X^C$ is independently N or $CR^X$, wherein $R^X$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$;

Y is —O— or —$NR^Y$—, wherein $R^Y$ is hydrogen, substituted or unsubstituted acyl, substituted or unsubstituted $C_{1-6}$ alkyl, or a nitrogen protecting group;

or when Y is —$NR^Y$— and $X^A$ is $CR^X$, $R^Y$ and $R^X$ of $X^A$ are joined to form a substituted or unsubstituted, monocyclic, 5- to 7-membered heterocyclic ring that is fused with Ring B;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$;

m is 0, 1, 2, 3, 4, or 5; and $R^D$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$.

In certain embodiments, a macrocyclic compound of Formula (I) for use in the present invention is of the formula:

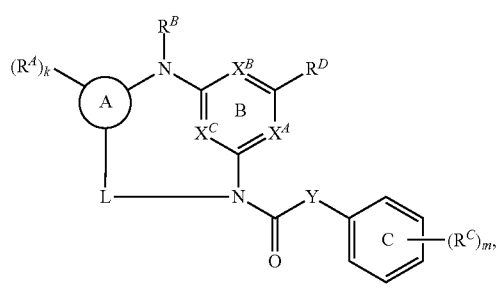

(I)

or a pharmaceutically acceptable salt, solvate, hydrate, polymorph, co-crystal, tautomer, stereoisomer, isotopically labeled derivative, or prodrug thereof, wherein:

Ring A is a substituted or unsubstituted phenyl ring or a substituted or unsubstituted, monocyclic, 5- to 6-membered heteroaryl ring, wherein one, two, three, or four atoms in the heteroaryl ring system are independently nitrogen, oxygen, or sulfur;

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

k is 0, 1, 2, 3, or 4;

L is a substituted or unsubstituted, saturated or unsaturated $C_{3-10}$ hydrocarbon chain, optionally wherein one or more chain atoms of the hydrocarbon chain are independently replaced with —O—, —S—, —$NR^N$—, —N=, or =N—, wherein each instance of $R^N$ is independently hydrogen, substituted or unsubstituted acyl, substituted or unsubstituted $C_{1-6}$ alkyl, or a nitrogen protecting group;

$R^B$ is hydrogen, substituted or unsubstituted acyl, substituted or unsubstituted $C_{1-6}$ alkyl, or a nitrogen protecting group;

each of $X^A$, $X^B$, and $X^C$ is independently N or $CR^X$, wherein $R^X$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$;

Y is —O— or —$NR^Y$—, wherein $R^Y$ is hydrogen, substituted or unsubstituted acyl, substituted or unsubstituted $C_{1-6}$ alkyl, or a nitrogen protecting group;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$;

m is 0, 1, 2, 3, 4, or 5; and $R^D$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

All embodiments of Ring A, Ring B, Ring C, L, X$^A$, X$^B$, X$^C$, Y, R$^A$, R$^a$, R$^B$, R$^C$, R$^D$, R$^E$, R$^N$, RX, R$^Y$, k, and m recited in subsection Compounds of Formula (I) apply only to Formula (I).

Formula (I) includes Ring A that is unsubstituted (e.g., when k is 0) or substituted with one or more substituents R$^A$ (e.g., when k is 1, 2, 3, or 4). In certain embodiments, Ring A is an unsubstituted phenyl ring. In certain embodiments, Ring A is a substituted phenyl ring. In certain embodiments, Ring A is a substituted or unsubstituted, monocyclic, 5-membered heteroaryl ring (e.g., furanyl, thienyl, pyrrolyl, imidazolyl, pyrazolyl, oxazolyl, isoxazolyl, thiazolyl, or isothiazolyl ring), wherein one, two, three, or four atoms in the heteroaryl ring system are independently nitrogen, oxygen, or sulfur. In certain embodiments, Ring A is a substituted or unsubstituted, monocyclic, 6-membered heteroaryl ring (e.g., a pyridyl, pyrazinyl, pyrimidinyl, or pyridazinyl ring), wherein one, two, three, or four atoms in the heteroaryl ring system are independently nitrogen, oxygen, or sulfur. In certain embodiments, Ring A is of the formula:

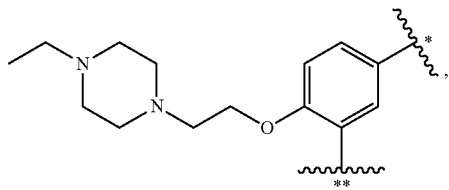

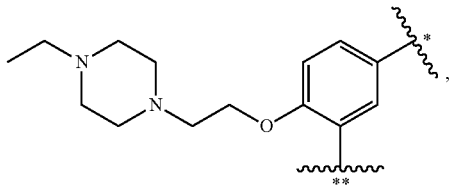

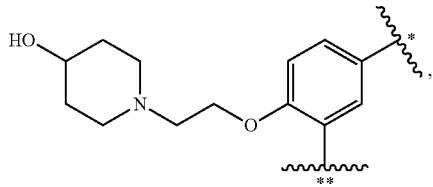

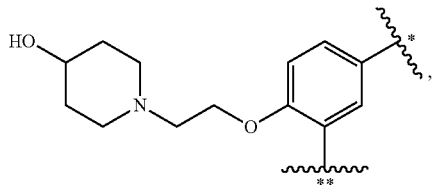

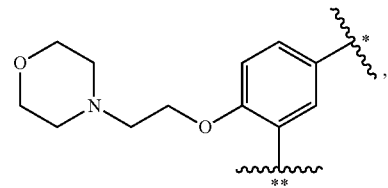

-continued

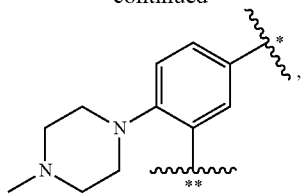

wherein the radical marked with "*" is directly attached to N(RB), and the radical marked with "**" is directly attached to L.

In Formula (I), Ring A may include one or more substituents R$^A$. In certain embodiments, at least two instances of R$^A$ are different. In certain embodiments, all instances of R$^A$ are the same. In certain embodiments, at least one instance of R$^A$ is halogen. In certain embodiments, at least one instance of R$^A$ is F. In certain embodiments, at least one instance of R$^A$ is Cl. In certain embodiments, at least one instance of R$^A$ is Br. In certain embodiments, at least one instance of R$^A$ is I (iodine). In certain embodiments, at least one instance of R$^A$ is substituted alkyl. In certain embodiments, at least one instance of R$^A$ is unsubstituted alkyl. In certain embodiments, at least one instance of R$^A$ is unsubstituted $C_{1-6}$ alkyl. In certain embodiments, all instances of R$^A$ are unsubstituted $C_{1-6}$ alkyl. In certain embodiments, at least one instance of R$^A$ is substituted $C_{1-6}$ alkyl. In certain embodiments, at least one instance of R$^A$ is $C_{1-6}$ alkyl substituted with at least one halogen. In certain embodiments, at least one instance of R$^A$ is —CH$_3$. In certain embodiments, all instances of R$^A$ are —CH$_3$. In certain embodiments, at least one instance of R$^A$ is substituted methyl. In certain embodiments, at least one instance of R$^A$ is —CH$_2$F. In certain embodiments, at least one instance of R$^A$ is —CHF$_2$. In certain embodiments, at least one instance of R$^A$ is —CF$_3$. In certain embodiments, at least one instance of R$^A$ is ethyl. In certain embodiments, at least one instance of R$^A$ is propyl. In certain embodiments, at least one instance of R$^A$ is butyl. In certain embodiments, at least one instance of R$^A$ is pentyl. In certain embodiments, at least one instance of R$^A$ is hexyl. In certain embodiments, at least one instance of R$^A$ is Bn. In certain embodiments, at least one instance of R$^A$ is substituted alkenyl. In certain embodiments, at least one instance of R$^A$ is unsubstituted alkenyl. In certain embodiments, at least one instance of R$^A$ is substituted alkynyl. In certain embodiments, at least one instance of R$^A$ is unsubstituted alkynyl. In certain embodiments, at least one instance of R$^A$ is substituted carbocyclyl. In certain embodiments, at least one instance of R$^A$ is unsubstituted carbocyclyl. In certain embodiments, at least one instance of R$^A$ is saturated carbocyclyl. In certain embodiments, at least one instance of R$^A$ is unsaturated carbocyclyl. In certain embodiments, at least one instance of R$^A$ is monocyclic carbocyclyl. In certain embodiments, at least one instance of R$^A$ is 3- to 7-membered, monocyclic carbocyclyl. In certain embodiments, at least one instance of R$^A$ is substituted heterocyclyl. In certain embodiments, at least one instance of R$^A$ is unsubstituted heterocyclyl. In certain embodiments, at least one instance of R$^A$ is saturated heterocyclyl. In certain embodiments, at least one instance of R$^A$ is unsaturated heterocyclyl. In certain embodiments, at least one instance of R$^A$ is heterocyclyl, wherein one, two, or three atoms in the heterocyclic ring system are independently selected from the group consisting of nitrogen, oxygen, and sulfur. In certain embodiments, at least one instance of R$^A$ is monocyclic heterocyclyl. In certain embodiments, at least one instance of R$^A$ is 3- to 7-membered, monocyclic heterocyclyl. In certain embodiments, at least one instance of $R^A$ is substituted or unsubstituted, monocyclic, 3- to 7-membered heterocyclyl, wherein one, two, or three atoms in the heterocyclic ring system are independently selected from the group consisting of nitrogen, oxygen, and sulfur. In certain embodiments, at least one instance of $R^A$ is substituted or unsubstituted oxetanyl, substituted or unsubstituted tetrahydrofuranyl, substituted or unsubstituted pyrrolidinyl, substituted or unsubstituted tetrahydropyranyl, substituted or unsubstituted piperidinyl, substituted or unsubstituted morpholinyl, or substituted or unsubstituted piperazinyl. In certain embodiments, at least one instance of $R^A$ is of the formula:

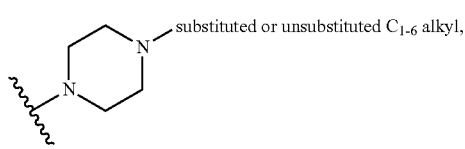

such as

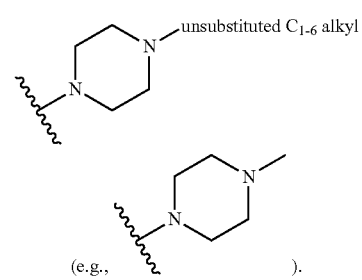

(e.g., ).

In certain embodiments, at least one instance of $R^A$ is substituted aryl. In certain embodiments, at least one instance of $R^A$ is unsubstituted aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms in the heteroaryl ring system are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9- or 10-membered, bicyclic heteroaryl. In certain embodiments, at least one instance of $R^A$ is —$OR^a$. In certain embodiments, at least one instance of $R^A$ is —OH. In certain embodiments, at least one instance of $R^A$ is —O(substituted or unsubstituted $C_{1-6}$ alkyl). In certain embodiments, at least one instance of $R^A$ is —OMe. In certain embodiments, at least one instance of $R^A$ is —OEt. In certain embodiments, at least one instance of $R^A$ is —OPr. In certain embodiments, at least one instance of $R^A$ is —OBu. In certain embodiments, at least one instance of $R^A$ is —OBn. In certain embodiments, at least one instance of $R^A$ is —OPh. In certain embodiments, at least one instance of $R^A$ is of the formula:

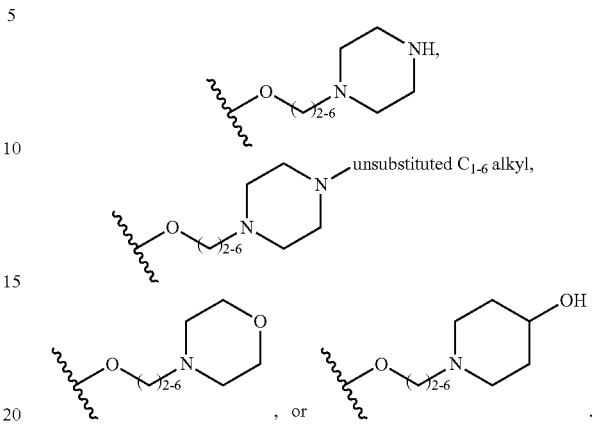

, or .

In certain embodiments, at least one instance of $R^A$ is of the formula:

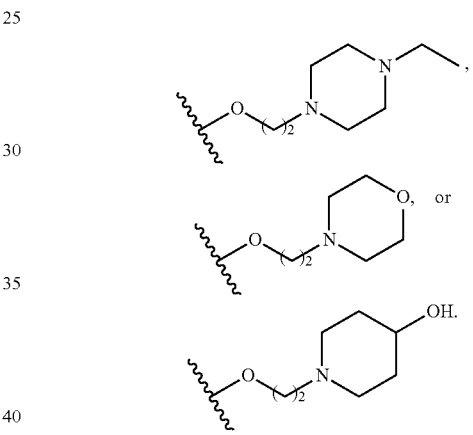

In certain embodiments, k is 1; and $R^A$ is of the formula:

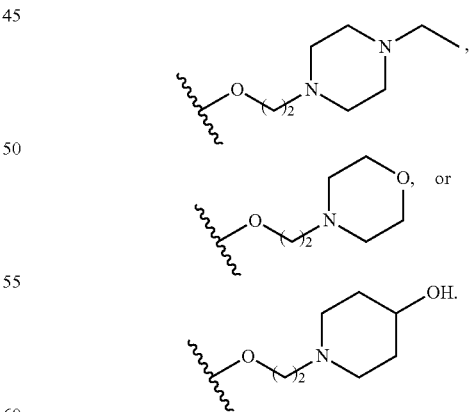

In certain embodiments, at least one instance of $R^A$ is —$SR^a$. In certain embodiments, at least one instance of $R^A$ is —SH. In certain embodiments, at least one instance of $R^A$ is —SMe. In certain embodiments, at least one instance of $R^A$ is —$N(R^a)_2$. In certain embodiments, at least one instance of $R^A$ is —$NH_2$. In certain embodiments, at least one instance of $R^A$ is —NHMe. In certain embodiments, at least one instance of $R^A$ is —NMe$_2$. In certain embodiments, at least one instance of $R^A$ is —CN. In certain embodiments, at least one instance of $R^A$ is —SCN. In certain embodiments, at least one instance of $R^A$ is —C(=NR$^a$)R$^a$, —C(=NR$^a$)OR$^a$, or —C(=NR$^a$)N(R$^a$)$_2$. In certain embodiments, at least one instance of $R^A$ is —C(=O)R$^a$ or —C(=O)OR$^a$. In certain embodiments, at least one instance of $R^A$ is —C(=O)N(R$^a$)$_2$. In certain embodiments, at least one instance of $R^A$ is —C(=O)NMe$_2$, —C(=O)NHMe, or —C(=O)NH$_2$. In certain embodiments, at least one instance of $R^A$ is —NO$_2$. In certain embodiments, at least one instance of $R^A$ is —NR$^a$C(=O)R$^a$, —NR$^a$C(=O)OR$^a$, or —NR$^a$C(=O)N(R$^a$)$_2$. In certain embodiments, at least one instance of $R^A$ is —OC(=O)R$^a$, —OC(=O)OR$^a$, or —OC(=O)N(R$^a$)$_2$.

Each instance of $R^A$, $R^C$, $R^D$, and $R^X$ may independently include one or more substituents $R^a$. In certain embodiments, all instances of $R^a$ are the same. In certain embodiments, at least two instances of $R^a$ are different. In certain embodiments, at least one instance of $R^a$ is H. In certain embodiments, each instance of $R^a$ is H. In certain embodiments, at least one instance of $R^a$ is substituted acyl. In certain embodiments, at least one instance of $R^a$ is unsubstituted acyl. In certain embodiments, at least one instance of $R^a$ is acetyl. In certain embodiments, at least one instance of $R^a$ is substituted alkyl. In certain embodiments, at least one instance of $R^a$ is unsubstituted alkyl. In certain embodiments, at least one instance of $R^a$ is unsubstituted $C_{1-6}$ alkyl. In certain embodiments, at least one instance of $R^a$ is methyl. In certain embodiments, at least one instance of $R^a$ is ethyl. In certain embodiments, at least one instance of $R^a$ is propyl. In certain embodiments, at least one instance of $R^a$ is butyl. In certain embodiments, at least one instance of $R^a$ is pentyl. In certain embodiments, at least one instance of $R^a$ is hexyl. In certain embodiments, at least one instance of $R^a$ is Bn. In certain embodiments, at least one instance of $R^a$ is substituted alkenyl. In certain embodiments, at least one instance of $R^a$ is unsubstituted alkenyl. In certain embodiments, at least one instance of $R^a$ is substituted alkynyl. In certain embodiments, at least one instance of $R^a$ is unsubstituted alkynyl. In certain embodiments, at least one instance of $R^a$ is substituted or unsubstituted carbocyclyl. In certain embodiments, at least one instance of $R^a$ is saturated carbocyclyl. In certain embodiments, at least one instance of $R^a$ is unsaturated carbocyclyl. In certain embodiments, at least one instance of $R^a$ is 3- to 7-membered, monocyclic carbocyclyl. In certain embodiments, at least one instance of $R^a$ is substituted or unsubstituted heterocyclyl. In certain embodiments, at least one instance of $R^a$ is saturated heterocyclyl. In certain embodiments, at least one instance of $R^a$ is unsaturated heterocyclyl. In certain embodiments, at least one instance of $R^a$ is heterocyclyl, wherein one, two, or three atoms of the heterocyclic ring system are independently selected from the group consisting of nitrogen, oxygen, and sulfur. In certain embodiments, at least one instance of $R^a$ is 3- to 7-membered, monocyclic heterocyclyl. In certain embodiments, at least one instance of $R^a$ is substituted or unsubstituted aryl. In certain embodiments, at least one instance of $R^a$ is 6- to 10-membered aryl. In certain embodiments, at least one instance of $R^a$ is monocyclic aryl. In certain embodiments, at least one instance of $R^a$ is substituted phenyl. In certain embodiments, at least one instance of $R^a$ is unsubstituted phenyl. In certain embodiments, at least one instance of $R^a$ is bicyclic aryl. In certain embodiments, at least one instance of $R^a$ is substituted or unsubstituted heteroaryl. In certain embodiments, at least one instance of $R^a$ is heteroaryl, wherein one, two, three, or four atoms of the heteroaryl ring system are independently selected from the group consisting of nitrogen, oxygen, and sulfur. In certain embodiments, at least one instance of $R^a$ is monocyclic heteroaryl. In certain embodiments, at least one instance of $R^a$ is 5- or 6-membered, monocyclic heteroaryl. In certain embodiments, at least one instance of $R^a$ is bicyclic heteroaryl, wherein the point of attachment may be on any atom of the bicyclic heteroaryl ring system, as valency permits. In certain embodiments, at least one instance of $R^a$ is a nitrogen protecting group when attached to a nitrogen atom. In certain embodiments, at least one instance of $R^a$ is Bn, Boc, Cbz, Fmoc, trifluoroacetyl, triphenylmethyl, acetyl, or Ts when attached to a nitrogen atom. In certain embodiments, $R^a$ is an oxygen protecting group when attached to an oxygen atom. In certain embodiments, $R^a$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^a$ is a sulfur protecting group when attached to a sulfur atom. In certain embodiments, $R^a$ is acetamidomethyl, t-Bu, 3-nitro-2-pyridine sulfenyl, 2-pyridine-sulfenyl, or triphenylmethyl when attached to a sulfur atom. In certain embodiments, two instances of R are joined to form a substituted or unsubstituted heterocyclic ring. In certain embodiments, two instances of $R^a$ are joined to form a saturated or unsaturated heterocyclic ring. In certain embodiments, two instances of $R^a$ are joined to form a heterocyclic ring, wherein one, two, or three atoms of the heterocyclic ring system are independently selected from the group consisting of nitrogen, oxygen, and sulfur. In certain embodiments, two instances of $R^a$ are joined to form a 3- to 7-membered, monocyclic heterocyclic ring. In certain embodiments, two instances of $R^a$ are joined to form a substituted or unsubstituted heteroaryl ring. In certain embodiments, two instances of $R^a$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, k is 0. In certain embodiments, k is 1. In certain embodiments, k is 2. In certain embodiments, k is 3. In certain embodiments, k is 4.

In certain embodiments, k is 1; and $R^A$ is —OR$^a$. In certain embodiments, k is 1; and $R^A$ is —O(substituted or unsubstituted $C_{1-6}$ alkyl).

Formula (I) includes divalent linker L. L consists of a chain, and optionally one or more hydrogen atoms and/or one or more substituents (e.g., =O) on the chain, where any two substituents may optionally be joined to form a ring. In certain embodiments, the molecular weight of L is not more than about 300 g/mol, not more than about 200 g/mol, not more than about 150 g/mol, not more than about 100 g/mol, or not more than 80 g/mol. In certain embodiments, the molecular weight of L is between 50 and 150 g/mol, inclusive. In certain embodiments, L consists of not more than about 70 atoms, not more than about 50 atoms, not more than about 30 atoms, not more than about 20 atoms, or not more than 15 atoms. In certain embodiments, L consists of between 10 and 30 atoms, inclusive. In certain embodiments, L does not include unsaturated bonds in the chain. In certain embodiments, L consists of one unsaturated bond in the chain. In certain embodiments, L consists of 2, 3, or 4 unsaturated bonds in the chain. In certain embodiments, L is a substituted or unsubstituted, saturated or unsaturated $C_{3-10}$ hydrocarbon chain (e.g., a $C_{5-6}$ hydrocarbon chain). In certain embodiments, L is a substituted or unsubstituted, saturated or unsaturated $C_{3-10}$ hydrocarbon chain (e.g., a $C_{5-6}$ hydrocarbon chain), wherein one chain atom of the hydrocarbon chain is replaced with —O—, —S—, —NR$^N$—, —N=, or =N—. In certain embodiments, L is a substituted or unsubstituted, saturated or unsaturated, $C_{3-10}$ hydrocarbon chain (e.g., a $C_{5-6}$ hydrocarbon chain), wherein 2, 3, 4, or 5 chain atoms of the hydrocarbon chain are independently replaced with —O—, —S—, —NR$^N$—, —N=, or =N—. In certain embodiments, L is a substituted or unsubstituted, saturated or unsaturated $C_{5-6}$ hydrocarbon chain, wherein one or two chain atoms of the hydrocarbon chain are independently replaced with —O—, —S—, or —NR$^N$-. In certain embodiments, L is of the formula:

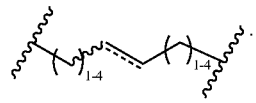

In certain embodiments, L is of the formula:

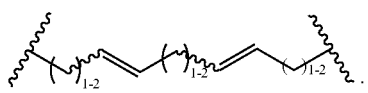

In certain embodiments, L is of the formula:

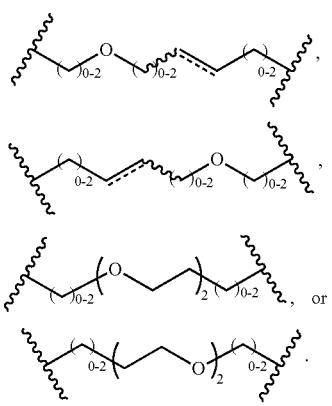

In certain embodiments, L is of the formula:

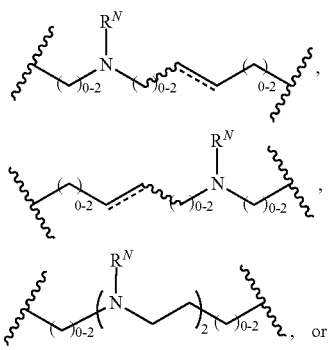

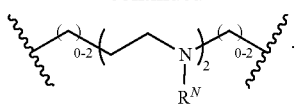

In certain embodiments, L is of the formula:

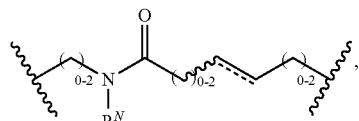

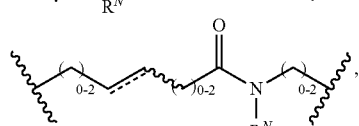

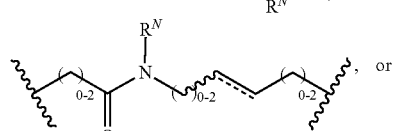

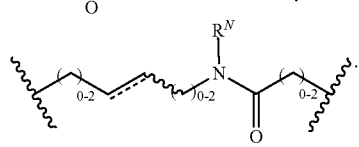

In certain embodiments, L is of the formula:

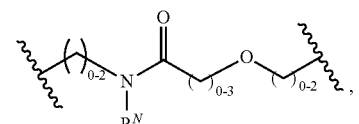

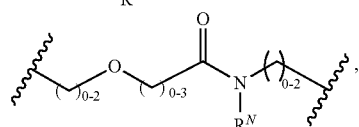

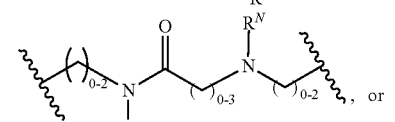

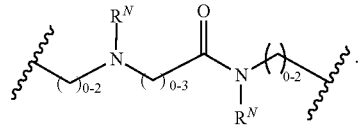

In certain embodiments, L is of the formula:

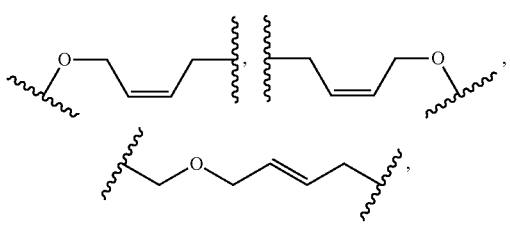

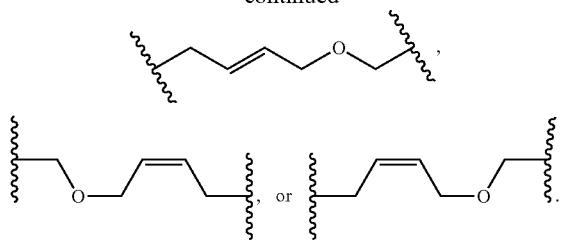

In certain embodiments, L is of the formula:

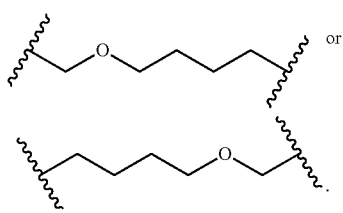

In certain embodiments, L is of the formula:

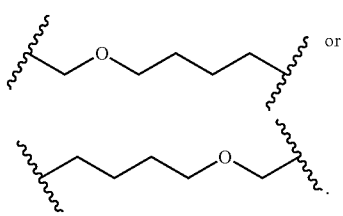

In certain embodiments, at least two instances of $R^N$ are different. In certain embodiments, all instances of $R^N$ are the same. In certain embodiments, at least one instance of $R^N$ is H. In certain embodiments, each instance of $R^N$ is H. In certain embodiments, at least one instance of $R^N$ is substituted acyl. In certain embodiments, at least one instance of $R^N$ is unsubstituted acyl. In certain embodiments, at least one instance of $R^N$ is acetyl. In certain embodiments, at least one instance of $R^N$ is unsubstituted $C_{1-6}$ alkyl. In certain embodiments, each instance of $R^N$ is independently unsubstituted $C_{1-6}$ alkyl. In certain embodiments, at least one instance of $R^N$ is substituted $C_{1-6}$ alkyl. In certain embodiments, at least one instance of $R^N$ is $C_{1-6}$ alkyl substituted with at least one halogen. In certain embodiments, at least one instance of $R^N$ is unsubstituted methyl. In certain embodiments, at least one instance of $R^N$ is substituted methyl. In certain embodiments, at least one instance of $R^N$ is —$CH_2F$. In certain embodiments, at least one instance of $R^N$ is —$CHF_2$. In certain embodiments, at least one instance of $R^N$ is —$CF_3$. In certain embodiments, at least one instance of $R^N$ is ethyl. In certain embodiments, at least one instance of $R^N$ is propyl. In certain embodiments, at least one instance of $R^N$ is butyl. In certain embodiments, at least one instance of $R^N$ is pentyl. In certain embodiments, at least one instance of $R^N$ is hexyl. In certain embodiments, at least one instance of $R^N$ is Bn. In certain embodiments, at least one instance of $R^N$ is a nitrogen protecting group. In certain embodiments, at least one instance of $R^N$ is Bn, Boc, Cbz, Fmoc, trifluoroacetyl, triphenylmethyl, acetyl, or Ts.

Formula (I) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is unsubstituted methyl. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is Bn. In certain embodiments, $R^B$ is a nitrogen protecting group. In certain embodiments, $R^B$ is Bn, Boc, Cbz, Fmoc, trifluoroacetyl, triphenylmethyl, acetyl, or Ts.

Formula (I) includes Ring B that includes moieties $X^A$, $X^B$, and $X^C$ in the ring system. In certain embodiments, $X^A$ is $CR^X$, and each of $X^B$ and $X^C$ is N. In certain embodiments, $X^A$ is CH, and each of $X^B$ and $X^C$ is N. In certain embodiments, $X^B$ is $CR^X$, and each of $X^A$ and $X^C$ is N. In certain embodiments, $X^B$ is CH, and each of $X^A$ and $X^C$ is N. In certain embodiments, $X^C$ is $CR^X$, and each of $X^A$ and $X^B$ is N. In certain embodiments, $X^C$ is CH, and each of $X^A$ and $X^B$ is N. In certain embodiments, $X^A$ is N, and each of $X^B$ and $X^C$ is independently $CR^X$. In certain embodiments, $X^A$ is N, and each of $X^B$ and $X^C$ is CH. In certain embodiments, $X^B$ is N, and each of $X^A$ and $X^C$ is independently $CR^X$. In certain embodiments, $X^B$ is N, and each of $X^A$ and $X^C$ is CH. In certain embodiments, $X^C$ is N, and each of $X^A$ and $X^B$ is independently $CR^X$. In certain embodiments, $X^C$ is N, and each of $X^A$ and $X^B$ is CH. In certain embodiments, each of $X^A$, $X^B$, and $X^C$ is independently $CR^X$. In certain embodiments, each of $X^A$, $X^B$, and $X^C$ is CH.

In certain embodiments, when $X^A$, $X^B$, or $X^C$ is $CR^X$, $R^X$ is H. In certain embodiments, $R^X$ is halogen. In certain embodiments, $R^X$ is F. In certain embodiments, $R^X$ is Cl. In certain embodiments, $R^X$ is Br. In certain embodiments, $R^X$ is I (iodine). In certain embodiments, $R^X$ is substituted alkyl. In certain embodiments, $R^X$ is unsubstituted alkyl. In certain embodiments, $R^X$ is unsubstituted $C_{1-6}$ alkyl. In certain embodiments, $R^X$ is substituted $C_{1-6}$ alkyl. In certain embodiments, $R^X$ is $C_{1-6}$ alkyl substituted with at least one halogen. In certain embodiments, $R^X$ is —$CH_3$. In certain embodiments, $R^X$ is substituted methyl. In certain embodiments, $R^X$ is —$CH_2F$. In certain embodiments, $R^X$ is —$CHF_2$. In certain embodiments, Rx is —$CF_3$. In certain embodiments, $R^X$ is ethyl. In certain embodiments, $R^X$ is propyl. In certain embodiments, $R^X$ is butyl. In certain embodiments, $R^X$ is pentyl. In certain embodiments, $R^X$ is hexyl. In certain embodiments, $R^X$ is Bn. In certain embodiments, $R^X$ is substituted alkenyl. In certain embodiments, $R^X$ is unsubstituted alkenyl. In certain embodiments, $R^X$ is substituted alkynyl. In certain embodiments, $R^X$ is unsubstituted alkynyl. In certain embodiments, $R^X$ is substituted carbocyclyl. In certain embodiments, $R^X$ is unsubstituted carbocyclyl. In certain embodiments, $R^X$ is saturated carbocyclyl. In certain embodiments, $R^X$ is unsaturated carbocyclyl. In certain embodiments, $R^X$ is monocyclic carbocyclyl. In certain embodiments, Rx is 3- to 7-membered, monocyclic carbocyclyl. In certain embodiments, $R^X$ is substituted heterocyclyl. In certain embodiments, $R^X$ is unsubstituted heterocyclyl. In certain embodiments, $R^X$ is saturated heterocyclyl. In certain embodiments, $R^X$ is unsaturated heterocyclyl. In certain embodiments, $R^X$ is heterocyclyl, wherein one, two, or three atoms in the heterocyclic ring system are independently selected from the group consisting of nitrogen, oxygen, and sulfur. In certain embodiments, $R^X$ is monocyclic heterocyclyl. In certain embodiments, $R^X$ is 3- to 7-membered, monocyclic heterocyclyl. In certain embodiments, $R^X$ is substituted aryl. In certain embodiments, $R^X$ is unsubstituted aryl. In certain embodiments, $R^X$ is 6- to 10-membered aryl. In certain embodiments, $R^X$ is substituted phenyl. In certain embodiments, $R^X$ is unsubstituted phenyl. In certain embodiments, $R^X$ is substituted heteroaryl. In certain embodiments, $R^X$ is unsubstituted heteroaryl. In certain embodiments, $R^X$ is heteroaryl, wherein one, two, three, or four atoms in the heteroaryl ring system are independently selected from the group consisting of nitrogen, oxygen, and sulfur. In certain embodiments, $R^X$ is monocyclic heteroaryl. In certain embodiments, $R^X$ is 5-membered, monocyclic heteroaryl. In certain embodiments, $R^X$ is 6-membered, monocyclic heteroaryl. In certain embodiments, $R^X$ is bicyclic heteroaryl, wherein the point of attachment may be on any atom of the bicyclic heteroaryl ring system, as valency permits. In certain embodiments, $R^X$ is —$OR^a$. In certain embodiments, $R^X$ is —OH. In certain embodiments, $R^X$ is —O(substituted or unsubstituted $C_{1-6}$ alkyl). In certain embodiments, $R^X$ is —OMe. In certain embodiments, $R^X$ is —OEt. In certain embodiments, $R^X$ is —OPr. In certain embodiments, $R^X$ is —OBu. In certain embodiments, $R^X$ is —OBn. In certain embodiments, $R^X$ is —OPh. In certain embodiments, $R^X$ is —$SR^a$. In certain embodiments, $R^X$ is —SH. In certain embodiments, $R^X$ is —SMe. In certain embodiments, $R^X$ is —$N(R^a)_2$. In certain embodiments, Rx is —$NH_2$. In certain embodiments, $R^X$ is —NHMe. In certain embodiments, $R^X$ is —$NMe_2$. In certain embodiments, $R^X$ is —CN. In certain embodiments, $R^X$ is —SCN. In certain embodiments, $R^X$ is —$C(=NR^a)R^a$, —$C(=NR^a)OR^a$, or —$C(=NR^a)N(R^a)_2$. In certain embodiments, $R^X$ is —$C(=O)R^a$ or —$C(=O)OR^a$. In certain embodiments, $R^X$ is —$C(=O)N(R^a)_2$. In certain embodiments, $R^X$ is —$C(=O)NMe_2$, —$C(=O)NHMe$, or —$C(=O)NH_2$. In certain embodiments, $R^X$ is —$NO_2$, In certain embodiments, $R^X$ is —$NR^aC(=O)R^a$, —$NR^aC(=O)OR^a$, or —$NR^aC(=O)N(R^a)_2$. In certain embodiments, $R^X$ is —$OC(=O)R^a$, —$OC(=O)OR^a$, or —$OC(=O)N(R^a)_2$.

Formula (I) includes divalent moiety Y. In certain embodiments, Y is —O—. In certain embodiments, Y is —$NR^Y$—. In certain embodiments, Y is —NH—. In certain embodiments, Y is —$NR^Y$—; $X^A$ is $CR^X$; and $R^Y$ and $R^X$ of $X^A$ are joined to form a substituted or unsubstituted, monocyclic, 5- to 7-membered heterocyclic ring that is fused with Ring B, optionally wherein there are 2 or 3 nitrogen atoms, 0 or 1 oxygen atom, and 0 or 1 sulfur atom, in the monocyclic heterocyclic ring system. The monocyclic heterocyclic ring formed by joining $R^Y$ and $R^X$ of $X^A$ is fused with Ring B to form a substituted or unsubstituted, bicyclic, 9- to 11-membered ring. In certain embodiments, Y is —$NR^Y$—; $X^A$ is $CR^X$; and $R^Y$ and $R^X$ of $X^A$ are joined to form a substituted or unsubstituted, monocyclic, 6-membered heterocyclic ring that is fused with Ring B.

In certain embodiments, when Y is —$NR^Y$—, $R^Y$ is H. In certain embodiments, $R^Y$ is substituted acyl. In certain embodiments, $R^Y$ is unsubstituted acyl. In certain embodiments, $R^Y$ is acetyl. In certain embodiments, $R^Y$ is unsubstituted $C_{1-6}$ alkyl. In certain embodiments, $R^Y$ is substituted $C_{1-6}$ alkyl. In certain embodiments, $R^Y$ is $C_{1-6}$ alkyl substituted with at least one halogen. In certain embodiments, $R^Y$ is unsubstituted methyl. In certain embodiments, $R^Y$ is substituted methyl. In certain embodiments, $R^Y$ is —$CH_2F$. In certain embodiments, $R^Y$ is —$CHF_2$. In certain embodiments, $R^Y$ is —$CF_3$. In certain embodiments, $R^Y$ is ethyl. In certain embodiments, $R^Y$ is propyl. In certain embodiments, $R^Y$ is butyl. In certain embodiments, $R^Y$ is pentyl. In certain embodiments, $R^Y$ is hexyl. In certain embodiments, $R^Y$ is Bn. In certain embodiments, $R^Y$ is a nitrogen protecting group. In certain embodiments, $R^Y$ is Bn, Boc, Cbz, Fmoc, trifluoroacetyl, triphenylmethyl, acetyl, or Ts.

In Formula (I), Ring B includes substituent $R^D$. In certain embodiments, $R^D$ is H. In certain embodiments, $R^D$ is halogen. In certain embodiments, $R^D$ is F. In certain embodiments, $R^D$ is Cl. In certain embodiments, $R^D$ is Br. In certain embodiments, $R^D$ is I (iodine). In certain embodiments, $R^D$ is substituted alkyl. In certain embodiments, $R^D$ is unsubstituted alkyl. In certain embodiments, $R^D$ is unsubstituted $C_{1-6}$ alkyl. In certain embodiments, $R^D$ is substituted $C_{1-6}$ alkyl. In certain embodiments, $R^D$ is $C_{1-6}$ alkyl substituted with at least one halogen. In certain embodiments, $R^D$ is —$CH_3$. In certain embodiments, $R^D$ is substituted methyl. In certain embodiments, $R^D$ is —$CH_2F$. In certain embodiments, $R^D$ is —$CHF_2$. In certain embodiments, $R^D$ is —$CF_3$. In certain embodiments, $R^D$ is ethyl. In certain embodiments, $R^D$ is propyl. In certain embodiments, $R^D$ is butyl. In certain embodiments, $R^D$ is pentyl. In certain embodiments, $R^D$ is hexyl. In certain embodiments, $R^D$ is Bn. In certain embodiments, $R^D$ is substituted alkenyl. In certain embodiments, $R^D$ is unsubstituted alkenyl. In certain embodiments, $R^D$ is substituted alkynyl. In certain embodiments, $R^D$ is unsubstituted alkynyl. In certain embodiments, $R^D$ is substituted carbocyclyl. In certain embodiments, $R^D$ is unsubstituted carbocyclyl. In certain embodiments, $R^D$ is saturated carbocyclyl. In certain embodiments, $R^D$ is unsaturated carbocyclyl. In certain embodiments, $R^D$ is monocyclic carbocyclyl. In certain embodiments, $R^D$ is 3- to 7-membered, monocyclic carbocyclyl. In certain embodiments, $R^D$ is substituted heterocyclyl. In certain embodiments, $R^D$ is unsubstituted heterocyclyl. In certain embodiments, $R^D$ is saturated heterocyclyl. In certain embodiments, $R^D$ is unsaturated heterocyclyl. In certain embodiments, $R^D$ is heterocyclyl, wherein one, two, or three atoms in the heterocyclic ring system are independently selected from the group consisting of nitrogen, oxygen, and sulfur. In certain embodiments, $R^D$ is monocyclic heterocyclyl. In certain embodiments, $R^D$ is 3- to 7-membered, monocyclic heterocyclyl. In certain embodiments, $R^D$ is substituted aryl. In certain embodiments, $R^D$ is unsubstituted aryl. In certain embodiments, $R^D$ is 6- to 10-membered aryl. In certain embodiments, $R^D$ is substituted phenyl. In certain embodiments, $R^D$ is unsubstituted phenyl. In certain embodiments, $R^D$ is substituted heteroaryl. In certain embodiments, $R^D$ is unsubstituted heteroaryl. In certain embodiments, $R^D$ is heteroaryl, wherein one, two, three, or four atoms in the heteroaryl ring system are independently selected from the group consisting of nitrogen, oxygen, and sulfur. In certain embodiments, $R^D$ is monocyclic heteroaryl. In certain embodiments, $R^D$ is 5-membered, monocyclic heteroaryl. In certain embodiments, $R^D$ is 6-membered, monocyclic heteroaryl. In certain embodiments, $R^D$ is bicyclic heteroaryl, wherein the point of attachment may be on any atom of the bicyclic heteroaryl ring system, as valency permits. In certain embodiments, $R^D$ is 9- or 10-membered, bicyclic heteroaryl. In certain embodiments, $R^D$ is —$OR^a$. In certain embodiments, $R^D$ is —OH. In certain embodiments, $R^D$ is —O(substituted or unsubstituted $C_{1-6}$ alkyl). In certain embodiments, $R^D$ is —OMe. In certain embodiments, $R^D$ is —OEt. In certain embodiments, $R^D$ is —OPr. In certain embodiments, $R^D$ is —OBu. In certain embodiments, $R^D$ is —OBn. In certain embodiments, $R^D$ is —OPh. In certain embodiments, $R^D$ is —$SR^a$. In certain embodiments, $R^D$ is —SH. In certain embodiments, $R^D$ is —SMe. In certain embodiments, $R^D$ is —N(R$^a$)$_2$. In certain embodiments, $R^D$ is —NH$_2$. In certain embodiments, $R^D$ is —NHMe. In certain embodiments, $R^D$ is —NMe$_2$. In certain embodiments, $R^D$ is —CN. In certain embodiments, $R^D$ is —SCN. In certain embodiments, $R^D$ is —C(=NR$^a$)R$^a$, —C(=NR$^a$)OR$^a$, or —C(=NR$^a$)N(R$^a$)$_2$. In certain embodiments, $R^D$ is —C(=O)R$^a$ or —C(=O)OR$^a$. In certain embodiments, $R^D$ is —C(=O)N(R$^a$)$_2$. In certain embodiments, $R^D$ is —C(=O)NMe$_2$, —C(=O)NHMe, or —C(=O)NH$_2$. In certain embodiments, $R^D$ is —NO$_2$, In certain embodiments, $R^D$ is —NR$^a$C(=O)R$^a$, —NR$^a$C(=O)OR$^a$, or —NR$^a$C(=O)N(R$^a$)$_2$. In certain embodiments, $R^D$ is —OC(=O)R$^a$, —OC(=O)OR$^a$, or —OC(=O)N(R$^a$)$_2$.

Formula (I) includes Ring C that is unsubstituted (e.g., when m is 0) or substituted with one or more substituents $R^C$ (e.g., when m is 1, 2, 3, 4, or 5). In certain embodiments, Ring C is of the formula:

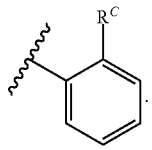

In certain embodiments, Ring C is of the formula:

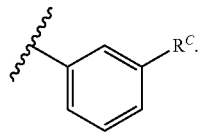

In certain embodiments, Ring C is of the formula:

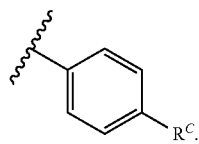

In certain embodiments, Ring C is of the formula:

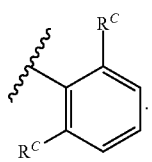

In certain embodiments, Ring C is of the formula:

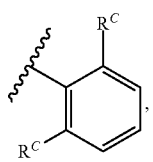

wherein each instance of $R^C$ is independently substituted or unsubstituted $C_{1-6}$ alkyl. In certain embodiments, Ring C is of the formula:

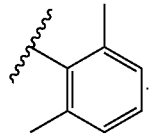 [SMILES: *c1c(C)cccc1C]

In certain embodiments, Ring C is of the formula:

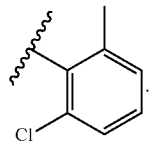 [SMILES: *c1c(C)cccc1Cl]

In certain embodiments, Ring C is of the formula:

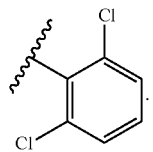 [SMILES: *c1c(Cl)cccc1Cl]

In certain embodiments, Ring C is of the formula:

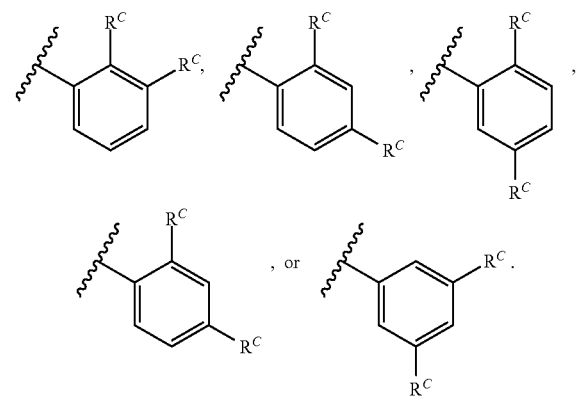

In certain embodiments, at least two instances of $R^C$ are different. In certain embodiments, all instances of $R^C$ are the same. In certain embodiments, at least one instance of $R^C$ is halogen. In certain embodiments, at least one instance of $R^C$ is F. In certain embodiments, at least one instance of $R^C$ is Cl. In certain embodiments, at least one instance of $R^C$ is Br. In certain embodiments, at least one instance of $R^C$ is I (iodine). In certain embodiments, at least one instance of $R^C$ is substituted alkyl. In certain embodiments, at least one instance of $R^C$ is unsubstituted alkyl. In certain embodiments, at least one instance of $R^C$ is unsubstituted $C_{1-6}$ alkyl. In certain embodiments, all instances of $R^C$ are unsubstituted $C_{1-6}$ alkyl. In certain embodiments, at least one instance of $R^C$ is substituted $C_{1-6}$ alkyl. In certain embodiments, at least one instance of $R^C$ is $C_{1-6}$ alkyl substituted with at least one halogen. In certain embodiments, at least one instance of $R^C$ is —$CH_3$. In certain embodiments, all instances of $R^C$ are —$CH_3$. In certain embodiments, at least one instance of $R^C$ is substituted methyl. In certain embodiments, at least one instance of $R^C$ is —$CH_2F$. In certain embodiments, at least one instance of $R^C$ is —$CHF_2$. In certain embodiments, at least one instance of $R^C$ is —$CF_3$. In certain embodiments, at least one instance of $R^C$ is ethyl. In certain embodiments, at least one instance of $R^C$ is propyl. In certain embodiments, at least one instance of $R^C$ is butyl. In certain embodiments, at least one instance of $R^C$ is pentyl. In certain embodiments, at least one instance of $R^C$ is hexyl. In certain embodiments, at least one instance of $R^C$ is Bn. In certain embodiments, each instance of $R^C$ is independently halogen (e.g., Cl) or substituted or unsubstituted $C_{1-6}$ alkyl (e.g., unsubstituted $C_{1-6}$ alkyl (e.g., Me)). In certain embodiments, at least one instance of $R^C$ is substituted alkenyl. In certain embodiments, at least one instance of $R^C$ is unsubstituted alkenyl. In certain embodiments, at least one instance of $R^C$ is substituted alkynyl. In certain embodiments, at least one instance of $R^C$ is unsubstituted alkynyl. In certain embodiments, at least one instance of $R^C$ is substituted carbocyclyl. In certain embodiments, at least one instance of $R^C$ is unsubstituted carbocyclyl. In certain embodiments, at least one instance of $R^C$ is saturated carbocyclyl. In certain embodiments, at least one instance of $R^C$ is unsaturated carbocyclyl. In certain embodiments, at least one instance of $R^C$ is monocyclic carbocyclyl. In certain embodiments, at least one instance of $R^C$ is 3- to 7-membered, monocyclic carbocyclyl. In certain embodiments, at least one instance of $R^C$ is substituted heterocyclyl. In certain embodiments, at least one instance of $R^C$ is unsubstituted heterocyclyl. In certain embodiments, at least one instance of $R^C$ is saturated heterocyclyl. In certain embodiments, at least one instance of $R^C$ is unsaturated heterocyclyl. In certain embodiments, at least one instance of $R^C$ is heterocyclyl, wherein one, two, or three atoms in the heterocyclic ring system are independently selected from the group consisting of nitrogen, oxygen, and sulfur. In certain embodiments, at least one instance of $R^C$ is monocyclic heterocyclyl. In certain embodiments, at least one instance of $R^C$ is 3- to 7-membered, monocyclic heterocyclyl. In certain embodiments, at least one instance of $R^C$ is substituted aryl. In certain embodiments, at least one instance of $R^C$ is unsubstituted aryl. In certain embodiments, at least one instance of $R^C$ is 6- to 10-membered aryl. In certain embodiments, at least one instance of $R^C$ is substituted phenyl. In certain embodiments, at least one instance of $R^C$ is unsubstituted phenyl. In certain embodiments, at least one instance of $R^C$ is substituted heteroaryl. In certain embodiments, at least one instance of $R^C$ is unsubstituted heteroaryl. In certain embodiments, at least one instance of $R^C$ is heteroaryl, wherein one, two, three, or four atoms in the heteroaryl ring system are independently selected from the group consisting of nitrogen, oxygen, and sulfur. In certain embodiments, at least one instance of $R^C$ is monocyclic heteroaryl. In certain embodiments, at least one instance of $R^C$ is 5-membered, monocyclic heteroaryl. In certain embodiments, at least one instance of $R^C$ is 6-membered, monocyclic heteroaryl. In certain embodiments, at least one instance of $R^C$ is bicyclic heteroaryl, wherein the point of attachment may be on any atom of the bicyclic heteroaryl ring system, as valency permits. In certain embodiments, at least one instance of $R^C$ is 9- or 10-membered, bicyclic heteroaryl. In certain embodiments, at least one instance of $R^C$ is —$OR^a$. In certain embodiments, at least one instance of $R^C$ is —OH. In certain embodiments, at least one instance of $R^C$ is —O(substituted or unsubstituted $C_{1-6}$ alkyl). In certain embodiments, at least one instance of $R^C$ is —OMe. In certain embodiments, at least one instance of $R^C$ is —OEt. In certain embodiments, at least one instance of $R^C$ is —OPr. In certain embodiments, at least one instance of $R^C$ is —OBu. In certain embodiments, at least one instance of $R^C$ is —OBn. In certain embodiments, at least one instance of $R^C$ is —OPh. In certain embodiments, at least one instance of $R^C$ is —$SR^a$. In certain embodiments, at least one instance of $R^C$ is —SH. In certain embodiments, at least one instance of $R^C$ is —SMe. In certain embodiments, at least one instance of $R^C$ is —$N(R^a)_2$. In certain embodiments, at least one instance of $R^C$ is —$NH_2$. In certain embodiments, at least one instance of $R^C$ is —NHMe. In certain embodiments, at least one instance of $R^C$ is —$NMe_2$. In certain embodiments, at least one instance of $R^C$ is —CN. In certain embodiments, at least one instance of $R^C$ is —SCN. In certain embodiments, at least one instance of $R^C$ is —$C(=NR^a)R^a$, —$C(=NR^a)OR^a$, or —$C(=NR^a)N(R^a)_2$. In certain embodiments, at least one instance of $R^C$ is —$C(=O)R^a$ or —$C(=O)OR^a$. In certain embodiments, at least one instance of $R^C$ is —$C(=O)N(R^a)_2$. In certain embodiments, at least one instance of $R^C$ is —$C(=O)NMe_2$, —$C(=O)NHMe$, or —$C(=O)NH_2$. In certain embodiments, at least one instance of $R^C$ is —$NO_2$. In certain embodiments, at least one instance of $R^C$ is —$NR^aC(=O)R^a$, —$NR^aC(=O)OR^a$, or —$NR^aC(=O)N(R^a)_2$. In certain embodiments, at least one instance of $R^C$ is —$OC(=O)R^a$, —$OC(=O)OR^a$, or —$OC(=O)N(R^a)_2$.

In certain embodiments, m is 0. In certain embodiments, m is 1. In certain embodiments, m is 2. In certain embodiments, m is 3. In certain embodiments, m is 4. In certain embodiments, m is 5.

In certain embodiments, m is 2; and each instance of $R^C$ is halogen (e.g., Cl). In certain embodiments, m is 2; and each instance of $R^C$ is substituted or unsubstituted $C_{1-6}$ alkyl. In certain embodiments, m is 2; and each instance of $R^C$ is methyl. In certain embodiments, m is 2; and each instance of $R^C$ is independently halogen (e.g., Cl) or substituted or unsubstituted $C_{1-6}$ alkyl (e.g., unsubstituted $C_{1-6}$ alkyl (e.g., Me)).

In certain embodiments, the compound of Formula (I) is of the formula:

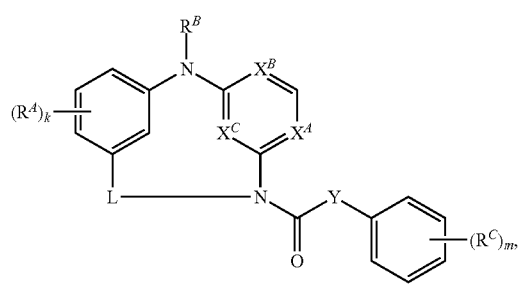

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

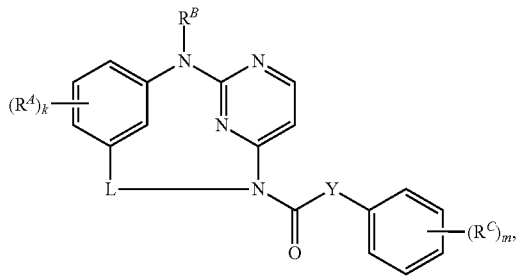

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

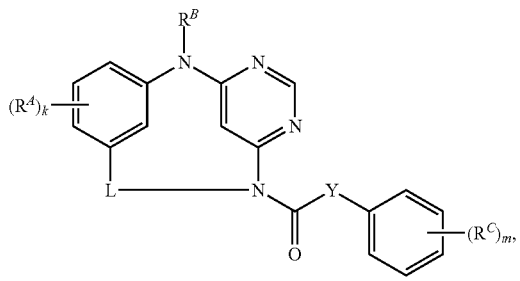

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

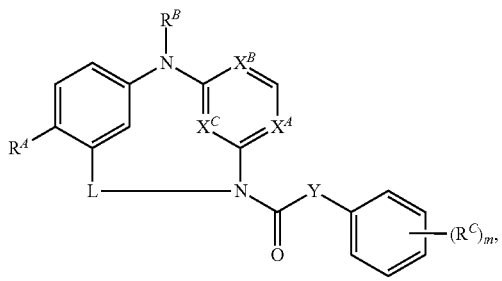

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

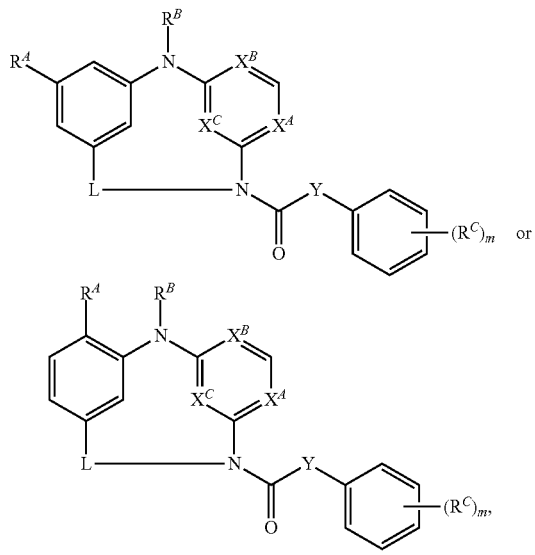

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

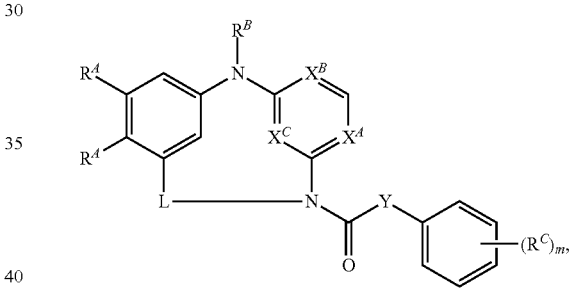

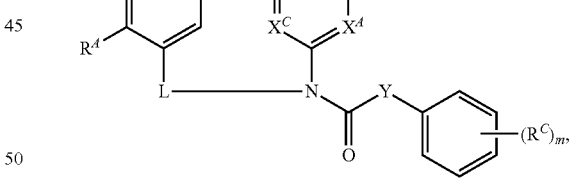

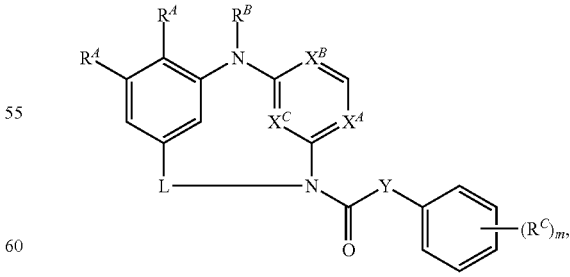

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

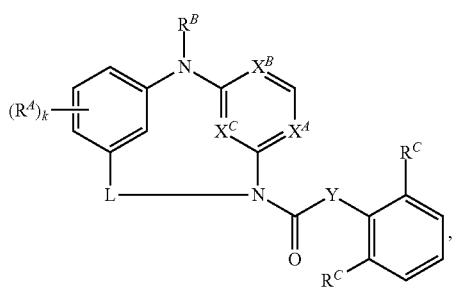

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

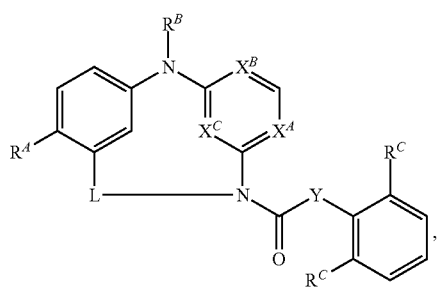

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

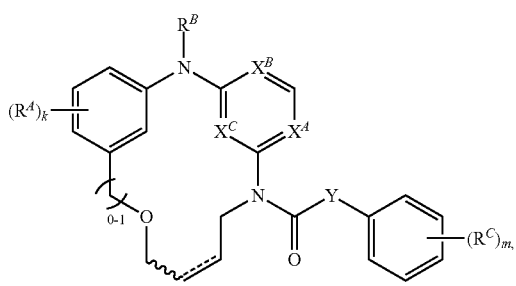

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

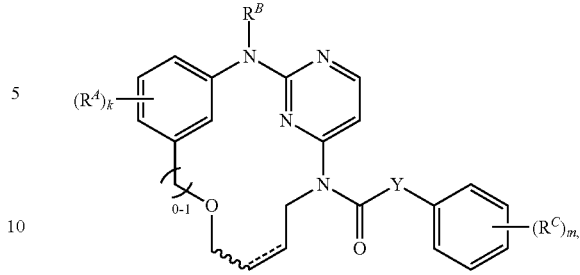

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

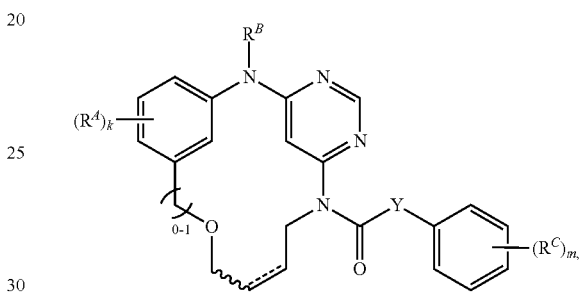

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

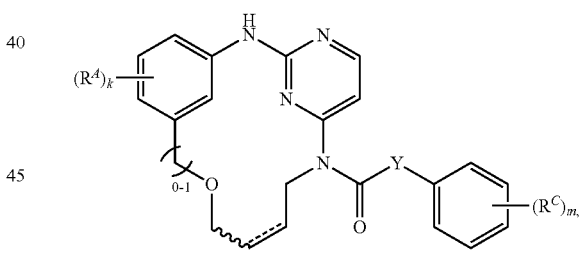

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

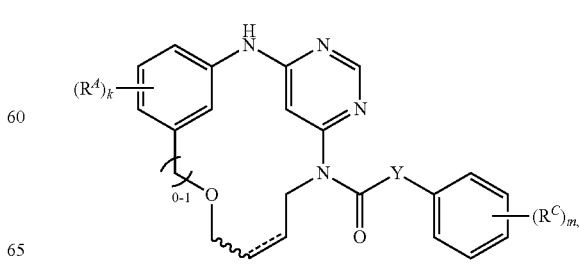

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

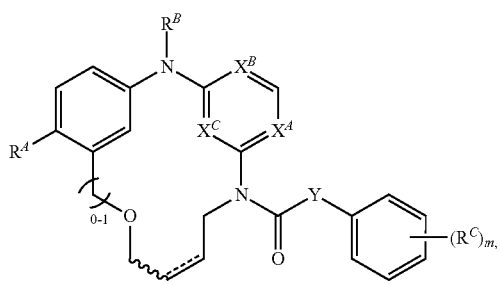

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

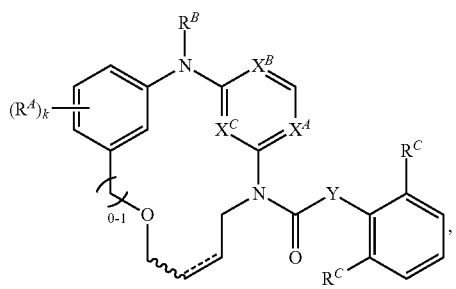

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

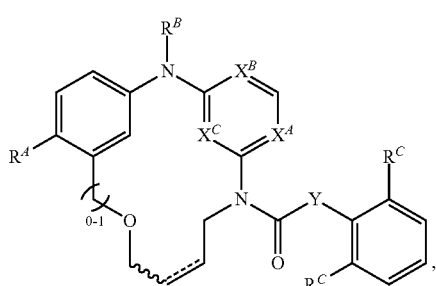

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

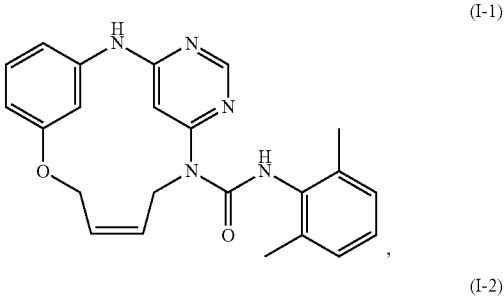
(I-1)

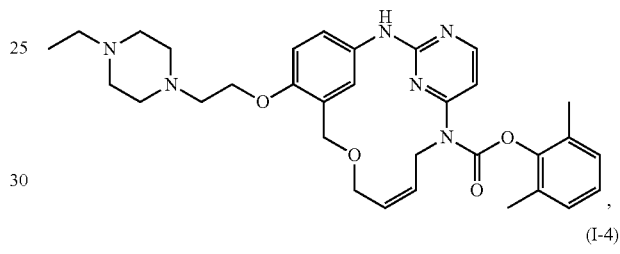
(I-2), (I--3)

(I-4)

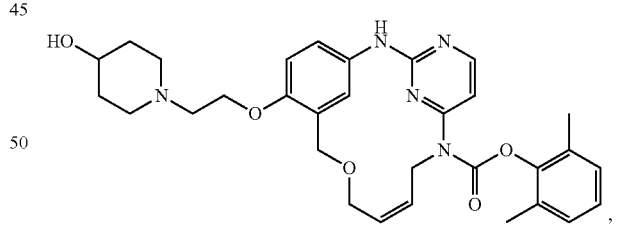
(I-5), (I-6)

-continued (I-7)

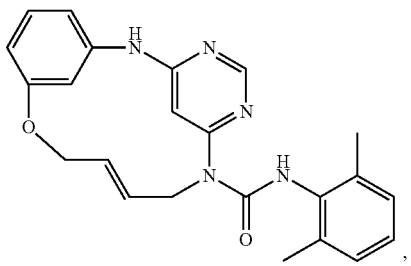

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

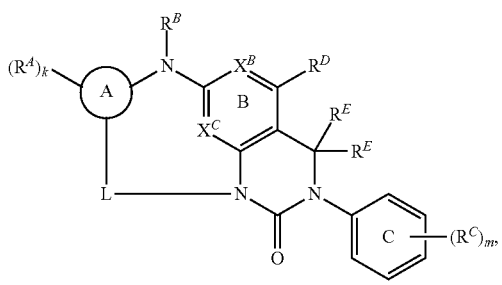

or a pharmaceutically acceptable salt, solvate, hydrate, polymorph, co-crystal, tautomer, stereoisomer, isotopically labeled derivative, or prodrug thereof, wherein each instance of $R^E$ is independently hydrogen, halogen, or substituted or unsubstituted $C_{1-6}$ alkyl. In certain embodiments, the two instances of $R^E$ are the same. In certain embodiments, the two instances of $R^E$ are not the same. In certain embodiments, at least one instance of $R^E$ is hydrogen. In certain embodiments, each instance of $R^E$ is hydrogen. In certain embodiments, at least one instance of $R^E$ is halogen (e.g., F, Cl, Br, or I). In certain embodiments, at least one instance of $R^E$ is substituted or unsubstituted $C_{1-6}$ alkyl. In certain embodiments, at least one instance of $R^E$ is Me. In certain embodiments, at least one instance of $R^E$ is substituted methyl (e.g., —CF$_3$ or Bn), Et, substituted ethyl (e.g., perfluoroethyl), Pr, substituted propyl (e.g., perfluoropropyl), Bu, or substituted butyl (e.g., perfluorobutyl).

In certain embodiments, the compound of Formula (I) is of the formula:

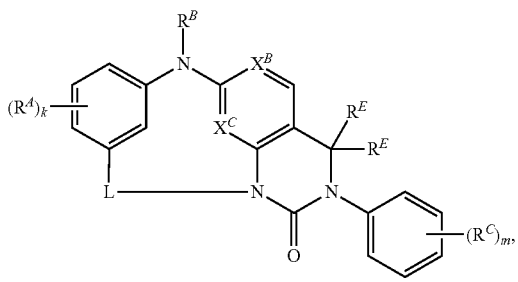

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

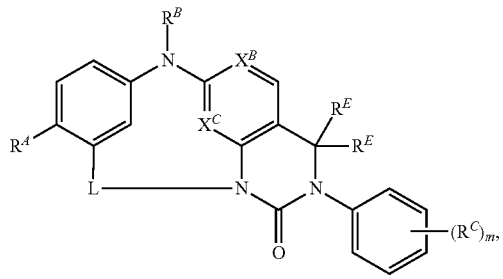

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

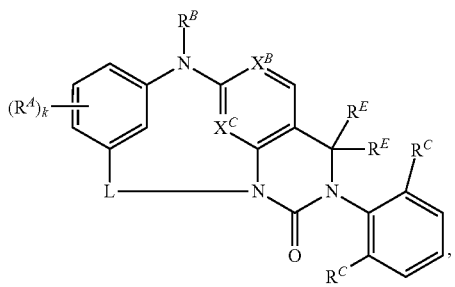

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

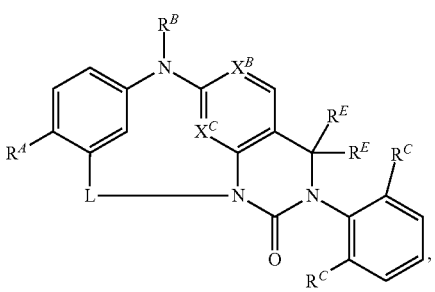

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

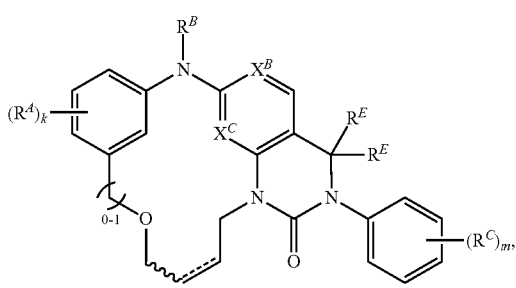

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

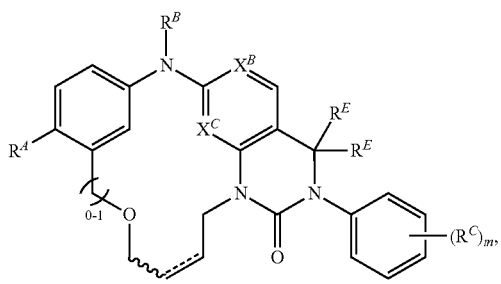

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

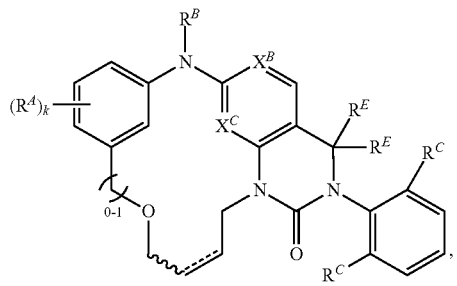

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

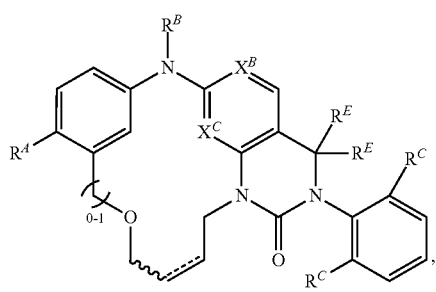

or a pharmaceutically acceptable salt, solvate, hydrate, polymorph, co-crystal, tautomer, stereoisomer, isotopically labeled derivative, or prodrug thereof.

In certain embodiments, the compound of Formula (I) is of the formula:

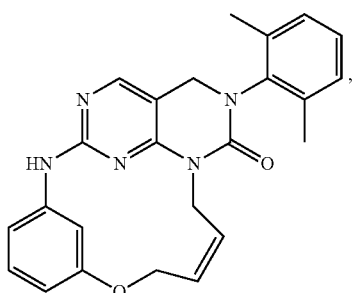
(YKL-05-120)

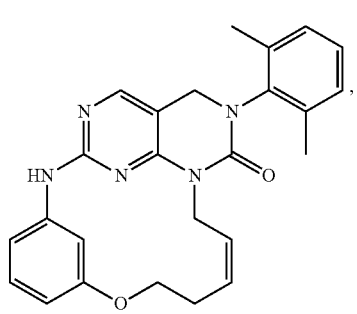
(YKL-05-200-1)

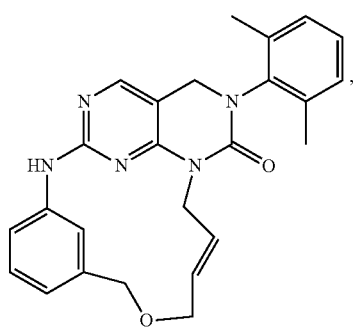
(YKL-05-200-2)

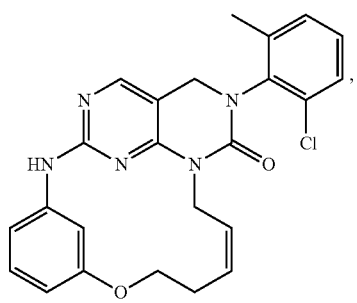
(YKL-05-201-1)

89
-continued
(YKL-05-201-2)
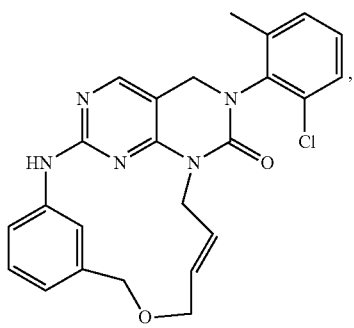
(YKL-05-202-1)
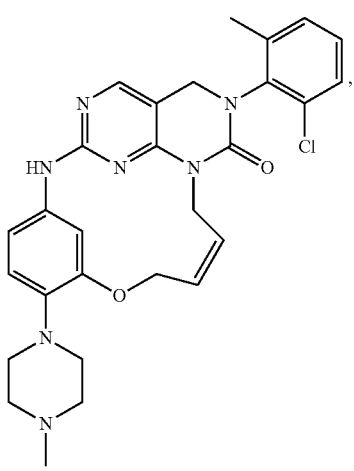
(YKL-05-202-2)
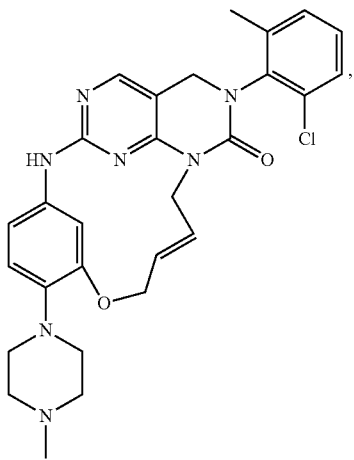
(YKL-05-203-1)
90
-continued
(YKL-05-203-2)
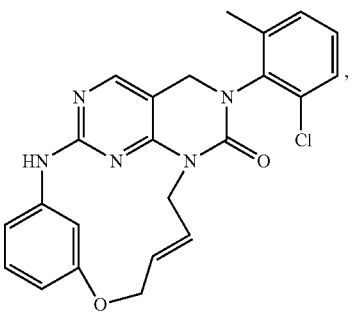
(YKL-05-204-1)
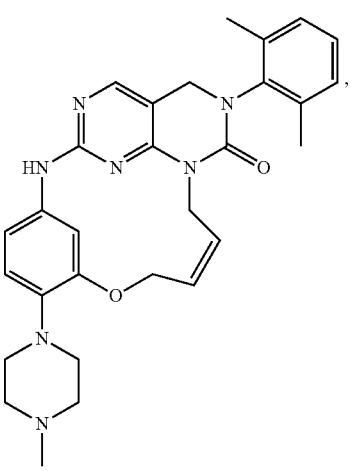
(YKL-05-204-2)
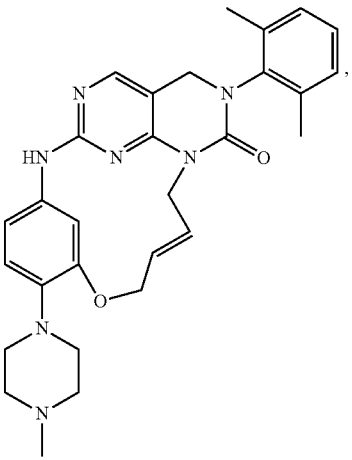
(YKL-05-205)
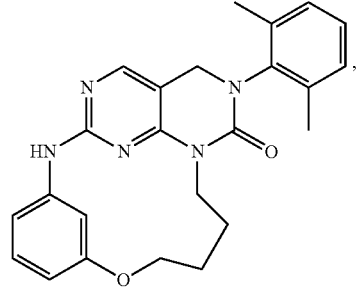

or a pharmaceutically acceptable salt, solvate, hydrate, polymorph, co-crystal, tautomer, stereoisomer, isotopically labeled derivative, or prodrug thereof.

Compounds of Formula (II)

In another aspect, the present disclosure provides imidazolyl compounds of Formula (II) for use in the invention:

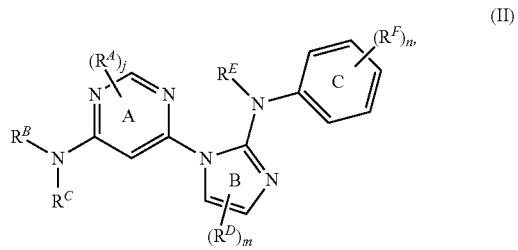

(II)

and pharmaceutically acceptable salts, solvates, hydrates, polymorphs, co-crystals, tautomers, stereoisomers, isotopically labeled derivatives, and prodrugs thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ are joined to form a substituted or unsubstituted heterocyclic or substituted or unsubstituted heteroaryl ring;

j is 0, 1, or 2;

$R^B$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$R^C$ is hydrogen, substituted or unsubstituted acyl, substituted or unsubstituted $C_{1-6}$ alkyl, or a nitrogen protecting group;

each instance of $R^D$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$;

m is 0, 1, or 2;

$R^E$ is hydrogen, substituted or unsubstituted acyl, substituted or unsubstituted $C_{1-6}$ alkyl, or a nitrogen protecting group;

each instance of $R^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$; and n is 0, 1, 2, 3, 4, or 5.

All embodiments of Ring A, Ring B, Ring C, Ring D, Ring E, Ring F, Ring G, $R^A$, $R^a$, $R^B$, $R^C$, $R^D$, $R^E$, $R^F$, $R^G$, $R^H$, $R^J$, $R^K$, j, k, m, n, and q recited in subsection Compounds of Formula (II) apply only to Formula (II).

Formula (II) includes as Ring A a pyrimidinyl ring that is unsubstituted (e.g., when j is 0) or substituted with one or two substituents $R^A$ (e.g., when j is 1 or 2). In certain embodiments, the two instances of $R^A$ are different. In certain embodiments, both instances of $R^A$ are the same. In certain embodiments, at least one instance of $R^A$ is halogen. In certain embodiments, at least one instance of $R^A$ is F. In certain embodiments, at least one instance of $R^A$ is Cl. In certain embodiments, at least one instance of $R^A$ is Br. In certain embodiments, at least one instance of $R^A$ is I (iodine). In certain embodiments, at least one instance of $R^A$ is substituted alkyl. In certain embodiments, at least one instance of $R^A$ is unsubstituted alkyl. In certain embodiments, at least one instance of $R^A$ is unsubstituted $C_{1-6}$ alkyl. In certain embodiments, both instances of $R^A$ are unsubstituted $C_{1-6}$ alkyl. In certain embodiments, at least one instance of $R^A$ is substituted $C_{1-6}$ alkyl. In certain embodiments, at least one instance of $R^A$ is $C_{1-6}$ alkyl substituted with at least one halogen. In certain embodiments, at least one instance of $R^A$ is —$CH_3$. In certain embodiments, at least one instance of $R^A$ is substituted methyl. In certain embodiments, at least one instance of $R^A$ is —$CH_2F$. In certain embodiments, at least one instance of $R^A$ is —$CHF_2$. In certain embodiments, at least one instance of $R^A$ is —$CF_3$. In certain embodiments, at least one instance of $R^A$ is ethyl. In certain embodiments, at least one instance of $R^A$ is propyl. In certain embodiments, at least one instance of $R^A$ is butyl. In certain embodiments, at least one instance of $R^A$ is pentyl. In certain embodiments, at least one instance of $R^A$ is hexyl. In certain embodiments, at least one instance of $R^A$ is Bn. In certain embodiments, at least one instance of $R^A$ is halogen or substituted or unsubstituted $C_{1-6}$ alkyl. In certain embodiments, at least one instance of $R^A$ is substituted alkenyl. In certain embodiments, at least one instance of $R^A$ is unsubstituted alkenyl. In certain embodiments, at least one instance of $R^A$ is substituted alkynyl. In certain embodiments, at least one instance of $R^A$ is unsubstituted alkynyl. In certain embodiments, at least one instance of $R^A$ is substituted carbocyclyl. In certain embodiments, at least one instance of $R^A$ is unsubstituted carbocyclyl. In certain embodiments, at least one instance of $R^A$ is saturated carbocyclyl. In certain embodiments, at least one instance of $R^A$ is unsaturated carbocyclyl. In certain embodiments, at least one instance of $R^A$ is monocyclic carbocyclyl. In certain embodiments, at least one instance of $R^A$ is 3- to 7-membered, monocyclic carbocyclyl. In certain embodiments, at least one instance of $R^A$ is substituted heterocyclyl. In certain embodiments, at least one instance of $R^A$ is unsubstituted heterocyclyl. In certain embodiments, at least one instance of $R^A$ is saturated heterocyclyl. In certain embodiments, at least one instance of $R^A$ is unsaturated heterocyclyl. In certain embodiments, at least one instance of $R^A$ is heterocyclyl, wherein one, two, or three atoms of the heterocyclic ring system are independently selected from the group consisting of nitrogen, oxygen, and sulfur. In certain embodiments, at least one instance of $R^A$ is monocyclic heterocyclyl. In certain embodiments, at least one instance of $R^A$ is 3- to 7-membered, monocyclic heterocyclyl. In certain embodiments, at least one instance of $R^A$ is substituted aryl. In certain embodiments, at least one instance of $R^A$ is unsubstituted aryl. In certain embodiments, at least one instance of $R^A$ is 6- to 10-membered aryl. In certain embodiments, at least one instance of $R^A$ is substituted phenyl. In certain embodiments, at least one instance of $R^A$ is unsubstituted phenyl. In certain embodiments, at least one instance of $R^A$ is substituted heteroaryl. In certain embodiments, at least one instance of $R^A$ is unsubstituted heteroaryl. In certain embodiments, at least one instance of $R^A$ is heteroaryl, wherein one, two, three, or four atoms of the heteroaryl ring system are independently selected from the group consisting of nitrogen, oxygen, and sulfur. In certain embodiments, at least one instance of $R^A$ is monocyclic heteroaryl. In certain embodiments, at least one instance of $R^A$ is 5-membered, monocyclic heteroaryl. In certain embodiments, at least one instance of $R^A$ is 6-membered, monocyclic heteroaryl. In certain embodiments, at least one instance of $R^A$ is bicyclic heteroaryl, wherein the point of attachment may be on any atom of the bicyclic heteroaryl ring system, as valency permits. In certain embodiments, at least one instance of $R^A$ is 9- or 10-membered, bicyclic heteroaryl. In certain embodiments, at least one instance of $R^A$ is —$OR^a$. In certain embodiments, at least one instance of $R^A$ is —OH. In certain embodiments, at least one instance of $R^A$ is —O(substituted or unsubstituted $C_{1-6}$ alkyl). In certain embodiments, at least one instance of $R^A$ is —OMe. In certain embodiments, at least one instance of $R^A$ is —OEt. In certain embodiments, at least one instance of $R^A$ is —OPr. In certain embodiments, at least one instance of $R^A$ is —OBu. In certain embodiments, at least one instance of $R^A$ is —OBn. In certain embodiments, at least one instance of $R^A$ is —OPh. In certain embodiments, at least one instance of $R^A$ is —$SR^a$. In certain embodiments, at least one instance of $R^A$ is —SH. In certain embodiments, at least one instance of $R^A$ is —SMe. In certain embodiments, at least one instance of $R^A$ is —$N(R^a)_2$. In certain embodiments, at least one instance of $R^A$ is —$NH_2$. In certain embodiments, at least one instance of $R^A$ is —NHMe. In certain embodiments, at least one instance of $R^A$ is —$NMe_2$. In certain embodiments, at least one instance of $R^A$ is —CN. In certain embodiments, at least one instance of $R^A$ is —SCN. In certain embodiments, at least one instance of $R^A$ is —$C(=NR^a)R^a$, —$C(=NR^a)OR^a$, or —$C(=NR^a)N(R^a)_2$. In certain embodiments, at least one instance of $R^A$ is —$C(=O)R^a$ or $C(=O)OR^a$. In certain embodiments, at least one instance of $R^A$ is —$C(=O)N(R^a)_2$. In certain embodiments, at least one instance of $R^A$ is —$C(=O)NMe_2$, —$C(=O)NHMe$, or —$C(=O)NH_2$. In certain embodiments, at least one instance of $R^A$ is —$NO_2$, In certain embodiments, at least one instance of $R^A$ is —$NR^aC(=O)R^a$, —$NR^aC(=O)OR^a$, or —$NR^aC(=O)N(R^a)_2$. In certain embodiments, at least one instance of $R^A$ is —$OC(=O)R^a$, —$OC(=O)OR^a$, or —$OC(=O)N(R^a)_2$.

Each instance of $R^A$, $R^D$, $R^F$, $R^G$, $R^J$, and $R^K$ may independently include one or more substituents $R^a$. In certain embodiments, all instances of $R^a$ are the same. In certain embodiments, at least two instances of $R^a$ are different. In certain embodiments, at least one instance of $R^a$ is H. In certain embodiments, each instance of $R^a$ is H. In certain embodiments, at least one instance of $R^a$ is substituted acyl. In certain embodiments, at least one instance of $R^a$ is unsubstituted acyl. In certain embodiments, at least one instance of $R^a$ is acetyl. In certain embodiments, at least one instance of $R^a$ is substituted alkyl. In certain embodiments, at least one instance of $R^a$ is unsubstituted alkyl. In certain embodiments, at least one instance of $R^a$ is unsubstituted $C_{1-6}$ alkyl. In certain embodiments, at least one instance of $R^a$ is methyl. In certain embodiments, at least one instance of $R^a$ is ethyl. In certain embodiments, at least one instance of $R^a$ is propyl. In certain embodiments, at least one instance of $R^a$ is butyl. In certain embodiments, at least one instance of $R^a$ is pentyl. In certain embodiments, at least one instance of $R^a$ is hexyl. In certain embodiments, at least one instance of $R^a$ is Bn. In certain embodiments, at least one instance of $R^a$ is substituted alkenyl. In certain embodiments, at least one instance of $R^a$ is unsubstituted alkenyl. In certain embodiments, at least one instance of $R^a$ is substituted alkynyl. In certain embodiments, at least one instance of $R^a$ is unsubstituted alkynyl. In certain embodiments, at least one instance of $R^a$ is substituted or unsubstituted carbocyclyl. In certain embodiments, at least one instance of $R^a$ is saturated carbocyclyl. In certain embodiments, at least one instance of $R^a$ is unsaturated carbocyclyl. In certain embodiments, at least one instance of $R^a$ is 3- to 7-membered, monocyclic carbocyclyl. In certain embodiments, at least one instance of $R^a$ is substituted or unsubstituted heterocyclyl. In certain embodiments, at least one instance of $R^a$ is saturated heterocyclyl. In certain embodiments, at least one instance of $R^a$ is unsaturated heterocyclyl. In certain embodiments, at least one instance of $R^a$ is heterocyclyl, wherein one, two, or three atoms of the heterocyclic ring system are independently selected from the group consisting of nitrogen, oxygen, and sulfur. In certain embodiments, at least one instance of $R^a$ is 3- to 7-membered, monocyclic heterocyclyl. In certain embodiments, at least one instance of $R^a$ is substituted or unsubstituted aryl. In certain embodiments, at least one instance of $R^a$ is 6- to 10-membered aryl. In certain embodiments, at least one instance of $R^a$ is monocyclic aryl. In certain embodiments, at least one instance of $R^a$ is substituted phenyl. In certain embodiments, at least one instance of $R^a$ is unsubstituted phenyl. In certain embodiments, at least one instance of $R^a$ is bicyclic aryl. In certain embodiments, at least one instance of $R^a$ is substituted or unsubstituted heteroaryl. In certain embodiments, at least one instance of $R^a$ is heteroaryl, wherein one, two, three, or four atoms of the heteroaryl ring system are independently selected from the group consisting of nitrogen, oxygen, and sulfur. In certain embodiments, at least one instance of $R^a$ is monocyclic heteroaryl. In certain embodiments, at least one instance of $R^a$ is 5- or 6-membered, monocyclic heteroaryl. In certain embodiments, at least one instance of $R^a$ is bicyclic heteroaryl, wherein the point of attachment may be on any atom of the bicyclic heteroaryl ring system, as valency permits. In certain embodiments, at least one instance of $R^a$ is a nitrogen protecting group when attached to a nitrogen atom. In certain embodiments, at least one instance of $R^a$ is Bn, Boc, Cbz, Fmoc, trifluoroacetyl, triphenylmethyl, acetyl, or Ts when attached to a nitrogen atom. In certain embodiments, $R^a$ is an oxygen protecting group when attached to an oxygen atom. In certain embodiments, $R^a$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, $R^a$ is a sulfur protecting group when attached to a sulfur atom. In certain embodiments, $R^a$ is acetamidomethyl, t-Bu, 3-nitro-2-pyridine sulfenyl, 2-pyridine-sulfenyl, or triphenylmethyl when attached to a sulfur atom. In certain embodiments, two instances of $R^a$ are joined to form a substituted or unsubstituted heterocyclic ring. In certain embodiments, two instances of $R^a$ are joined to form a saturated or unsaturated heterocyclic ring. In certain embodiments, two instances of $R^a$ are joined to form a heterocyclic ring, wherein one, two, or three atoms of the heterocyclic ring system are independently selected from the group consisting of nitrogen, oxygen, and sulfur. In certain embodiments, two instances of $R^a$ are joined to form a 3- to 7-membered, monocyclic heterocyclic ring. In certain embodiments, two instances of $R^a$ are joined to form a substituted or unsubstituted heteroaryl ring. In certain embodiments, two instances of $R^a$ are joined to form a substituted or unsubstituted, 5- to 6-membered, monocyclic heteroaryl ring, wherein one, two, three, or four atoms of the heteroaryl ring system are independently nitrogen, oxygen, or sulfur.

In certain embodiments, j is 0. In certain embodiments, j is 1. In certain embodiments, j is 2.

Formula (II) includes substituent $R^B$ on a nitrogen atom. In certain embodiments, $R^B$ is H. In certain embodiments, $R^B$ is substituted acyl. In certain embodiments, $R^B$ is unsubstituted acyl. In certain embodiments, $R^B$ is acetyl. In certain embodiments, $R^B$ is substituted alkyl. In certain embodiments, $R^B$ is unsubstituted alkyl. In certain embodiments, $R^B$ is unsubstituted $C_{1-6}$ alkyl. In certain embodiments, $R^B$ is substituted $C_{1-6}$ alkyl. In certain embodiments, $R^B$ is $C_{1-6}$ alkyl substituted with at least one halogen. In certain embodiments, $R^B$ is —$CH_3$. In certain embodiments, $R^B$ is substituted methyl. In certain embodiments, $R^B$ is —$CH_2F$. In certain embodiments, $R^B$ is —$CHF_2$. In certain embodiments, $R^B$ is —$CF_3$. In certain embodiments, $R^B$ is ethyl. In certain embodiments, $R^B$ is propyl. In certain embodiments, $R^B$ is butyl. In certain embodiments, $R^B$ is pentyl. In certain embodiments, $R^B$ is hexyl. In certain embodiments, $R^B$ is Bn. In certain embodiments, $R^B$ is —$(CH_2)_{1-4}$-(Ring F), wherein Ring F is a substituted or unsubstituted, 3- to 7-membered, monocyclic heterocyclic ring. In certain embodiments, $R^B$ is —$(CH_2)_{1-4}$-(substituted or unsubstituted pyrrolidinyl). In certain embodiments, $R^B$ is of the formula:

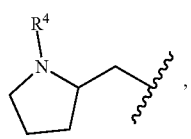

wherein $R^4$ is H, substituted or unsubstituted $C_{1-6}$ alkyl, or a nitrogen protecting group. In certain embodiments, $R^B$ is of the formula:

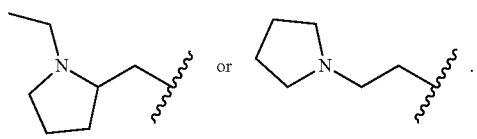

In certain embodiments, $R^B$ is —$(CH_2)_{1-4}$-(Ring F), wherein Ring F is a substituted or unsubstituted oxetanyl, substituted or unsubstituted azetidinyl, substituted or unsubstituted tetrahydrofuranyl, substituted or unsubstituted tetrahydropyranyl, substituted or unsubstituted piperidinyl, substituted or unsubstituted piperazinyl, or substituted or unsubstituted morpholinyl ring. In certain embodiments, $R^B$ is substituted alkenyl. In certain embodiments, $R^B$ is unsubstituted alkenyl. In certain embodiments, $R^B$ is substituted alkynyl. In certain embodiments, $R^B$ is unsubstituted alkynyl. In certain embodiments, $R^B$ is substituted carbocyclyl. In certain embodiments, $R^B$ is unsubstituted carbocyclyl. In certain embodiments, $R^B$ is saturated carbocyclyl. In certain embodiments, $R^B$ is unsaturated carbocyclyl. In certain embodiments, $R^B$ is monocyclic carbocyclyl. In certain embodiments, $R^B$ is 3- to 7-membered, monocyclic carbocyclyl. In certain embodiments, $R^B$ is unsubstituted cyclopropyl. In certain embodiments, $R^B$ is substituted cyclopropyl. In certain embodiments, $R^B$ is substituted heterocyclyl. In certain embodiments, $R^B$ is unsubstituted heterocyclyl. In certain embodiments, RB is saturated heterocyclyl. In certain embodiments, $R^B$ is unsaturated heterocyclyl. In certain embodiments, $R^B$ is heterocyclyl, wherein one, two, or three atoms of the heterocyclic ring system are independently selected from the group consisting of nitrogen, oxygen, and sulfur. In certain embodiments, $R^B$ is monocyclic heterocyclyl. In certain embodiments, $R^B$ is 3- to 7-membered, monocyclic heterocyclyl. In certain embodiments, $R^B$ is substituted aryl. In certain embodiments, $R^B$ is unsubstituted aryl. In certain embodiments, $R^B$ is 6- to 10-membered aryl. In certain embodiments, $R^B$ is substituted phenyl. In certain embodiments, $R^B$ is unsubstituted phenyl. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur. In certain embodiments, $R^B$ is substituted or unsubstituted pyrazolyl. In certain embodiments, $R^B$ is of the formula:

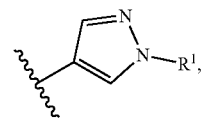

wherein $R^1$ is H, substituted or unsubstituted $C_{1-6}$ alkyl, or a nitrogen protecting group. In certain embodiments, $R^B$ is of the formula:

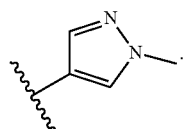 [SMILES: *c1cnn(C)c1]

In certain embodiments, $R^B$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^B$ is substituted or unsubstituted pyridyl, substituted or unsubstituted pyrazinyl, substituted or unsubstituted pyrimidinyl, or substituted or unsubstituted pyridazinyl. In certain embodiments, $R^B$ is substituted or unsubstituted, 9- to 10-membered, bicyclic heteroaryl, wherein one, two, three, or four atoms of the heteroaryl ring system are independently nitrogen, oxygen, or sulfur. In certain embodiments, RB is a nitrogen protecting group. In certain embodiments, $R^B$ is Bn, Boc, Cbz, Fmoc, trifluoroacetyl, triphenylmethyl, acetyl, or Ts.

Formula (II) includes substituent $R^C$ on a nitrogen atom. In certain embodiments, $R^C$ is H. In certain embodiments, $R^C$ is substituted acyl. In certain embodiments, $R^C$ is unsubstituted acyl. In certain embodiments, $R^C$ is acetyl. In certain embodiments, $R^C$ is unsubstituted $C_{1-6}$ alkyl. In certain embodiments, $R^C$ is substituted $C_{1-6}$ alkyl. In certain embodiments, $R^C$ is $C_{1-6}$ alkyl substituted with at least one halogen. In certain embodiments, $R^C$ is unsubstituted methyl. In certain embodiments, $R^C$ is substituted methyl. In certain embodiments, $R^C$ is —CH$_2$F. In certain embodiments, $R^C$ is —CHF$_2$. In certain embodiments, $R^C$ is —CF$_3$. In certain embodiments, $R^C$ is ethyl. In certain embodiments, $R^C$ is propyl. In certain embodiments, $R^C$ is butyl. In certain embodiments, $R^C$ is pentyl. In certain embodiments, $R^C$ is hexyl. In certain embodiments, $R^C$ is Bn. In certain embodiments, $R^C$ is a nitrogen protecting group. In certain embodiments, $R^C$ is Bn, Boc, Cbz, Fmoc, trifluoroacetyl, triphenylmethyl, acetyl, or Ts.

In certain embodiments, $R^B$ is substituted or unsubstituted $C_{1-6}$ alkyl, and $R^C$ is H. In certain embodiments, $R^B$ is —(CH$_2$)$_{1-4}$-(Ring F), wherein Ring F is a substituted or unsubstituted, 3- to 7-membered, monocyclic heterocyclic ring; and $R^C$ is H. In certain embodiments, $R^B$ is substituted or unsubstituted phenyl (e.g., para-substituted phenyl), and $R^C$ is H. In certain embodiments, $R^B$ is substituted or unsubstituted, 5- to 6-membered, monocyclic heteroaryl, wherein one, two, three, or four atoms of the heteroaryl ring system are independently nitrogen, oxygen, or sulfur; and $R^C$ is H. In certain embodiments, $R^B$ is substituted or unsubstituted pyrazolyl, and $R^C$ is H. In certain embodiments, $R^B$ is substituted or unsubstituted, 3- to 7-membered, monocyclic carbocyclyl; and $R^C$ is H. In certain embodiments, $R^B$ is substituted or unsubstituted cyclopropyl, and $R^C$ is H.

Formula (II) includes as Ring B an imidazolyl ring that is unsubstituted (e.g., when m is 0) or substituted with one or two substituents $R^D$ (e.g., when m is 1 or 2). In certain embodiments, Ring B does not include substituents $R^D$, that is, m is 0. In certain embodiments, the two instances of $R^D$ are different. In certain embodiments, both instances of $R^D$ are the same. In certain embodiments, at least one instance of $R^D$ is halogen. In certain embodiments, at least one instance of $R^D$ is F. In certain embodiments, at least one instance of $R^D$ is Cl. In certain embodiments, at least one instance of $R^D$ is Br. In certain embodiments, at least one instance of $R^D$ is I (iodine). In certain embodiments, at least one instance of $R^D$ is substituted alkyl. In certain embodiments, at least one instance of $R^D$ is unsubstituted alkyl. In certain embodiments, at least one instance of $R^D$ is unsubstituted $C_{1-6}$ alkyl. In certain embodiments, both instances of $R^D$ are unsubstituted $C_{1-6}$ alkyl. In certain embodiments, at least one instance of $R^D$ is substituted $C_{1-6}$ alkyl. In certain embodiments, at least one instance of $R^D$ is $C_{1-6}$ alkyl substituted with at least one halogen. In certain embodiments, at least one instance of $R^D$ is —CH$_3$. In certain embodiments, at least one instance of $R^D$ is substituted methyl. In certain embodiments, at least one instance of $R^D$ is —CH$_2$F. In certain embodiments, at least one instance of $R^D$ is —CHF$_2$. In certain embodiments, at least one instance of $R^D$ is —CF$_3$. In certain embodiments, at least one instance of $R^D$ is ethyl. In certain embodiments, at least one instance of $R^D$ is propyl. In certain embodiments, at least one instance of $R^D$ is butyl. In certain embodiments, at least one instance of $R^D$ is pentyl. In certain embodiments, at least one instance of $R^D$ is hexyl. In certain embodiments, at least one instance of $R^D$ is Bn. In certain embodiments, at least one instance of $R^D$ is halogen or substituted or unsubstituted $C_{1-6}$ alkyl. In certain embodiments, at least one instance of $R^D$ is substituted alkenyl. In certain embodiments, at least one instance of $R^D$ is unsubstituted alkenyl. In certain embodiments, at least one instance of $R^D$ is substituted alkynyl. In certain embodiments, at least one instance of $R^D$ is unsubstituted alkynyl. In certain embodiments, at least one instance of $R^D$ is substituted carbocyclyl. In certain embodiments, at least one instance of $R^D$ is unsubstituted carbocyclyl. In certain embodiments, at least one instance of $R^D$ is saturated carbocyclyl. In certain embodiments, at least one instance of $R^D$ is unsaturated carbocyclyl. In certain embodiments, at least one instance of $R^D$ is monocyclic carbocyclyl. In certain embodiments, at least one instance of $R^D$ is 3- to 7-membered, monocyclic carbocyclyl. In certain embodiments, at least one instance of $R^D$ is substituted heterocyclyl. In certain embodiments, at least one instance of $R^D$ is unsubstituted heterocyclyl. In certain embodiments, at least one instance of $R^D$ is saturated heterocyclyl. In certain embodiments, at least one instance of $R^D$ is unsaturated heterocyclyl. In certain embodiments, at least one instance of $R^D$ is heterocyclyl, wherein one, two, or three atoms of the heterocyclic ring system are independently selected from the group consisting of nitrogen, oxygen, and sulfur. In certain embodiments, at least one instance of $R^D$ is monocyclic heterocyclyl. In certain embodiments, at least one instance of $R^D$ is 3- to 7-membered, monocyclic heterocyclyl. In certain embodiments, at least one instance of $R^D$ is substituted aryl. In certain embodiments, at least one instance of $R^D$ is unsubstituted aryl. In certain embodiments, at least one instance of $R^D$ is 6- to 10-membered aryl. In certain embodiments, at least one instance of $R^D$ is substituted phenyl. In certain embodiments, at least one instance of $R^D$ is unsubstituted phenyl. In certain embodiments, at least one instance of $R^D$ is substituted heteroaryl. In certain embodiments, at least one instance of $R^D$ is unsubstituted heteroaryl. In certain embodiments, at least one instance of $R^D$ is heteroaryl, wherein one, two, three, or four atoms of the heteroaryl ring system are independently selected from the group consisting of nitrogen, oxygen, and sulfur. In certain embodiments, at least one instance of $R^D$ is monocyclic heteroaryl. In certain embodiments, at least one instance of $R^D$ is 5-membered, monocyclic heteroaryl. In certain embodiments, at least one instance of $R^D$ is 6-membered, monocyclic heteroaryl. In certain embodiments, at least one instance of $R^D$ is bicyclic heteroaryl, wherein the point of attachment may be on any atom of the bicyclic heteroaryl ring system, as valency permits. In certain embodiments, at least one instance of $R^D$ is 9- or 10-membered, bicyclic heteroaryl. In certain embodiments, at least one instance of $R^D$ is —OR$^a$. In certain embodiments, at least one instance of $R^D$ is —OH. In certain embodiments, at least one instance of $R^D$ is —O(substituted or unsubstituted $C_{1-6}$ alkyl). In certain embodiments, at least one instance of $R^D$ is —OMe. In certain embodiments, at least one instance of $R^D$ is —OEt. In certain embodiments, at least one instance of $R^D$ is —OPr. In certain embodiments, at least one instance of $R^D$ is —OBu. In certain embodiments, at least one instance of $R^D$ is —OBn. In certain embodiments, at least one instance of $R^D$ is —OPh. In certain embodiments, at least one instance of $R^D$ is —SR$^a$. In certain embodiments, at least one instance of $R^D$ is —SH. In certain embodiments, at least one instance of $R^D$ is —SMe. In certain embodiments, at least one instance of $R^D$ is —$N(R^a)_2$. In certain embodiments, at least one instance of $R^D$ is —$NH_2$. In certain embodiments, at least one instance of $R^D$ is —NHMe. In certain embodiments, at least one instance of $R^D$ is —$NMe_2$. In certain embodiments, at least one instance of $R^D$ is —CN. In certain embodiments, at least one instance of $R^D$ is —SCN. In certain embodiments, at least one instance of $R^D$ is —C(=$NR^a$)$R^a$, —C(=$NR^a$)$OR^a$, or —C(=$NR^a$)$N(R^a)_2$. In certain embodiments, at least one instance of $R^D$ is —C(=O)$R^a$ or —C(=O)$OR^a$. In certain embodiments, at least one instance of $R^D$ is —C(=O)$N(R^a)_2$. In certain embodiments, at least one instance of $R^D$ is —C(=O)$NMe_2$, —C(=O)NHMe, or —C(=O)$NH_2$. In certain embodiments, at least one instance of $R^D$ is —$NO_2$. In certain embodiments, at least one instance of $R^D$ is —$NR^a$C(=O)$R^a$, —$NR^a$C(=O)$OR^a$, or —$NR^a$C(=O)$N(R^a)_2$. In certain embodiments, at least one instance of $R^D$ is —OC(=O)$R^a$, —OC(=O)$OR^a$, or —OC(=O)$N(R^a)_2$.

In certain embodiments, m is 0. In certain embodiments, m is 1. In certain embodiments, m is 2.

Formula (II) includes substituent $R^E$ on a nitrogen atom. In certain embodiments, $R^E$ is H. In certain embodiments, $R^E$ is substituted acyl. In certain embodiments, $R^E$ is unsubstituted acyl. In certain embodiments, $R^E$ is acetyl. In certain embodiments, $R^E$ is unsubstituted $C_{1-6}$ alkyl. In certain embodiments, $R^E$ is substituted $C_{1-6}$ alkyl. In certain embodiments, $R^E$ is $C_{1-6}$ alkyl substituted with at least one halogen. In certain embodiments, $R^E$ is unsubstituted methyl. In certain embodiments, $R^E$ is substituted methyl. In certain embodiments, $R^E$ is —$CH_2F$. In certain embodiments, $R^E$ is —$CHF_2$. In certain embodiments, $R^E$ is —$CF_3$. In certain embodiments, $R^E$ is ethyl. In certain embodiments, $R^E$ is propyl. In certain embodiments, $R^E$ is butyl. In certain embodiments, $R^E$ is pentyl. In certain embodiments, $R^E$ is hexyl. In certain embodiments, $R^E$ is Bn. In certain embodiments, $R^E$ is a nitrogen protecting group. In certain embodiments, $R^E$ is Bn, Boc, Cbz, Fmoc, trifluoroacetyl, triphenylmethyl, acetyl, or Ts.

In certain embodiments, each of $R^C$ and $R^E$ is H.

Formula (II) includes as Ring C a phenyl ring that is unsubstituted (e.g., when n is 0) or substituted with one or more substituents $R^F$ (e.g., when n is 1, 2, 3, 4, or 5). In certain embodiments, Ring C is of the formula:

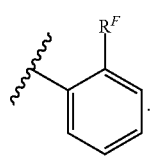

In certain embodiments, Ring C is of the formula:

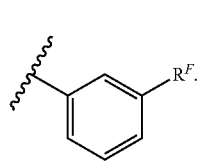

In certain embodiments, Ring C is of the formula:

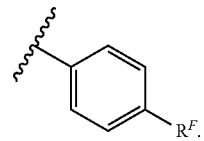

In certain embodiments, Ring C is of the formula:

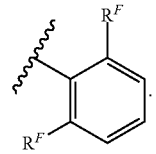

In certain embodiments, Ring C is of the formula:

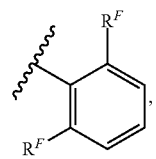

wherein each instance of $R^F$ is independently halogen or substituted or unsubstituted $C_{1-6}$ alkyl. In certain embodiments, Ring C is of the formula:

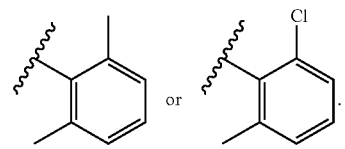

In certain embodiments, Ring C is of the formula:

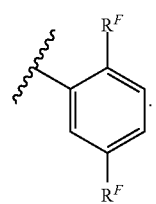

In certain embodiments, Ring C is of the formula:

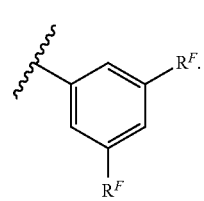

In certain embodiments, Ring C is of the formula:

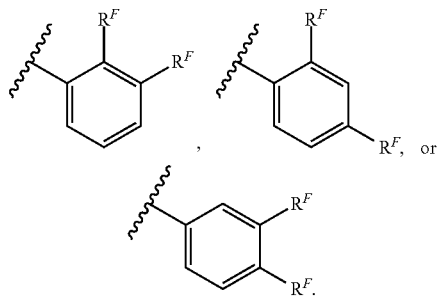

In certain embodiments, at least two instances of $R^F$ are different. In certain embodiments, all instances of $R^F$ are the same. In certain embodiments, at least one instance of $R^F$ is halogen. In certain embodiments, at least one instance of $R^F$ is F. In certain embodiments, at least one instance of $R^F$ is Cl. In certain embodiments, at least one instance of $R^F$ is Br. In certain embodiments, at least one instance of $R^F$ is I (iodine). In certain embodiments, at least one instance of $R^F$ is substituted alkyl. In certain embodiments, at least one instance of $R^F$ is unsubstituted alkyl. In certain embodiments, at least one instance of $R^F$ is unsubstituted $C_{1-6}$ alkyl. In certain embodiments, all instances of $R^F$ are unsubstituted $C_{1-6}$ alkyl. In certain embodiments, at least one instance of $R^F$ is substituted $C_{1-6}$ alkyl. In certain embodiments, at least one instance of $R^F$ is $C_{1-6}$ alkyl substituted with at least one halogen. In certain embodiments, at least one instance of $R^F$ is —$CH_3$. In certain embodiments, all instances of $R^F$ are —$CH_3$. In certain embodiments, at least one instance of $R^F$ is substituted methyl. In certain embodiments, at least one instance of $R^F$ is —$CH_2F$. In certain embodiments, at least one instance of $R^F$ is —$CHF_2$. In certain embodiments, at least one instance of $R^F$ is —$CF_3$. In certain embodiments, at least one instance of $R^F$ is ethyl. In certain embodiments, at least one instance of $R^F$ is propyl. In certain embodiments, at least one instance of $R^F$ is butyl. In certain embodiments, at least one instance of $R^F$ is pentyl. In certain embodiments, at least one instance of $R^F$ is hexyl. In certain embodiments, at least one instance of $R^F$ is Bn. In certain embodiments, at least one instance of $R^F$ is substituted alkenyl. In certain embodiments, at least one instance of $R^F$ is unsubstituted alkenyl. In certain embodiments, at least one instance of $R^F$ is substituted alkynyl. In certain embodiments, at least one instance of $R^F$ is unsubstituted alkynyl. In certain embodiments, at least one instance of $R^F$ is substituted carbocyclyl. In certain embodiments, at least one instance of $R^F$ is unsubstituted carbocyclyl. In certain embodiments, at least one instance of $R^F$ is saturated carbocyclyl. In certain embodiments, at least one instance of $R^F$ is unsaturated carbocyclyl. In certain embodiments, at least one instance of $R^F$ is monocyclic carbocyclyl. In certain embodiments, at least one instance of $R^F$ is 3- to 7-membered, monocyclic carbocyclyl. In certain embodiments, at least one instance of $R^F$ is substituted heterocyclyl. In certain embodiments, at least one instance of $R^F$ is unsubstituted heterocyclyl. In certain embodiments, at least one instance of $R^F$ is saturated heterocyclyl. In certain embodiments, at least one instance of $R^F$ is unsaturated heterocyclyl. In certain embodiments, at least one instance of $R^F$ is heterocyclyl, wherein one, two, or three atoms of the heterocyclic ring system are independently selected from the group consisting of nitrogen, oxygen, and sulfur. In certain embodiments, at least one instance of $R^F$ is monocyclic heterocyclyl. In certain embodiments, at least one instance of $R^F$ is 3- to 7-membered, monocyclic heterocyclyl. In certain embodiments, at least one instance of $R^F$ is substituted aryl. In certain embodiments, at least one instance of $R^F$ is unsubstituted aryl. In certain embodiments, at least one instance of $R^F$ is 6- to 10-membered aryl. In certain embodiments, at least one instance of $R^F$ is substituted phenyl. In certain embodiments, at least one instance of $R^F$ is unsubstituted phenyl. In certain embodiments, at least one instance of $R^F$ is substituted heteroaryl. In certain embodiments, at least one instance of $R^F$ is unsubstituted heteroaryl. In certain embodiments, at least one instance of $R^F$ is heteroaryl, wherein one, two, three, or four atoms of the heteroaryl ring system are independently selected from the group consisting of nitrogen, oxygen, and sulfur. In certain embodiments, at least one instance of $R^F$ is monocyclic heteroaryl. In certain embodiments, at least one instance of $R^F$ is 5-membered, monocyclic heteroaryl. In certain embodiments, at least one instance of $R^F$ is 6-membered, monocyclic heteroaryl. In certain embodiments, at least one instance of $R^F$ is bicyclic heteroaryl, wherein the point of attachment may be on any atom of the bicyclic heteroaryl ring system, as valency permits. In certain embodiments, at least one instance of $R^F$ is 9- or 10-membered, bicyclic heteroaryl. In certain embodiments, at least one instance of $R^F$ is —$OR^a$. In certain embodiments, at least one instance of $R^F$ is —OH. In certain embodiments, at least one instance of $R^F$ is —O(substituted or unsubstituted $C_{1-6}$ alkyl). In certain embodiments, at least one instance of $R^F$ is —OMe. In certain embodiments, at least one instance of $R^F$ is —OEt. In certain embodiments, at least one instance of $R^F$ is —OPr. In certain embodiments, at least one instance of $R^F$ is —OBu. In certain embodiments, at least one instance of $R^F$ is —OBn. In certain embodiments, at least one instance of $R^F$ is —OPh. In certain embodiments, at least one instance of $R^F$ is —$SR^a$. In certain embodiments, at least one instance of $R^F$ is —SH. In certain embodiments, at least one instance of $R^F$ is —SMe. In certain embodiments, at least one instance of $R^F$ is —$N(R^a)_2$. In certain embodiments, at least one instance of $R^F$ is —$NH_2$. In certain embodiments, at least one instance of $R^F$ is —NHMe. In certain embodiments, at least one instance of $R^F$ is —$NMe_2$. In certain embodiments, at least one instance of $R^F$ is —CN. In certain embodiments, at least one instance of $R^F$ is —SCN. In certain embodiments, at least one instance of $R^F$ is —$C(=NR^a)R^a$, —$C(=NR^a)OR^a$, or —$C(=NR^a)N(R^a)_2$. In certain embodiments, at least one instance of $R^F$ is —$C(=O)R^a$ or —$C(=O)OR^a$. In certain embodiments, at least one instance of $R^F$ is —$C(=O)N(R^a)_2$.

In certain embodiments, at least one instance of $R^F$ is —$C(=O)N(R^a)_2$, wherein each instance of $R^a$ is independently hydrogen, substituted or unsubstituted $C_{1-6}$ alkyl, substituted or unsubstituted phenyl, or a nitrogen protecting group. In certain embodiments, at least one instance of $R^F$ is —$C(=O)NHR^a$, wherein $R^a$ is substituted or unsubstituted phenyl. In certain embodiments, at least one instance of $R^F$ is —$C(=O)NHR^a$, wherein $R^a$ is phenyl substituted with one, two, three, four, or five substituents independently selected from the group consisting of halogen and substituted or unsubstituted $C_{1-6}$ alkyl. In certain embodiments, at least one instance of $R^F$ is —$C(=O)NMeR^a$, wherein $R^a$ is substituted or unsubstituted phenyl. In certain embodiments, at least one instance of $R^F$ is —$C(=O)NMeR^a$, wherein $R^a$ is phenyl substituted with one, two, three, four, or five substituents independently selected from the group consisting of halogen and substituted or unsubstituted $C_{1-6}$ alkyl. In certain embodiments, at least one instance of $R^F$ is —$C(=O)NMe_2$, —$C(=O)NHMe$, or —$C(=O)NH_2$. In certain embodiments, at least one instance of $R^F$ is —$NO_2$. In certain embodiments, at least one instance of $R^F$ is —$NR^aC(=O)R^a$, —$NR^WC(=O)OR^a$, or —$NR^aC(=O)N(R^a)_2$. In certain embodiments, at least one instance of $R^F$ is —$OC(=O)R^a$, —$OC(=O)OR^a$, or —$OC(=O)N(R^a)_2$.

In certain embodiments, at least one instance of $R^F$ is halogen, substituted or unsubstituted $C_{1-6}$ alkyl, or —$OR^a$. In certain embodiments, at least one instance of $R^F$ is halogen, substituted or unsubstituted $C_{1-6}$ alkyl, or —$OR^a$, wherein $R^a$ is hydrogen, substituted or unsubstituted $C_{1-6}$ alkyl, or an oxygen protecting group. In certain embodiments, at least one instance of $R^F$ is halogen, unsubstituted $C_{1-6}$ alkyl, or —$OR^a$, wherein $R^a$ is unsubstituted $C_{1-6}$ alkyl. In certain embodiments, at least one instance of $R^F$ is —$CH_3$ or Cl.

In certain embodiments, n is 0. In certain embodiments, n is 1. In certain embodiments, n is 2. In certain embodiments, n is 3. In certain embodiments, n is 4. In certain embodiments, n is 5.

In certain embodiments, n is 1; and $R^F$ is —$C(=O)N(R^a)_2$. In certain embodiments, n is 1; and $R^F$ is —$C(=O)N(R^a)_2$, wherein each instance of $R^a$ is independently hydrogen, substituted or unsubstituted $C_{1-6}$ alkyl, substituted or unsubstituted phenyl, or a nitrogen protecting group. In certain embodiments, n is 2; and each instance of $R^F$ is independently halogen or substituted or unsubstituted $C_{1-6}$ alkyl. In certain embodiments, n is 2; and each instance of $R^F$ is independently halogen or unsubstituted $C_{1-6}$ alkyl (e.g., —$CH_3$). In certain embodiments, n is 2; and each instance of $R^F$ is independently halogen, substituted or unsubstituted $C_{1-6}$ alkyl, —$OR^a$, or —$C(=O)N(R^a)_2$. In certain embodiments, n is 2; and each instance of $R^F$ is independently halogen, substituted or unsubstituted $C_{1-6}$ alkyl, —$OR^a$, or —$C(=O)N(R^a)_2$, wherein each instance of $R^a$ is independently hydrogen, substituted or unsubstituted $C_{1-6}$ alkyl, substituted or unsubstituted phenyl, an oxygen protecting group when attached to an oxygen atom, or a nitrogen protecting group when attached to a nitrogen atom.

In certain embodiments, the compound of Formula (II) is of Formula (II-A):

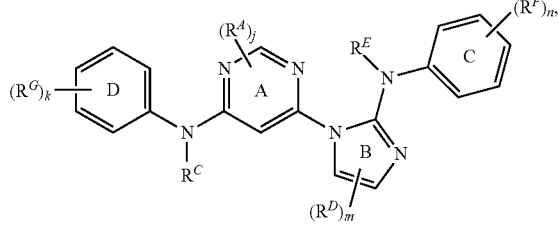

(II-A)

or a pharmaceutically acceptable salt, solvate, hydrate, polymorph, co-crystal, tautomer, stereoisomer, isotopically labeled derivative, or prodrug thereof, wherein:

each instance of $R^G$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$; and k is 0, 1, 2, 3, 4, or 5.

Formula (II-A) includes as Ring D a phenyl ring that is unsubstituted (e.g., when k is 0) or substituted with one or more substituents $R^G$ (e.g., when k is 1, 2, 3, 4, or 5). In certain embodiments, Ring D is of the formula:

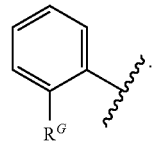

In certain embodiments, Ring D is of the formula:

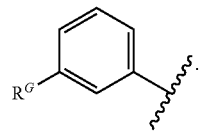

In certain embodiments, Ring D is of the formula:

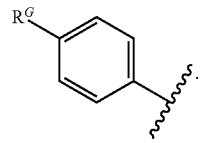

In certain embodiments, Ring D is of the formula:

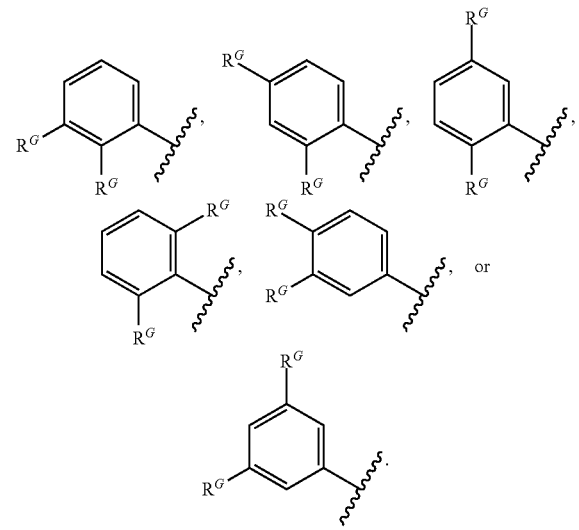

In certain embodiments, at least two instances of $R^G$ are different. In certain embodiments, all instances of $R^G$ are the same. In certain embodiments, at least one instance of $R^G$ is halogen. In certain embodiments, at least one instance of $R^G$ is F. In certain embodiments, at least one instance of $R^G$ is Cl. In certain embodiments, at least one instance of $R^G$ is Br. In certain embodiments, at least one instance of $R^G$ is I (iodine). In certain embodiments, at least one instance of $R^G$ is substituted alkyl. In certain embodiments, at least one instance of $R^G$ is unsubstituted alkyl. In certain embodiments, at least one instance of $R^G$ is unsubstituted $C_{1-6}$ alkyl. In certain embodiments, all instances of $R^G$ are unsubstituted $C_{1-6}$ alkyl. In certain embodiments, at least one instance of $R^G$ is substituted $C_{1-6}$ alkyl. In certain embodiments, at least one instance of $R^G$ is $C_{1-6}$ alkyl substituted with at least one halogen. In certain embodiments, at least one instance of $R^G$ is —$CH_3$. In certain embodiments, all instances of $R^G$ are —$CH_3$. In certain embodiments, at least one instance of $R^G$ is substituted methyl. In certain embodiments, at least one instance of $R^G$ is —$CH_2F$. In certain embodiments, at least one instance of $R^G$ is —$CHF_2$. In certain embodiments, at least one instance of $R^G$ is —$CF_3$. In certain embodiments, at least one instance of $R^G$ is ethyl. In certain embodiments, at least one instance of $R^G$ is propyl. In certain embodiments, at least one instance of $R^G$ is butyl. In certain embodiments, at least one instance of $R^G$ is pentyl. In certain embodiments, at least one instance of $R^G$ is hexyl. In certain embodiments, at least one instance of $R^G$ is Bn. In certain embodiments, at least one instance of $R^G$ is substituted alkenyl. In certain embodiments, at least one instance of $R^G$ is unsubstituted alkenyl. In certain embodiments, at least one instance of $R^G$ is substituted alkynyl. In certain embodiments, at least one instance of $R^G$ is unsubstituted alkynyl. In certain embodiments, at least one instance of $R^G$ is substituted carbocyclyl. In certain embodiments, at least one instance of $R^G$ is unsubstituted carbocyclyl. In certain embodiments, at least one instance of $R^G$ is saturated carbocyclyl. In certain embodiments, at least one instance of $R^G$ is unsaturated carbocyclyl. In certain embodiments, at least one instance of $R^G$ is monocyclic carbocyclyl. In certain embodiments, at least one instance of $R^G$ is 3- to 7-membered, monocyclic carbocyclyl. In certain embodiments, at least one instance of $R^G$ is substituted heterocyclyl. In certain embodiments, at least one instance of $R^G$ is unsubstituted heterocyclyl. In certain embodiments, at least one instance of $R^G$ is saturated heterocyclyl. In certain embodiments, at least one instance of $R^G$ is unsaturated heterocyclyl. In certain embodiments, at least one instance of $R^G$ is heterocyclyl, wherein one, two, or three atoms of the heterocyclic ring system are independently selected from the group consisting of nitrogen, oxygen, and sulfur. In certain embodiments, at least one instance of $R^G$ is monocyclic heterocyclyl. In certain embodiments, at least one instance of $R^G$ is 3- to 7-membered, monocyclic heterocyclyl. In certain embodiments, at least one instance of $R^G$ is substituted or unsubstituted piperazinyl. In certain embodiments, at least one instance of $R^G$ is of the formula:

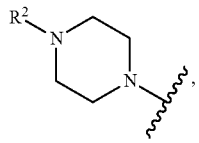

wherein $R^2$ is H, substituted or unsubstituted $C_{1-6}$ alkyl, or a nitrogen protecting group. In certain embodiments, at least one instance of $R^G$ is of the formula:

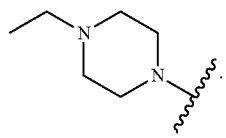 [SMILES: *N1CCN(CC)CC1]

In certain embodiments, at least one instance of $R^G$ is substituted aryl. In certain embodiments, at least one instance of $R^G$ is unsubstituted aryl. In certain embodiments, at least one instance of $R^G$ is 6- to 10-membered aryl. In certain embodiments, at least one instance of $R^G$ is substituted phenyl. In certain embodiments, at least one instance of $R^G$ is unsubstituted phenyl. In certain embodiments, at least one instance of $R^G$ is substituted heteroaryl. In certain embodiments, at least one instance of $R^G$ is unsubstituted heteroaryl. In certain embodiments, at least one instance of $R^G$ is heteroaryl, wherein one, two, three, or four atoms of the heteroaryl ring system are independently selected from the group consisting of nitrogen, oxygen, and sulfur. In certain embodiments, at least one instance of $R^G$ is monocyclic heteroaryl. In certain embodiments, at least one instance of $R^G$ is 5-membered, monocyclic heteroaryl. In certain embodiments, at least one instance of $R^G$ is 6-membered, monocyclic heteroaryl. In certain embodiments, at least one instance of $R^G$ is bicyclic heteroaryl, wherein the point of attachment may be on any atom of the bicyclic heteroaryl ring system, as valency permits. In certain embodiments, at least one instance of $R^G$ is 9- or 10-membered, bicyclic heteroaryl. In certain embodiments, at least one instance of $R^G$ is —$OR^a$. In certain embodiments, at least one instance of $R^G$ is —OH. In certain embodiments, at least one instance of $R^G$ is —O(substituted or unsubstituted $C_{1-6}$ alkyl). In certain embodiments, at least one instance of $R^G$ is —O—$(CH_2)_{2-4}$—O-(substituted or unsubstituted $C_{1-6}$ alkyl). In certain embodiments, at least one instance of $R^G$ is —O—$(CH_2)_2$—OMe. In certain embodiments, at least one instance of $R^G$ is —OMe. In certain embodiments, at least one instance of $R^G$ is —OEt. In certain embodiments, at least one instance of $R^G$ is —OPr. In certain embodiments, at least one instance of $R^G$ is —OBu. In certain embodiments, at least one instance of $R^G$ is —OBn. In certain embodiments, at least one instance of $R^G$ is —OPh. In certain embodiments, at least one instance of $R^G$ is —$SR^a$. In certain embodiments, at least one instance of $R^G$ is —SH. In certain embodiments, at least one instance of $R^G$ is —SMe. In certain embodiments, at least one instance of $R^G$ is —$N(R^a)_2$. In certain embodiments, at least one instance of $R^G$ is —$N(R^a)_2$, wherein each instance of $R^a$ is independently hydrogen, substituted or unsubstituted $C_{1-6}$ alkyl, or a nitrogen protecting group, or two instances of $R^a$ are joined to form a substituted or unsubstituted, 3- to 7-membered, monocyclic heterocyclic ring. In certain embodiments, at least one instance of $R^G$ is —$NH_2$. In certain embodiments, at least one instance of $R^G$ is —NHMe. In certain embodiments, at least one instance of $R^G$ is —$NMe_2$. In certain embodiments, at least one instance of $R^G$ is —CN. In certain embodiments, at least one instance of $R^G$ is —SCN. In certain embodiments, at least one instance of $R^G$ is —$C(=NR^a)R^a$, —$C(=NR^a)OR^a$, or —$C(=NR^a)N(R^a)_2$. In certain embodiments, at least one instance of $R^G$ is —$C(=O)R^a$ or $C(=O)OR^a$. In certain embodiments, at least one instance of $R^G$ is —$C(=O)N(R^a)_2$. In certain embodiments, at least one instance of $R^G$ is —$C(=O)NMe_2$, —$C(=O)NHMe$, or —$C(=O)NH_2$. In certain embodiments, at least one instance of $R^G$ is —$NO_2$. In certain embodiments, at least one instance of $R^G$ is —$NR^aC(=O)R^a$, —$NR^aC(=O)OR^a$, or —$NR^aC(=O)N(R^a)_2$. In certain embodiments, at least one instance of $R^G$ is —$OC(=O)R^a$, —$OC(=O)OR^a$, or —$OC(=O)N(R^a)_2$.

In certain embodiments, at least one instance of $R^G$ is —$OR^a$, —$N(R^a)_2$, or substituted or unsubstituted, 3- to 7-membered, monocyclic heterocyclyl, wherein one, two, or three atoms of the heterocyclic ring system are independently nitrogen, oxygen, or sulfur.

In certain embodiments, k is 0. In certain embodiments, k is 1. In certain embodiments, k is 2. In certain embodiments, k is 3. In certain embodiments, k is 4. In certain embodiments, k is 5.

In certain embodiments, k is 1; and $R^G$ is —$OR^a$, —$N(R^a)_2$, or substituted or unsubstituted, 3- to 7-membered, monocyclic heterocyclyl, wherein one, two, or three atoms of the heterocyclic ring system are independently nitrogen, oxygen, or sulfur. In certain embodiments, k is 1; and $R^G$ is —$OR^a$, —$N(R^a)_2$, or substituted or unsubstituted, 3- to 7-membered, monocyclic heterocyclyl, wherein one, two, or three atoms of the heterocyclic ring system are independently nitrogen, oxygen, or sulfur; and each instance of $R^a$ is independently H, substituted or unsubstituted $C_{1-6}$ alkyl, an oxygen protecting group when attached to an oxygen atom, or a nitrogen protecting group when attached to a nitrogen group.

In certain embodiments, the compound of Formula (II) is of the formula:

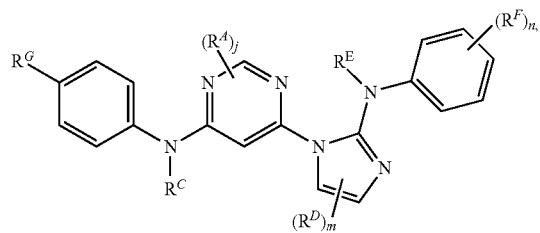

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

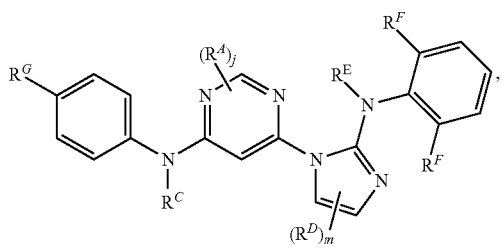

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

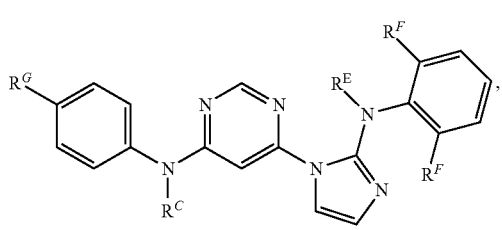

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

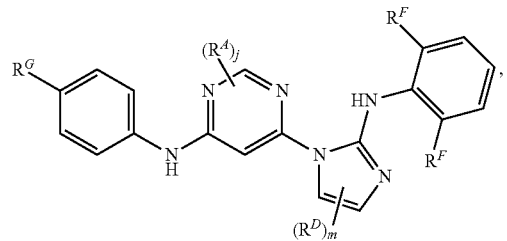

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

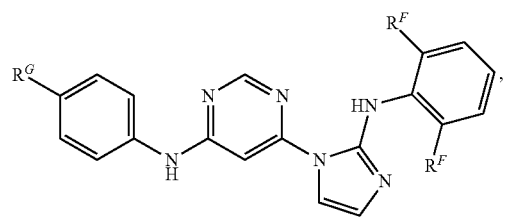

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of Formula (II-B):

(II-B)

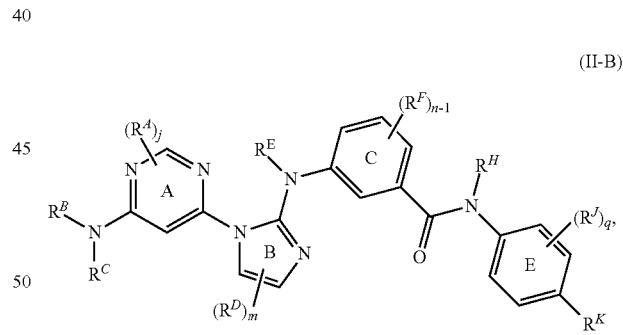

or a pharmaceutically acceptable salt, solvate, hydrate, polymorph, co-crystal, tautomer, stereoisomer, isotopically labeled derivative, or prodrug thereof, wherein:

$R^H$ is hydrogen, substituted or unsubstituted acyl, substituted or unsubstituted $C_{1-6}$ alkyl, or a nitrogen protecting group;

each instance of $R^J$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

q is 0, 1, 2, 3, or 4; and

R$^K$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$.

In certain embodiments, a compound of Formula (II) is of Formula (II-B), wherein when R$^C$ is hydrogen, R$^B$ is not unsubstituted cyclopropyl or

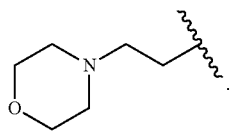 [SMILES: *CCN1CCOCC1]

Formula (II-B) includes substituent R$^H$ on a nitrogen atom. In certain embodiments, R$^H$ is H. In certain embodiments, R$^H$ is not H. In certain embodiments, R$^H$ is substituted acyl. In certain embodiments, R$^H$ is unsubstituted acyl. In certain embodiments, R$^H$ is acetyl. In certain embodiments, R$^H$ is unsubstituted C$_{1-6}$ alkyl. In certain embodiments, R$^H$ is substituted C$_{1-6}$ alkyl. In certain embodiments, R$^H$ is C$_{1-6}$ alkyl substituted with at least one halogen. In certain embodiments, R$^H$ is unsubstituted methyl. In certain embodiments, R$^H$ is substituted methyl. In certain embodiments, R$^H$ is —CH$_2$F. In certain embodiments, R$^H$ is —CHF$_2$. In certain embodiments, R$^H$ is —CF$_3$. In certain embodiments, R$^H$ is ethyl. In certain embodiments, R$^H$ is propyl. In certain embodiments, R$^H$ is butyl. In certain embodiments, R$^H$ is pentyl. In certain embodiments, R$^H$ is hexyl. In certain embodiments, R$^H$ is Bn. In certain embodiments, R$^H$ is a nitrogen protecting group. In certain embodiments, R$^H$ is Bn, Boc, Cbz, Fmoc, trifluoroacetyl, triphenylmethyl, acetyl, or Ts. In certain embodiments, R$^H$ is hydrogen or unsubstituted C$_{1-6}$ alkyl.

Formula (II-B) includes as Ring E a phenyl ring that is substituted with R$^K$ and optionally one or more substituents R$^J$. In certain embodiments, Ring E is of the formula:

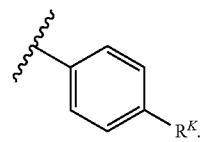

In certain embodiments, Ring E is of the formula:

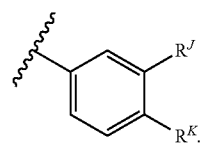

In certain embodiments, Ring E is of the formula:

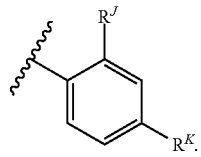

In certain embodiments, Ring E is of the formula:

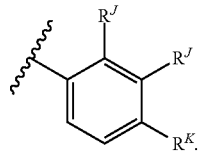

In certain embodiments, Ring E is of the formula:

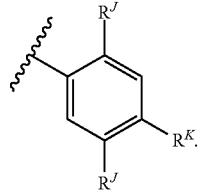

In certain embodiments, Ring E is of the formula:

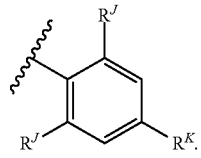

In certain embodiments, Ring E is of the formula:

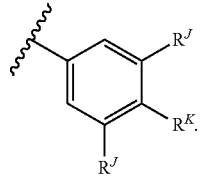

In certain embodiments, R$^K$ is H. In certain embodiments, R$^K$ is halogen. In certain embodiments, R$^K$ is F. In certain embodiments, R$^K$ is Cl. In certain embodiments, R$^K$ is Br. In certain embodiments, R$^K$ is I (iodine). In certain embodiments, R$^K$ is substituted alkyl. In certain embodiments, R$^K$ is unsubstituted alkyl. In certain embodiments, R$^K$ is unsubstituted C$_{1-6}$ alkyl. In certain embodiments, R$^K$ is substituted C$_{1-6}$ alkyl. In certain embodiments, R$^K$ is C$_{1-6}$ alkyl substituted with at least one halogen. In certain embodiments, R$^K$ is —CH$_3$. In certain embodiments, R$^K$ is substituted methyl. In certain embodiments, R$^K$ is —CH$_2$F. In certain embodiments, R$^K$ is —CHF$_2$. In certain embodiments, R$^K$ is —CF$_3$. In certain embodiments, R$^K$ is ethyl. In certain embodiments, $R^K$ is propyl. In certain embodiments, $R^K$ is butyl. In certain embodiments, $R^K$ is pentyl. In certain embodiments, $R^K$ is hexyl. In certain embodiments, $R^K$ is Bn. In certain embodiments, $R^K$ is substituted alkenyl. In certain embodiments, $R^K$ is unsubstituted alkenyl. In certain embodiments, $R^K$ is substituted alkynyl. In certain embodiments, $R^K$ is unsubstituted alkynyl. In certain embodiments, $R^K$ is substituted carbocyclyl. In certain embodiments, $R^K$ is unsubstituted carbocyclyl. In certain embodiments, $R^K$ is saturated carbocyclyl. In certain embodiments, $R^K$ is unsaturated carbocyclyl. In certain embodiments, $R^K$ is monocyclic carbocyclyl. In certain embodiments, $R^K$ is 3- to 7-membered, monocyclic carbocyclyl. In certain embodiments, $R^K$ is substituted heterocyclyl. In certain embodiments, $R^K$ is unsubstituted heterocyclyl. In certain embodiments, $R^K$ is saturated heterocyclyl. In certain embodiments, $R^K$ is unsaturated heterocyclyl. In certain embodiments, $R^K$ is heterocyclyl, wherein one, two, or three atoms of the heterocyclic ring system are independently selected from the group consisting of nitrogen, oxygen, and sulfur. In certain embodiments, $R^K$ is monocyclic heterocyclyl. In certain embodiments, $R^K$ is 3- to 7-membered, monocyclic heterocyclyl. In certain embodiments, $R^K$ is substituted aryl. In certain embodiments, $R^K$ is unsubstituted aryl. In certain embodiments, $R^K$ is 6- to 10-membered aryl. In certain embodiments, $R^K$ is substituted phenyl. In certain embodiments, $R^K$ is unsubstituted phenyl. In certain embodiments, $R^K$ is substituted heteroaryl. In certain embodiments, $R^K$ is unsubstituted heteroaryl. In certain embodiments, $R^K$ is heteroaryl, wherein one, two, three, or four atoms of the heteroaryl ring system are independently selected from the group consisting of nitrogen, oxygen, and sulfur. In certain embodiments, $R^K$ is monocyclic heteroaryl. In certain embodiments, $R^K$ is 5-membered, monocyclic heteroaryl. In certain embodiments, $R^K$ is not substituted imidazolyl. In certain embodiments, $R^K$ is 6-membered, monocyclic heteroaryl. In certain embodiments, $R^K$ is bicyclic heteroaryl, wherein the point of attachment may be on any atom of the bicyclic heteroaryl ring system, as valency permits. In certain embodiments, $R^K$ is 9- or 10-membered, bicyclic heteroaryl. In certain embodiments, $R^K$ is —$OR^a$. In certain embodiments, $R^K$ is —OH. In certain embodiments, $R^K$ is —O(substituted or unsubstituted $C_{1-6}$ alkyl). In certain embodiments, $R^K$ is —OMe. In certain embodiments, $R^K$ is —OEt. In certain embodiments, $R^K$ is —OPr. In certain embodiments, $R^K$ is —OBu. In certain embodiments, $R^K$ is —OBn. In certain embodiments, $R^K$ is —OPh. In certain embodiments, $R^K$ is —$SR^a$. In certain embodiments, $R^K$ is —SH. In certain embodiments, $R^K$ is —SMe. In certain embodiments, $R^K$ is —$N(R^a)_2$. In certain embodiments, $R^K$ is —$NH_2$. In certain embodiments, $R^K$ is —NHMe. In certain embodiments, $R^K$ is —$NMe_2$. In certain embodiments, $R^K$ is —CN. In certain embodiments, $R^K$ is —SCN. In certain embodiments, $R^K$ is —C(=$NR^a$)$R^a$, —C(=$NR^a$)$OR^a$, or —C(=$NR^a$)N$(R^a)_2$. In certain embodiments, $R^K$ is —C(=O)$R^a$ or C(=O)$OR^a$. In certain embodiments, $R^K$ is —C(=O)N$(R^a)_2$. In certain embodiments, $R^K$ is —C(=O)NMe$_2$, —C(=O)NHMe, or —C(=O)NH$_2$. In certain embodiments, $R^K$ is —$NO_2$, In certain embodiments, $R^K$ is —$NR^aC$(=O)$R^a$, —$NR^aC$(=O)$OR^a$, or —$NR^aC$(=O)N$(R^a)_2$. In certain embodiments, $R^K$ is —OC(=O)$R^a$, —OC(=O)$OR^a$, or —OC(=O)N$(R^a)_2$.

In certain embodiments, $R^K$ is —$(CH_2)_{1-3}$-(Ring G), wherein Ring G is a substituted or unsubstituted, 3- to 7-membered, monocyclic heterocyclic ring. In certain embodiments, $R^K$ is —$(CH_2)_{1-3}$-(substituted or unsubstituted piperazinyl). In certain embodiments, $R^K$ is of the formula:

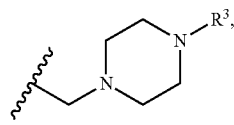

wherein $R^3$ is H, substituted or unsubstituted $C_{2-6}$ alkyl, substituted methyl, or a nitrogen protecting group. In certain embodiments, $R^K$ is of the formula:

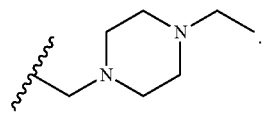 [SMILES: *CN1CCN(CC)CC1]

In certain embodiments, $R^K$ is not of the formula:

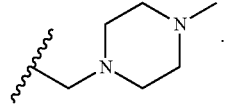 [SMILES: *CN1CCN(C)CC1]

In certain embodiments, $R^K$ is —$(CH_2)_{1-3}$-(Ring G), wherein Ring G is a substituted or unsubstituted oxetanyl, substituted or unsubstituted azetidinyl, substituted or unsubstituted tetrahydrofuranyl, substituted or unsubstituted pyrrolidinyl, substituted or unsubstituted tetrahydropyranyl, substituted or unsubstituted piperidinyl, or substituted or unsubstituted morpholinyl ring.

Ring E of Formula (II-B) may include one or more substituents $R^J$. In certain embodiments, at least two instances of $R^J$ are different. In certain embodiments, all instances of $R^J$ are the same. In certain embodiments, at least one instance of $R^J$ is halogen. In certain embodiments, at least one instance of $R^J$ is F. In certain embodiments, at least one instance of $R^J$ is Cl. In certain embodiments, at least one instance of $R^J$ is Br. In certain embodiments, at least one instance of $R^J$ is I (iodine). In certain embodiments, at least one instance of $R^J$ is substituted alkyl. In certain embodiments, at least one instance of $R^J$ is unsubstituted alkyl. In certain embodiments, at least one instance of $R^J$ is unsubstituted $C_{1-6}$ alkyl. In certain embodiments, all instances of $R^J$ are unsubstituted $C_{1-6}$ alkyl. In certain embodiments, at least one instance of $R^J$ is substituted $C_{1-6}$ alkyl. In certain embodiments, at least one instance of $R^J$ is $C_{1-6}$ alkyl substituted with at least one halogen. In certain embodiments, at least one instance of $R^J$ is —$CH_3$. In certain embodiments, all instances of $R^J$ are —$CH_3$. In certain embodiments, at least one instance of $R^J$ is substituted methyl. In certain embodiments, at least one instance of $R^J$ is —$CH_2F$. In certain embodiments, at least one instance of $R^J$ is —$CHF_2$. In certain embodiments, at least one instance of $R^J$ is —$CF_3$. In certain embodiments, at least one instance of $R^J$ is ethyl. In certain embodiments, at least one instance of $R^J$ is propyl. In certain embodiments, at least one instance of $R^J$ is butyl. In certain embodiments, at least one instance of $R^J$ is pentyl. In certain embodiments, at least one instance of $R^J$ is hexyl. In certain embodiments, at least one instance of $R^J$ is Bn. In certain embodiments, at least one instance of $R^J$ is halogen or substituted or unsubstituted $C_{1-6}$ alkyl. In certain embodiments, at least one instance of $R^J$ is substituted alkenyl. In certain embodiments, at least one instance of $R^J$ is unsubstituted alkenyl. In certain embodiments, at least one instance of $R^J$ is substituted alkynyl. In certain embodiments, at least one instance of $R^J$ is unsubstituted alkynyl. In certain embodiments, at least one instance of $R^J$ is substituted carbocyclyl. In certain embodiments, at least one instance of $R^J$ is unsubstituted carbocyclyl. In certain embodiments, at least one instance of $R^J$ is saturated carbocyclyl. In certain embodiments, at least one instance of $R^J$ is unsaturated carbocyclyl. In certain embodiments, at least one instance of $R^J$ is monocyclic carbocyclyl. In certain embodiments, at least one instance of $R^J$ is 3- to 7-membered, monocyclic carbocyclyl. In certain embodiments, at least one instance of $R^J$ is substituted heterocyclyl. In certain embodiments, at least one instance of $R^J$ is unsubstituted heterocyclyl. In certain embodiments, at least one instance of $R^J$ is saturated heterocyclyl. In certain embodiments, at least one instance of $R^J$ is unsaturated heterocyclyl. In certain embodiments, at least one instance of $R^J$ is heterocyclyl, wherein one, two, or three atoms of the heterocyclic ring system are independently selected from the group consisting of nitrogen, oxygen, and sulfur. In certain embodiments, at least one instance of $R^J$ is monocyclic heterocyclyl. In certain embodiments, at least one instance of $R^J$ is 3- to 7-membered, monocyclic heterocyclyl. In certain embodiments, at least one instance of $R^J$ is substituted aryl. In certain embodiments, at least one instance of $R^J$ is unsubstituted aryl. In certain embodiments, at least one instance of $R^J$ is 6- to 10-membered aryl. In certain embodiments, at least one instance of $R^J$ is substituted phenyl. In certain embodiments, at least one instance of $R^J$ is unsubstituted phenyl. In certain embodiments, at least one instance of $R^J$ is substituted heteroaryl. In certain embodiments, at least one instance of $R^J$ is unsubstituted heteroaryl. In certain embodiments, at least one instance of $R^J$ is heteroaryl, wherein one, two, three, or four atoms of the heteroaryl ring system are independently selected from the group consisting of nitrogen, oxygen, and sulfur. In certain embodiments, at least one instance of $R^J$ is monocyclic heteroaryl. In certain embodiments, at least one instance of $R^J$ is 5-membered, monocyclic heteroaryl. In certain embodiments, no instance of $R^J$ is substituted imidazolyl. In certain embodiments, at least one instance of $R^J$ is 6-membered, monocyclic heteroaryl. In certain embodiments, at least one instance of $R^J$ is bicyclic heteroaryl, wherein the point of attachment may be on any atom of the bicyclic heteroaryl ring system, as valency permits. In certain embodiments, at least one instance of $R^J$ is 9- or 10-membered, bicyclic heteroaryl. In certain embodiments, at least one instance of $R^J$ is —$OR^a$. In certain embodiments, at least one instance of $R^J$ is —OH. In certain embodiments, at least one instance of $R^J$ is —O(substituted or unsubstituted $C_{1-6}$ alkyl). In certain embodiments, at least one instance of $R^J$ is —OMe. In certain embodiments, at least one instance of $R^J$ is —OEt. In certain embodiments, at least one instance of $R^J$ is —OPr. In certain embodiments, at least one instance of $R^J$ is —OBu. In certain embodiments, at least one instance of $R^J$ is —OBn. In certain embodiments, at least one instance of $R^J$ is —OPh. In certain embodiments, at least one instance of $R^J$ is —$SR^a$. In certain embodiments, at least one instance of $R^J$ is —SH. In certain embodiments, at least one instance of $R^J$ is —SMe. In certain embodiments, at least one instance of $R^J$ is —$N(R^a)_2$. In certain embodiments, at least one instance of $R^J$ is —$NH_2$. In certain embodiments, at least one instance of $R^J$ is —NHMe. In certain embodiments, at least one instance of $R^J$ is —$NMe_2$. In certain embodiments, at least one instance of $R^J$ is —CN. In certain embodiments, at least one instance of $R^J$ is —SCN. In certain embodiments, at least one instance of $R^J$ is —$C(=NR^a)R^a$, —$C(=NR^a)OR^a$, or —$C(=NR^a)N(R^a)_2$. In certain embodiments, at least one instance of $R^J$ is —$C(=O)R^a$ or $C(=O)OR^a$. In certain embodiments, at least one instance of $R^J$ is —$C(=O)N(R^a)_2$. In certain embodiments, at least one instance of $R^J$ is —$C(=O)NMe_2$, —$C(=O)NHMe$, or —$C(=O)NH_2$. In certain embodiments, at least one instance of $R^J$ is —$NO_2$. In certain embodiments, at least one instance of $R^J$ is —$NR^aC(=O)R^a$, —$NR^WC(=O)OR^a$, or —$NR^aC(=O)N(R^a)_2$. In certain embodiments, at least one instance of $R^J$ is —$OC(=O)R^a$, —$OC(=O)OR^a$, or —$OC(=O)N(R^a)_2$.

In certain embodiments, at least one instance of $R^J$ is halogen or substituted or unsubstituted $C_{1-6}$ alkyl. In certain embodiments, at least one instance of $R^J$ is halogen, unsubstituted $C_{1-6}$ alkyl, or $C_{1-6}$ alkyl substituted with at least one halogen.

In certain embodiments, q is 0. In certain embodiments, q is 1. In certain embodiments, q is 2. In certain embodiments, q is 3. In certain embodiments, q is 4.

In certain embodiments, no instance of $R^J$ and $R^K$ is substituted or unsubstituted heteroaryl. In certain embodiments, no instance of $R^J$ and $R^K$ is substituted or unsubstituted imidazolyl. In certain embodiments, no instance of $R^J$ and $R^K$ is substituted imidazolyl.

In certain embodiments, the compound of Formula (II) is of the formula:

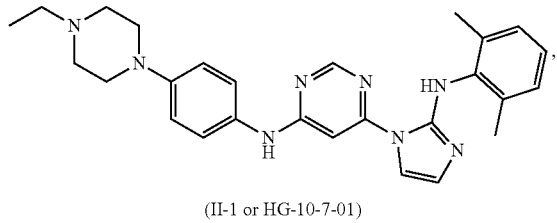

(II-1 or HG-10-7-01)

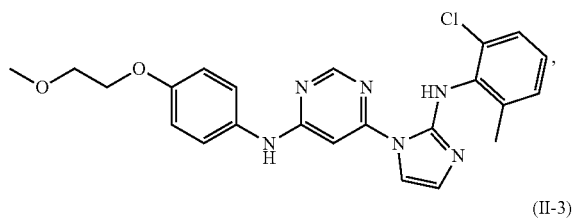

(II-2)

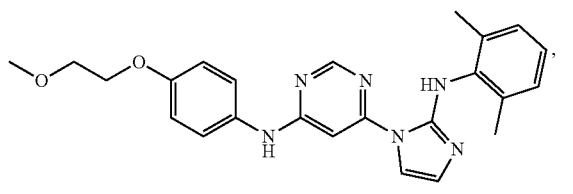

(II-3)

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:

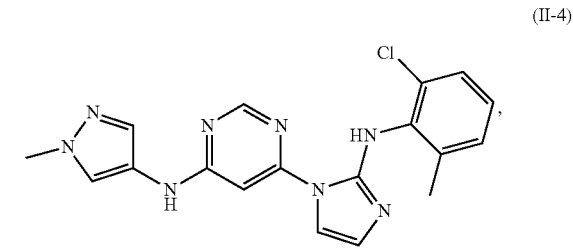 [SMILES: Cc1cccc(Cl)c1Nc1nccn1-c1cc(Nc2cnn(C)c2)ncn1]

(II-4)

or a pharmaceutically acceptable salt, solvate, hydrate, polymorph, co-crystal, tautomer, stereoisomer, isotopically labeled derivative, or prodrug thereof.

In certain embodiments, the compound of Formula (II) is of the formula:
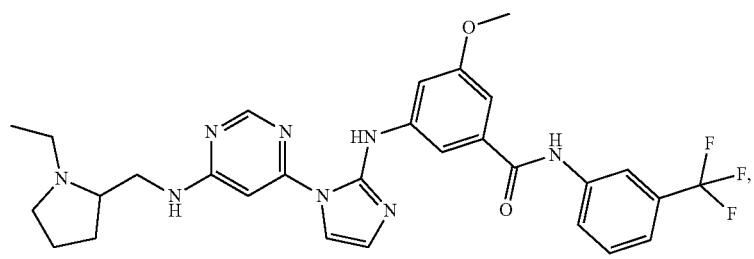
(II-5)
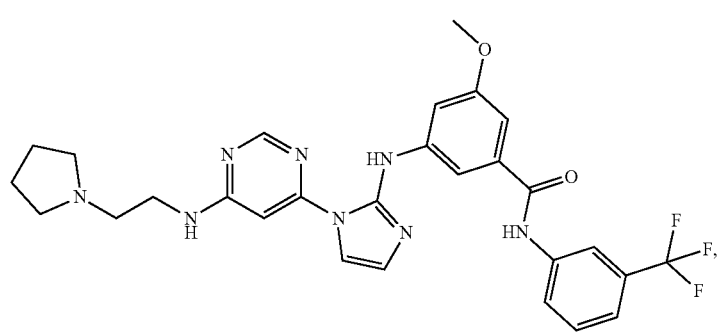
(II-6)
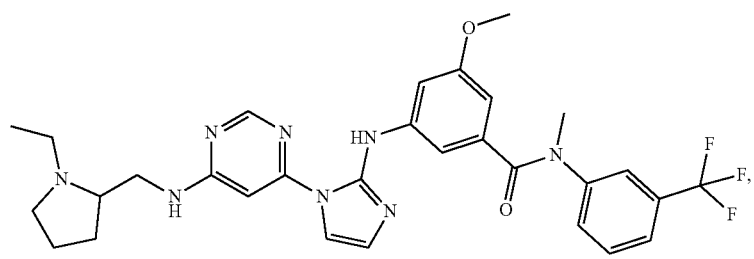
(II-7)
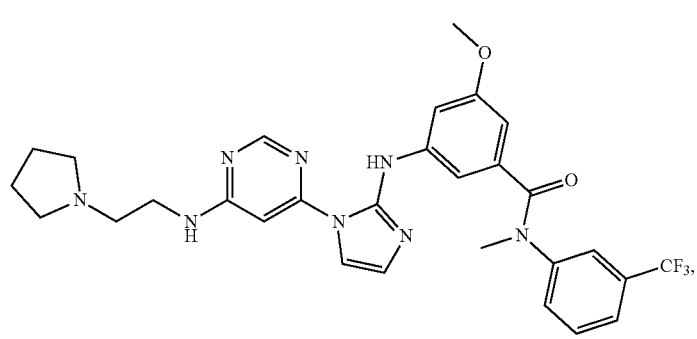
(II-8)
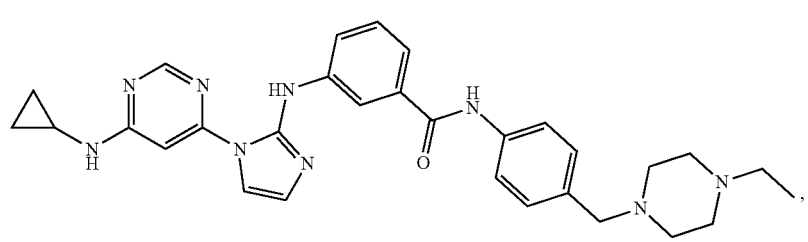
(II-9)

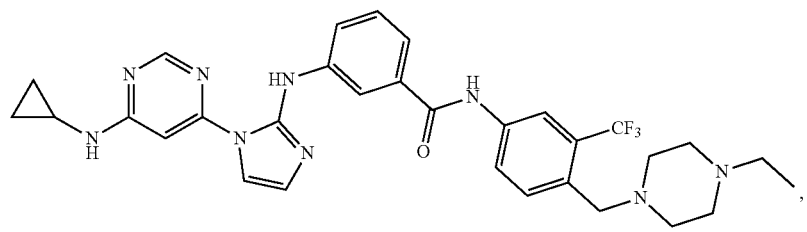
(II-10)
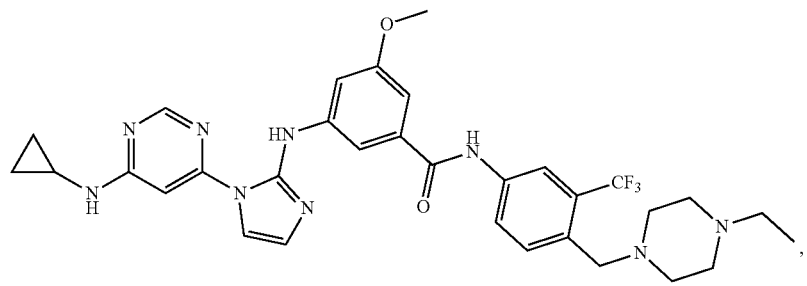
(II-11)
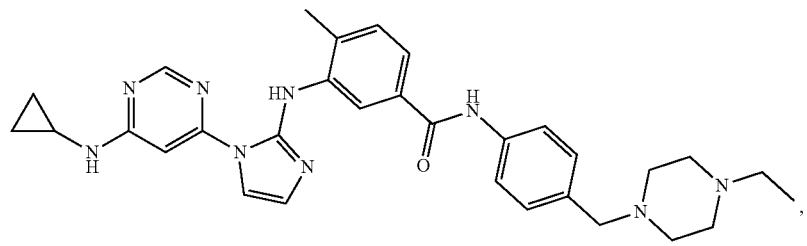
(II-12)
or a pharmaceutically acceptable salt, solvate, hydrate, polymorph, co-crystal, tautomer, stereoisomer, isotopically labeled derivative, or prodrug thereof.
In certain embodiments, a compound of Formula (II) is not of the formula:
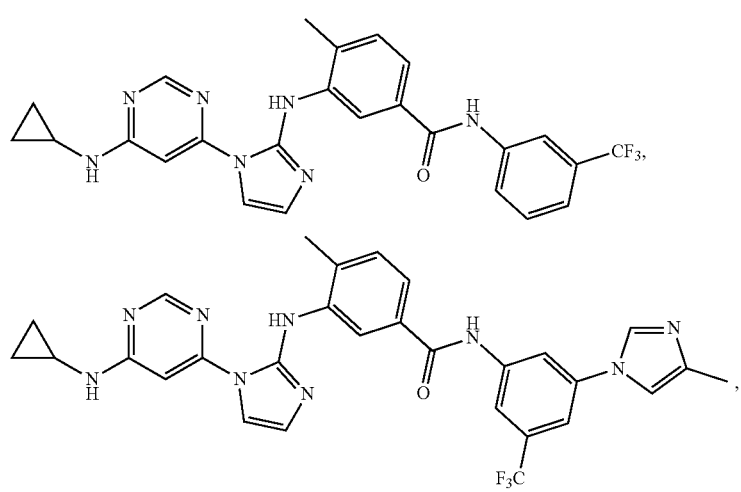

-continued
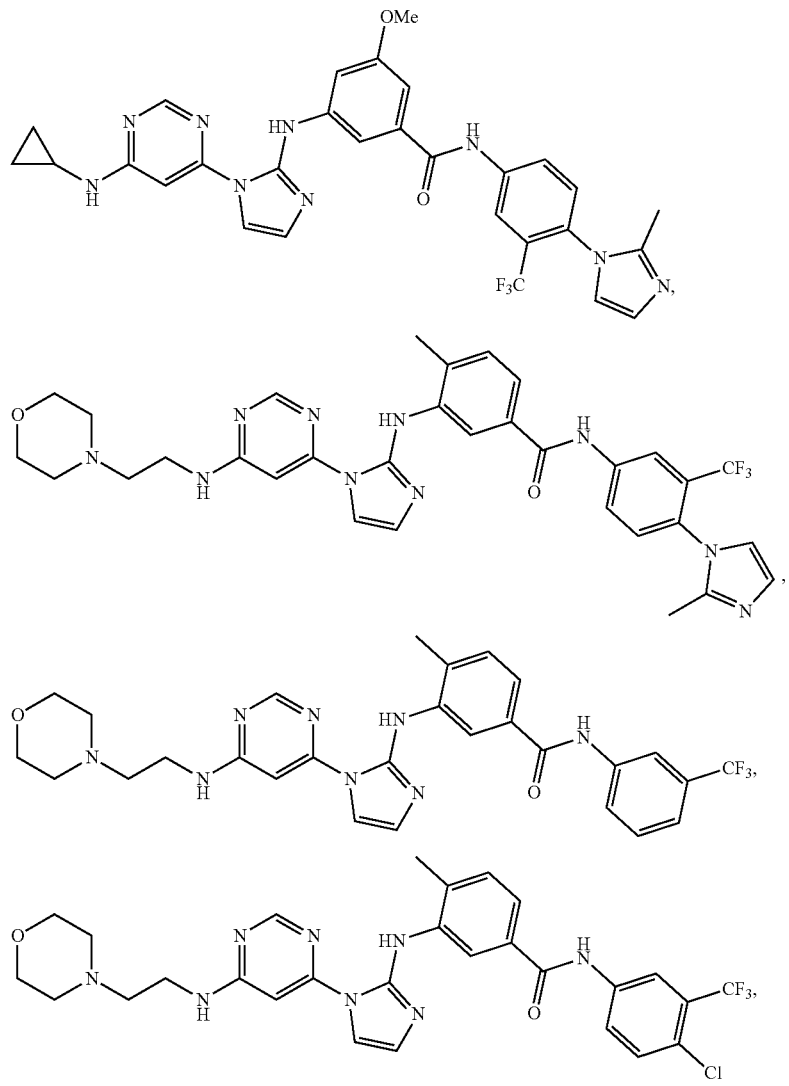
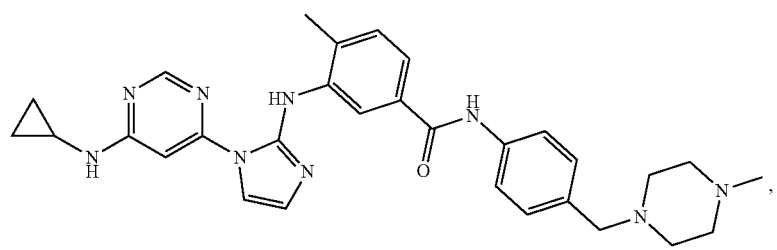
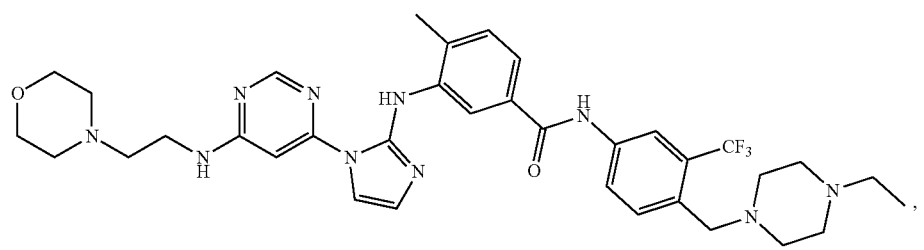

-continued

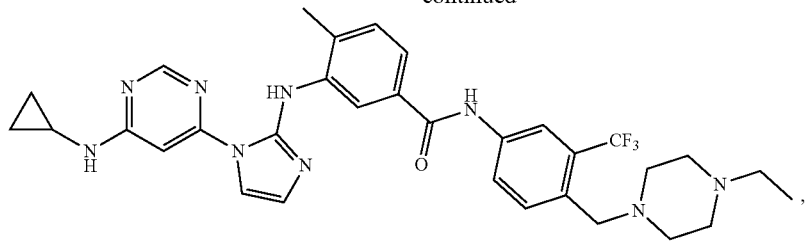

or a pharmaceutically acceptable salt, solvate, hydrate, polymorph, co-crystal, or tautomer thereof.

Compounds of Formula (III-A)

In another aspect, the present disclosure provides urea or carbamate compounds of Formula (III-A) for use in the present invention:

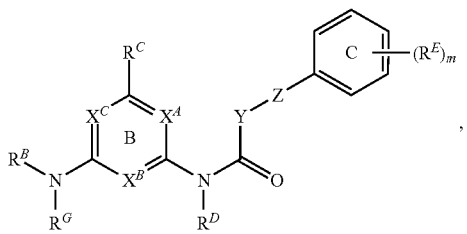

(III-A)

and pharmaceutically acceptable salts, solvates, hydrates, polymorphs, co-crystals, tautomers, stereoisomers, isotopically labeled derivatives, and prodrugs thereof, wherein:

$R^G$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted heteroaryl, or of the formula:

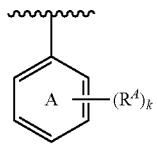

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N(R^a)_2$, —C(=O)$R^a$, —C(=O)$OR^a$, —C(=O)N(R^a)_2$, —NO_2$, —$NR^aC$(=O)$R^a$, —$NR^aC$(=O)$OR^a$, —$NR^aC$(=O)N(R^a)_2$, —OC(=O)$R^a$, —OC(=O)$OR^a$, or —OC(=O)N(R^a)_2$, or two $R^A$ groups are joined to form a substituted or unsubstituted carbocyclic ring, substituted or unsubstituted heterocyclic ring, substituted or unsubstituted aryl ring, or substituted or unsubstituted heteroaryl ring;

each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;

k is 0, 1, 2, 3, 4, or 5;

$R^B$ is hydrogen, substituted or unsubstituted acyl, substituted or unsubstituted $C_{1-6}$ alkyl, or a nitrogen protecting group;

each of $X^A$, $X^B$, and $X^C$ is independently N or $CR^X$, wherein each instance of $R^X$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N(R^a)_2$, —C(=O)$R^a$, —C(=O)$OR^a$, —C(=O)N(R^a)_2$, —NO_2$, —$NR^aC$(=O)$R^a$, —$NR^aC$(=O)$OR^a$, —$NR^aC$(=O)N(R^a)_2$, —OC(=O)$R^a$, —OC(=O)$OR^a$, or —OC(=O)N(R^a)_2$;

or: $X^B$ is $CR^X$, and $R^G$ and $R^X$ of $X^B$ are joined to form a substituted or unsubstituted heterocyclic or substituted or unsubstituted heteroaryl ring;

$R^C$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N(R^a)_2$, —C(=O)$R^a$, —C(=O)$OR^a$, —C(=O)N(R^a)_2$, —NO_2$, —$NR^aC$(=O)$R^a$, —$NR^aC$(=O)$OR^a$, —$NR^aC$(=O)N(R^a)_2$, —OC(=O)$R^a$, —OC(=O)$OR^a$, or —OC(=O)N(R^a)_2$;

$R^D$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

Y is —O— or —$NR^Y$—, wherein $R^Y$ is hydrogen, substituted or unsubstituted acyl, substituted or unsubstituted $C_{1-6}$ alkyl, or a nitrogen protecting group;

Z is a bond or —$C(R^Z)_2$—, wherein each instance of $R^Z$ is independently hydrogen, halogen, or substituted or unsubstituted $C_{1-6}$ alkyl;

each instance of $R^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, or —OC(=O)N(R$^a$)$_2$; and m is 0, 1, 2, 3, 4, or 5.

In certain embodiments, a compound of Formula (III-A) is of Formula (III):

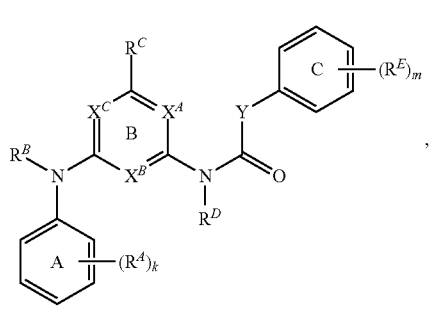

(III)

or a pharmaceutically acceptable salt, solvate, hydrate, polymorph, co-crystal, tautomer, stereoisomer, isotopically labeled derivative, or prodrug thereof, wherein:

each instance of R$^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^a$ groups are joined to form a substituted or unsubstituted heterocyclic or substituted or unsubstituted heteroaryl ring;

k is 0, 1, 2, 3, 4, or 5;

R$^B$ is hydrogen, substituted or unsubstituted acyl, substituted or unsubstituted C$_{1-6}$ alkyl, or a nitrogen protecting group;

each of X$^A$, X$^B$, and X$^C$ is independently N or CR$^X$, wherein each instance of R$^X$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^C$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

R$^D$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

Y is —O— or —NR$^Y$—, wherein R$^Y$ is hydrogen, substituted or unsubstituted acyl, substituted or unsubstituted C$_{1-6}$ alkyl, or a nitrogen protecting group;

each instance of R$^E$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$; and m is 0, 1, 2, 3, 4, or 5.

All embodiments of Ring A, Ring B, Ring C, X$^A$, X$^B$, X$^C$, Y, Z, R$^A$, R$^B$, R$^C$, R$^D$, R$^E$, R$^F$, R$^G$, R$^X$, R$^Y$, R$^Z$, R$^a$, k, m, and n recited in subsection Compounds of Formula (III-A) (e.g., compounds of Formula (III)) apply only to Formula (III-A) (e.g., Formula (III)).

Formula (III-A) includes substituent R$^G$. In certain embodiments, R$^G$ is hydrogen. In certain embodiments, R$^G$ is substituted or unsubstituted alkyl. In certain embodiments, R$^G$ is substituted C$_{1-6}$ alkyl (e.g., —CF$_3$, perfluoroethyl, perfluoropropyl, perfluorobutyl, Bn, or C$_{1-6}$ alkyl substituted with at least one instance of halogen and/or —OR$^a$). In certain embodiments, R$^G$ is C$_{1-6}$ alkyl substituted with at least one instance of —OR$^a$, optionally wherein R$^a$ is hydrogen or substituted or unsubstituted C$_{1-6}$ alkyl. In certain embodiments, R$^G$ is of the formula:

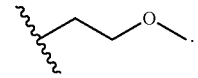 [SMILES: *CCOC]

In certain embodiments, R$^G$ is unsubstituted C$_{1-6}$ alkyl (e.g., Me, Et, Pr, or Bu). In certain embodiments, R$^G$ is substituted or unsubstituted alkenyl (e.g., substituted or unsubstituted C$_{1-6}$ alkenyl). In certain embodiments, R$^G$ is substituted or unsubstituted alkynyl (e.g., substituted or unsubstituted C$_{1-6}$ alkynyl). In certain embodiments, R$^G$ is substituted or unsubstituted carbocyclyl (e.g., substituted or unsubstituted, monocyclic, 3- to 7-membered carbocyclyl). In certain embodiments, R$^G$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^G$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^G$ is substituted or unsubstituted 2-pyridyl. In certain embodiments, $R^G$ is substituted or unsubstituted 3-pyridyl. In certain embodiments, $R^G$ is of the formula:

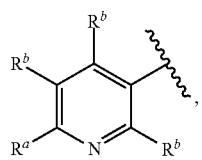

wherein $R^a$ is hydrogen, halogen, substituted or unsubstituted $C_{1-6}$ alkyl, —OH, —O(substituted or unsubstituted $C_{1-6}$ alkyl), or substituted or unsubstituted, monocyclic, 5- to 6-membered heterocyclyl, wherein one, two, or three atoms in the heterocyclic ring system are independently nitrogen, oxygen, or sulfur; and each instance of $R^b$ is independently hydrogen, halogen, substituted or unsubstituted $C_{1-6}$ alkyl, —OH, or —O(substituted or unsubstituted $C_{1-6}$ alkyl). In certain embodiments, $R^G$ is of the formula:

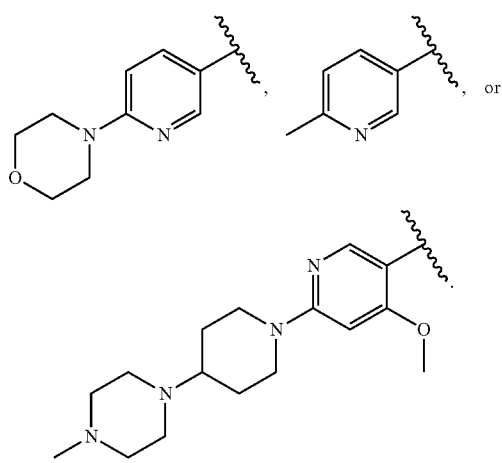

In certain embodiments, $R^G$ is substituted or unsubstituted 4-pyridyl. In certain embodiments, $R^G$ is substituted or unsubstituted 1-pyrazolyl. In certain embodiments, $R^G$ is substituted or unsubstituted 3-pyrazolyl. In certain embodiments, $R^G$ is substituted or unsubstituted 4-pyrazolyl. In certain embodiments, $R^G$ is of the formula:

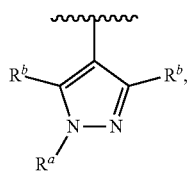

wherein $R^a$ is hydrogen, substituted or unsubstituted $C_{1-6}$ alkyl, a nitrogen protecting group, or -(substituted or unsubstituted $C_{1-6}$ alkylene)-(substituted or unsubstituted, mono-cyclic, 5- to 6-membered heterocyclyl, wherein one, two, or three atoms in the heterocyclic ring system are independently nitrogen, oxygen, or sulfur); and each instance of $R^b$ is independently hydrogen, halogen, substituted or unsubstituted $C_{1-6}$ alkyl, —OH, or —O(substituted or unsubstituted $C_{1-6}$ alkyl). In certain embodiments, $R^G$ is of the formula:

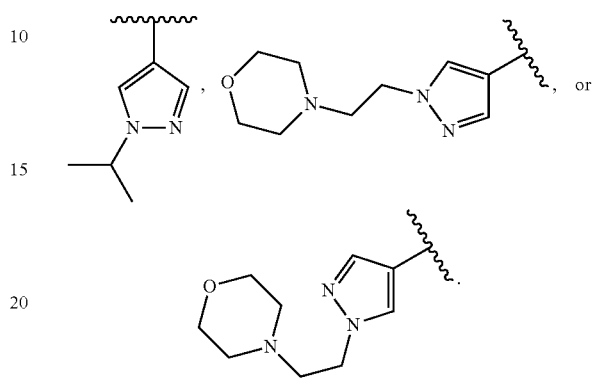

In certain embodiments, $R^G$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, substituted or unsubstituted isothiazolyl, or substituted or unsubstituted tetrazolyl. In certain embodiments, $R^G$ is substituted or unsubstituted pyrazinyl, substituted or unsubstituted pyrimidinyl, or substituted or unsubstituted pyridazinyl. In certain embodiments, $R^G$ is substituted or unsubstituted, bicyclic, 9- to 10-membered heteroaryl, wherein one, two, three, or four atoms in the heteroaryl ring system are independently nitrogen, oxygen, or sulfur.

In certain embodiments, $R^G$ is of the formula:

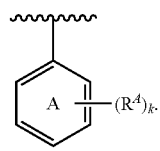

Ring A is unsubstituted (e.g., when k is 0) or substituted with one or more substituents $R^A$ (e.g., when k is 1, 2, 3, 4, or 5). In certain embodiments, Ring A is an unsubstituted phenyl ring. In certain embodiments, Ring A is a substituted phenyl ring. In certain embodiments, Ring A is of the formula:

optionally wherein $R^A$ is substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

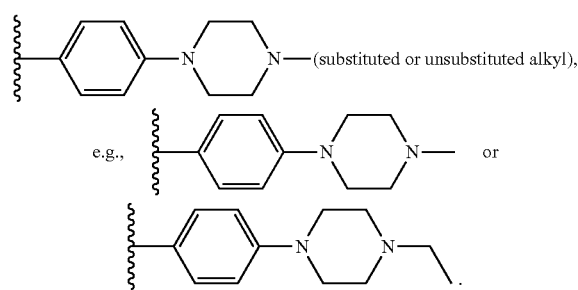

e.g.,

In certain embodiments, Ring A is of the formula:

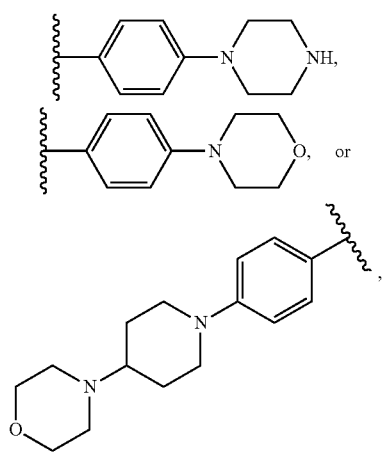

In certain embodiments, Ring A is of the formula:

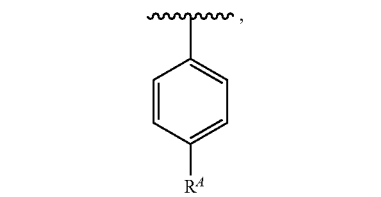

optionally wherein $R^A$ is halogen, substituted or unsubstituted $C_{1-6}$ alkyl, or —$OR^a$. In certain embodiments, Ring A is of the formula:

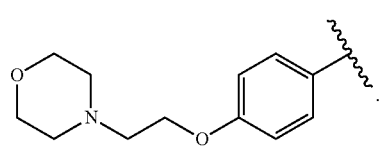 [SMILES: *c1ccc(OCCN2CCOCC2)cc1]

In certain embodiments, Ring A is of the formula:

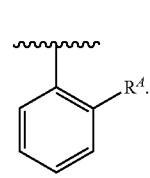

In certain embodiments, Ring A is of the formula:

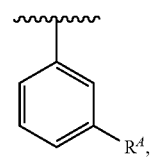

optionally wherein $R^A$ is halogen, substituted or unsubstituted $C_{1-6}$ alkyl, or —$OR^a$. In certain embodiments, Ring A is of the formula:

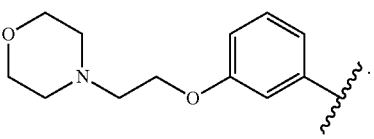 [SMILES: *c1cccc(OCCN2CCOCC2)c1]

In certain embodiments, Ring A is of the formula:

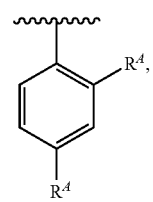

optionally wherein each instance of $R^A$ is independently halogen, substituted or unsubstituted $C_{1-6}$ alkyl, —$OR^a$, —$C(=O)R^a$, —$C(=O)OR^a$, —$C(=O)N(R^a)_2$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

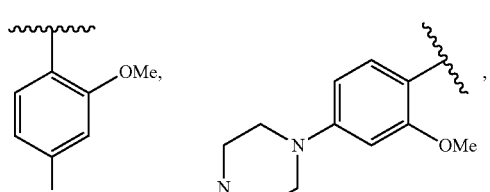

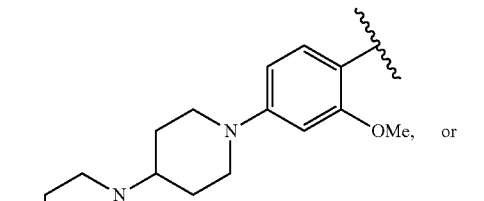

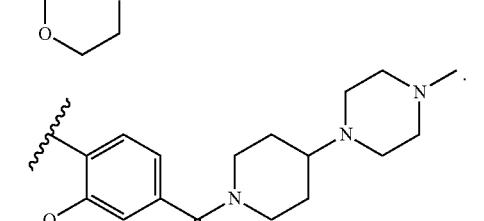

In certain embodiments, Ring A is of the formula:

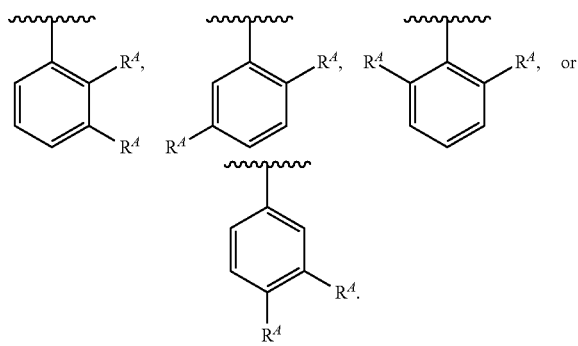

In certain embodiments, Ring A is of the formula:

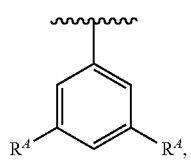

optionally wherein each instance of $R^A$ is independently halogen, substituted or unsubstituted $C_{1-6}$ alkyl, —$OR^a$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

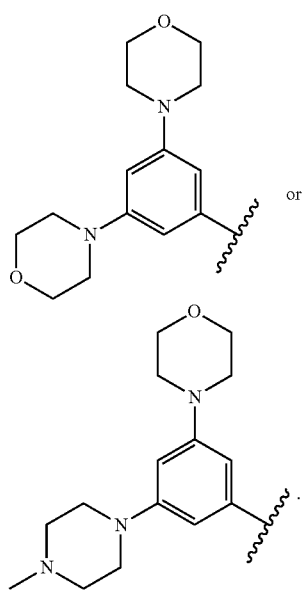

In certain embodiments, Ring A is of the formula:

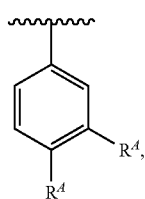

wherein the two instances of $R^A$ are joined to form a substituted or unsubstituted carbocyclic ring (e.g., substituted or unsubstituted, 3- to 7-membered, monocyclic carbocyclic ring), substituted or unsubstituted heterocyclic ring (e.g., substituted or unsubstituted, monocyclic, 5- to 6-membered heterocyclic ring, wherein one or two atoms in the heterocyclic ring system are independently nitrogen, oxygen, or sulfur), substituted or unsubstituted aryl ring (e.g., substituted or unsubstituted phenyl ring), or substituted or unsubstituted heteroaryl ring (e.g., substituted or unsubstituted, monocyclic, 5- to 6-membered heteroaryl ring, wherein one or two atoms in the heteroaryl ring system are independently nitrogen, oxygen, or sulfur). In certain embodiments, Ring A is of the formula:

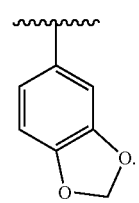 [SMILES: *c1ccc2c(c1)OCO2]

In certain embodiments, Ring A is of the formula:

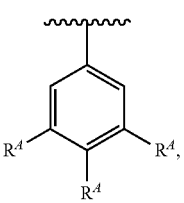

optionally wherein each instance of $R^A$ is independently halogen, substituted or unsubstituted $C_{1-6}$ alkyl, —$OR^a$, or substituted or unsubstituted, monocyclic, 5- to 6-membered heterocyclic ring, wherein one or two atoms in the heterocyclic ring system are independently nitrogen, oxygen, or sulfur. In certain embodiments, Ring A is of the formula:

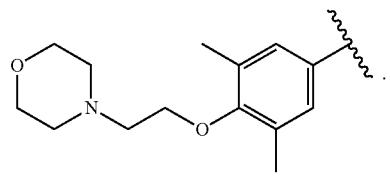 [SMILES: *c1cc(C)c(OCCN2CCOCC2)c(C)c1]

In certain embodiments, Ring A is of the formula:

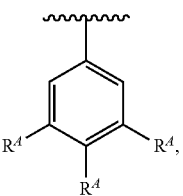

wherein each instance of $R^A$ is independently —$OR^a$. In certain embodiments, Ring A is of the formula:

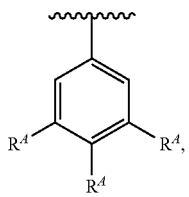

wherein each instance of $R^A$ is independently —O(substituted or unsubstituted alkyl). In certain embodiments, Ring A is of the formula:

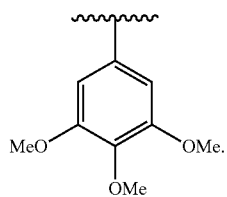

In certain embodiments, Ring A is of the formula:

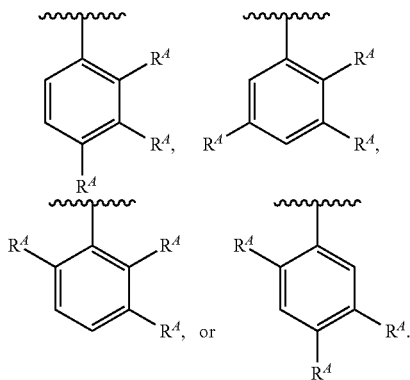

In Formula (III-A), Ring A may include one or more substituents $R^A$. In certain embodiments, all instances of $R^A$ are the same. In certain embodiments, at least two instances of $R^A$ are different. In certain embodiments, at least one instance of $R^A$ is halogen (e.g., F, Cl, Br, or I). In certain embodiments, at least one instance of $R^A$ is substituted or unsubstituted alkyl (e.g., substituted or unsubstituted $C_{1-6}$ alkyl). In certain embodiments, at least one instance of $R^A$ is —$CH_3$. In certain embodiments, at least one instance of $R^A$ is —$CF_3$, unsubstituted ethyl, perfluoroethyl, unsubstituted propyl, perfluoropropyl, unsubstituted butyl, perfluorobutyl, or Bn. In certain embodiments, at least one instance of $R^A$ is substituted or unsubstituted alkenyl (e.g., substituted or unsubstituted $C_{1-6}$ alkenyl). In certain embodiments, at least one instance of $R^A$ is substituted or unsubstituted alkynyl (e.g., substituted or unsubstituted $C_{1-6}$ alkynyl). In certain embodiments, at least one instance of $R^A$ is substituted or unsubstituted carbocyclyl (e.g., substituted or unsubstituted, monocyclic, 3- to 7-membered carbocyclyl). In certain embodiments, at least one instance of $R^A$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^A$ is of the formula:

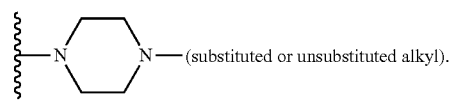

In certain embodiments, at least one instance of $R^A$ is of the formula:

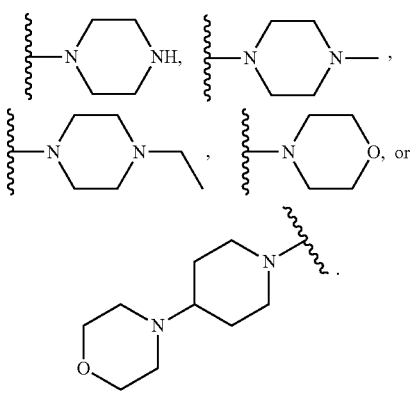

In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted phenyl. In certain embodiments, at least one instance of $R^A$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^A$ is —$OR^a$. In certain embodiments, at least one instance of $R^A$ is —OH. In certain embodiments, at least one instance of $R^A$ is —O(substituted or unsubstituted alkyl), such as —O(substituted or unsubstituted $C_{1-6}$ alkyl) (e.g., —OMe, —OEt, —OPr, —OBu, —OBn, or

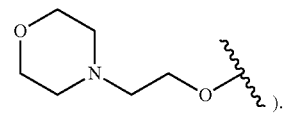 [SMILES: *OCCN1CCOCC1]

In certain embodiments, at least one instance of $R^A$ is —O(substituted or unsubstituted phenyl) (e.g., —OPh)). In certain embodiments, at least one instance of $R^A$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^A$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^A$ is —CN, —SCN, or —$NO_2$, In certain embodiments, at least one instance of $R^A$ is —C(=$NR^a$)$R^a$, —C(=$NR^a$)$OR^a$, or —C(=$NR^a$)N($R^a$)$_2$. In certain embodiments, at least one instance of $R^A$ is —C(=O)$R^a$ or —C(=O)$OR^a$. In certain embodiments, at least one instance of $R^A$ is —C(=O)N($R^a$)$_2$ (e.g., —C(=O)$NH_2$, —C(=O)NHMe, —C(=O)$NMe_2$, or

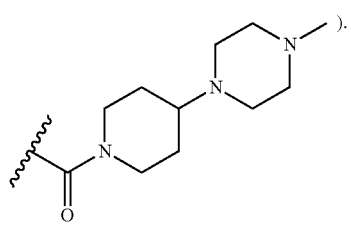 [SMILES: *C(=O)N1CCC(N2CCN(C)CC2)CC1]

In certain embodiments, at least one instance of $R^A$ is —NR$^a$C(=O)R$^a$, —NR$^a$C(=O)OR$^a$, or —NR$^a$C(=O)N(R$^a$)$_2$. In certain embodiments, at least one instance of $R^A$ is —OC(=O)R$^a$, —OC(=O)OR$^a$, or —OC(=O)N(R$^a$)$_2$.

Each instance of $R^A$, $R^C$, $R^E$, and $R^X$ may independently include one or more substituents $R^a$. In certain embodiments, all instances of $R^a$ are the same. In certain embodiments, at least two instances of $R^a$ are different. In certain embodiments, at least one instance of $R^a$ is H. In certain embodiments, each instance of $R^a$ is H. In certain embodiments, at least one instance of $R^a$ is substituted or unsubstituted acyl (e.g., acetyl). In certain embodiments, at least one instance of $R^a$ is substituted or unsubstituted alkyl (e.g., substituted or unsubstituted $C_{1-6}$ alkyl). In certain embodiments, at least one instance of $R^a$ is —CH$_3$. In certain embodiments, at least one instance of $R^a$ is —CF$_3$, unsubstituted ethyl, perfluoroethyl, unsubstituted propyl, perfluoropropyl, unsubstituted butyl, perfluorobutyl, or Bn. In certain embodiments, at least one instance of $R^a$ is substituted or unsubstituted alkenyl (e.g., substituted or unsubstituted $C_{1-6}$ alkenyl). In certain embodiments, at least one instance of $R^a$ is substituted or unsubstituted alkynyl (e.g., substituted or unsubstituted $C_{1-6}$ alkynyl). In certain embodiments, at least one instance of $R^a$ is substituted or unsubstituted carbocyclyl (e.g., substituted or unsubstituted, monocyclic, 3- to 7-membered carbocyclyl). In certain embodiments, at least one instance of $R^a$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^a$ is substituted or unsubstituted aryl (e.g., substituted or unsubstituted, 6- to 10-membered aryl). In certain embodiments, at least one instance of $R^a$ is substituted or unsubstituted phenyl. In certain embodiments, at least one instance of $R^a$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^a$ is a nitrogen protecting group (e.g., Bn, Boc, Cbz, Fmoc, trifluoroacetyl, triphenylmethyl, acetyl, or Ts) when attached to a nitrogen atom. In certain embodiments, at least one instance of $R^a$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, at least one instance of $R^a$ is a sulfur protecting group (e.g., acetamidomethyl, t-Bu, 3-nitro-2-pyridine sulfenyl, 2-pyridine-sulfenyl, or triphenylmethyl) when attached to a sulfur atom. In certain embodiments, two instances of $R^a$ are joined to form a substituted or unsubstituted heterocyclic ring (e.g., substituted or unsubstituted, monocyclic, 5- to 6-membered heterocyclic ring, wherein one, two, or three atoms in the heterocyclic ring system are independently nitrogen, oxygen, or sulfur). In certain embodiments, two instances of $R^a$ are joined to form a substituted or unsubstituted heteroaryl ring (e.g., substituted or unsubstituted, monocyclic, 5- to 6-membered heteroaryl ring, wherein one, two, three, or four atoms in the heteroaryl ring system are independently nitrogen, oxygen, or sulfur).

In certain embodiments, k is 0. In certain embodiments, k is 1. In certain embodiments, k is 2. In certain embodiments, k is 3. In certain embodiments, k is 4. In certain embodiments, k is 5.

Formula (III-A) includes substituent $R^B$ on the nitrogen atom that connects Rings A and B. In certain embodiments, $R^B$ is hydrogen. In certain embodiments, $R^B$ is substituted or unsubstituted acyl (e.g., acetyl). In certain embodiments, $R^B$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, perfluorobutyl, or Bn). In certain embodiments, $R^B$ is a nitrogen protecting group (e.g., Bn, Boc, Cbz, Fmoc, trifluoroacetyl, triphenylmethyl, acetyl, or Ts).

Formula (III-A) includes a heteroaryl ring as Ring B that includes moieties $X^A$, $X^B$, and $X^C$ in the heteroaryl ring system. In certain embodiments, $X^A$ is CR$^X$, and each of $X^B$ and $X^C$ is N. In certain embodiments, $X^A$ is CH, and each of $X^B$ and $X^C$ is N. In certain embodiments, $X^B$ is CR$^X$, and each of $X^A$ and $X^C$ is N. In certain embodiments, $X^B$ is CH, and each of $X^A$ and $X^C$ is N. In certain embodiments, $X^C$ is CR$^X$, and each of $X^A$ and $X^B$ is N. In certain embodiments, $X^C$ is CH, and each of $X^A$ and $X^B$ is N. In certain embodiments, $X^A$ is N, and each of $X^B$ and $X^C$ is independently CR$^X$. In certain embodiments, $X^A$ is N, and each of $X^B$ and $X^C$ is CH. In certain embodiments, $X^B$ is N, and each of $X^A$ and $X^C$ is independently CR$^X$. In certain embodiments, $X^B$ is N, and each of $X^A$ and $X^C$ is CH. In certain embodiments, $X^C$ is N, and each of $X^A$ and $X^B$ is independently CR$^X$. In certain embodiments, $X^C$ is N, and each of $X^A$ and $X^B$ is CH. In certain embodiments, each of $X^A$, $X^B$, and $X^C$ is independently CR$^X$. In certain embodiments, each of $X^A$, $X^B$, and $X^C$ is CH.

In certain embodiments, $X^B$ is CR$^X$, and $R^G$ and $R^X$ of $X^B$ are joined to form a substituted or unsubstituted heterocyclic ring (e.g., substituted or unsubstituted, monocyclic, 5- to 6-membered heterocyclic ring, wherein one or two atoms in the heterocyclic ring system are independently nitrogen, oxygen, or sulfur, further wherein at least one atom in the heterocyclic ring system is nitrogen). In certain embodiments, $X^B$ is CR$^X$, and $R^G$ and $R^X$ of $X^B$ are joined to form a substituted or unsubstituted heteroaryl ring (e.g., substituted or unsubstituted, monocyclic, 5- to 6-membered heteroaryl ring, wherein one or two atoms in the heterocyclic ring system are independently nitrogen, oxygen, or sulfur, further wherein at least one atom in the heteroaryl ring system is nitrogen). In certain embodiments, $X^B$ is CR$^X$, and $R^G$ and $R^X$ of $X^B$ are joined to form substituted or unsubstituted pyrrolyl ring.

In certain embodiments, all instances of $R^X$ are the same. In certain embodiments, at least two instances of $R^X$ are different. In certain embodiments, at least one instance of $R^X$ is hydrogen. In certain embodiments, at least one instance of $R^X$ is halogen (e.g., F, Cl, Br, or I). In certain embodiments, at least one instance of $R^X$ is substituted or unsubstituted alkyl (e.g., substituted or unsubstituted $C_{1-6}$ alkyl). In certain embodiments, at least one instance of $R^X$ is —CH$_3$. In certain embodiments, at least one instance of $R^X$ is —CF$_3$, unsubstituted ethyl, perfluoroethyl, unsubstituted propyl, perfluoropropyl, unsubstituted butyl, perfluorobutyl, or Bn. In certain embodiments, at least one instance of $R^X$ is substituted or unsubstituted alkenyl (e.g., substituted or unsubstituted $C_{1-6}$ alkenyl). In certain embodiments, at least one instance of $R^X$ is substituted or unsubstituted alkynyl (e.g., substituted or unsubstituted $C_{1-6}$ alkynyl). In certain embodiments, at least one instance of $R^X$ is substituted or unsubstituted carbocyclyl (e.g., substituted or unsubstituted, monocyclic, 3- to 7-membered carbocyclyl). In certain embodiments, at least one instance of $R^X$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^X$ is substituted or unsubstituted aryl (e.g., substituted or unsubstituted, 6- to 10-membered aryl). In certain embodiments, at least one instance of $R^X$ is substituted or unsubstituted phenyl. In certain embodiments, at least one instance of $R^X$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^X$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^X$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^X$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^X$ is —CN, —SCN, or —$NO_2$, In certain embodiments, at least one instance of $R^X$ is —$C(=NR^a)R^a$, —$C(=NR^a)OR^a$, or —$C(=NR^a)N(R^a)_2$. In certain embodiments, at least one instance of $R^X$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, at least one instance of $R^X$ is —$NR^aC(=O)R^a$, —$NR^aC(=O)OR^a$, or —$NR^aC(=O)N(R^a)_2$. In certain embodiments, at least one instance of $R^X$ is —$OC(=O)R^a$, —$OC(=O)OR^a$, or —$OC(=O)N(R^a)_2$.

Formula (III-A) includes substituent $R^C$ on Ring B. In certain embodiments, $R^C$ is hydrogen. In certain embodiments, $R^C$ is halogen (e.g., F, Cl, Br, or I). In certain embodiments, $R^C$ is substituted or unsubstituted alkyl (e.g., substituted or unsubstituted $C_{1-6}$ alkyl). In certain embodiments, $R^C$ is —$CH_3$. In certain embodiments, $R^C$ is —$CF_3$, unsubstituted ethyl, perfluoroethyl, unsubstituted propyl, perfluoropropyl, unsubstituted butyl, perfluorobutyl, or Bn. In certain embodiments, $R^C$ is substituted or unsubstituted alkenyl (e.g., substituted or unsubstituted $C_{1-6}$ alkenyl). In certain embodiments, $R^C$ is substituted or unsubstituted alkynyl (e.g., substituted or unsubstituted $C_{1-6}$ alkynyl). In certain embodiments, $R^C$ is substituted or unsubstituted carbocyclyl (e.g., substituted or unsubstituted, monocyclic, 3- to 7-membered carbocyclyl). In certain embodiments, $R^C$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted phenyl. In certain embodiments, $R^C$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^C$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, $R^C$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^C$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^C$ is —CN, —SCN, or —$NO_2$, In certain embodiments, $R^C$ is —$C(=NR^a)R^a$, —$C(=NR^a)OR^a$, or —$C(=NR^a)N(R^a)_2$. In certain embodiments, $R^C$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, $R^C$ is —$NR^aC(=O)R^a$, —$NR^aC(=O)OR^a$, or —$NR^aC(=O)N(R^a)_2$. In certain embodiments, $R^C$ is —$OC(=O)R^a$, —$OC(=O)OR^a$, or —$OC(=O)N(R^a)_2$.

Formula (III-A) includes substituent $R^D$ on a nitrogen atom of the urea or carbamate moiety. In certain embodiments, $R^D$ is hydrogen. In certain embodiments, $R^D$ is substituted or unsubstituted alkyl, such as substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn). In certain embodiments, $R^D$ is substituted or unsubstituted alkenyl (e.g., substituted or unsubstituted $C_{1-6}$ alkenyl). In certain embodiments, $R^D$ is substituted or unsubstituted alkynyl (e.g., substituted or unsubstituted $C_{1-6}$ alkynyl). In certain embodiments, $R^D$ is substituted or unsubstituted carbocyclyl (e.g., substituted or unsubstituted, monocyclic, 3- to 7-membered carbocyclyl). In certain embodiments, $R^D$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, $R^D$ is substituted or unsubstituted oxetanyl, substituted or unsubstituted azetidinyl, substituted or unsubstituted tetrahydrofuranyl, substituted or unsubstituted tetrahydropyranyl, substituted or unsubstituted pyrrolidinyl, substituted or unsubstituted piperidinyl, substituted or unsubstituted piperazinyl, or substituted or unsubstituted morpholinyl. In certain embodiments, $R^D$ is of the formula:

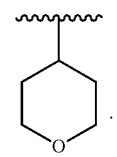

In certain embodiments, $R^D$ is substituted or unsubstituted aryl (e.g., substituted or unsubstituted, 6- to 10-membered aryl). In certain embodiments, $R^D$ is substituted or unsubstituted phenyl. In certain embodiments, $R^D$ is of the formula:

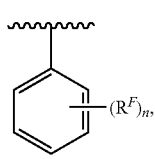

wherein each instance of $R^F$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)$N(R^a)_2$, —C(=O)$R^a$, —C(=O)$OR^a$, —C(=O)$N(R^a)_2$, —$NO_2$, —$NR^a$C(=O)$R^a$, —$NR^a$C(=O)$OR^a$, —$NR^a$C(=O)$N(R^a)_2$, —OC(=O)$R^a$, —OC(=O)$OR^a$, or —OC(=O)$N(R^a)_2$; and n is 0, 1, 2, 3, 4, or 5. In certain embodiments, $R^D$ is of the formula:

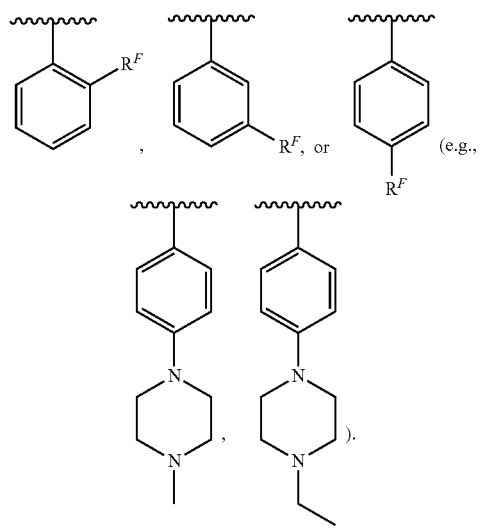

In certain embodiments, $R^D$ is of the formula:

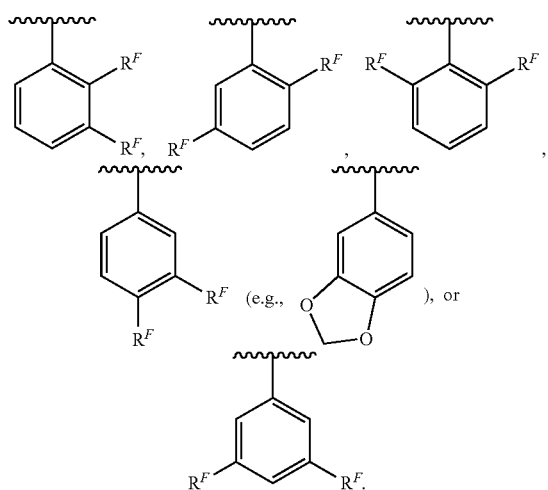

In certain embodiments, $R^D$ is of the formula:

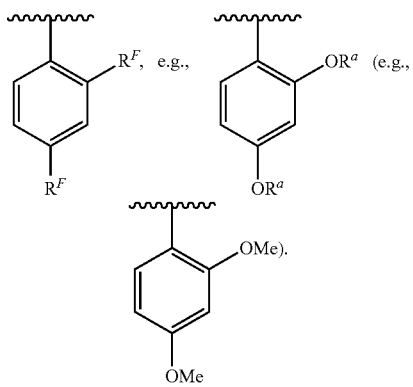

In certain embodiments, $R^D$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, $R^D$ is substituted or unsubstituted 1-pyrazolyl, substituted or unsubstituted 3-pyrazolyl, or substituted or unsubstituted 4-pyrazolyl (e.g.,

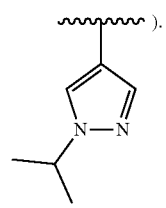 [SMILES: *c1cnn(C(C)C)c1]

).

In certain embodiments, $R^D$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, substituted or unsubstituted isothiazolyl, or substituted or unsubstituted tetrazolyl. In certain embodiments, $R^D$ is substituted or unsubstituted pyridyl, substituted or unsubstituted pyrazinyl, substituted or unsubstituted pyrimidinyl, or substituted or unsubstituted pyridazinyl.

In certain embodiments, $R^D$ is a nitrogen protecting group (e.g., Bn, Boc, Cbz, Fmoc, trifluoroacetyl, triphenylmethyl, acetyl, or Ts).

Formula (III-A) includes divalent moiety Y. In certain embodiments, Y is —O—. In certain embodiments, Y is —$NR^Y$—. In certain embodiments, Y is —NH—.

In certain embodiments, $R^Y$ is hydrogen. In certain embodiments, $R^Y$ is substituted or unsubstituted acyl (e.g., acetyl). In certain embodiments, $R^Y$ is substituted or unsubstituted $C_{1-6}$ alkyl (e.g., —$CH_3$, —$CF_3$, unsubstituted ethyl, perfluoroethyl, unsubstituted propyl, perfluoropropyl, unsubstituted butyl, perfluorobutyl, or Bn). In certain embodiments, $R^Y$ is a nitrogen protecting group (e.g., Bn, Boc, Cbz, Fmoc, trifluoroacetyl, triphenylmethyl, acetyl, or Ts).

Formula (III-A) includes divalent moiety Z. In certain embodiments, Z is a bond. In certain embodiments, Z is —$C(R^Z)_2$—. In certain embodiments, Z is —$CH_2$—. In certain embodiments, Z is —CHF— or —$CF_2$—.

In certain embodiments, the two instances of $R^Z$ are the same. In certain embodiments, the two instances of $R^Z$ are not the same. In certain embodiments, at least one instance of $R^Z$ is hydrogen. In certain embodiments, each instance of $R^Z$ is hydrogen. In certain embodiments, at least one instance of $R^Z$ is halogen (e.g., F, Cl, Br, or I). In certain embodiments, at least one instance of $R^Z$ is substituted or unsubstituted $C_{1-6}$ alkyl (e.g., —CH$_3$, —CF$_3$, unsubstituted ethyl, perfluoroethyl, unsubstituted propyl, perfluoropropyl, unsubstituted butyl, perfluorobutyl, or Bn).

In certain embodiments, —Y—Z— is —N(R$^Y$)—. In certain embodiments, —Y—Z— is —NH—. In certain embodiments, —Y—Z— is —N(Me)-. In certain embodiments, —Y—Z— is —O—. In certain embodiments, —Y—Z— is —N(R$^Y$)—C(R$^Z$)$_2$— (e.g., —N(R$^Y$)—CH$_2$—). In certain embodiments, —Y—Z— is —NH—CH$_2$—. In certain embodiments, —Y—Z— is —N(Me)-CH$_2$—. In certain embodiments, —Y—Z— is —O—C(R$^Z$)$_2$— (e.g., —O—CH$_2$—).

Formula (III-A) includes a phenyl ring as Ring C, which is unsubstituted (e.g., when m is 0) or substituted with one or more substituents $R^E$ (e.g., when m is 1, 2, 3, 4, or 5). In certain embodiments, Ring C is an unsubstituted phenyl ring. In certain embodiments, Ring C is a substituted phenyl ring. In certain embodiments, Ring C is of the formula:

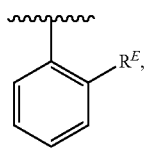

optionally wherein $R^E$ is halogen, substituted or unsubstituted $C_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$, In certain embodiments, Ring C is of the formula:

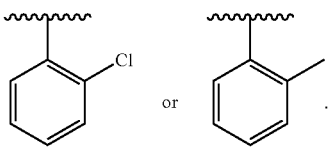

In certain embodiments, Ring C is of the formula:

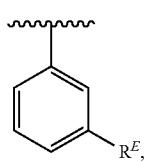

optionally wherein $R^E$ is halogen, substituted or unsubstituted $C_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$, In certain embodiments, Ring C is of the formula:

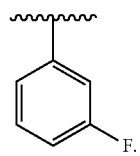 [SMILES: *c1cccc(F)c1]

In certain embodiments, Ring C is of the formula:

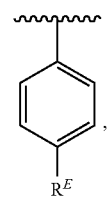

optionally wherein $R^E$ is halogen, substituted or unsubstituted $C_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$, In certain embodiments, Ring C is of the formula:

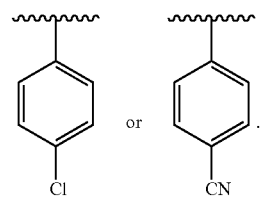 [SMILES: *c1ccc(Cl)cc1 ; *c1ccc(C#N)cc1]

In certain embodiments, Ring C is of the formula:

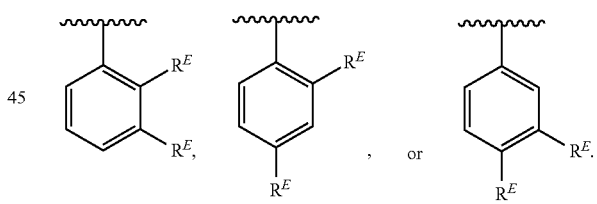

In certain embodiments, Ring C is of the formula:

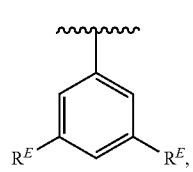

optionally wherein each instance of $R^E$ is independently halogen, substituted or unsubstituted $C_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$, In certain embodiments, Ring C is of the formula:

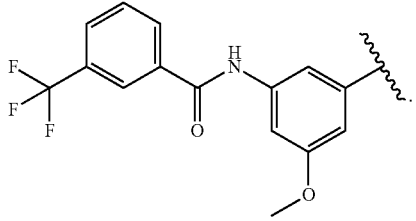 [SMILES: *c1cc(NC(=O)c2cccc(C(F)(F)F)c2)cc(OC)c1]

In certain embodiments, Ring C is of the formula:

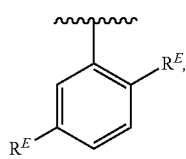

optionally wherein each instance of R$^E$ is independently halogen, substituted or unsubstituted C$_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$, In certain embodiments, Ring C is of the formula:

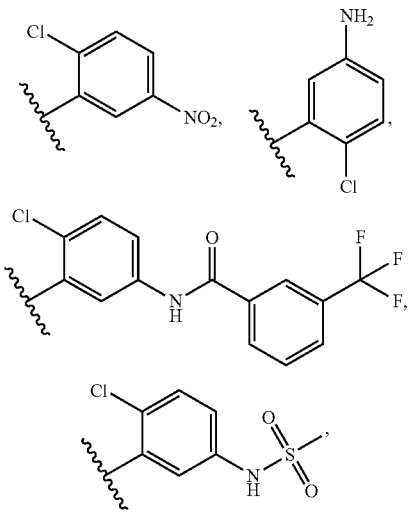

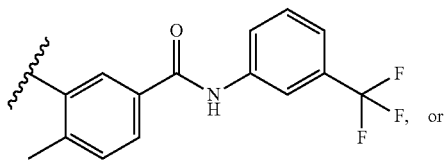

, or

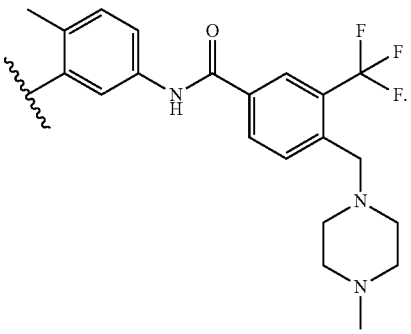

In certain embodiments, Ring C is of the formula:

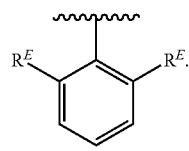

In certain embodiments, Ring C is of the formula:

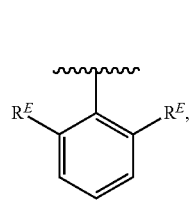

wherein each instance of R$^E$ is independently substituted or unsubstituted alkyl. In certain embodiments, Ring C is of the formula:

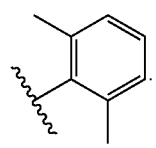

wherein each instance of R$^E$ is independently halogen, substituted or unsubstituted C$_{1-6}$ alkyl, —OR$^a$, —N(R$^a$)$_2$, —C(=O)R$^a$, —C(=O)OR$^a$, —C(=O)N(R$^a$)$_2$, —NR$^a$C(=O)R$^a$, —NR$^a$C(=O)OR$^a$, —NR$^a$C(=O)N(R$^a$)$_2$, —NR$^a$S(=O)R$^a$, —NR$^a$S(=O)OR$^a$, —NR$^a$S(=O)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OC(=O)R$^a$, —OC(=O)OR$^a$, —OC(=O)N(R$^a$)$_2$, —CN, —SCN, or —NO$_2$, In certain embodiments, Ring C is of the formula:

In certain embodiments, Ring C is of the formula:

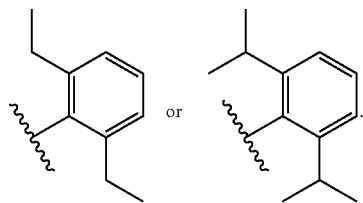 [SMILES: *c1c(CC)cccc1CC ; *c1c(C(C)C)cccc1C(C)C]

In certain embodiments, Ring C is of the formula:

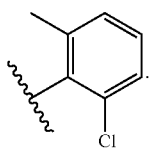 [SMILES: *c1c(C)cccc1Cl]

In certain embodiments, Ring C is of the formula:

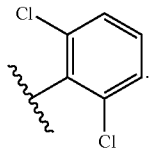 [SMILES: *c1c(Cl)cccc1Cl]

In certain embodiments, Ring C is of the formula:

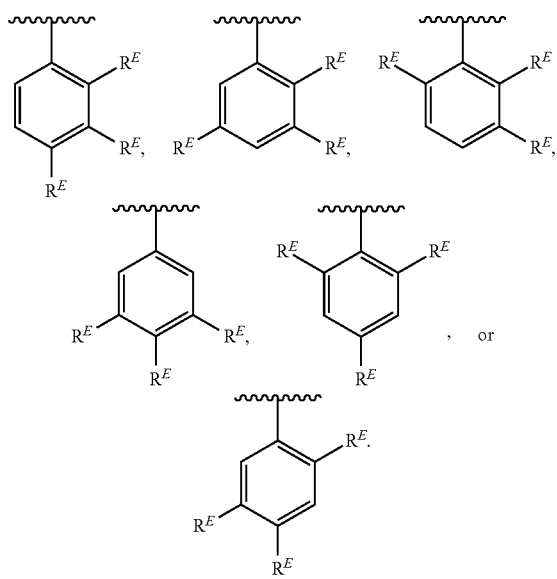

In certain embodiments, Ring C is of the formula:

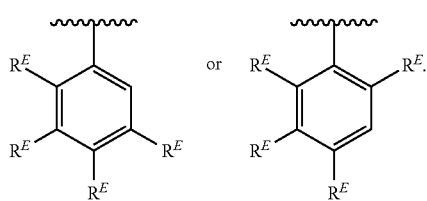

In certain embodiments, Ring C is of the formula:

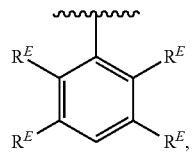

optionally wherein each instance of $R^E$ is independently halogen, substituted or unsubstituted $C_{1-6}$ alkyl, —$OR^a$, —$N(R^a)_2$, —C(=O)$R^a$, —C(=O)$OR^a$, —C(=O)N($R^a$)$_2$, —$NR^aC(=O)R^a$, —$NR^aC(=O)OR^a$, —$NR^aC(=O)N(R^a)_2$, —$NR^aS(=O)R^a$, —$NR^aS(=O)OR^a$, —$NR^aS(=O)N(R^a)_2$, —$NR^aS(=O)_2R^a$, —$NR^aS(=O)_2OR^a$, —$NR^aS(=O)_2N(R^a)_2$, —OC(=O)$R^a$, —OC(=O)$OR^a$, —OC(=O)N($R^a$)$_2$, —CN, —SCN, or —NO$_2$, In certain embodiments, Ring C is of the formula:

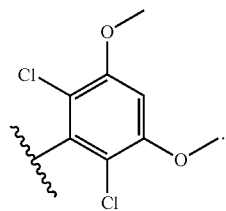 [SMILES: *c1c(Cl)c(OC)cc(OC)c1Cl]

In certain embodiments, Ring C is of the formula:

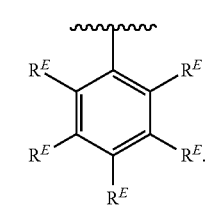

In Formula (I-A), Ring C may include one or more substituents $R^E$. In certain embodiments, all instances of $R^E$ are the same. In certain embodiments, at least two instances of $R^E$ are different. In certain embodiments, at least one instance of $R^E$ is halogen (e.g., F, Cl, Br, or I). In certain embodiments, at least one instance of $R^E$ is substituted or unsubstituted alkyl (e.g., substituted or unsubstituted $C_{1-6}$ alkyl). In certain embodiments, at least one instance of $R^E$ is —CH$_3$. In certain embodiments, at least one instance of $R^E$ is —CF$_3$, unsubstituted ethyl, perfluoroethyl, unsubstituted propyl, perfluoropropyl, unsubstituted butyl, perfluorobutyl, or Bn. In certain embodiments, at least one instance of $R^E$ is substituted or unsubstituted alkenyl (e.g., substituted or unsubstituted $C_{1-6}$ alkenyl). In certain embodiments, at least one instance of $R^E$ is substituted or unsubstituted alkynyl (e.g., substituted or unsubstituted $C_{1-6}$ alkynyl). In certain embodiments, at least one instance of $R^E$ is substituted or unsubstituted carbocyclyl (e.g., substituted or unsubstituted, monocyclic, 3- to 7-membered carbocyclyl). In certain embodiments, at least one instance of $R^E$ is substituted or unsubstituted heterocyclyl (e.g., substituted or unsubstituted, monocyclic, 5- to 6-membered heterocyclyl, wherein one, two, or three atoms in the heterocyclic ring system are independently nitrogen, oxygen, or sulfur). In certain embodiments, at least one instance of $R^E$ is substituted or unsubstituted aryl (e.g., substituted or unsubstituted, 6- to 10-membered aryl). In certain embodiments, at least one instance of $R^E$ is substituted or unsubstituted phenyl. In certain embodiments, at least one instance of $R^E$ is substituted or unsubstituted heteroaryl (e.g., substituted or unsubstituted, monocyclic, 5- to 6-membered heteroaryl, wherein one, two, three, or four atoms in the heteroaryl ring system are independently nitrogen, oxygen, or sulfur). In certain embodiments, at least one instance of $R^E$ is —$OR^a$ (e.g., —OH, —O(substituted or unsubstituted $C_{1-6}$ alkyl) (e.g., —OMe, —OEt, —OPr, —OBu, or —OBn), or —O(substituted or unsubstituted phenyl) (e.g., —OPh)). In certain embodiments, at least one instance of $R^E$ is —$SR^a$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, at least one instance of $R^E$ is —$N(R^a)_2$ (e.g., —$NH_2$, —NH(substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^E$ is —CN, —SCN, or —$NO_2$. In certain embodiments, at least one instance of $R^E$ is —$C(=NR^a)R^a$, —$C(=NR^a)OR^a$, or —$C(=NR^a)N(R^a)_2$. In certain embodiments, at least one instance of $R^E$ is —$C(=O)R^a$, —$C(=O)OR^a$, or —$C(=O)N(R^a)_2$ (e.g., —$C(=O)NH_2$, —$C(=O)NHMe$, or —$C(=O)NMe_2$). In certain embodiments, at least one instance of $R^E$ is —$NR^aC(=O)R^a$, optionally wherein each instance of $R^a$ is independently H, substituted or unsubstituted $C_{1-6}$ alkyl, substituted or unsubstituted phenyl, or a nitrogen protecting group when attached to a nitrogen atom. In certain embodiments, at least one instance of $R^E$ is —$NHC(=O)R^a$, wherein $R^a$ is substituted or unsubstituted phenyl. In certain embodiments, at least one instance of $R^E$ is of the formula:

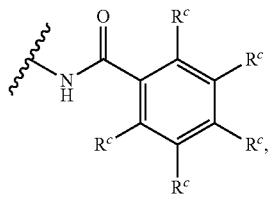

optionally wherein each instance of $R^C$ is independently H, halogen, substituted or unsubstituted $C_{1-6}$ alkyl, —OH, or —O(substituted or unsubstituted $C_{1-6}$ alkyl). In certain embodiments, at least one instance of $R^E$ is of the formula:

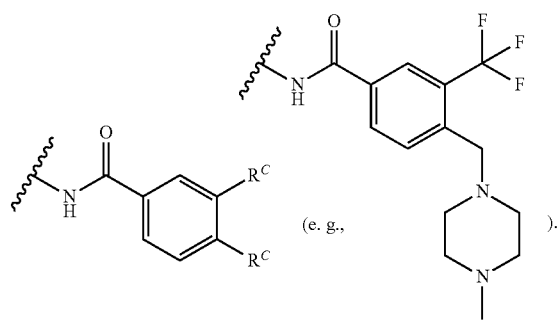

In certain embodiments, at least one instance of $R^E$ is —$NR^aC(=O)OR^a$ or —$NR^aC(=O)N(R^a)_2$. In certain embodiments, at least one instance of $R^E$ is —$OC(=O)R^a$, —$OC(=O)OR^a$, or —$OC(=O)N(R^a)_2$. In certain embodiments, at least one instance of $R^E$ is —$NR^aS(=O)R^a$, —$NR^aS(=O)OR^a$, or —$NR^aS(=O)N(R^a)_2$, optionally wherein each instance of $R^a$ is independently H, substituted or unsubstituted $C_{1-6}$ alkyl, nitrogen protecting group when attached to a nitrogen atom, or an oxygen protecting group when attached to an oxygen atom. In certain embodiments, at least one instance of $R^E$ is —$NR^aS(=O)_2R^a$, —$NR^aS(=O)_2OR^a$, or —$NR^aS(=O)_2N(R^a)_2$, optionally wherein each instance of $R^a$ is independently H, substituted or unsubstituted $C_{1-6}$ alkyl, nitrogen protecting group when attached to a nitrogen atom, or an oxygen protecting group when attached to an oxygen atom. In certain embodiments, at least one instance of $R^E$ is —$NHS(=O)_2R^a$, optionally wherein $R^a$ is substituted or unsubstituted $C_{1-6}$ alkyl. In certain embodiments, at least one instance of $R^E$ is —$NHS(=O)_2Me$.

In certain embodiments, m is 0. In certain embodiments, m is 1. In certain embodiments, m is 2. In certain embodiments, m is 3. In certain embodiments, m is 4. In certain embodiments, m is 5.

In certain embodiments, the compound of Formula (III-A) is of the formula:

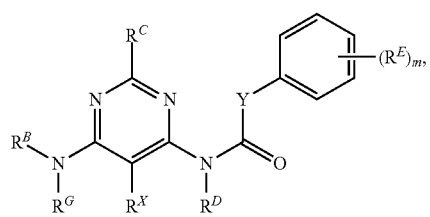

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

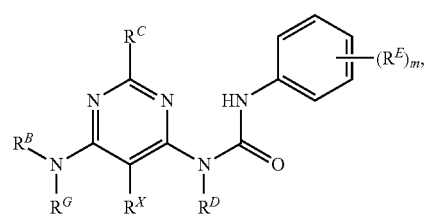

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

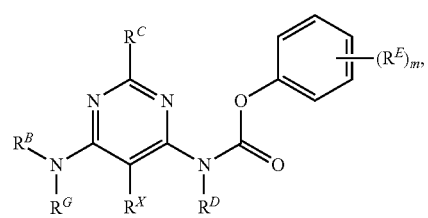

In certain embodiments, the compound of Formula (III-A) is of the formula:

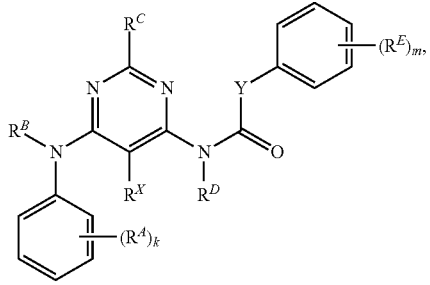

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

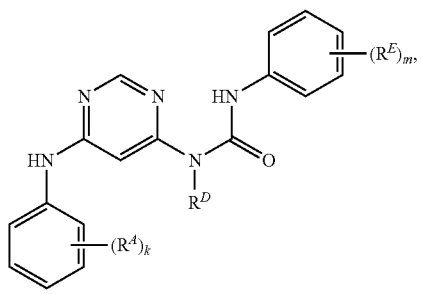

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

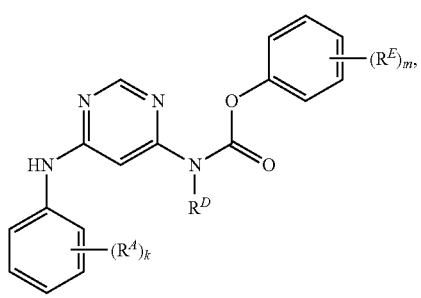

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

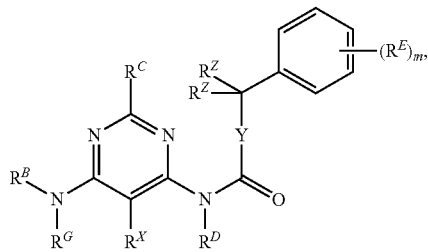

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

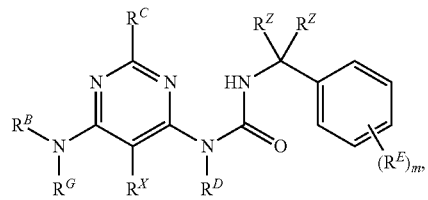

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

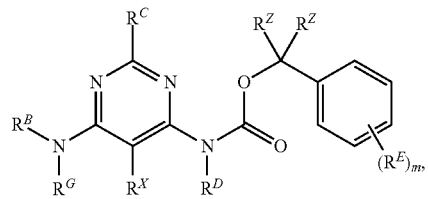

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

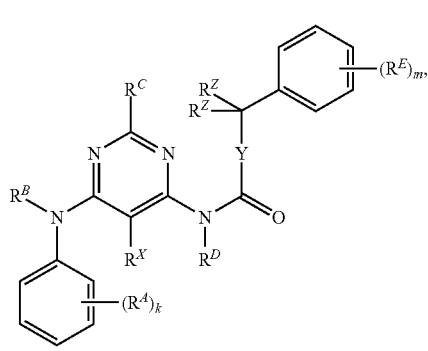

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

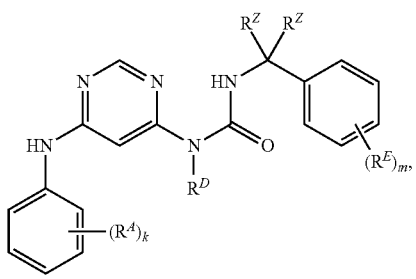

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

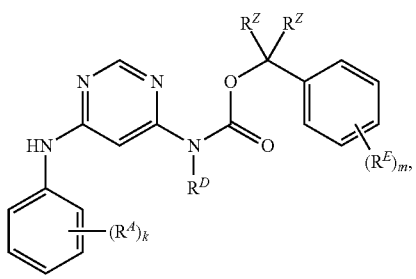

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

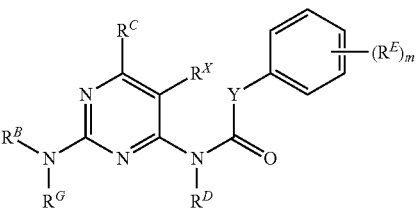

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

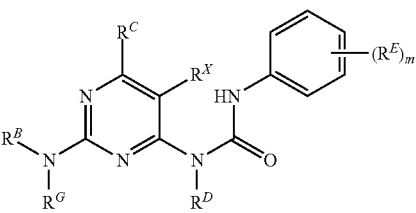

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

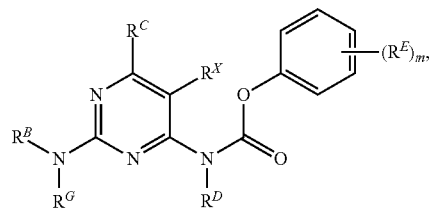

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

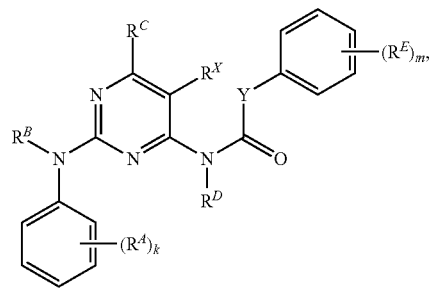

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

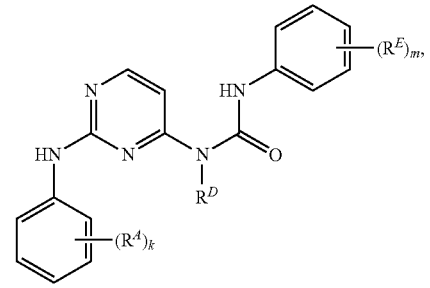

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

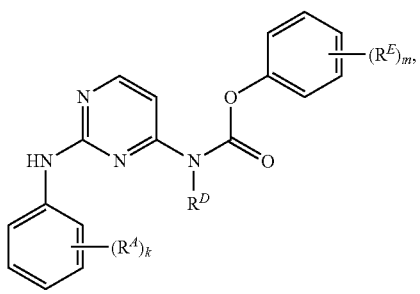

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

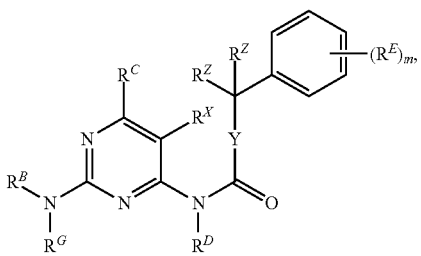

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

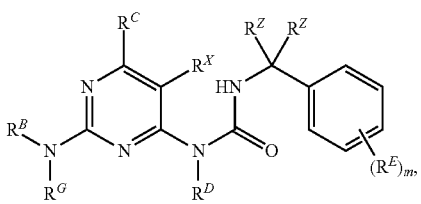

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

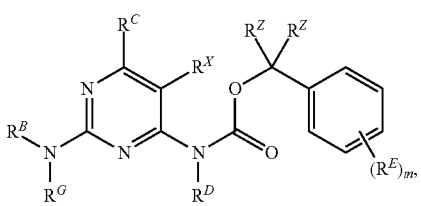

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

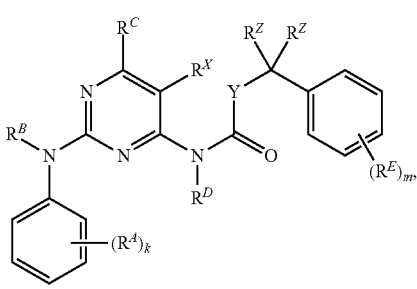

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

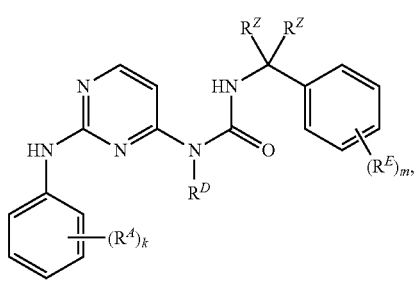

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

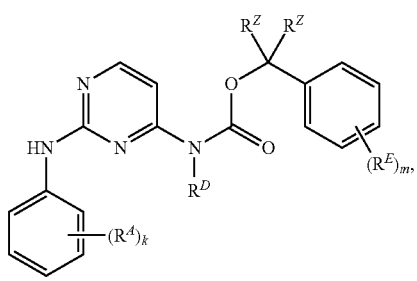

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is not of the formula:

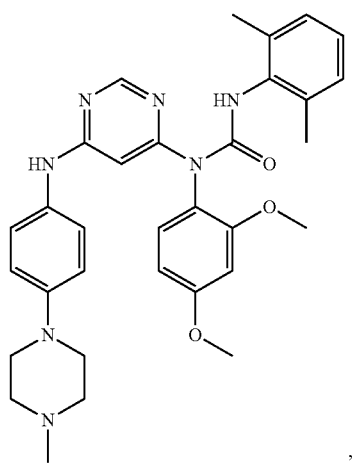

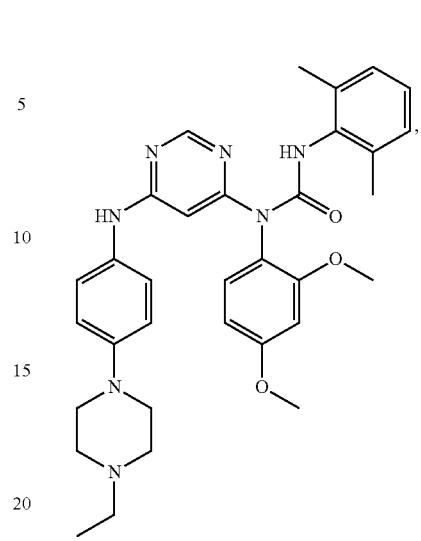

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

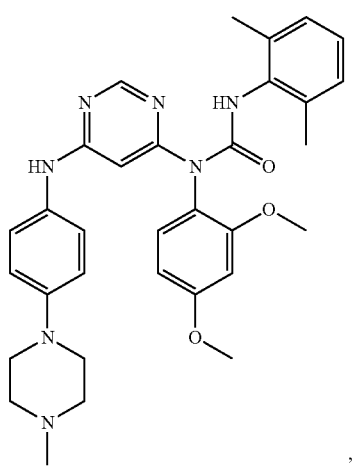 [SMILES: COc1ccc(N(C(=O)Nc2c(C)cccc2C)c2cc(Nc3ccc(N4CCN(C)CC4)cc3)ncn2)c(OC)c1]

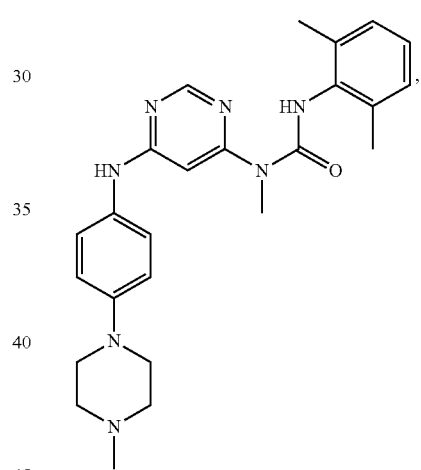

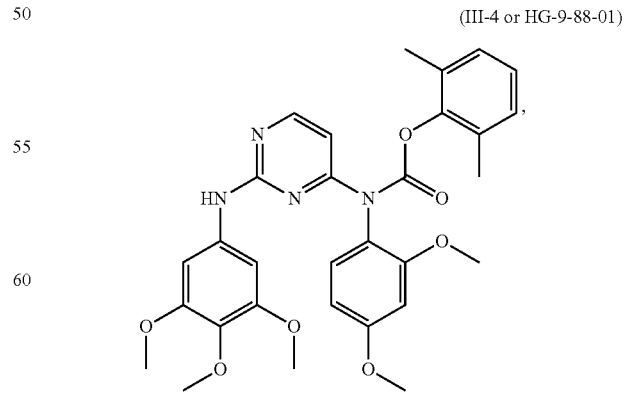

or a pharmaceutically acceptable salt, solvate, hydrate, polymorph, co-crystal, tautomer, stereoisomer, isotopically labeled derivative, or prodrug thereof.

In certain embodiments, the compound of Formula (III-A) is of the formula:

(III-5 or HG-9-150-01)
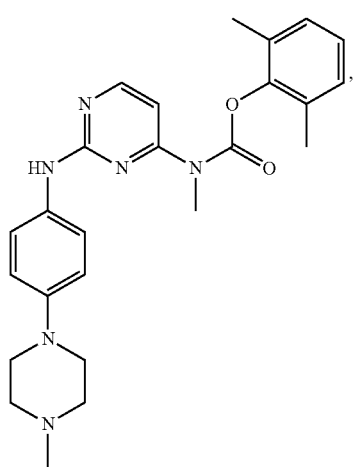
HG-10-8-01
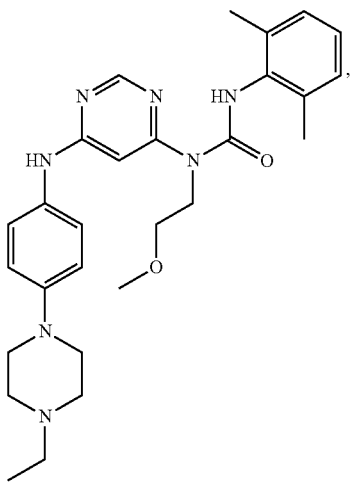
or a pharmaceutically acceptable salt, solvate, hydrate, polymorph, co-crystal, tautomer, stereoisomer, isotopically labeled derivative, or prodrug thereof.
In certain embodiments, the compound of Formula (III-A) is of the formula:
HG-9-96-01
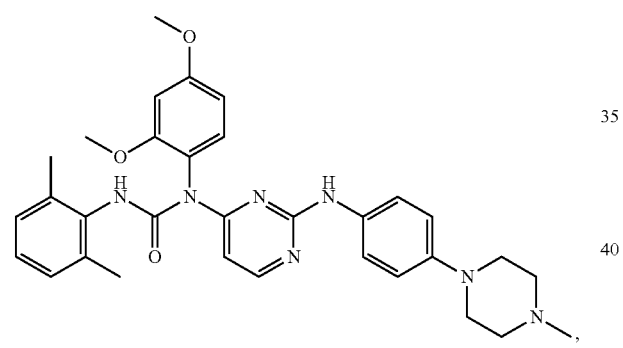
HG-10-8-02
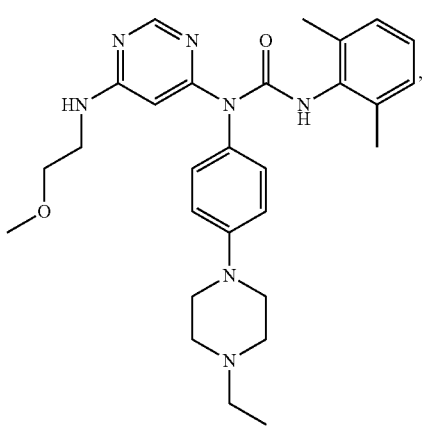
HG-9-148-02
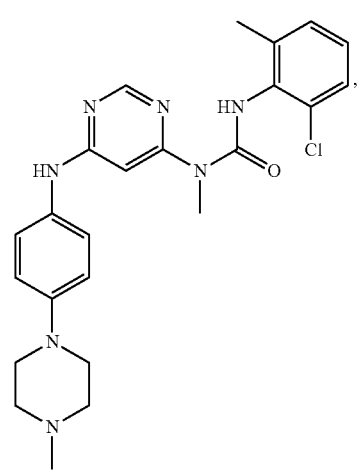
HG-10-9-01

-continued
HG-10-15-02
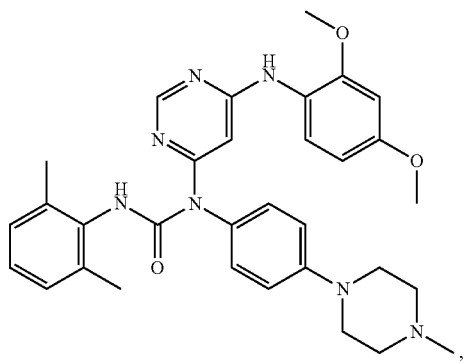
HG-10-15-03
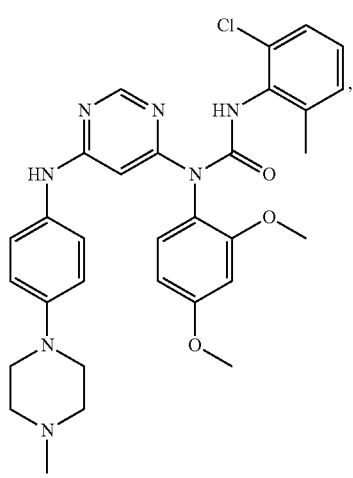
HG-10-15-04
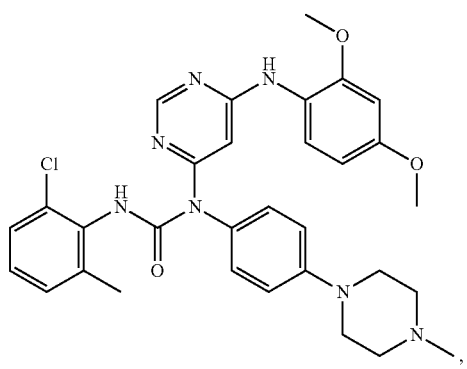
-continued
HG-10-27-01
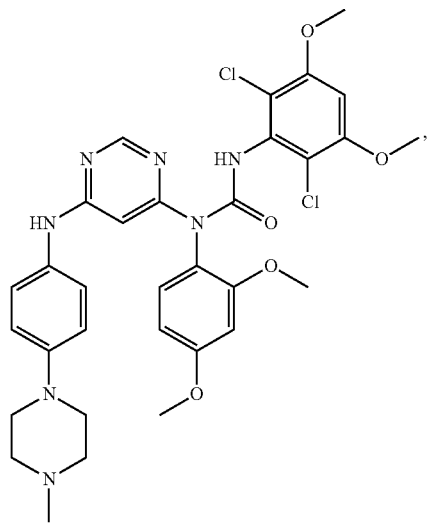
HG-10-27-02
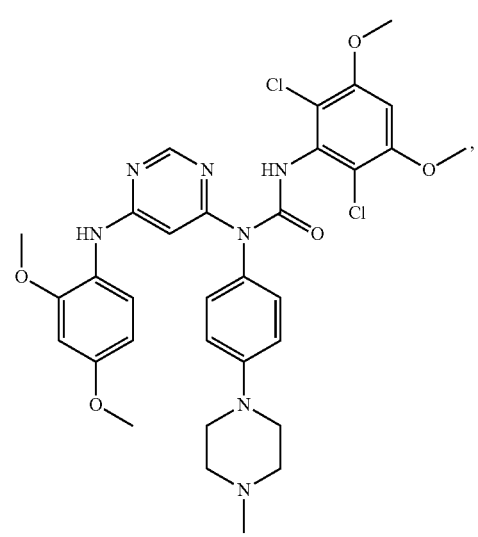
HG-10-28-01
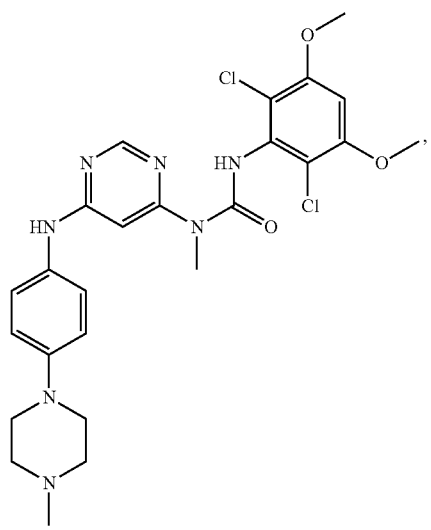

HG-10-31-01
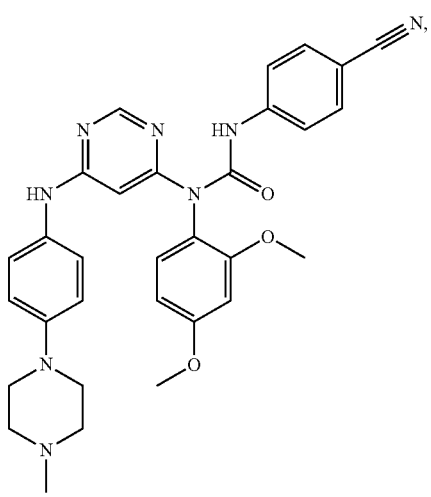
HG-10-36-02
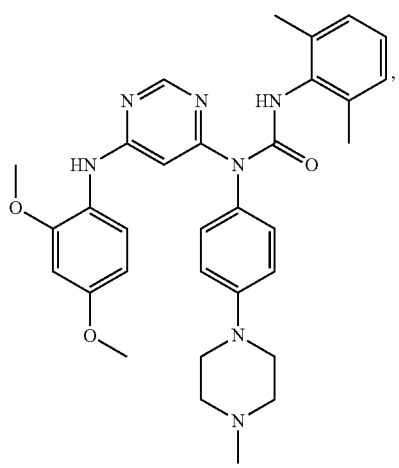
HG-10-31-02
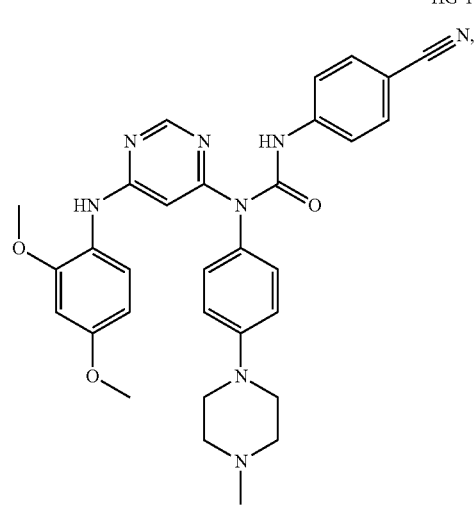
HG-10-59-02
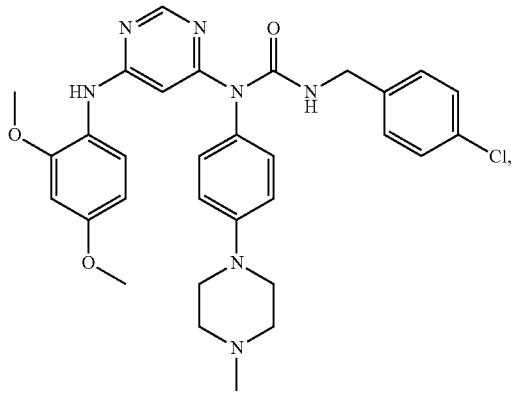
HG-10-36-01
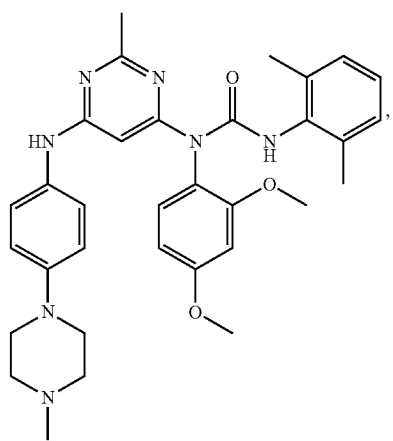
H 10-60-01
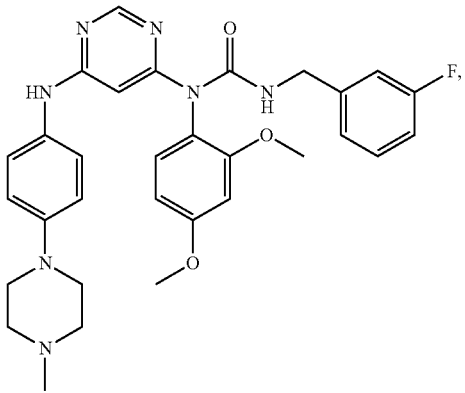

161
-continued
HG 10-60-02
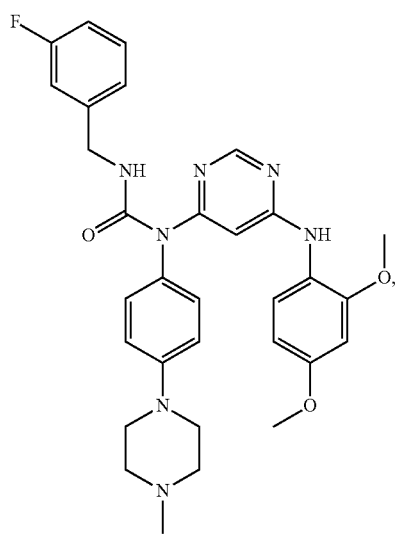
HG 10-61-01
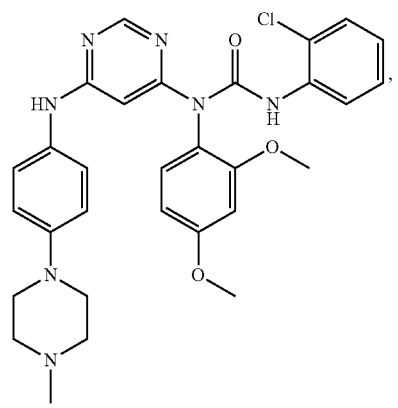
HG 10-61-02
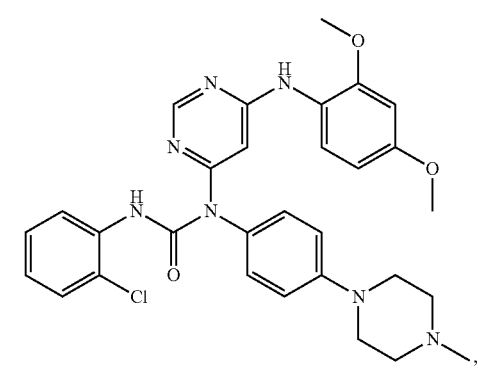
162
-continued
HG 10-62-01
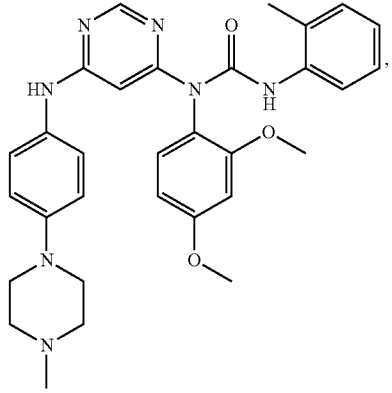
HG 10-62-02
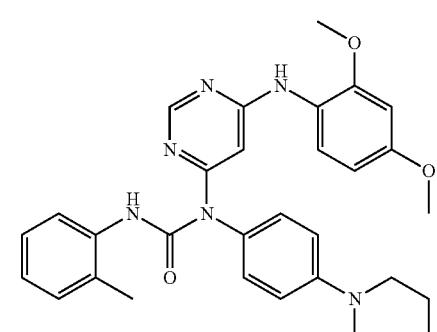
HG 10-63-01
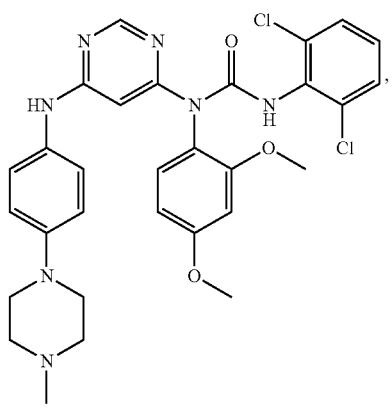
HG 10-63-02
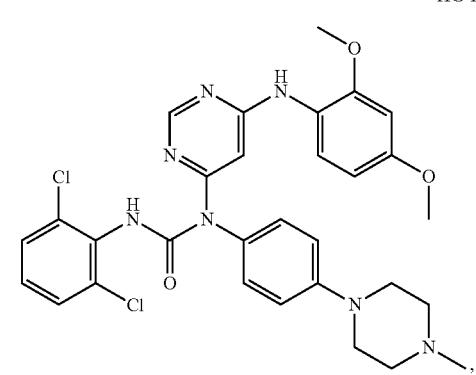

HG 10-64-01
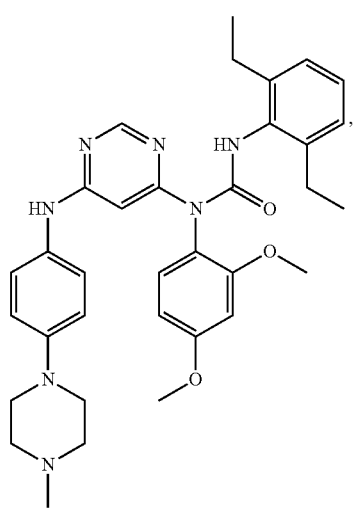
HG 10-65-02
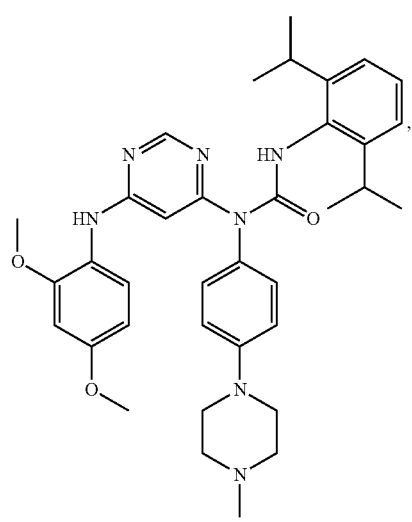
HG 10-64-02
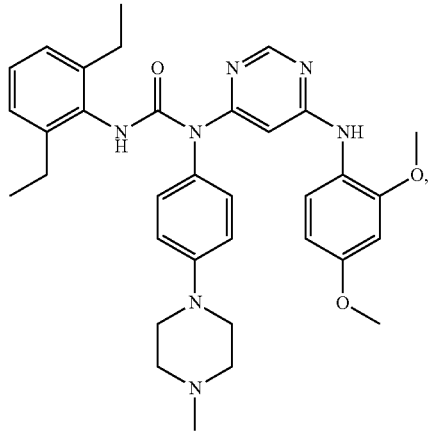
HG-10-149-01
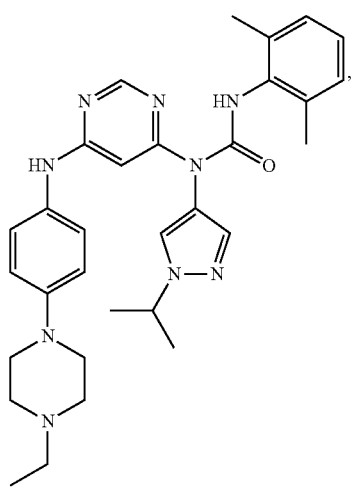
HG 10-65-01
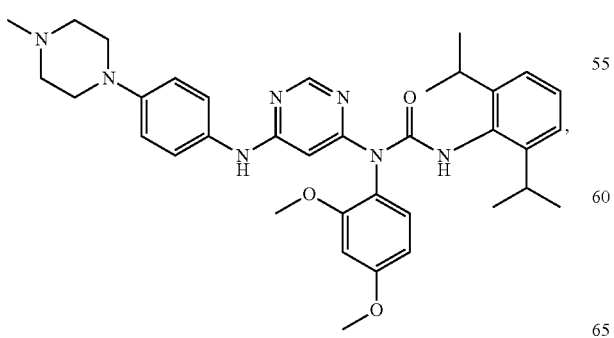
HG-10-149-02
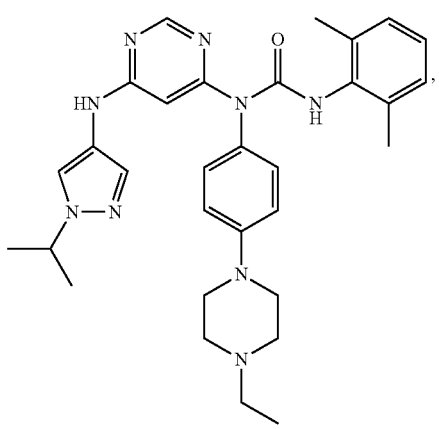

HG-10-150-01
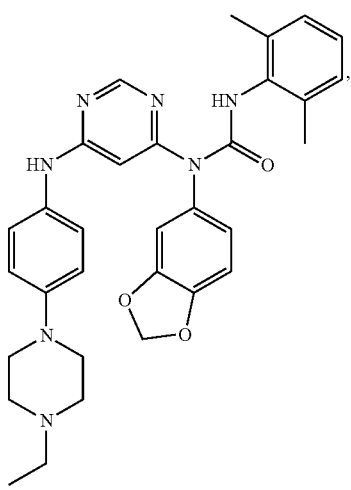
HG-11-18-02
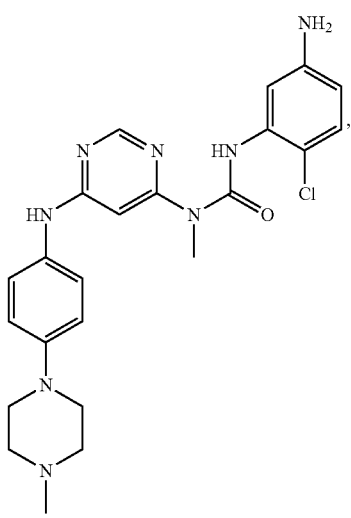
HG-10-150-02
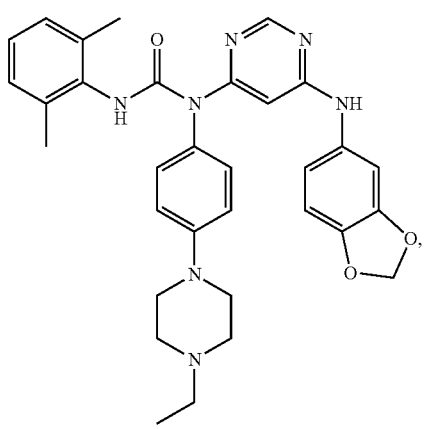
HG-11-21-01
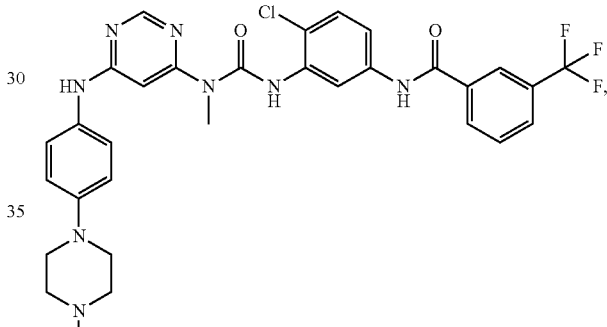
HG-11-18-01
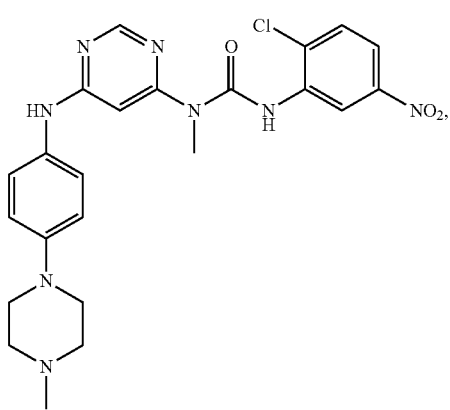
HG-11-22-01
or a pharmaceutically acceptable salt, solvate, hydrate, polymorph, co-crystal, tautomer, stereoisomer, isotopically labeled derivative, or prodrug thereof.
In certain embodiments, the compound of Formula (III-A) is of the formula:

HG-3-09-01 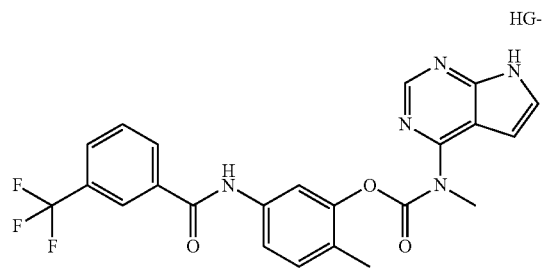 HG-9-87-02 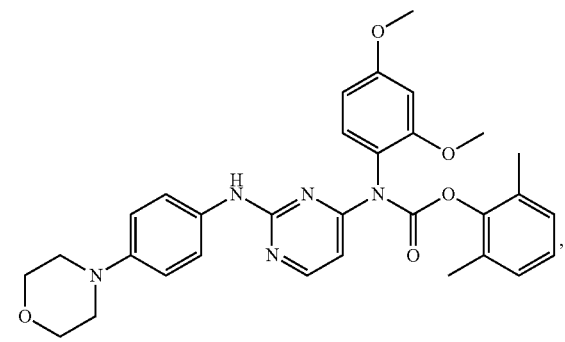
HG-9-87-03 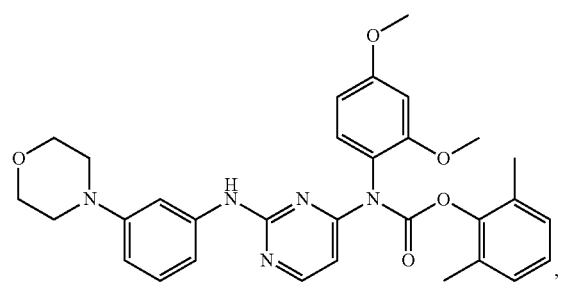 HG-9-87-04 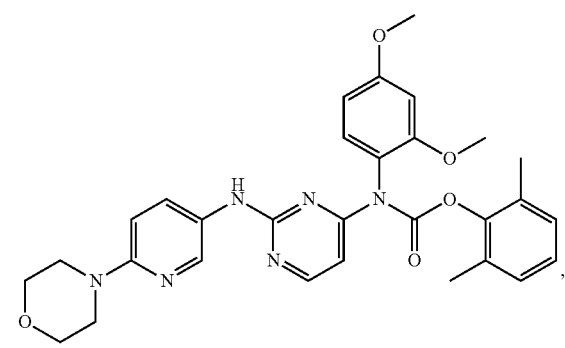
HG-9-88-02 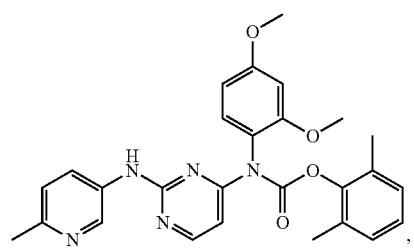 HG-9-88-03 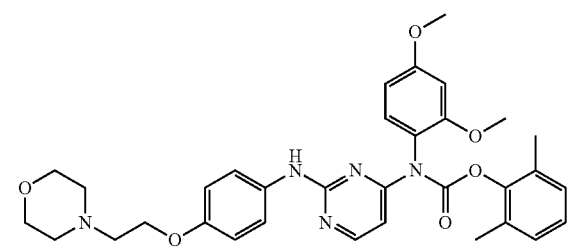
HG-9-88-04 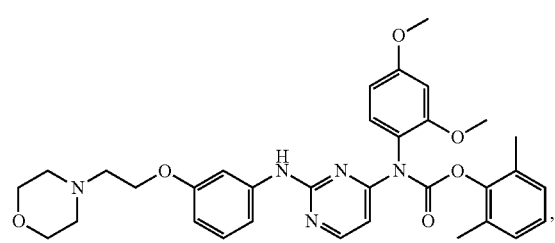 HG-9-88-05 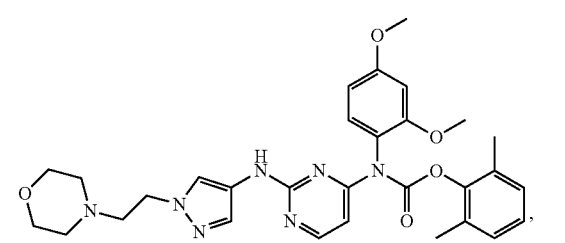
HG-9-90-01 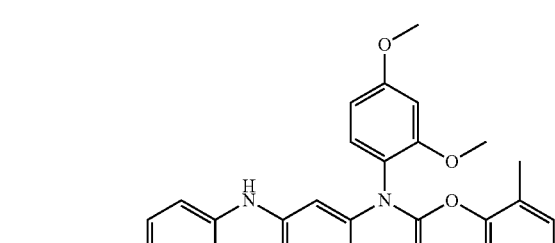 HG-9-90-02 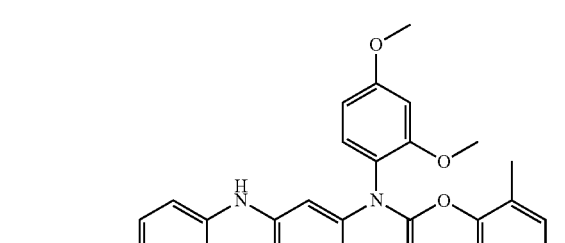
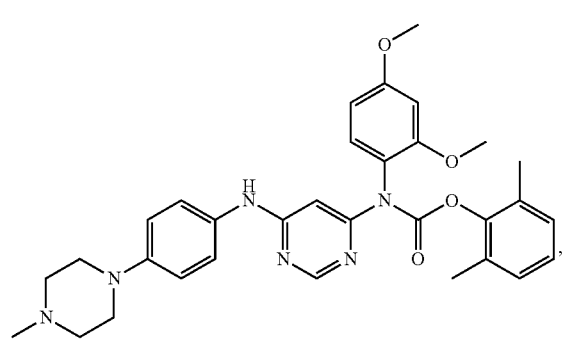 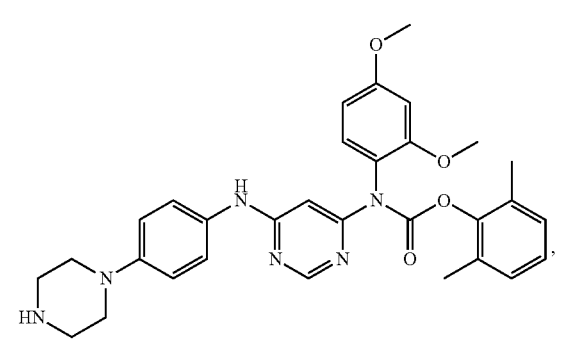

-continued
HG-9-90-03
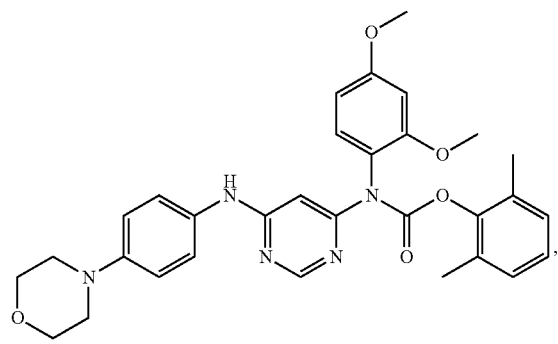
HG-9-139-02
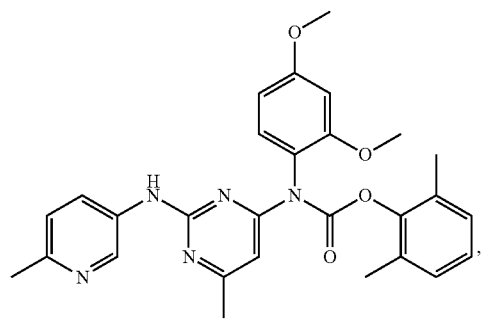
HG-9-139-03
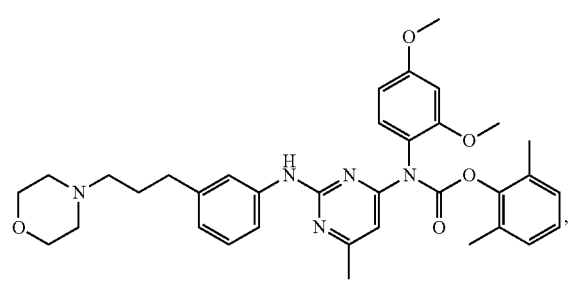
HG-9-139-04
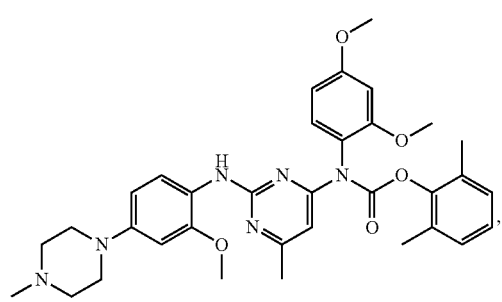
HG-9-139-05
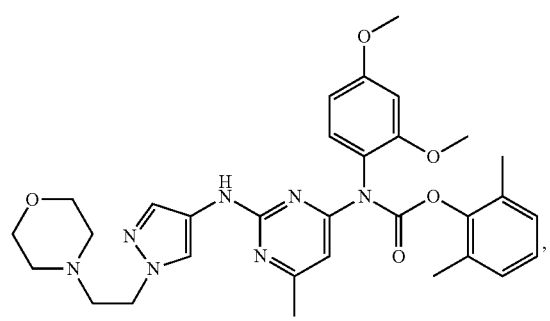
HG-9-140-01
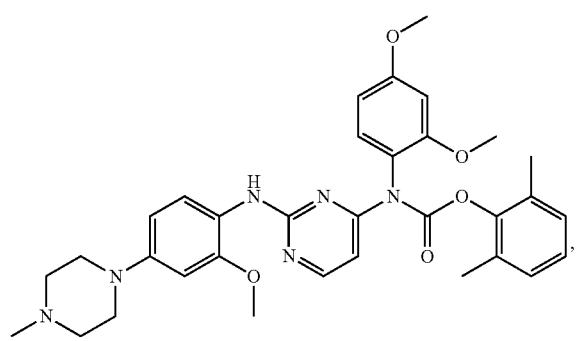
HG-9-144-01
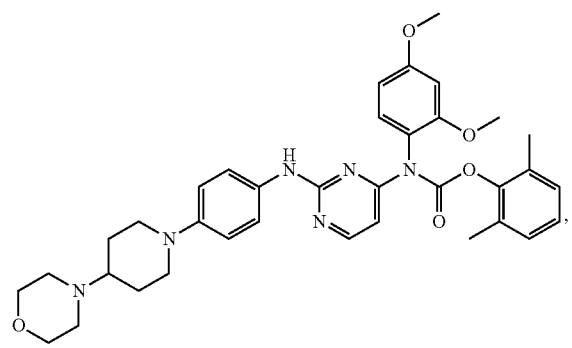
HG-9-144-02
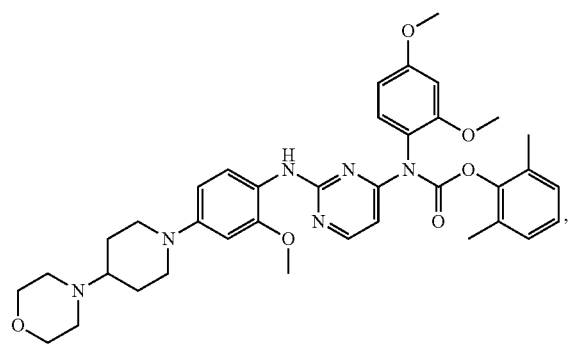

-continued
HG-9-144-03
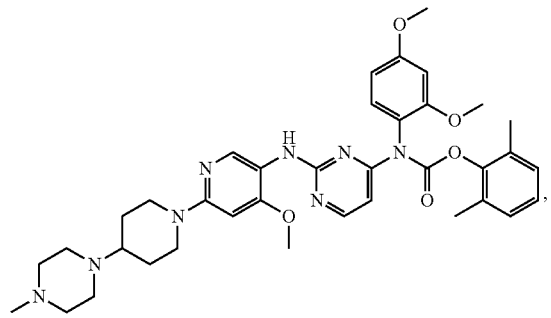
HG-9-144-04
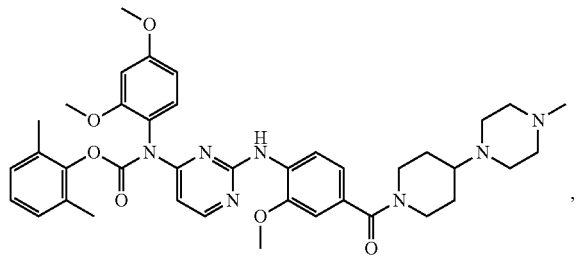
HG-9-144-05
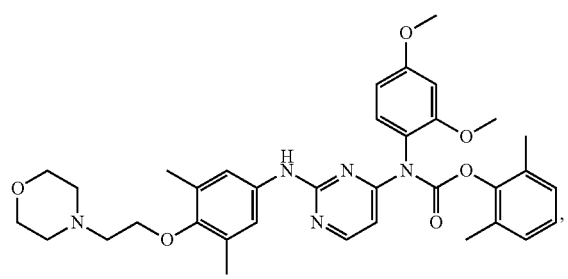
HG-9-150-02
HG-11-6-01
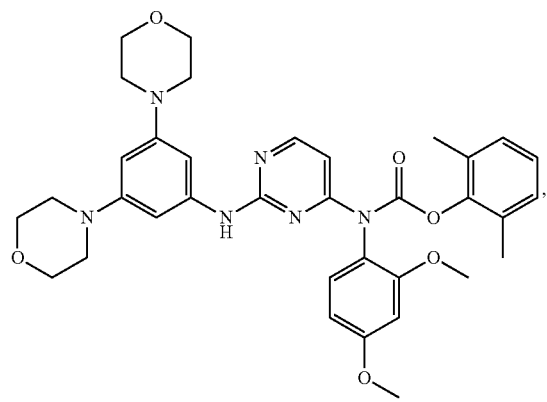
HG-11-6-02
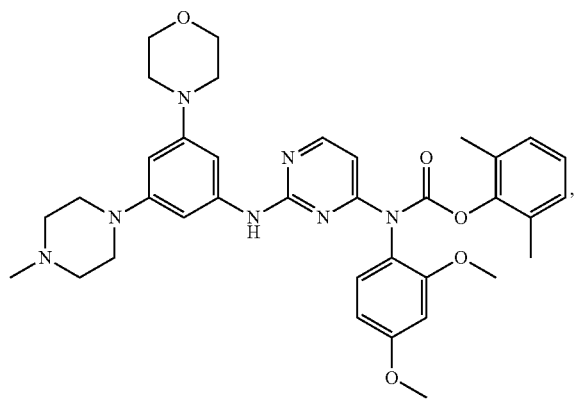
WH-4-023
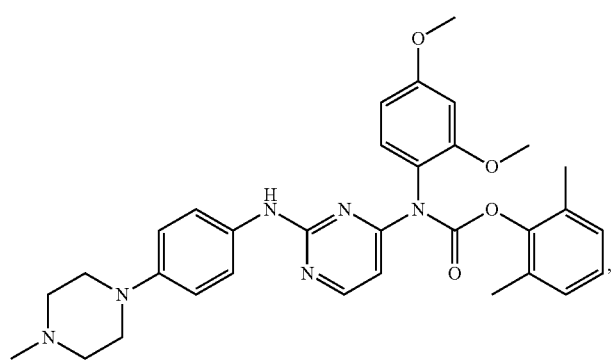

-continued
WH-4-025
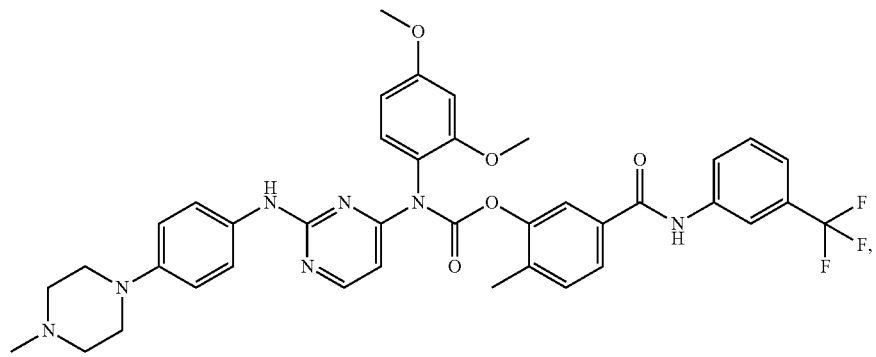
WH4-113
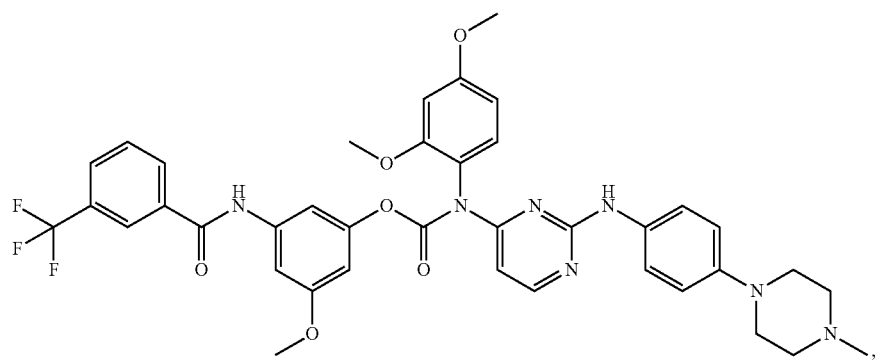
WH4-124-1
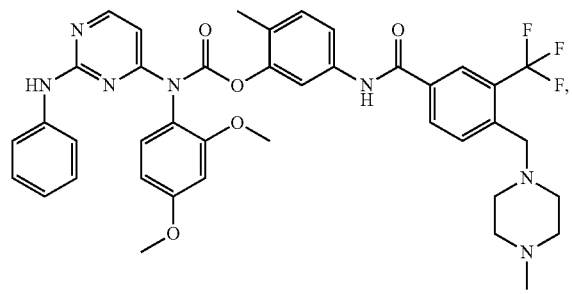
WH4-124-2
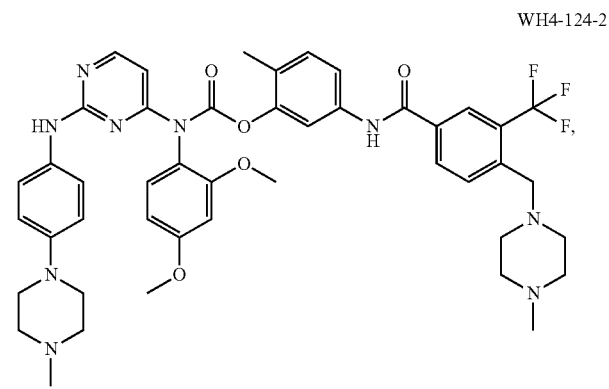
WH4-199-1
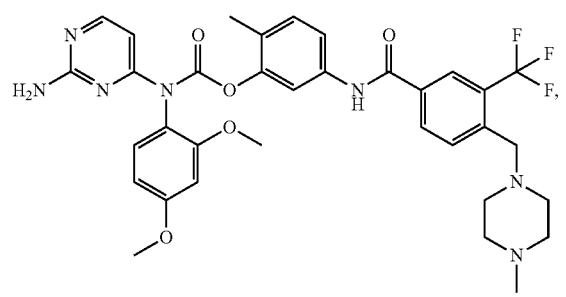
WH4-199-2
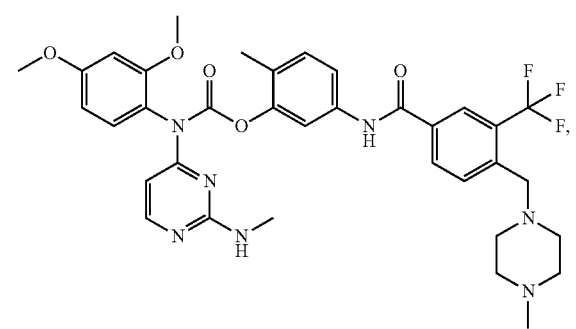

WH4-200-1

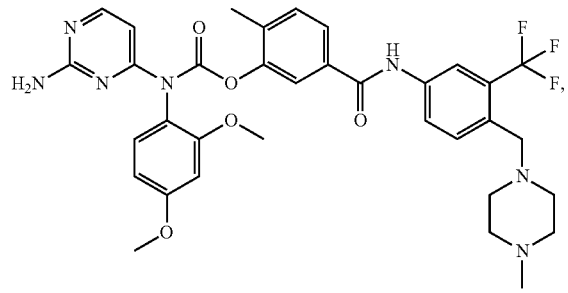

WH4-200-2

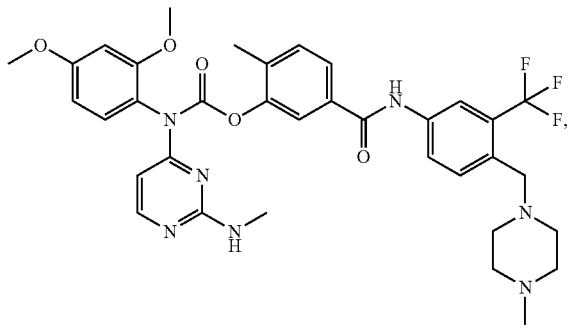

or a pharmaceutically acceptable salt, solvate, hydrate, polymorph, co-crystal, tautomer, stereoisomer, isotopically labeled derivative, or prodrug thereof.

SIK Inhibitors

In certain embodiments, a SIK inhibitor for use in the invention described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a SIK inhibitor for use in the invention described herein is a compound of Formula (I), or a pharmaceutically acceptable salt thereof. In certain embodiments, a SIK inhibitor for use in the invention described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a SIK inhibitor for use in the invention described herein is a compound of Formula (II), or a pharmaceutically acceptable salt thereof. In certain embodiments, a SIK inhibitor for use in the invention described herein is a compound of Formula (III-A), or a pharmaceutically acceptable salt, solvate, hydrate, polymorph, co-crystal, tautomer, stereoisomer, isotopically labeled derivative, or prodrug thereof. In certain embodiments, a SIK inhibitor for use in the invention described herein is a compound of Formula (III-A), or a pharmaceutically acceptable salt thereof.

The SIK inhibitors described herein may be able to bind a SIK (e.g., SIK1, SIK2, or SIK3). In certain embodiments, the SIK inhibitor covalently binds to a SIK. In certain embodiments, the SIK inhibitor non-covalently binds to a SIK. In certain embodiments, the SIK inhibitor reversibly binds to a SIK. In certain embodiments, the SIK inhibitor non-reversibly binds to the SIK. In certain embodiments, the SIK inhibitor modulates (e.g., inhibit) the activity (e.g., aberrant activity, such as increased activity) of a SIK. In certain embodiments, the SIK inhibitor inhibits the activity of a SIK. The inhibition of SIK may be in the context of a disease associated with aberrant or increased SIK activity.

The binding affinity of a SIK inhibitor described herein to a SIK may be measured by the dissociation constant ($K_d$) value of an adduct of the SIK inhibitor and the SIK using methods known in the art (e.g., isothermal titration calorimetry (ITC)). In certain embodiments, the adduct comprises the SIK inhibitor and the SIK, which are bound (e.g., non-covalently bound) to each other. In certain embodiments, the $K_d$ value of the adduct is not more than about 100 μM, not more than about 10 μM, not more than about 1 μM, not more than about 100 nM, not more than about 10 nM, or not more than about 1 nM. In certain embodiments, the $K_d$ value of the adduct is at least about 1 nM, at least about 10 nM, at least about 100 nM, at least about 1 μM, at least about 10 μM, or at least about 100 μM. Combinations of the above-referenced ranges are also within the scope of the disclosure.

In certain embodiments, the activity of a SIK is inhibited by a SIK inhibitor described herein. The inhibition of the activity of a SIK by a SIK inhibitor described herein may be measured by the half maximal inhibitory concentration ($IC_{50}$) value of the SIK inhibitor when the SIK inhibitor, or a pharmaceutical composition thereof, is contacted with the SIK. The $IC_{50}$ values may be obtained using methods known in the art (e.g., by a competition binding assay). In certain embodiments, the $IC_{50}$ value of a SIK inhibitor described herein is not more than about 1 mM, not more than about 100 μM, not more than about 10 μM, not more than about 1 μM, not more than about 100 nM, not more than about 10 nM, or not more than about 1 nM. In certain embodiments, the $IC_{50}$ value of a SIK inhibitor described herein is at least about 1 nM, at least about 10 nM, at least about 100 nM, at least about 1 μM, at least about 10 μM, at least about 100 μM, or at least about 1 mM. Combinations of the above-referenced ranges are also within the scope of the disclosure.

The SIK inhibitors described herein may selectively modulate the activity of a SIK. In certain embodiments, the SIK inhibitors selectively inhibit the activity of a SIK, compared to a different SIK or a protein kinase that is not a SIK.

The selectivity of a SIK inhibitor described herein in inhibiting the activity of a first SIK over a second SIK or a protein kinase that is not a SIK (e.g., the serine/threonine-protein kinase SGK1, SGK2, or SGK3) may be measured by the quotient of the $IC_{50}$ value of the SIK inhibitor in inhibiting the activity of the second SIK or the protein kinase that is not a SIK over the $IC_{50}$ value of the SIK inhibitor in inhibiting the activity of the first SIK. The selectivity of a SIK inhibitor described herein in modulating the activity of a first SIK over a second SIK or a protein kinase that is not a SIK may also be measured by the quotient of the $K_d$ value of an adduct of the SIK inhibitor and the second SIK or the protein kinase that is not a SIK over the $K_d$ value of an adduct of the SIK inhibitor and the first SIK. In certain embodiments, the selectivity is at least about 1-fold, at least about 3-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold.

In certain embodiments, the SIK inhibitors described herein are useful in treating and/or preventing inflammatory bowel disease (IBD) and/or graft-versus-host disease (GVHD) in a subject in need thereof.

Pharmaceutical Compositions, Kits, and Administration

The present disclosure provides pharmaceutical compositions comprising a SIK inhibitor described herein, or a pharmaceutically acceptable salt thereof, and optionally a pharmaceutically acceptable excipient for use in treating and/or preventing IBD or GVHD. In certain embodiments, the pharmaceutical composition described herein comprises a SIK inhibitor described herein, or a pharmaceutically acceptable salt thereof, and a pharmaceutically acceptable excipient.

In certain embodiments, the SIK inhibitor described herein is provided in an effective amount in the pharmaceutical composition. In certain embodiments, the effective amount is a therapeutically effective amount (e.g., amount effective for treating IBD or GVHD). In certain embodiments, the effective amount is a prophylactically effective amount (e.g., amount effective for preventing IBD or GVHD). In certain embodiments, the effective amount is an amount effective for inhibiting the activity (e.g., aberrant activity, increased activity) of a SIK in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the cell is in vitro. In certain embodiments, the cell is ex vivo. In certain embodiments, the cell is in vivo.

An effective amount of a SIK inhibitor may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the effective amount is an amount effective for inhibiting the activity of a SIK by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a SIK by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting the activity of a SIK by a range between a percentage described in this paragraph and another percentage described in this paragraph, inclusive.

Pharmaceutical compositions described herein can be prepared by any method known in the art of pharmacology. In general, such preparatory methods include bringing the SIK inhibitor described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a SIK inhibitor described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the SIK inhibitor in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

SIK inhibitors provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The SIK inhibitors and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the SIK inhibitor or pharmaceutical composition described herein is suitable for topical administration to the eye of a subject.

The exact amount of a SIK inhibitor required to achieve an effective amount will vary from subject to subject, depending, for example, on species, age, and general condition of a subject, severity of the side effects or disorder, identity of the particular SIK inhibitor, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a SIK inhibitor for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a SIK inhibitor per unit dosage form.

In certain embodiments, the SIK inhibitors described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A SIK inhibitor or composition, as described herein, can be administered in combination with one or more additional pharmaceutical agents (e.g., therapeutically and/or prophylactically active agents) useful in treating and/or preventing IBD or GVHD. The SIK inhibitors or compositions can be administered in combination with additional pharmaceutical agents that improve their activity (e.g., activity (e.g., potency and/or efficacy) in treating IBD or GVHD in a subject in need thereof, in preventing IBD or GVHD in a subject in need thereof, and/or in inhibiting the activity of a SIK in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a SIK inhibitor described herein and an additional pharmaceutical agent shows a synergistic effect that is absent in a pharmaceutical composition including one of the SIK inhibitor and the additional pharmaceutical agent, but not both.

The SIK inhibitor or composition can be administered concurrently with, prior to, or subsequent to one or more additional pharmaceutical agents, which may be useful as, e.g., combination therapies in treating IBD or GVHD. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing IBD or GVHD. In certain embodiments, the additional pharmaceutical agent is a pharmaceutical agent approved by a regulatory agency (e.g., the US FDA) for treating and/or preventing IBD or GVHD. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the SIK inhibitor described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an anti-inflammatory agent (e.g., an anti-inflammatory agent for treating IBD or GVHD, such as sulfasalazine (AZULFIDINE), mesalamine (APRISO, ASACOL, or LIALDA), balsalazide (COLAZAL), olsalazine (DIPENTUM), a corticosteroid (e.g., prednisone, methylprednisolone, budesonide, or beclomethasone dipropionate), or a combination thereof). In certain embodiments, the additional pharmaceutical agent is an immunosuppressant (e.g., immunosuppressant for treating IBD or GVHD, such as azathioprine (AZASAN or IMURAN), mercaptopurine (PURINETHOL), cyclosporine (GENGRAF, NEORAL, or SANDIMMUNE), infliximab (REMICADE), adalimumab (HUMIRA), certolizumab pegol (CIMZIA), methotrexate (RHEUMATREX), natalizumab (TYSABRI), mycophenolate mofetil (CELLCEPT), sirolimus (RAPAMUNE), tacrolimus (PROGRAF), thalidomide (THALOMID), or a combination thereof). In certain embodiments, the additional pharmaceutical agent is antithymocyte globulin (e.g., antithymocyte globulin for treating IBD or GVHD, such as rabbit ATG or THYMOGLOBULIN), daclizumab (ZENA- PAX), infliximab (REMICADE), alemtuzumab (CAMPATH), etanercept (ENBREL), rituximab (RITUXAN), or a combination thereof. In certain embodiments, the additional pharmaceutical agent is an antibiotic (e.g., antibiotic for treating IBD or GVHD, such as metronidazole (FLAGYL) or ciprofloxacin (CIPRO)). In certain embodiments, the additional pharmaceutical agent is a protein kinase inhibitor (e.g., protein kinase inhibitor for treating IBD or GVHD, such as BCR-Abl inhibitor, c-Kit inhibitor, Raf inhibitor, Alk inhibitor, Wee1 inhibitor, JAK inhibitor, or GSK3 inhibitor). In certain embodiments, the additional pharmaceutical agent is dasatinib, DGC-0879, bosutinib, dabrafenib, TAE-684 (Tae684), MK 1775, vemurafenib, ruxolitinib, CHIR-99021, saracatinib, imatinib, or a combination thereof. Examples of the additional pharmaceutical agents also include, but are not limited to, anti-diarrheal agents, laxatives, pain relievers, iron supplements, vitamin B-12, and calcium and vitamin D supplements. Examples of the additional pharmaceutical agents further include, but are not limited to, anti-proliferative agents, anti-cancer agents (e.g., denileukin diftitox (ONTAK), pentostatin (NIPENT), imatinib mesylate (GLEEVEC)), anti-angiogenesis agents, cardiovascular agents, cholesterol-lowering agents, anti-diabetic agents, and anti-allergic agents. In certain embodiments, the additional pharmaceutical agent is a binder or inhibitor of a SIK. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine SIK inhibitors), modulators of protein stability (e.g., proteasome inhibitors), Hsp90 inhibitors, glucocorticoids, all-trans retinoic acids, and other agents that promote differentiation. In certain embodiments, the SIK inhibitors described herein or pharmaceutical compositions can be administered in combination with an anti-cancer therapy including, but not limited to, surgery, radiation therapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating IBD or GVHD in a subject in need thereof. In certain embodiments, the kits are useful for preventing IBD or GVHD in a subject in need thereof. In certain embodiments, the kits are useful for inhibiting the activity of a SIK in a subject or cell. In certain embodiments, the kits are useful for increasing the level of IL-10 in a subject or cell. In certain embodiments, the kits are useful for decreasing the level of a pro-inflammatory cytokine (e.g., IL-1β, IL-6, IL-12, or TNF-α) in a subject or cell. In certain embodiments, the kits are useful for converting bone marrow-derived dendritic cells (BMDCs) to an anti-inflammatory phenotype in a subject.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating IBD and/or GVHD in a subject in need thereof, for preventing IBD and/or GVHD in a subject in need thereof, for inhibiting the activity of a SIK in a subject or cell, for increasing the level of IL-10 in a subject or cell, for decreasing the level of a pro-inflammatory cytokine (e.g., IL-1β, IL-6, IL-12, or TNF-α) in a subject or cell, for converting bone marrow-derived dendritic cells (BMDCs) to an anti-inflammatory phenotype in a subject. A kit described herein may include one or more additional pharmaceutical agents described herein as a separate composition.

Methods of Treatment

The present disclosure provides methods for the treatment and prevention of inflammatory bowel disease (IBD) and graft-versus-host disease (GVHD).

Recent research has established a rationale for modulating IL-10 (e.g., increasing) in both IBD and GVHD. Although the etiology of IBD is complex, impaired function of anti-inflammatory immune mechanisms is observed in many patients. For instance, single nucleotide polymorphisms (SNPs) in genetic loci containing IL10 or its receptor (IL10RA) are associated with an increased risk of Crohn's disease and ulcerative colitis, and rare loss-of-function mutations in the coding regions of IL10 or IL10RA lead to severe, pediatric-onset enterocolitis. The link between gut inflammation and defective IL-10 signaling in humans is recapitulated in Il10−/− and Il10ra−/− mice, which both develop spontaneous colitis. Conversely, prophylactic administration of recombinant IL-10 partially alleviates gut inflammation and weight loss in murine models of chemically induced colitis. Unfortunately, well-tolerated doses of recombinant IL-10 therapy did not show efficacy in clinical trials for Crohn's disease. Potential explanations of this lack of efficacy include insufficient delivery of IL-10 to the gut mucosa by systemic administration and/or the need to combine IL-10 supplementation with neutralization of inflammatory cytokines. Of note, disease activity is reduced in Crohn's disease patients following oral administration of *L. lactis* engineered to express IL-10, which suggests that specifically increasing IL-10 levels in the gut microenvironment can be therapeutically beneficial in the absence of toxicities (e.g., headache, anemia and thrombocytopenia) that limit systemic treatment.

As with IBD, recent research has also established a compelling rationale for treating GVHD by enhancing IL-10. For example, certain IL-10 promoter-region halotypes had a protective effect against GVHD. Recipients of allogenic bone marrow who have the interleukin-10 (IL-10)-592A/A genotype (having high level of IL-10 production) have a lower risk of severe acute GVHD than recipients who have the −592C/C genotype. Studies using IL-10-deficient donor or host mice (BALB/c or C57BL/6, respectively) in a MHC-mismatched model for acute GVHD, found a strongly aggravated course of the disease with increased mortality when either donor or host cells could not produce IL-10. Notably, IL-10 is a potent suppressor of TNF-α, interleukin-1a, interleukin-1b, interleukin-6, interleukin-12, and interferon-gamma production and may facilitate the induction of tolerance after allogeneic transplantation. Indeed, clinical studies suggest that elevated levels of endogenous IL-10 may be associated with immunologic tolerance. These observations underscore the utility and therapeutic potential of enhancing IL-10 production in both IBD (e.g., Crohn's disease and ulcerative colitis) and GVHD.

The present disclosure is based in part on the discovery that inhibiting salt-inducible kinases (SIKs) using the SIK inhibitors described herein enhanced IL-10 production by macrophages and dendritic cells of the gut.

In another aspect, the present disclosure provides methods of inhibiting the activity of a salt-inducible kinase (SIK) in a subject or cell. In certain embodiments, the SIK is a member of the serine/threonine SIK kinase subfamily (e.g., SIK1, SIK2, SIK3). In certain embodiments, the activity of a SIK in a subject or cell is inhibited by the SIK inhibitors or pharmaceutical compositions described herein. In certain embodiments, the activity of a SIK in a subject or cell is inhibited by the methods described herein by at least about 10%, at least about 20%, at least about 30%, at least about 40%, at least about 50%, at least about 60%, at least about 70%, at least about 80%, at least about 90%, or at least about 95%. In certain embodiments, the activity of a SIK in a subject or cell is inhibited by the methods described herein by at most about 90%, at most about 80%, at most about 70%, at most about 60%, at most about 50%, at most about 40%, at most about 30%, at most about 20%, at most about 10%, at most about 3%, or at most about 1%. Combinations of the above-referenced ranges (e.g., at least about 10% and at most about 50%) are also within the scope of the disclosure. Other ranges are also possible. In some embodiments, the activity of a SIK in a subject or cell is selectively inhibited by the methods described herein. In certain embodiments, a SIK is inhibited by a method described herein to a greater extent, compared to a protein kinase that is not a SIK. In certain embodiments, a SIK (e.g., SIK1, SIK2, or SIK3) is inhibited by a method described herein to a greater extent, compared to a different SIK. In certain embodiments, SIK1 is selectively inhibited by the methods described herein, compared to SIK2, SIK3, or a protein kinase that is not a SIK. In certain embodiments, SIK2 is selectively inhibited by the methods described herein, compared to SIK1, SIK3, or a protein kinase that is not a SIK. In certain embodiments, SIK3 is selectively inhibited by the methods described herein, compared to SIK1, SIK2, or a protein kinase that is not a SIK. In some embodiments, the activity of a SIK in a subject or cell is non-selectively inhibited by the methods described herein. In certain embodiments, the level of interleukin 10 (IL-10) is reduced. In certain embodiments, the level of IL-10 is reduced by at least about 10%, at least about 20%, at least about 30%, at least about 40%, at least about 50%, at least about 60%, at least about 70%, at least about 80%, at least about 90%, or at least about 95%. In some embodiments, bone marrow derived cells (BDMCs) are converted to an anti-inflammatory phenotype. For example, the BDMCs produce reduced levels of pro-inflammatory cytokines (e.g., IL-1β, IL-6, IL-12 and TNF-α). In some embodiments, the BDMCs are macrophages or dendritic cells.

In certain embodiments, the activity of a SIK is an aberrant activity of the SIK. In certain embodiments, the activity of a SIK is an increased activity of the SIK.

In another aspect, the present disclosure provides methods of increasing the level of IL-10 in a subject.

In another aspect, the present disclosure provides methods of increasing the level of IL-10 in a cell.

In certain embodiments, the level of IL-10 in a subject or cell is at an aberrant level before treatment by the inventive methods. In certain embodiments, the level of IL-10 in a subject or cell is decreased by the inventive method. In certain embodiments, the level of IL-10 in a subject or cell is normal.

Another aspect of the present disclosure relates to methods of decreasing the level of a pro-inflammatory cytokine in a subject.

Another aspect of the present disclosure relates to methods of decreasing the level of a pro-inflammatory cytokine in a cell.

In some embodiments, the pro-inflammatory cytokine is IL-10, IL-6, IL-12, or TNF-α. In certain embodiments, the level of the pro-inflammatory cytokine is reduced (e.g., reduced by at least about 10%, at least about 20%, at least about 30%, at least about 40%, at least about 50%, at least about 60%, at least about 70%, at least about 80%, at least about 90%, or at least about 95%) by a method described herein. In certain embodiments, the level of the pro-inflammatory cytokine is measured by an enzyme-linked immunosorbent assay (ELISA). In certain embodiments, the level of the pro-inflammatory cytokine is measured by a bead-based multiplex assay (e.g., a luminex assay). In certain embodiments, the level of the pro-inflammatory cytokine is measured transcriptionally. In certain embodiments, the level of a pro-inflammatory cytokine in a subject or cell is normal.

In another aspect, the present disclosure provides methods of converting bone marrow-derived dendritic cells (BM-DCs) to an anti-inflammatory phenotype in a subject. In certain embodiments, the BMDCs are immune cells. In certain embodiments, the BMDCs are dendritic cells or macrophages. In certain embodiments, the BMDCs have a pro-inflammatory phenotype. For example, the pro-inflammatory phenotype may include the production of a pro-inflammatory cytokine (e.g., IL-10, IL-6, IL-12, or TNF-α). In certain embodiments, converting BDMCs to an anti-inflammatory phenotype comprises decreasing the production of a pro-inflammatory cytokine (e.g., IL-1β, IL-6, IL-12, or TNF-α). In certain embodiments, a method of converting BDMCs to an anti-inflammatory phenotype decreases the production of a pro-inflammatory cytokine by at least about 10%, at least about 20%, at least about 30%, at least about 40%, at least about 50%, at least about 60%, at least about 70%, at least about 80%, at least about 90%, or at least about 95%.

Another aspect of the present disclosure relates to methods of treating IBD or GVHD in a subject in need thereof.

Another aspect of the present disclosure relates to methods of preventing IBD or GVHD in a subject in need thereof.

In certain embodiments, the IBD is Crohn's disease or ulcerative colitis. In certain embodiments, the IBD is collagenous colitis, lymphocytic colitis, diversion colitis, Behçet's disease, or indeterminate colitis. In certain embodiments, the GVHD is acute graft-versus-host disease (aGVHD) or chronic graft-versus-host disease (cGVHD).

In certain embodiments, the methods of the disclosure include administering to a subject in need thereof an effective amount (e.g., therapeutically effective amount or prophylactically effective amount) of a SIK inhibitor or pharmaceutical composition described herein. In certain embodiments, the methods of the disclosure further include performing a surgery on the subject. In certain embodiments, the surgery is strictureplasty, resection (e.g., bowel resection, colon resection), colectomy, surgery for abscesses and fistulas, proctocolectomy, restorative proctocolectomy, vaginal surgery, cataract surgery, or a combination thereof. In certain embodiments, the methods of the disclosure include contacting a cell with an effective amount (e.g., therapeutically effective amount or prophylactically effective amount) of a SIK inhibitor or pharmaceutical composition described herein.

Uses

In another aspect, the present disclosure provides the SIK inhibitors described herein for use in a method described herein (e.g., a method of treating IBD and/or GVHD, method of preventing IBD and/or GVHD, method of inhibiting the activity of a SIK, method of increasing the level of IL-10, method of decreasing the level of a pro-inflammatory cytokine, or method of converting bone marrow-derived dendritic cells (BMDCs) to an anti-inflammatory phenotype).

In still another aspect, the present disclosure provides the pharmaceutical compositions described herein for use in a method described herein (e.g., a method of treating IBD and/or GVHD, method of preventing IBD and/or GVHD, method of inhibiting the activity of a SIK, method of increasing the level of IL-10, method of decreasing the level of a pro-inflammatory cytokine, or method of converting bone marrow-derived dendritic cells (BMDCs) to an anti-inflammatory phenotype).

EXAMPLES

In order that the disclosure may be more fully understood, the following examples are set forth. The synthetic and biological examples described in this application are offered to illustrate the SIK inhibitors, pharmaceutical compositions, uses, and methods provided herein and are not to be construed in any way as limiting their scope.

Example 1. Preparation of the SIK Inhibitors

The SIK inhibitors of any one of Formulae (I), (II), and (I-A) can be prepared from readily available starting materials using the following general methods and procedures (e.g., the methods shown in Schemes 1 to 9). It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization.

A SIK inhibitor of Formula (I) can be prepared according to the methods shown in Scheme 1.

Scheme 1. An exemplary preparation of the SIK inhibitors of Formula (I)

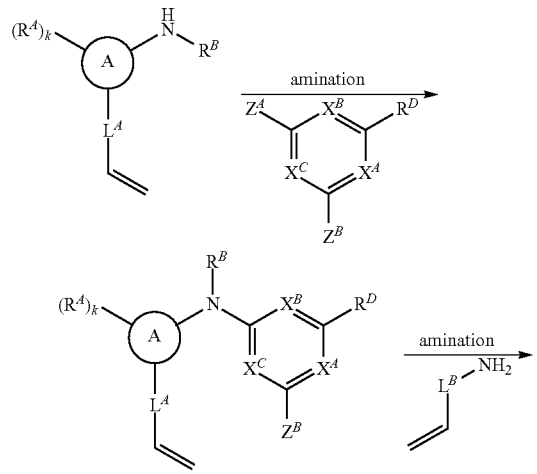

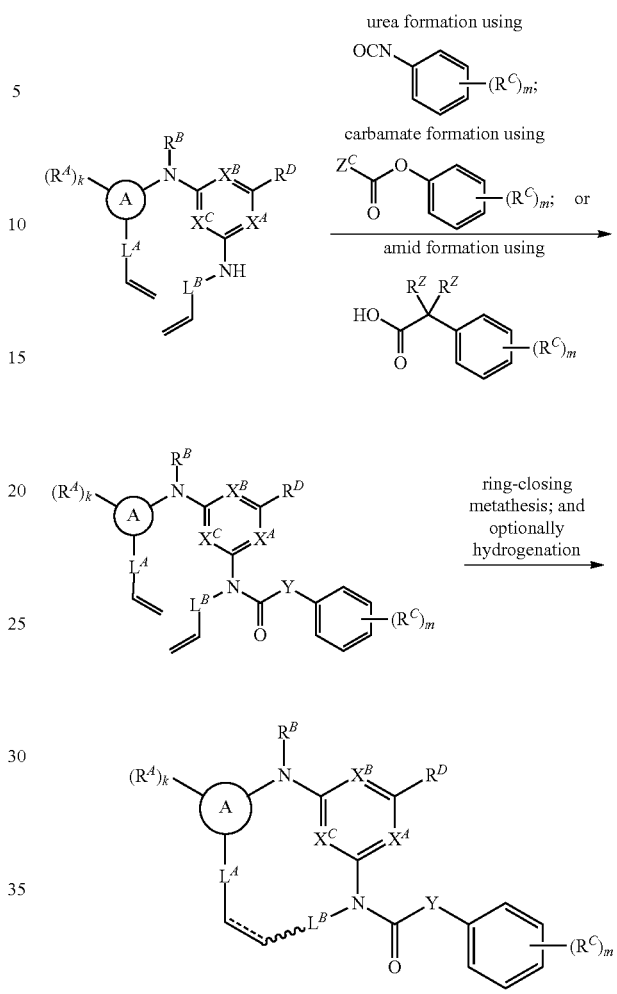

In Scheme 1, each of $Z^A$, $Z^B$, and $Z^C$ is independently a leaving group. In certain embodiments, each of $Z^A$, $Z^B$, and $Z^C$ is independently halogen (e.g., F, Cl, Br, or I (iodine)), —OTs, —OMs, —OBs, or —OTf. In certain embodiments, each of $Z^A$ and $Z^B$ is Cl. In certain embodiments, $Z^C$ is —OR$^{ZC}$ or of the formula:

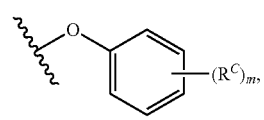

wherein $R^{ZC}$ is substituted or unsubstituted $C_{1-6}$ alkyl (e.g., —CH$_3$) or an oxygen protecting group.

When Y is —NR$^Y$—, $X^A$ is CR$^X$, and R$^Y$ and R$^X$ of $X^A$ are joined to form a substituted or unsubstituted, 5- to 7-membered heterocyclic ring that is fused with Ring B, the SIK inhibitors of Formula (I) can be prepared using the methods known in the art, such as the methods described in U.S. Patent Application Publication, US 2006/0258687, which is incorporated herein by reference.

A SIK inhibitor of Formula (II) can be prepared according to the methods shown in Scheme 2.

Scheme 2. An exemplary preparation of the SIK inhibitors of Formula (II)
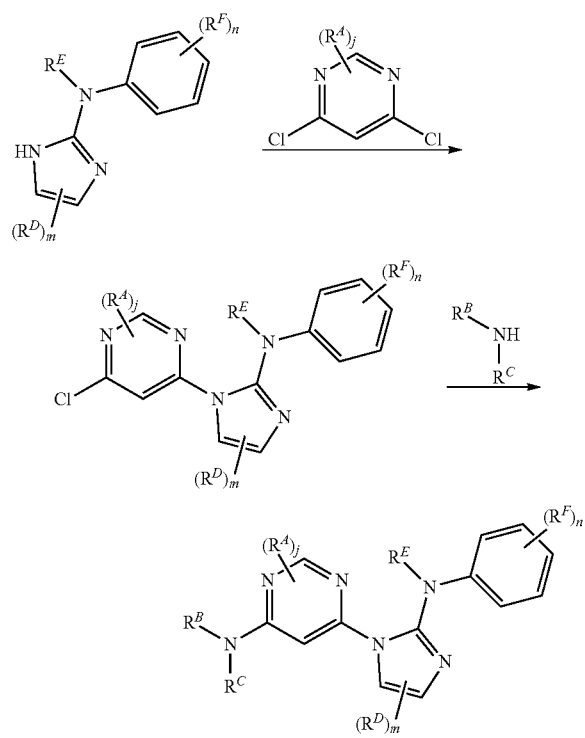
A SIK inhibitor of Formula (II) can be prepared according to the methods shown in Schemes 3A and 3B.
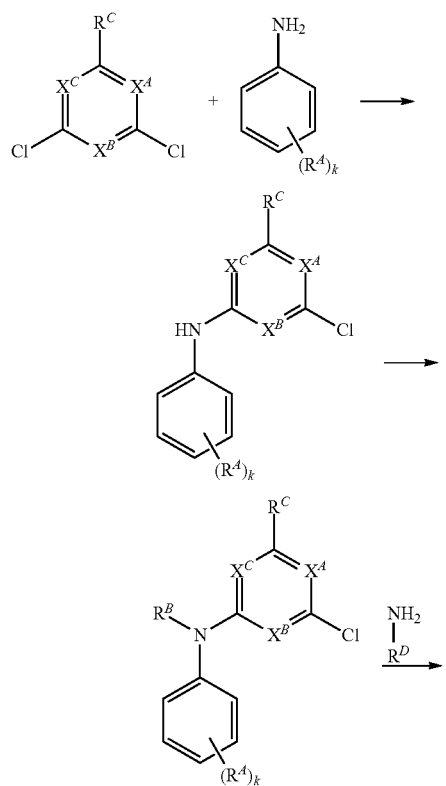
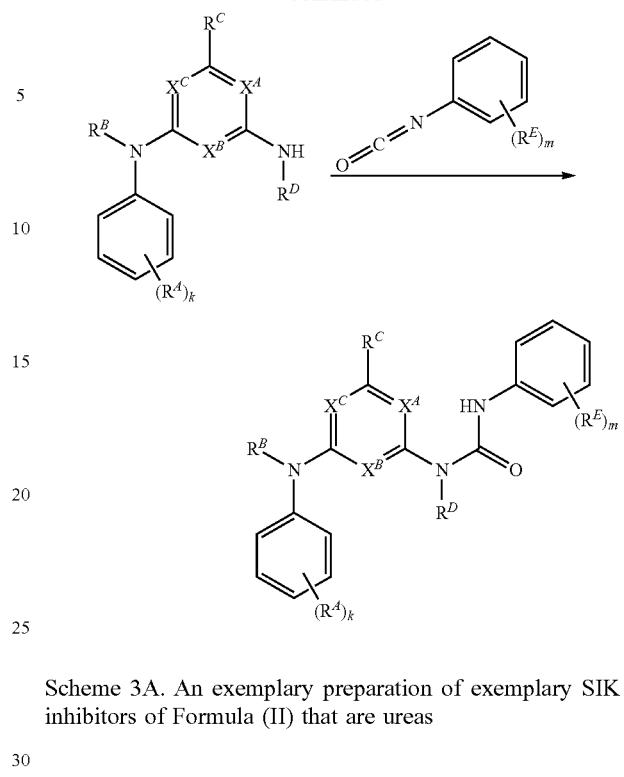
Scheme 3A. An exemplary preparation of exemplary SIK inhibitors of Formula (II) that are ureas
Scheme 3B. An exemplary preparation of exemplary SIK inhibitors of Formula (III) that are carbamates

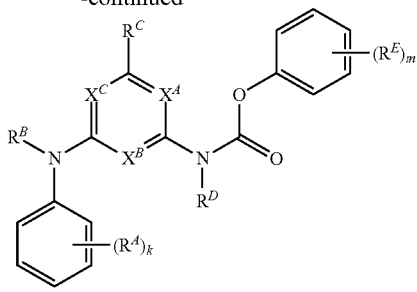

A SIK inhibitor of Formula (III-A) can be prepared using methods similar to the methods of preparing a compound of Formula (II).

General.

The urea formation was performed using a Biotage® Initiator⁺ Microwave Synthesizer. All reactions were monitored by thin layer chromatography (TLC) with 0.25 mm E. Merck pre-coated silica gel plates (60 $F_{254}$) and Waters LC/MS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ C18 column (4.6×50 mm, 5 μm particle size) (solvent gradient=97% A at 0 min, 0% A at 5 min; solvent A=0.035% TFA in water; solvent B=0.035% TFA in acetonitrile; flow rate=2.5 mL/min). Retention time (Rt) was determined using the above Waters LC/MS system. Purification of reaction products was carried out by flash chromatography using CombiFlash® Rf with Teledyne Isco RediSep® Rf High Performance Gold or Silicycle SiliaSep™ High Performance columns (4 g, 12 g, 24 g, 40 g, 80 g, or 120 g). The purity of all compounds was over 95% and was analyzed with Waters LCMS system. ¹H NMR and ¹³C NMR spectra were obtained using a Varian Inova-600 (600 MHz for ¹H and 125 MHz for ¹³C) or Varian Inova-400 (400 MHz for ¹H) spectrometer. Chemical shifts are reported relative to chloroform (δ=7.24 ppm) or dimethyl sulfoxide (δ=2.50 ppm) for ¹H NMR and relative to dimethyl sulfoxide (δ=39.51 ppm) for ¹³C NMR. Data are reported as (br=broad, s=singlet, d=doublet, t=triplet, q=quartet, m=multiplet).

Example 1.1. Preparation of SIK Inhibitor I-7

In an exemplary experiment, SIK inhibitor I-7 was prepared according to the methods shown in Scheme 4.

Scheme 4. An exemplary preparation of SIK inhibitor I-7

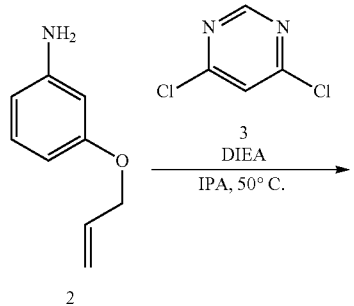

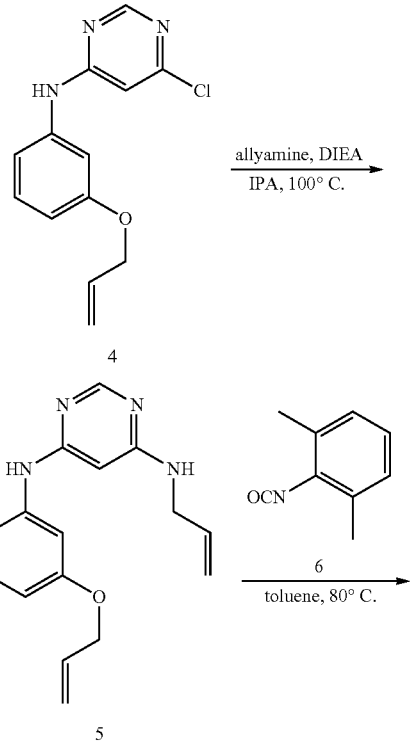

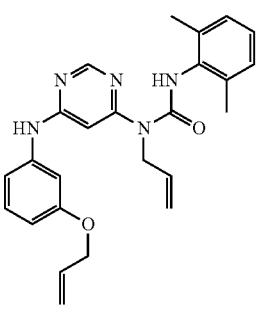

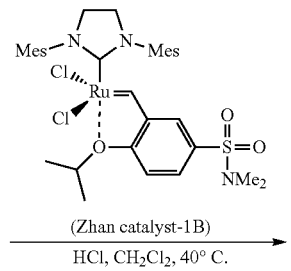

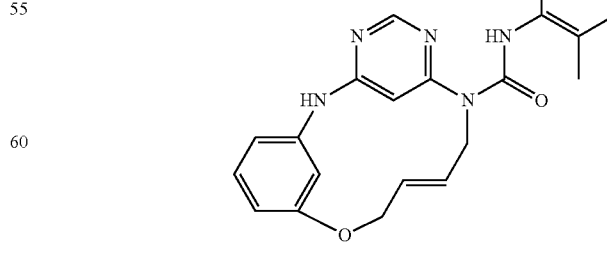

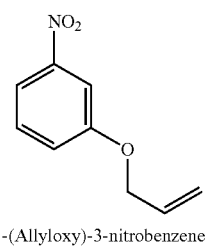

1-(Allyloxy)-3-nitrobenzene (1)

To a solution of 3-nitrophenol (5.0 g, 33.79 mmol) and K$_2$CO$_3$ (14.9 g, 107.88 mmol) in acetone (50 mL) was added allyl bromide. The reaction mixture was refluxed for 6 h and partitioned between ethyl acetate and water. The organic layer was dried over anhydrous sodium sulfate, filtered through a pad of CELITE, and concentrated under reduced pressure. The residue was purified by column chromatography on silica gel (0/100 to 20/80, ethyl acetate:hexane) to afford 1-(allyloxy)-3-nitrobenzene (4.3 g, 66% yield) as a yellow oil.

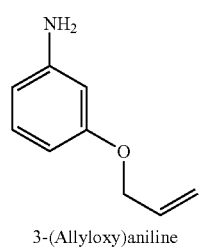

3-(Allyloxy)aniline (2)

To a solution 1-(allyloxy)-3-nitrobenzene (3.0 g, 16.75 mmol) and fine iron powder (2.81 g, 50.26 mmol) in EtOH (30 mL) was added NH$_4$Cl solution (5.4 g, 100.52 mmol, in 6 mL water). The reaction mixture was refluxed for 6 h, and EtOH was removed from the reaction mixture under reduced pressure. The residue was basified with a NaHCO$_3$ solution until pH 7-8 and extracted with CH$_2$Cl$_2$. The organic layer was dried over anhydrous sodium sulfate, filtered through a pad of CELITE, and concentrated under reduced pressure. The residue was purified by column chromatography on silica gel (10/100 to 40/60, ethyl acetate:hexane) to afford 3-(allyloxy)aniline (2.3 g; yield, 92%) as a brown oil. Rt: 1.53 min; MS m/z: 149.92 [M+1]$^+$.

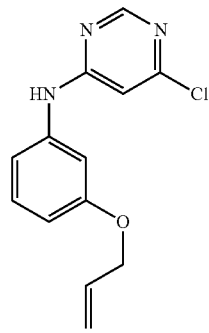

N-(3-(Allyloxy)phenyl)-6-chloropyrimidin-4-amine (4)

To a solution of 4,6-dichloropyrimidine (1.2 g, 8.05 mmol) in 2-propanol (IPA, 34 mL) was added 2,4-dimethoxyaniline (1.0 g, 6.71 mmol) and N,N-diisopropylethylamine (DIEA, 2.82 ml, 16.22 mmol). The reaction mixture was stirred at 50° C. for 24 h and partitioned between ethyl acetate and a saturated aqueous sodium bicarbonate solution. The organic layer was washed with brine, dried over anhydrous sodium sulfate, filtered through a pad of CELITE, and concentrated under reduced pressure. The residue was purified by column chromatography on silica gel (1:9 to 3:7, ethyl acetate/hexane) to afford N-(3-(allyloxy)phenyl)-6-chloropyrimidin-4-amine (1.1 g, 63% yield) as a violet solid. Rt: 3.37 min; MS m/z: 262.29 [M+1]$^+$.

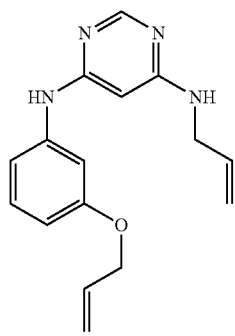

N4-Allyl-N6-(3-(allyloxy)phenyl)pyrimidine-4,6-diamine (5)

To a solution of N-(3-(allyloxy)phenyl)-6-chloropyrimidin-4-amine (1.0 g, 3.82 mmol) in 2-propanol (10 mL) was added allylamine (0.428 mL, 5.73 mmol) and N,N-diisopropylethylamine (1.39 ml, 7.64 mmol). The reaction mixture was stirred at 100° C. for 24 h and partitioned between ethyl acetate and a saturated aqueous sodium bicarbonate solution. The organic layer was washed with brine, dried over anhydrous sodium sulfate, filtered through a pad of CELITE, and concentrated under reduced pressure. The residue was purified by column chromatography on silica gel (1:9 to 5:5, ethyl acetate/hexane) to afford N4-allyl-N6-(3-(allyloxy)phenyl)pyrimidine-4,6-diamine (830 mg, 77% yield).

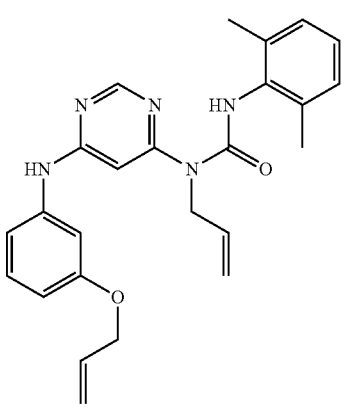

1-Allyl-1-(6-((3-(allyloxy)phenyl)amino)pyrimidin-4-yl)-3-(2,6-dimethylphenyl)urea (7)

To a solution of N4-allyl-N6-(3-(allyloxy)phenyl)pyrimidine-4,6-diamine (200 mg, 0.71 mmol) in toluene (2 mL) was added 2,6-dimethylphenyl isocyanate (0.11 mL, 0.85 mmol) and heated at 80° C. for 6 h. The reaction mixture was concentrated under reduced pressure. The residue was purified by column chromatography on silica gel (0:100 to 3:97, methanol/dichloromethane) to afford 1-allyl-1-(6-((3-(allyloxy)phenyl)amino)pyrimidin-4-yl)-3-(2,6-dimethylphenyl)urea (160 mg, 53% yield) as an off-white solid.

SIK Inhibitor I-7

To a solution of 1-allyl-1-(6-((3-(allyloxy)phenyl)amino)pyrimidin-4-yl)-3-(2,6-dimethylphenyl)urea (100 mg, 0.23 mmol) in dichloromethane (10 mL) was added 6 N HCl solution (1 mL) and degassed. Zhan catayst-1B (17 mg, 0.02 mmol) was added in two portions at 2 h intervals. The resulting mixture was heated at 40° C. for 8 h and partitioned between methylene chloride and water. The organic layer was washed with brine, dried over anhydrous sodium sulfate, filtered through a pad of CELITE, and concentrated under reduced pressure. The crude product was purified by preparative HPLC to afford SIK inhibitor I-7 (36 mg, 39% yield) as an off-white solid. Rt: 3.63 min; $^1$H NMR 400 MHz (DMSO-$d_6$) δ 12.29 (s, 1H), 9.84 (s, 1H), 8.51 (s, 1H), 7.29 (t, J=8.0 Hz, 1H), 7.15 (m, 3H), 6.88 (m, 1H), 6.74 (m, 2H), 6.41 (s, 1H), 5.85 (m, 1H), 5.66 (m, 1H), 4.95 (m, 2H), 4.16 (m, 2H), 2.57 (s, 6H) ppm; MS m/z: 402.45 [M+1]$^+$.

Example 1.2. Preparation of SIK Inhibitors I-2 to I-6

In another set of experiments, SIK inhibitors I-2 to I-6 were prepared using methods similar to the ones of Example 1.1. Exemplary analytical data of these SIK inhibitors are shown in Table 1. Exemplary analytical data of additional SIK inhibitors of Formula (I) are also shown in Table 1.

TABLE 1

Exemplary analytical data of select SIK inhibitors of Formula (I)

| SIK inhibitor | LC/MS retention time (min) | $^1$H NMR chemical shift, 400 MHz or 500 MHz$^a$, DMSO-$d_6$ or CDCl$_3$$^b$ (ppm) | MS m/z, [M + 1]$^+$ |
|---|---|---|---|
| I-2 | 2.10 | 9.57 (s, 1H), 8.41 (d, J = 6.0 Hz, 1H), 7.87 (d, J = 2.0 Hz, 1H), 7.29 (d, J = 5.6 Hz, 1H), 7.19 (m, 3H), 7.04 (dd, J = 2.8 Hz, J = 8.4 Hz, 1H), 6.98 (d, J = 8.4 Hz, 1H), 5.96 (m, 1H), 5.80 (m, 1H), 4.71 (m, 2H), 4.51 (m, 2H), 4.26 (t, 2H), 4.23 (d, J = 6.4 Hz, 2H), 3.63 (m, 2H), 3.29 (m, 4H), 3.22 (m, 6H), 2.21 (s, 6H), 1.29 (t, J = 6.8 Hz, 3H) | 573.65 |
| I-3 | 2.15 | 9.56 (s, 1H), 8.39 (d, J = 5.6 Hz, 1H), 7.87 (d, J = 2.4 Hz, 1H), 7.53 (d, J = 6.0 Hz, 1H), 7.21 (m, 3H), 7.10 (m, 2H), 5.86 (m, 2H), 4.96 (m, 2H), 4.65 (m, 2H), 4.28 (t, 2H), 4.17 (d, J = 6.4 Hz, 2H), 3.60 (m, 2H), 3.28 (m, 4H), 3.22 (m, 6H), 2.22 (s, 6H), 1.27 (t, J = 6.8 Hz, 3H) | 573.63 |
| I-4 | 2.22 | | 560.65 |
| I-5 | 2.28 | | 560.58 |
| I-6 | 2.37 | 9.66 (s, 1H), 8.42 (d, J = 2.4 Hz, 1H), 8.39 (d, J = 5.6 Hz, 1H), 7.51 (d, J = 6.0 Hz, 1H), 7.23 (m, 3H), 7.10 (dd, J = 2.8 Hz, J = 8.4 Hz, 1H), 7.06 (d, J = 8.4 Hz, 1H), 4.86 (s, 2H), 4.37 (m, 2H), 4.32 (m, 2H), 4.03 (m, 2H), 3.80 (m, 4H), 3.65 (m, 2H), 3.35 (m, 4H), 2.21 (s, 6H), 2.13 (m, 2H), 1.80 (m, 2H) | 548.61 |
| YKL-05-120 | | $^a$ 9.82 (s, 1H), 9.34 (s, 1H), 8.16 (s, 1H), 7.18 (m, 3H), 7.06 (t, J = 6.5 Hz, 1H), 6.67 (d, J = 7.0 Hz, 1H), 6.41 (dd, J$_1$ = 8.0 Hz, J$_2$ = 2.0 Hz, 1H), 5.58 (m, 2H), 5.10 (dd, J$_1$ = 14.0 Hz, J$_2$ = 10.0 Hz, 1H), 4.78-4.86 (m, 1H), 4.62-4.70 (m, 2H), 4.55 (d, J = 14.5 Hz, 1H), 4.44 (d, J = 15.0 Hz, 1H), 2.23 (s, 3H), 2.16 (s, 3H) | 414.3 |
| YKL-05-200-1 | | 9.60 (s, 1H), 8.14 (s, 1H), 7.88 (s, 1H), 7.26 (t, J = 7.6 Hz, 1H), 7.18-7.15 (m, 3H), 6.98 (d, J = 8.0 Hz, 1H), 6.85 (d, J = 7.6 Hz, 1H), 5.80-5.74 (m, 1H), 5.60-5.54 (m, 1H), 4.61 (s, 2H), 4.56 (d, J = 3.6 Hz, 2H), 4.52 (s, 2H), 4.17 (d, J = 6.0 Hz, 2H), 2.20 (s, 6H) | 428.4 |
| YKL-05-200-2 | | $^b$ 7.75 (s, 1H), 7.62 (s, 1H), 7.36 (t, J = 7.6 Hz, 1H), 7.25-7.14 (m, 4H), 7.07(d, J = 7.6 Hz, 3H), 5.75-5.59 (m, 2H), 4.79 (s, 2H), 4.51 (s, 2H), 4.46 (d, J = 5.6 Hz, 2H), 4.20 (d, J = 6.8 Hz, 4H), 2.28 (s, 6H) | 428.4 |
| YKL-05-201-1 | | 9.69 (s, 1H), 8.17 (s, 1H), 7.86 (s, 1H), 7.46 (dd, J$_1$ = 6.8 Hz, J$_2$ = 2.8 Hz, 1H), 7.36-7.31 (m, 2H), 7.27 (t, J = 8.0 Hz, 1H), 6.98 (d, J = 9.2 Hz, 1H), 6.86 (d, J = 7.6 Hz, 1H), 5.79-5.74 (m, 1H), 5.58-5.54 (m, 1H), 4.61 (s, 2H), 4.57 (s, 4H), 4.16 (d, J = 6.0 Hz, 2H), 2.27 (s, 3H) | 448.3 |
| YKL-05-201-2 | | 9.58 (s, 1H), 8.17 (s, 1H), 7.74 (s, 1H), 7.45 (dd, J$_1$ = 6.4 Hz, J$_2$ = 2.8 Hz, 1H), 7.36-7.31 (m, 2H), 7.20 (t, J = 8.0 Hz, 1H), 6.91 (d, J = 8.8 Hz, 1H), 6.82 (d, J = 7.2 Hz, 1H), 5.82-5.75 (m, 1H), 5.66-5.60 (m, 1H), 4.69 (s, 2H), 4.57 (s, 2H), 4.33 (d, J = 5.6 Hz, 2H), 4.11 (d, J = 6.8 Hz, 2H), 2.27 (s, 3H) | 448.3 |

TABLE 1-continued

Exemplary analytical data of select SIK inhibitors of Formula (I)

| SIK inhibitor | LC/MS retention time (min) | $^1$H NMR chemical shift, 400 MHz or 500 MHz$^a$, DMSO-d$_6$ or CDCl$_3$$^b$ (ppm) | MS m/z, [M + 1]$^+$ |
|---|---|---|---|
| YKL-05-202-1 | | 9.64 (s, 1H), 9.21 (s, 1H), 8.15 (s, 1H), 7.46-7.44 (m, 1H), 7.34-7.33 (m, 2H), 6.74 (d, J = 8.4 Hz, 1H), 6.62 (dd, J$_1$ = 8.4 Hz, J$_2$ = 2.0 Hz, 1H), 5.66-5.49 (m, 2H), 5.11-5.04 (m, 1H), 4.86-4.78 (m, 1H), 4.72-4.59 (m, 3H), 4.46 (dd, J$_1$ = 14.0 Hz, J$_2$ = 5.2 Hz, 1H), 2.93 (s, 4H), 2.46 (s, 4H), 2.30-2.22 (m, 6H) | 532.4 |
| YKL-05-202-2 | | 8.12 (s, 1H), 7.52 (d, J = 2.0 Hz, 1H), 7.43-7.41 (m, 1H), 7.32-7.28 (m, 2H), 6.75 (d, J = 8.4 Hz, 1H), 6.53 (dd, J$_1$ = 8.4 Hz, J$_2$ = 2.0 Hz, 1H), 5.80 (dt, J$_1$ = 16 Hz, J$_2$ = 4.0 Hz, 1H), 5.49-5.45 (m, 1H), 4.80 (d, J = 5.2 Hz, 2H), 4.55-4.47 (m, 4H), 2.95 (s, 4H), 2.62 (s, 4H), 2.32 (s, 3H), 2.22 (s, 3H) | 532.4 |
| YKL-05-203-1 | | 9.81 (s, 1H), 9.32 (s, 1H), 8.19 (s, 1H), 7.46-7.45 (m, 1H), 7.35-7.33 (m, 2H), 7.06 (t, J = 8.0 Hz, 1H), 6.68 (d, J = 8.0 Hz, 1H), 6.42 (dd, J$_1$ = 8.8 Hz, J$_2$ = 1.6 Hz, 1H), 5.65-5.50 (m, 2H), 5.13-5.07 (m, 1H), 4.89-4.81 (m, 1H), 4.74-4.63 (m, 2H), 4.57-4.47 (m, 2H), 2.31 (s, 1.5H), 2.24 (s, 1.5H) | 434.3 |
| YKL-05-203-2 | | 9.72 (s, 1H), 8.18 (s, 1H), 7.64 (s, 1H), 7.44 (dd, J$_1$ = 6.4 Hz, J$_2$ = 4.0 Hz, 1H), 7.34-7.32 (m, 2H), 7.06 (t, J = 8.4 Hz, 1H), 6.59 (d, J = 7.6 Hz, 1H), 6.47 (d, J = 8.4 Hz, 1H), 5.86 (dt, J$_1$ = 15.6 Hz, J$_2$ = 4.4 Hz, 1H), 5.52 (dt, J$_1$ = 16.4 Hz, J$_2$ = 6.4 Hz, 1H), 4.77 (d, J = 4.8 Hz, 2H), 4.55 (dd, J$_1$ = 18.4 Hz, J$_2$ = 14.4 Hz, 4H), 2.25 (s, 3H) | 434.3 |
| YKL-05-204-1 | | 9.61 (s, 1H), 9.23 (d, J = 2.0 Hz 1H), 8.39 (s, 1H), 8.12 (s, 1H), 7.17(m, 3H), 6.73 (d, J = 8.4 Hz, 1H), 6.61(dd, J$_1$ = 8.4 Hz, J$_2$ = 2.0 Hz, 1H), 5.63 (t, J = 10.8 Hz, 1H), 5.54 (t, J = 9.6 Hz, 1H), 5.07 (dd, J$_1$ = 14 Hz, J$_2$ = 10.8 Hz, 1H), 4.80 (dd, J$_1$ = 16 Hz, J$_2$ = 9.6 Hz, 1H), 4.67-4.61 (m, 3H), 4.40 (d, J = 14.4 Hz, 1H), 2.92 (s, 4H), 2.45 (s, 4H), 2.22 (d, J = 5.6 Hz, 6H), 2.15 (s, 3H) | 512.4 |
| YKL-05-204-2 | | 9.47 (s, 1H), 8.41 (s, 1H), 8.12 (s, 1H), 7.57 (d, J = 1.6 Hz, 1H), 7.16 (s, 3H), 6.73 (d, J = 8.4 Hz, 1H), 6.53 (dd, J$_1$ = 8.4 Hz, J$_2$ = 1.6 Hz, 1H), 5.84 (dt, J$_1$ = 16.4 Hz, J$_2$ = 4.8 Hz, 1H), 5.48 (dt, J$_1$ = 16.4 Hz, J$_2$ = 5.6 Hz, 1H), 4.81 (d, J = 5.6 Hz, 2H), 4.51-4.47 (m, 4H), 2.92 (m, 4H), 2.45 (m, 4H), 2.21 (s, 3H), 2.18 (s, 6H) | 512.4 |
| YKL-05-205 | | | 416.4 |

Example 1.3. Preparation of SIK Inhibitor II-1

In an exemplary experiment, SIK inhibitor II-1 was prepared according to the method shown in Scheme 2.

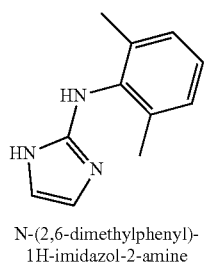

N-(2,6-dimethylphenyl)-1H-imidazol-2-amine

To a solution of cyanogen bromide (25 g, 236.03 mmol) in hexane (80 mL) was added a solution of the aminoacetaldehyde diethyl acetal (34.3 mL, 236.03 mmol) in diethyl ether (80 mL) at room temperature. The resulting mixture was stirred overnight. A white solid was formed and was removed by filtration and washed with diethyl ether. The filtrate was concentrated and purified by flash chromatography on silica gel (eluted with 0/100 to 5/95 methanol/dichloromethane) to afford N-(2,2-diethyloxyethyl)carbodiimide (27 g, 72% yield) as a bright yellow oil. Rt (retention time)=1.82 min; MS m/z: 159.20 [M+1].

To a solution of 2,6-dimethylaniline (5.0 g, 41.29 mmol) and N-(2,2-diethyloxyethyl)carbodiimide (7.8 g, 49.55 mmol) in ethanol (100 mL) was added methanesulfonic acid (3.2 mL, 49.55 mL). The resulting mixture was refluxed for 20 h, concentrated, and dissolved in a 6.0 N HCl solution (30 mL). After stirring for 8 h, the resulting mixture was neutralized with a 10 N NaOH solution at 0° C. to pH 6. A saturated sodium carbonate solution was added so that the pH of the resulting mixture was about 13. A solid was produced and was filtered and dried to afford N-(2,6-dimethylphenyl)-1H-imidazol-2-amine (3.8 g, 49% yield). Rt=1.57 min; $^1$H NMR (600 MHz; DMSO-d$_6$) δ 10.25 (s, 1H), 7.28 (s, 1H), 6.97 (m, 2H), 6.92 (m, 1H), 6.49 (s, 1H), 6.36 (s, 1H), 2.07 (s, 6H) ppm; MS m/z: 188.23 [M+1].

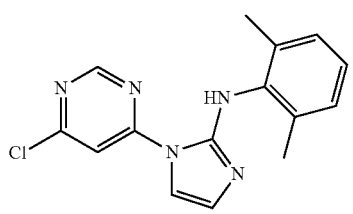

1-(6-Chloropyrimidin-4-yl)-N-(2,6-dimethylphenyl)-1H-imidazol-2-amine

To a solution of N-(2,6-dimethylphenyl)-1H-imidazol-2-amine (1.0 g, 5.34 mmol) and N,N-diisopropylethylamine (1.8 mL, 10.69 mmol) in 2-butanol (10 mL) was added 4,6-dichloropyrimidine (1.2 g, 8.02 mmol). The resulting mixture was heated at 120° C. overnight, cooled, and partitioned between a saturated aqueous potassium carbonate solution and a mixed solvents of $CHCl_3$/2-propanol (4/1). The organic phase was separated, dried over anhydrous sodium sulfate, filtered through a pad of CELITE, and concentrated. The residue was purified by flash chromatography on silica gel (eluted with 1/99 to 5/95 ammonia (7.0 N in methanol) in methanol/dichloromethane) to afford 1-(6-chloropyrimidin-4-yl)-N-(2,6-dimethylphenyl)-1H-imidazol-2-amine (1.3 g, 81% yield) as an off-white solid. Rt=1.97 min, $^1$H NMR (600 MHz; DMSO-$d_6$) δ 9.46 (s, 1H), 9.01 (d, J=4.2 Hz, 1H), 8.15 (d, J=4.2 Hz, 1H), 7.71 (m, 1H), 7.16 (m, 3H), 6.70 (s, 1H), 2.25 (m, 6H) ppm; MS m/z: 300.19 [M+1].

SIK Inhibitor II-1

To a solution of 1-(6-chloropyrimidin-4-yl)-N-(2,6-dimethylphenyl)-1H-imidazol-2-amine (100 mg, 0.33 mmol) and 4-(4-ethylpiperazin-1-yl)aniline (68 mg, 0.33 mmol) in 2-butanol (1 mL) was added trifluoroacetic acid (TFA, 0.1 mL). The resulting mixture was stirred at 120° C. for 4 h, concentrated, and diluted with dimethyl sulfoxide (6 mL). The resulting mixture was purified with preparative HPLC to afford 6-(2-((2,6-dimethylphenyl)amino)-1H-imidazol-1-yl)-N-(4-(4-ethylpiperazin-1-yl)phenyl)pyrimidin-4-amine TFA salt (78 mg, 41% yield) as an off-white solid. Rt=1.93 min; $^1$H NMR (600 MHz; DMSO-$d_6$) δ 10.71 (br, 1H), 10.02 (s, 1H), 9.97 (br, 1H), 8.54 (s, 1H), 7.65 (s, 1H), 7.48 (d, J=6.6 Hz, 2H), 7.20 (m, 4H), 7.10 (s, 1H), 7.01 (d, J=9.0 Hz, 2H), 6.95 (s, 1H), 3.78 (m, 2H), 3.56 (m, 2H), 3.17 (m, 2H), 3.09 (m, 2H), 2.94 (m, 2H), 2.18 (s, 6H), 1.23 (m, 3H) ppm; MS m/z: 469.46 [M+1].

Example 1.4. Preparation of SIK Inhibitors II-2 to II-12

In another set of experiments, SIK inhibitors II-2 to II-12 were prepared using methods similar to the ones of Example 1.3. Exemplary analytical data of these SIK inhibitors are shown in Table 2.

TABLE 2

Exemplary analytical data of SIK inhibitors II-2 to II-12

| SIK inhibitor | LC/MS retention time (min) | MS m/z, [M + 1]+ |
|---|---|---|
| II-2 | 3.05 | 451.31 |
| II-3 | 3.02 | 431.40 |
| II-4 | 2.73 | 381.31 |
| II-5 | | 581.7 |
| II-6 | | 567.7 |
| II-7 | | 594.7 |
| II-8 | | 581.6 |
| II-9 | | 537.7 |
| II-10 | | 606.7 |
| II-11 | | 636.6 |
| II-12 | | 552.7 |

Example 1.5. Preparation of SIK Inhibitor III-1

In an exemplary experiment, SIK inhibitor III-1 was prepared according to the methods shown in Scheme 5.

Scheme 5. An exemplary preparation of SIK inhibitor III-1

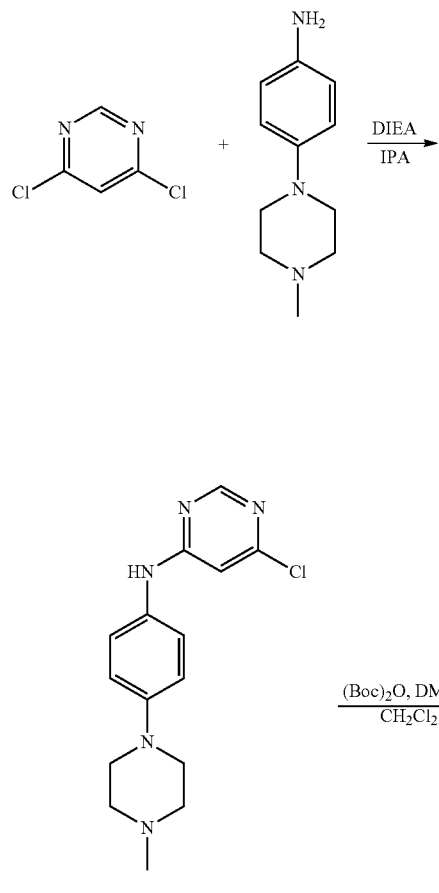

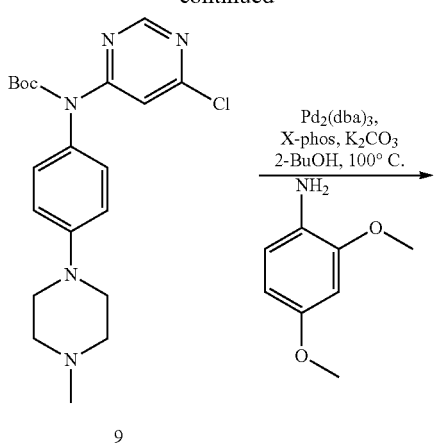

9

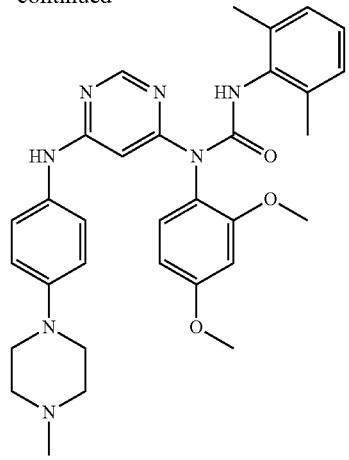

III-1

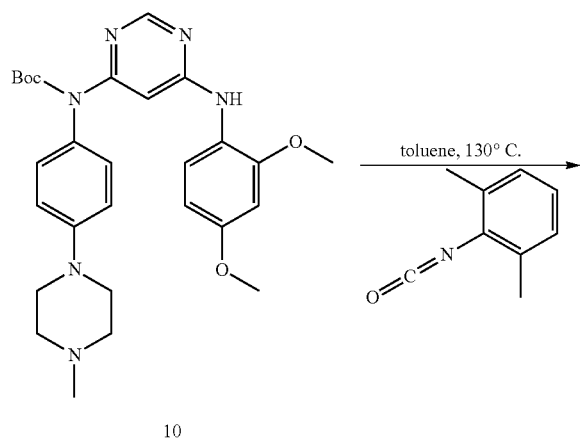

10

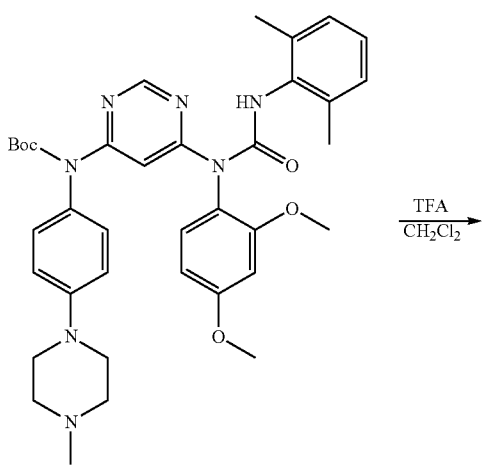

11

6-Chloro-N-(4-(4-methylpiperazin-1-yl)phenyl)pyrimidin-4-amine (8)

To a solution of 4-(4-methylpiperazin-1-yl)aniline (5.0 g, 26.16 mmol) and N,N-diisopropylethylamine (6.8 g, 39.24 mmol) in 2-propanol (50 mL) was added 4,6-dichloropyrimidine (5.8 g, 39.24 mmol) and stirred at room temperature for 24 h. The reaction mixture was partitioned between saturated aqueous potassium carbonate solution and CHCl$_3$/2-propanol (4/1) solvents. The organic phase was separated, dried over anhydrous sodium sulfate, filtered through a pad of CELITE, and concentrated. The residue was purified by column chromatography on silica gel (1/99 to 7/93, ammonia solution 7.0 N in methanol/dichloromethane) to afford 6-chloro-N-(4-(4-methylpiperazin-1-yl)phenyl)pyrimidin-4-amine (6.2 g, 78% yield) as a dark violet solid. Rt=1.68 min, $^1$H NMR 600 MHz (CDCl$_3$) δ 8.32 (s, 1H), 7.09 (d, J=9.0 Hz, 2H), 6.91 (br, 1H), 6.89 (d, J=9.0 Hz, 2H), 6.44 (s, 1H), 3.17 (m, 4H), 2.53 (m, 4H), 2.30 (s, 3H) ppm; MS m/z: 304.16 [M+1].

tert-Butyl (6-chloropyrimidin-4-yl)(4-(4-methylpiperazin-1-yl)phenyl)carbamate (9)

To a solution of 6-chloro-N-(4-(4-methylpiperazin-1-yl)phenyl)pyrimidin-4-amine (6.0 g, 19.79 mmol) and 4-dimethylaminopyridine (3.6 g, 29.69 mmol) in dichloromethane (60 mL) was added di-tert-butyl dicarbonate (5.2 g, 23.75 mmol). The mixture was stirred at room temperature for 4 h and partitioned between ethyl acetate and water. The organic layer was washed with brine, dried over anhydrous sodium sulfate, filtered through a pad of CELITE, and concentrated under reduced pressure. The residue was purified by column chromatography on silica gel (1/99 to 15/85, methanol/dichloromethane) to afford tert-butyl (6-chloropyrimidin-4-yl)(4-(4-methylpiperazin-1-yl)phenyl)carbamate (7.1 g, 89% yield) as an off-white solid. Rt=2.45 min, $^1$H NMR 600 MHz (CDCl$_3$) δ 8.51 (s, 1H), 7.94 (s, 1H), 6.91 (d, J=7.8 Hz, 2H), 6.87 (d, J=8.4 Hz, 2H), 3.19 (m, 4H), 2.51 (m, 4H), 2.29 (s, 3H), 1.35 (s, 9H) ppm; MS m/z: 404.47 [M+1].

tert-Butyl (6-((2,4-dimethoxyphenyl)amino)pyrimidin-4-yl)(4-(4-methylpiperazin-1-yl)phenyl)carbamate (10)

A mixture of tert-butyl (6-chloropyrimidin-4-yl)(4-(4-methylpiperazin-1-yl)phenyl)carbamate (3.0 g, 7.44 mmol), 2,4-dimethoxyaniline (2.3 g, 14.88 mmol), and K$_2$CO$_3$ (4.1 g, 29.76 mmol) in 2-butanol (30 mL) was degassed for 10 min. To the reaction mixture were added Pd$_2$(dba)$_3$ (408 mg, 0.45 mmol) and X-phos (2-dicyclohexylphosphino-2',4',6'-triisopropylbiphenyl, 319 mg, 0.67 mmol). The resulting mixture was heated at 100° C. for 4 hours and filtered with a pad of CELITE. The filtrate was concentrated under reduced pressure. The residue was purified by column chromatography on silica gel (3/97 to 15/85, methanol/dichloromethane) to afford tert-butyl (6-((2,4-dimethoxyphenyl)amino)pyrimidin-4-yl)(4-(4-methylpiperazin-1-yl)phenyl)carbamate (2.2 g, 57% yield) as a yellow solid. Rt=2.13 min; MS m/z: 521.43 [M+1].

tert-Butyl (6-(1-(2,4-dimethoxyphenyl)-3-(2,6-dimethylphenyl)ureido)pyrimidin-4-yl)(4-(4-methylpiperazin-1-yl)phenyl)carbamate (11)

A 5 mL microwave vial was charged with tert-butyl (6-((2,4-dimethoxyphenyl)amino)pyrimidin-4-yl)(4-(4-methylpiperazin-1-yl)phenyl)carbamate (300 mg, 0.58 mmol), 2,6-dimethylphenyl isocyanate (0.32 mL, 2.31 mmol), and toluene (2 mL). The vial was sealed and heated at 130° C. for 1 h. To the vial was additionally added 2,6-dimethylphenyl isocyanate (0.16 mL, 2.35 mmol), and the resulting mixture was heated at 130° C. for 1 h. The reaction mixture was concentrated under reduced pressure. The residue was purified by column chromatography on silica gel (1/99 to 10/90, methanol/dichloromethane) to afford tert-butyl (6-(1-(2,4-dimethoxyphenyl)-3-(2,6-dimethylphenyl)ureido)pyrimidin-4-yl)(4-(4-methylpiperazin-1-yl)phenyl)carbamate (290 mg, 75% yield) as an off-white solid. Rt=2.85 min; MS m/z: 668.48 [M+1].

1-(2,4-Dimethoxyphenyl)-3-(2,6-dimethylphenyl)-1-(6-((4-(4-methylpiperazin-1-yl)phenyl)amino)pyrimidin-4-yl)urea (III-1)

To a solution of tert-butyl (6-(1-(2,4-dimethoxyphenyl)-3-(2,6-dimethylphenyl)ureido)pyrimidin-4-yl)(4-(4-methylpiperazin-1-yl)phenyl)carbamate (200 mg, 0.30 mmol) in dichloromethane (2 mL) was added trifluoroacetic acid (0.11 mL, 1.50 mmol). The resulting mixture was stirred for 4 h, concentrated, and diluted with dimethyl sulfoxide (6 mL). The resulting mixture was purified with preparative HPLC to afford 1-(2,4-dimethoxyphenyl)-3-(2,6-dimethylphenyl)-1-(6-((4-(4-methylpiperazin-1-yl)phenyl)amino)pyrimidin-4-yl)urea (186 mg, 93% yield) as an off-white TFA salt. Rt=2.25 min; $^1$H NMR 600 MHz (DMSO-d$_6$) δ 11.54 (s, 1H), 9.19 (s, 1H), 8.38 (s, 1H), 7.29 (m, 2H), 7.15 (d, J=9.0 Hz, 1H), 7.07 (m, 3H), 6.85 (d, J=8.4 Hz, 2H), 6.74 (d, J=2.4 Hz, 1H), 6.63 (dd, J=8.4 Hz, J=2.4 Hz, 1H), 5.70 (s, 1H), 3.82 (s, 3H), 3.74 (s, 3H), 3.05 (m, 4H), 2.44 (m, 4H), 2.23 (s, 6H), 2.22 (s, 3H) ppm; $^{13}$C NMR 125 MHz (DMSO-d$_6$) δ 161.24, 160.34, 160.28, 156.51, 156.03, 152.59, 146.88, 135.46, 134.90, 131.38, 127.64, 125.99, 121.43, 120.62, 115.76, 105.42, 99.68, 55.75, 55.41, 48.57, 45.68, 18.30 ppm; MS m/z: 568.41 [M+1].

Example 1.6. Preparation of SIK Inhibitor III-2

In an exemplary experiment, SIK inhibitor III-2 was prepared according to the methods shown in Scheme 6.

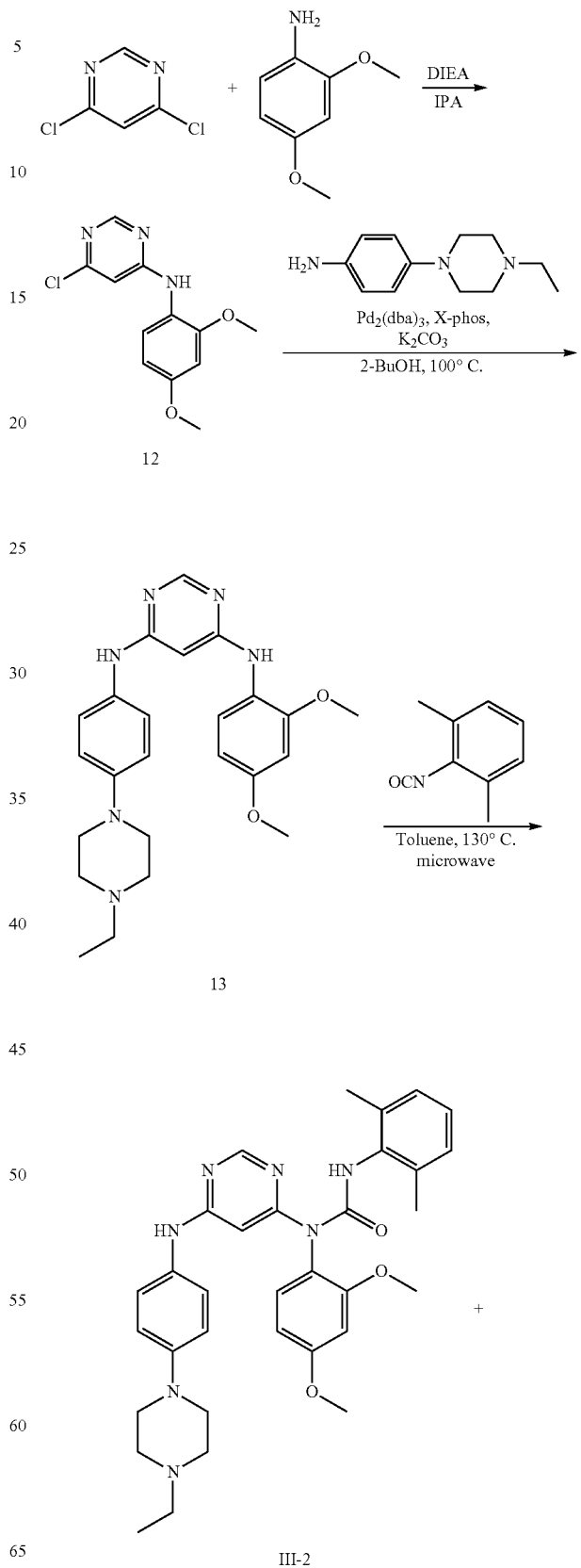

Scheme 6. An exemplary preparation of SIK inhibitor III-2

1-(2,4-Dimethoxyphenyl)-3-(2,6-dimethylphenyl)-1-(6-((4-(4-ethylpiperazin-1-yl)phenyl)amino)pyrimidin-4-yl)urea (III-2)

A 5 mL microwave vial was charged with N4-(2,4-dimethoxyphenyl)-N6-(4-(4-ethylpiperazin-1-yl)phenyl)pyrimidine-4,6-diamine (200 mg, 0.46 mmol), 2,6-dimethylphenyl isocyanate (338 mg, 2.30 mmol) and toluene (2 mL). The vial was sealed and heated at 130° C. for 1 h. To the vial was additionally added 2,6-dimethylphenyl isocyanate (338 mg, 2.30 mmol), and the resulting mixture was heated at 130° C. for 1 h. Two regioisomers, 1-(2,4-dimethoxyphenyl)-3-(2,6-dimethylphenyl)-1-(6-((4-(4-ethylpiperazin-1-yl)phenyl)amino)pyrimidin-4-yl)urea and 1-(6-((2,4-dimethoxyphenyl)amino)pyrimidin-4-yl)-3-(2,6-dimethylphenyl)-1-(4-(4-ethylpiperazin-1-yl)phenyl)urea were generated in a ratio of 1:1, as indicated by HPLC analysis. The reaction mixture was concentrated under reduced pressure. The residue was purified by column chromatography on silica gel (1:99 to 7:93, methanol/dichloromethane) and additionally purified with HPLC to afford 1-(2,4-dimethoxyphenyl)-3-(2,6-dimethylphenyl)-1-(6-((4-(4-ethylpiperazin-1-yl)phenyl)amino)pyrimidin-4-yl)urea (72 mg, 23% yield) as an off-white solid. Rt=2.28 min; $^1$H NMR 600 MHz (DMSO-$d_6$) δ 9.44 (br, 1H), 9.36 (br, 1H), 8.39 (s, 1H), 7.38 (m, 2H), 7.17 (d, J=8.4 Hz, 1H), 7.06 (m, 3H), 6.93 (d, J=8.4 Hz, 2H), 6.74 (m, 1H), 6.63 (d, J=6.6 Hz, 1H), 5.76 (s, 1H), 3.90 (m, 2H), 3.72 (s, 3H), 3.69 (s, 3H), 3.61 (m, 2H), 3.22 (m, 2H), 3.11 (m, 2H), 3.00 (m, 2H), 2.20 (s, 6H), 1.23 (m, 3H) ppm; MS m/z: 582.64 [M+1].

1-(6-((2,4-Dimethoxyphenyl)amino)pyrimidin-4-yl)-3-(2,6-dimethylphenyl)-1-(4-(4-ethylpiperazin-1-yl)phenyl)urea Rt=2.38 min; $^1$H NMR 600 MHz (DMSO-$d_6$) δ 9.65 (br, 1H), 9.35 (br, 1H), 8.32 (s, 1H), 8.31 (s, 1H), 7.24 (br, 1H), 7.18 (d, J=7.8 Hz, 2H), 7.11 (d, J=7.8 Hz, 2H), 7.06 (m, 3H), 6.54 (s, 1H), 6.45 (d, J=8.4 Hz, 1H), 5.56 (br, 1H), 3.90 (m, 2H), 3.72 (s, 3H), 3.69 (s, 3H), 3.61 (m, 2H), 3.28 (m, 2H), 3.11 (m, 2H), 3.00 (m, 2H), 2.20 (s, 6H), 1.25 (m, 3H) ppm; MS m/z: 582.64 [M+1].

Example 1.7. Preparation of SIK Inhibitor III-3

In an exemplary experiment, SIK inhibitor III-3 was prepared according to the methods shown in Scheme 7.

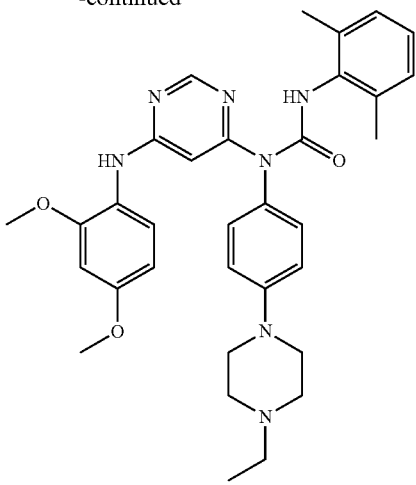

6-Chloro-N-(2,4-dimethoxyphenyl)pyrimidin-4-amine (12)

To a solution of 4,6-dichloropyrimidine (1.2 g, 8.11 mmol) in 2-propanol (34 mL) was added 2,4-dimethoxyaniline (1.03 g, 6.75 mmol) and N,N-diisopropylethylamine (2.82 ml, 16.22 mmol). The reaction mixture was stirred at 50° C. for 24 h and partitioned between ethyl acetate and saturated aqueous sodium bicarbonate solution. The organic layer was washed with brine, dried over anhydrous sodium sulfate, filtered through a pad of CELITE, and concentrated under reduced pressure. The residue was purified by column chromatography on silica gel (1:9 to 3:7, ethyl acetate/hexane) to afford 6-chloro-N-(2,4-dimethoxyphenyl)pyrimidin-4-amine (1.4 g, 78% yield) as a violet solid. Rt=2.88 min; $^1$H NMR 600 MHz (CDCl$_3$) δ 8.39 (s, 1H), 7.44 (bs, 1H), 7.37 (bs, 1H), 6.49-6.52 (m, 3H), 3.81 (m, 6H) ppm; $^1$H NMR 600 MHz (DMSO-$d_6$) δ 9.02 (s, 1H), 8.23 (s, 1H), 7.36 (bs, 1H), 6.60 (d, J=2.4 Hz, 1H), 6.47 (m, 1H), 3.68 (m, 6H) ppm; MS m/z: 266.13 [M+1].

N4-(2,4-Dimethoxyphenyl)-N6-(4-(4-ethylpiperazin-1-yl)phenyl)pyrimidine-4,6-diamine (13)

A mixture of 6-chloro-N-(2,4-dimethoxyphenyl)pyrimidin-4-amine (1.24 g, 4.68 mmol), 4-(4-ethylpiperazin-1-yl)aniline (800 mg, 3.90 mmol), and K$_2$CO$_3$ (1.6 g, 11.70 mmol) in 2-butanol (10 mL) was degassed for 10 min. To the reaction mixture were added Pd$_2$(dba)$_3$ (214 mg, 0.23 mmol) and X-phos (2-dicyclohexylphosphino-2',4',6'-triisopropylbiphenyl, 167 mg, 0.35 mmol), and the resulting mixture was heated at 100° C. for 4 hours after which and filtered with a pad of CELITE. The filtrate was concentrated under reduced pressure. The residue was purified by column chromatography on silica gel (3/97 to 15/85, methanol/dichloromethane) to afford N4-(2,4-dimethoxyphenyl)-N6-(4-(4-ethylpiperazin-1-yl)phenyl)pyrimidine-4,6-diamine (1.3 g, 77% yield) as a violet solid. Rt=1.68 min; $^1$H NMR 600 MHz (DMSO-$d_6$) δ 8.63 (s, 1H), 8.04 (s, 1H), 7.99 (s, 1H), 7.35 (d, J=7.8 Hz, 1H), 7.27 (d, J=9.0 Hz, 2H), 6.84 (d, J=8.4 Hz, 2H), 6.61 (d, J=2.4 Hz, 1H), 6.48 (m, 1H), 5.68 (s, 1H), 3.75 (s, 3H), 3.74 (s, 3H), 3.03 (m, 4H), 2.48 (m, 4H), 2.36 (q, 2H), 1.01 (t, J=6.6 Hz, 3H) ppm; MS m/z: 435.49 [M+1].

Scheme 7. An exemplary preparation of SIK inhibitor III-3

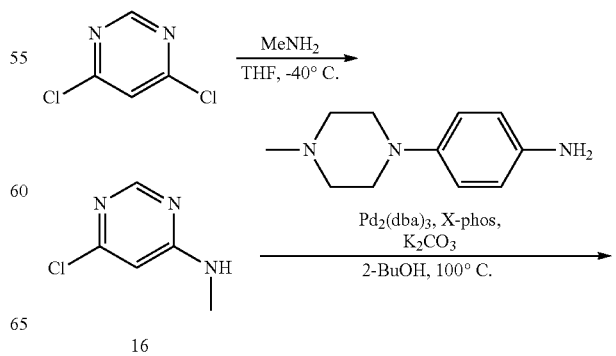

16

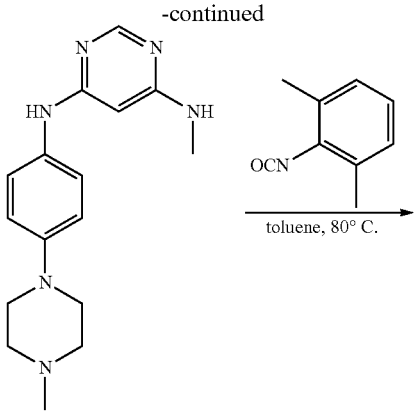

17

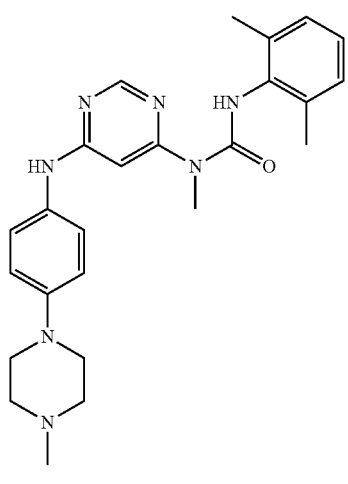

III-3

6-Chloro-N-methylpyrimidin-4-amine (16)

To a solution of 4,6-dichloropyrimidine (5.0 g, 33.79 mmol) in anhydrous THF (50 mL) was slowly added 2.0 M methylamine solution in THF (42.2 mL, 84.48 mmol) at −40° C. The reaction mixture was stirred at 0° C. for 4 h and partitioned between CHCl$_3$/2-propanol (4/1) and water. The organic layer was dried over anhydrous sodium sulfate, filtered through a pad of CELITE, and concentrated under reduced pressure. The white solid 6-chloro-N-methylpyrimidin-4-amine (4.2 g, 87% yield) was used in the next reaction without purification. Rt=1.55 min; $^1$H NMR 600 MHz (CDCl$_3$) δ 8.13 (br, 1H), 6.54 (m, 1H), 5.37 (br, 1H), 2.99 (m, 3H) ppm; MS m/z: 144.05 [M+1].

N4-Methyl-N6-(4-(4-methylpiperazin-1-yl)phenyl)pyrimidine-4,6-diamine (17)

A mixture of 4-(4-methylpiperazin-1-yl)aniline (500 mg, 2.62 mmol), 6-chloro-N-methylpyrimidin-4-amine (580 mg, 3.92 mmol), and K$_2$CO$_3$ (1.8 g, 13.08 mmol) in 2-butanol (5 mL) was degassed for 10 min. To the resulting mixture were added Pd$_2$(dba)$_3$ (143 mg, 0.16 mmol) and X-phos (2-dicyclohexylphosphino-2',4',6'-triisopropylbiphenyl, 112 mg, 0.24 mmol), and the resulting mixture was heated at 100° C. for 4 hours and filtered with a pad of CELITE. The filtrate was concentrated under reduced pressure. The residue was purified by column chromatography on silica gel (1/99 to 7/93, ammonia solution 7.0 N in methanol/dichloromethane) to afford N$_4$-methyl-N$_6$-(4-(4-methylpiperazin-1-yl)phenyl)pyrimidine-4,6-diamine (680 mg, 87% yield) as a brown solid. Rt=1.23 min; $^1$H NMR 600 MHz (CDCl$_3$) δ 8.11 (m, 1H), 7.15 (m, 2H), 6.92 (m, 2H), 6.60 (m, 1H), 5.49 (m, 1H), 4.78 (m, 1H), 3.17 (m, 4H), 2.77 (m, 3H), 2.56 (m, 4H), 2.33 (s, 3H) ppm; MS m/z: 299.43 [M+1].

3-(2,6-Dimethylphenyl)-1-methyl-1-(6-((4-(4-methylpiperazin-1-yl)phenyl)amino)pyrimidin-4-yl)urea (III-3)

To a solution of N4-methyl-N6-(4-(4-methylpiperazin-1-yl)phenyl)pyrimidine-4,6-diamine (200 mg, 0.67 mmol) in toluene (2 mL) was added 2,6-dimethylphenyl isocyanate (0.11 mL, 0.80 mmol). The resulting mixture was heated at 80° C. for 6 h and concentrated under reduced pressure. The residue was purified by column chromatography on silica gel (1:99 to 15:85, methanol/dichloromethane) and additionally purified with preparative HPLC to afford 3-(2,6-dimethylphenyl)-1-methyl-1-(6-((4-(4-methylpiperazin-1-yl)phenyl)amino)pyrimidin-4-yl)urea (110 mg, 30% yield) as an off-white TFA salt. Rt=2.52 min; $^1$H NMR 600 MHz (DMSO-d$_6$) δ 11.47 (s, 1H), 9.96 (br, 1H), 9.48 (s, 1H), 8.37 (s, 1H), 7.44 (m, 2H), 7.05 (m, 3H), 7.01 (m, 2H), 6.41 (s, 1H), 3.74 (m, 2H), 3.49 (m, 2H), 3.28 (s, 3H), 3.13 (m, 2H), 2.90 (m, 2H), 2.82 (s, 3H), 2.15 (s, 6H) ppm; MS m/z: 446.33 [M+1].

Example 1.8. Preparation of SIK Inhibitor III-4

In an exemplary experiment, SIK inhibitor III-4 was prepared according to the methods shown in Scheme 8.

Scheme 8. An exemplary preparation of SIK inhibitor III-4

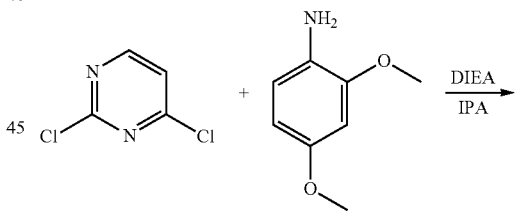

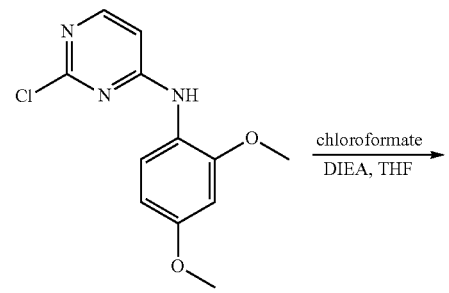

14

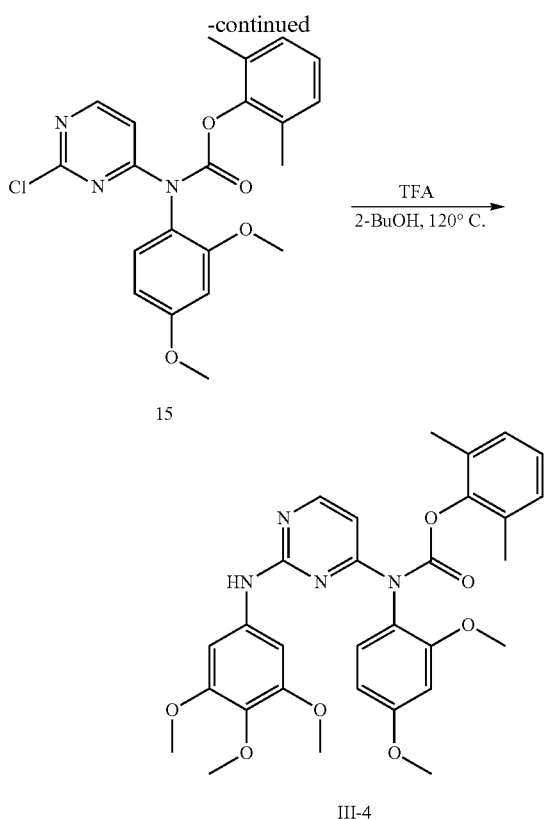

2-Chloro-N-(2,4-dimethoxyphenyl)pyrimidin-4-amine (14)

To a solution of 2,4-dichloropyrimidine (6.0 g, 40 mmol) and N,N-diisopropylethylamine (15.6 g, 120 mmol) in 2-propanol (40 mL) was added 2,4-dimethoxyaniline (6.2 g, 40 mmol). The resulting mixture was stirred at room temperature for 2 days. The reaction mixture was partitioned between saturated aqueous potassium carbonate solution and CHCl$_3$/2-propanol (4/1) solvents. The organic phase was separated, dried over anhydrous sodium sulfate, filtered through a pad of CELITE, and concentrated to afford crude 2-chloro-N-(2,4-dimethoxyphenyl)pyrimidin-4-amine (9.3 g, 87% yield) as a violet solid. The product was used without further purification. Rt=2.82 min; $^1$H NMR 600 MHz (CDCl$_3$) δ 8.11 (m, 1H), 7.32 (m, 1H), 6.99 (br, 1H), 6.57 (m, 2H), 6.46 (m, 1H), 3.89 (s, 3H), 3.87 (s, 3H) ppm; MS m/z: 266.20 [M+1].

2,6-Dimethylphenyl (2-chloropyrimidin-4-yl)(2,4-dimethoxyphenyl)carbamate (15)

To a solution of 2,6-dimethylphenol (3.44 g, 28.18 mmol) in dichloromethane (140 mL) was added slowly a solution of 15 wt. % phosgene in toluene (20 mL, 28.18 mmol) at 0° C. Pyridine (2.30 mL, 28.18 mmol) was added dropwise and the reaction was allowed to warm to room temperature overnight. The reaction mixture was diluted with ethyl acetate and partitioned between ethyl acetate and 1 N HCl solution. The organic layer was separated and washed with 1 N HCl solution and brine, dried over anhydrous sodium sulfate, filtered with a pad of CELITE, and concentrated to afford 2,6-dimethylphenyl chloroformate (4.8 g, 93% yield) as a yellow oil. The product used without further purification.

To a solution 2-chloro-N-(2,4-dimethoxyphenyl)pyrimidin-4-amine (2.0 g, 7.55 mmol) and N,N-diisopropylethylamine (3.94 mL, 22.64 mmol) in tetrahydrofuran (20 mL) was added 2,6-dimethylphenyl chloroformate (1.52 g, 8.30 mmol). The resulting mixture was stirred at room temperature for 24 h and diluted with ethyl acetate. The resulting mixture was partitioned between ethyl acetate and saturated aqueous sodium carbonate solution. The organic layer was washed with brine, dried over anhydrous sodium sulfate, filtered with a pad of CELITE, and concentrated under reduced pressure. The residue was purified by column chromatography on silica gel (0/100 to 3/97, methanol/dichloromethane) to afford 2,6-dimethylphenyl (2-chloropyrimidin-4-yl)(2,4-dimethoxyphenyl)carbamate (2.7 g, 87% yield) as an orange solid. Rt=3.95 min; $^1$H NMR 600 MHz (CDCl$_3$) δ 8.38 (d, J=6.0 Hz, 1H), 8.09 (d, J=6.0 Hz, 1H), 7.12 (d, J=9.0 Hz, 1H), 6.95 (m, 3H), 6.51 (m, 2H), 6.46 (m, 1H), 3.78 (s, 3H), 3.71 (s, 3H), 2.08 (s, 6H) ppm; MS m/z: 414.31 [M+1].

2,6-Dimethylphenyl (2,4-dimethoxyphenyl)(2-((3,4,5-trimethoxyphenyl)amino)pyrimidin-4-yl)carbamate (III-4)

To a solution of 2,6-dimethylphenyl (2-chloropyrimidin-4-yl)(2,4-dimethoxyphenyl)carbamate (100 mg, 0.24 mmol) in 2-butanol (1 mL) was added trifluoroacetic acid (0.1 mL). The resulting mixture was stirred at 120° C. for 8 h, concentrated, and diluted with dimethyl sulfoxide (6 mL). The resulting mixture was purified with preparative HPLC to afford 2,6-dimethylphenyl (2,4-dimethoxyphenyl)(2-((3,4,5-trimethoxyphenyl)amino)pyrimidin-4-yl)carbamate (121 mg, 76% yield) as an off-white TFA salt. Rt=3.40 min; $^1$H NMR 600 MHz (DMSO-d$_6$) δ 9.12 (s, 1H), 8.29 (m, 1H), 7.26 (m, 1H), 7.06 (m, 1H), 7.00 (m, 3H), 6.86 (m, 2H), 6.65 (m, 1H), 6.53 (m, 1H), 3.72 (m, 6H), 3.57 (m, 6H), 3.51 (m, 3H), 2.01 (m, 6H) ppm; MS m/z: 561.53 [M+1].

Example 1.9. Preparation of SIK Inhibitor III-5

In an exemplary experiment, SIK inhibitor III-5 was prepared according to the methods shown in Scheme 9.

Scheme 9. An exemplary preparation of SIK inhibitor III-5

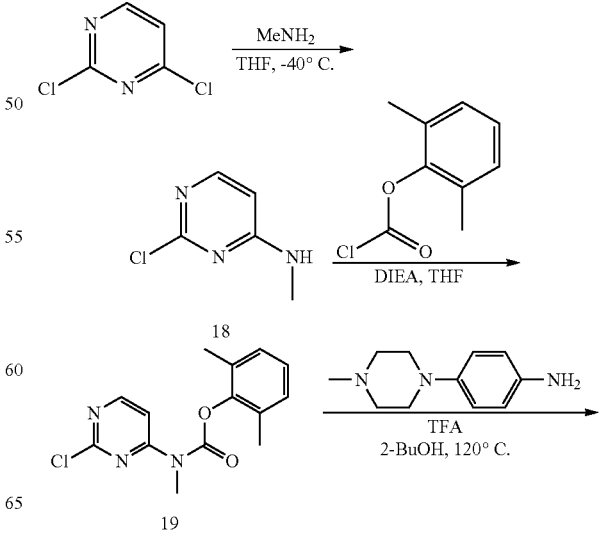

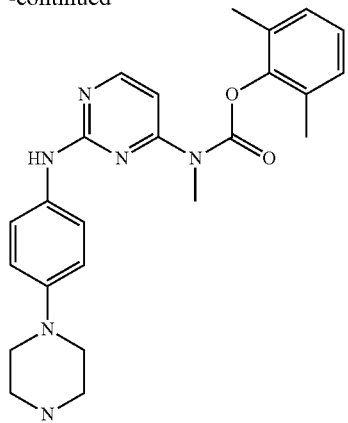

III-5

2-Chloro-N-methylpyrimidin-4-amine (18)

To a solution of 2,4-dichloropyrimidine (5.0 g, 33.79 mmol) in anhydrous THF (50 mL) was slowly added 2.0 M methylamine solution in THF (42.2 mL, 84.48 mmol) at −40° C. The reaction mixture was stirred at 0° C. for 4 h and partitioned between $CHCl_3$/2-propanol (4/1) and water. The organic layer was dried over anhydrous sodium sulfate, filtered through a pad of CELITE, and concentrated under reduced pressure. The residue was purified by column chromatography on silica gel (100% dichloromethane) to afford 2-chloro-N-methylpyrimidin-4-amine (2.8 g, 58% yield) as a white solid. Rt=1.15 min; $^1$H NMR 600 MHz (DMSO-$d_6$) δ 8.02 (s, 1H), 6.22 (m, 1H), 2.86 (d, J=4.8 Hz, 3H) ppm; MS m/z: 144.12 [M+1].

2,6-Dimethylphenyl (2-chloropyrimidin-4-yl)(methyl)carbamate (19)

To a solution 2-chloro-N-methylpyrimidin-4-amine (1.0 g, 6.99 mmol) and N,N-diisopropylethylamine (3.65 mL, 20.97 mmol) in tetrahydrofuran (10 mL) was added 2,6-dimethylphenyl chloroformate (1.92 g, 10.49 mmol). The resulting mixture was stirred at room temperature for 24 h and diluted with ethyl acetate. The resulting mixture was partitioned between ethyl acetate and saturated aqueous sodium carbonate solution. The organic layer was washed with brine, dried over anhydrous sodium sulfate, filtered with a pad of CELITE, and concentrated under reduced pressure. The residue was purified by column chromatography on silica gel (0/100 to 1/97, methanol/dichloromethane) to afford 2,6-dimethylphenyl (2-chloropyrimidin-4-yl)(methyl)carbamate (1.65 g, 81% yield) as a white solid. Rt=3.87 min; $^1$H NMR 600 MHz ($CDCl_3$) δ 8.36 (d, J=6.0 Hz, 1H), 8.06 (d, J=6.0 Hz, 1H), 7.03 (m, 3H), 3.68 (s, 3H), 2.14 (s, 6H) ppm; MS m/z: 292.24 [M+1].

2,6-Dimethylphenyl methyl(2-((4-(4-methylpiperazin-1-yl)phenyl)amino)pyrimidin-4-yl)carbamate (III-5)

To a solution of 2,6-dimethylphenyl (2-chloropyrimidin-4-yl)(methyl)carbamate (100 mg, 0.34 mmol) and 4-(4-methylpiperazin-1-yl)aniline (98 mg, 0.52 mmol) in 2-butanol (1 mL) was added trifluoroacetic acid (0.1 mL). The resulting mixture was stirred at 120° C. for 8 h, concentrated, and diluted with dimethyl sulfoxide (6 mL). The resulting mixture was purified with preparative HPLC to afford 2,6-dimethylphenyl methyl(2-((4-(4-methylpiperazin-1-yl)phenyl)amino)pyrimidin-4-yl)carbamate (123 mg, 66% yield) as an off-white TFA salt. Rt=2.50 min; $^1$H NMR 600 MHz (DMSO-$d_6$) δ 10.14 (s, 1H), 9.50 (s, 1H), 8.28 (m, 1H), 7.57 (m, 2H), 7.29 (m, 1H), 7.10 (m, 3H), 6.94 (m, 2H), 3.71 (m, 2H), 3.59 (s, 3H), 3.38 (m, 2H), 3.13 (m, 2H), 2.91 (m, 2H), 2.81 (s, 3H), 2.12 (m, 6H) ppm; MS m/z: 447.52 [M+1].

Exemplary preparations and analytical data of additional exemplary compounds of Formula (III-A) are shown in Tables 2A and 2B.

TABLE 2A

Exemplary preparations and analytical data of additional exemplary compounds of Formula (III-A)

| Compound | Preparation method; retention time (Rt); MS m/z |
|---|---|
| HG-9-96-01 | Scheme 6; Rt = 2.49 min; MS m/z: 568.71 [M + 1] |
| HG-9-148-02 | Scheme 7; MS m/z: 466.99 [M + 1] |
| HG-10-8-01 | Scheme 6; Rt = 1.90 min; MS m/z: 504.69 [M + 1] |
| HG-10-8-02 | Scheme 6; Rt = 2.27 min; MS m/z: 504.69 [M + 1] |
| HG-10-9-01 | Scheme 7; Rt = 2.02 min; MS m/z: 530.65 [M + 1] |
| HG-10-15-02 | Rt = 2.34 min; MS m/z: 568.71 [M + 1] |
| HG-10-15-03 | Scheme 6; Rt = 2.27 min; MS m/z: 588.81 [M + 1] |
| HG-10-15-04 | Scheme 6; Rt = 2.45 min; MS m/z: 588.81 [M + 1] |
| HG-10-27-01 | Scheme 6; MS m/z: 669.77 [M + 1] |
| HG-10-27-02 | Scheme 6; MS m/z: 669.77 [M + 1] |
| HG-10-28-01 | Scheme 7; Rt = 2.25 min; MS m/z: 547.53 [M + 1] |
| HG-10-31-01 | Scheme 6; Rt = 2.45 min; MS m/z: 565.69 [M + 1] |
| HG-10-31-02 | Scheme 6; Rt = 2.48 min; MS m/z: 565.69 [M + 1] |
| HG-10-36-01 | Scheme 6; Rt = 2.23 min; MS m/z: 582.76 [M + 1] |
| HG-10-36-02 | Scheme 6; Rt = 2.32 min; MS m/z: 582.76 [M + 1] |
| HG 10-59-02 | Scheme 6; Rt = 2.22 min; MS m/z: 588.69 [M + 1] |
| HG 10-60-01 | Scheme 6; Rt = 2.10 min; MS m/z: 572.62 [M + 1] |
| HG 10-60-02 | Scheme 6; Rt = 2.20 min; MS m/z: 572.62 [M + 1] |
| HG 10-61-01 | Scheme 6; Rt = 2.65 min; MS m/z: 574.70 [M + 1] |

TABLE 2A-continued

Exemplary preparations and analytical data of additional exemplary compounds of Formula (III-A)

| Compound | Preparation method; retention time (Rt); MS m/z |
|---|---|
| HG 10-61-02 | Scheme 6; Rt = 2.53 min; MS m/z: 574.70 [M + 1] |
| HG 10-62-01 | Scheme 6; Rt = 2.40 min; MS m/z: 554.72 [M + 1] |
| HG 10-62-02 | Scheme 6; Rt = 2.53 min; MS m/z: 554.72 [M + 1] |
| HG 10-63-01 | Scheme 6; Rt = 2.48 min; MS m/z: 609.72 [M + 1] |
| HG 10-63-02 | Scheme 6; Rt = 2.75 min; MS m/z: 609.72 [M + 1] |
| HG 10-64-01 | Scheme 6; Rt = 2.44 min; MS m/z: 596.82 [M + 1] |
| HG 10-64-02 | Scheme 6; Rt = 2.68 min; MS m/z: 596.82 [M + 1] |
| HG 10-65-01 | Scheme 6; Rt = 2.62 min; MS m/z: 624.79 [M + 1] |
| HG 10-65-02 | Scheme 6; Rt = 2.73 min; MS m/z: 624.79 [M + 1] |
| HG-10-149-01 | Scheme 6; Rt = 2.18 min; MS m/z: 554.79 [M + 1] |
| HG-10-149-02 | Scheme 6; Rt = 2.27 min; MS m/z: 554.79 [M + 1] |
| HG-10-150-01 | Scheme 6; Rt = 2.28 min; MS m/z: 566.76 [M + 1] |
| HG-10-150-02 | Scheme 6; Rt = 2.45 min; MS m/z: 566.76 [M + 1] |
| HG-11-18-01 | Scheme 7; Rt = 2.67 min; MS m/z: 497.57 [M + 1] |
| HG-11-18-02 | Rt = 1.80 min; MS m/z: 467.57 [M + 1] |
| HG-11-21-01 | Rt = 2.92 min; MS m/z: 639.66 [M + 1] |
| HG-11-22-01 | Scheme 7; Rt = 2.25 min; MS m/z: 545.71 [M + 1] |

TABLE 2B

Exemplary analytical data of additional exemplary compounds of Formula (III-A)

| Compound | Retention time (Rt); $^1$H NMR; MS m/z |
|---|---|
| HG-3-09-01 | MS m/z: 470.52 [M + 1]. |
| HG-9-87-02 | Rt = 3.13 min; MS m/z: 556.61 [M + 1]. |
| HG-9-87-03 | Rt = 3.43 min; MS m/z: 556.61 [M + 1]. |
| HG-9-87-04 | Rt = 2.77 min; MS m/z: 557.37 [M + 1]. |
| HG-9-88-02 | Rt = 2.70 min; MS m/z: 486.22 [M + 1]. |
| HG-9-88-03 | Rt = 2.55 min; MS m/z: 600.60 [M + 1]. |
| HG-9-88-04 | Rt = 2.73 min; MS m/z: 600.60 [M + 1]. |
| HG-9-88-05 | Rt = 2.48 min; MS m/z: 574.64 [M + 1]. |
| HG-9-90-01 | Rt = 2.53 min; $^1$H NMR 600 MHz (DMSO-$d_6$) δ 9.67 (s, 1H), 9.43 (s, 1H), 8.23 (s, 1H), 7.44 (d, J = 7.8 Hz, 2H), 7.31 (s, 1H), 7.24 (d, J = 9.0 Hz, 1H), 7.05 (m, 2H), 6.96 (d, J = 9.0 Hz, 2H), 6.68 (d, J = 2.4 Hz, 1H), 6.57 (dd, J = 3.0 Hz, J = 8.4 Hz, 1H), 3.78 (s, 3H), 3.76 (s, 3H), 3.74 (m, 4H), 3.12 (m, 2H), 2.98 (m, 2H), 2.83 (s, 3H), 2.06 (s, 6H); MS m/z: 569.72 [M + 1]. |
| HG-9-90-02 | Rt = 2.53 min; $^1$H NMR 600 MHz (DMSO-$d_6$) 8.22 (s, 1H), 7.38 (s, 1H), 7.20 (m, 3H), 7.04 (m, 6H), 6.67 (d, J = 2.4 Hz, 1H), 6.57 (dd, J = 2.4 Hz, J = 7.8 Hz, 1H), 3.78 (s, 3H), 3.75 (s, 3H), 3.72 (m, 4H), 3.27 (m, 4H), 2.06 (s, 6H); MS m/z: 565.61 [M + 1]. |
| HG-9-90-03 | Rt = 3.18 min; $^1$H NMR 600 MHz (DMSO-$d_6$) 9.65 (s, 1H), 8.37 (s, 1H), 7.54 (m, 2H), 7.40 (m, 2H), 7.17 (m, 5H), 6.80 (d, 1H), 6.71 (dd, 1H), 3.91 (s, 3H), 3.86 (s, 3H), 3.81 (m, 4H), 3.22 (m, 4H), 2.10 (s, 6H); MS m/z: 566.61 [M + 1]. |

TABLE 2B-continued

Exemplary analytical data of additional exemplary compounds of Formula (III-A)

| Compound | Retention time (Rt);<br>$^1$H NMR;<br>MS m/z |
|---|---|
| HG-9-139-02 | Rt = 2.75 min;<br>$^1$H NMR 600 MHz (DMSO-$d_6$) 10.19 (s, 1H), 8.63 (s, 1H), 8.11 (m, 1H), 7.36 (m, 3H), 7.06 (m, 3H), 6.80 (d, 1H), 6.71 (dd, 1H), 3.84 (s, 3H), 3.76 (s, 3H), 2.56 (s, 3H), 2.38 (s, 3H), 2.07 (s, 6H);<br>MS m/z: 500.57 [M + 1]. |
| HG-9-139-03 | Rt = 2.72 min;<br>$^1$H NMR 600 MHz (DMSO-$d_6$) 9.44 (s, 1H), 7.34 (m, 1H), 7.30 (d, J = 7.8 Hz, 1H), 7.07 (m, 3H), 6.97 (d, J = 7.8 Hz, 1H), 6.85 (s, 1H), 6.79 (d, 1H), 6.77 (d, 1H), 6.65 (dd, 1H), 6.49 (dd, 1H), 4.23 (m, 2H), 3.95 (m, 2H), 3.83 (S, 3H), 3.74 (s, 3H), 3.67 (m, 2H), 3.51 (m, 2H), 3.14 (m, 4H), 2.33 (s, 3H), 2.07 (s, 6H);<br>MS m/z: 614.71 [M + 1]. |
| HG-9-139-04 | Rt = 2.53 min;<br>MS m/z: 613.71 [M + 1]. |
| HG-9-139-05 | Rt = 2.47 min;<br>MS m/z: 588.69 [M + 1]. |
| HG-9-140-01 | Rt = 2.47 min;<br>$^1$H NMR 600 MHz (DMSO-$d_6$) 9.49 (s, 1H), 8.07 (s, 1H), 7.58 (s, 1H), 7.23 (m, 1H), 7.06 (d, J = 8.4 Hz, 1H), 6.84 (m, 3H), 6.54 (m, 2H), 6.38 (m, 1H), 6.36 (m, 1H), 3.59 (s, 3H), 3.52 (s, 3H), 3.48 (s, 3H), 3.44 (m, 4H), 2.87 (m, 4H), 2.60 (s, 3H), 1.84 (s, 6H);<br>MS m/z: 599.71 [M + 1]. |
| HG-9-144-01 | Rt = 2.45 min;<br>$^1$H NMR 600 MHz (DMSO-$d_6$) 9.80 (s, 1H), 9.32 (s, 1H), 8.32 (d, 1H), 7.54 (d, 1H), 7.32 (d, 1H), 7.07 (m, 3H), 6.79 (m, 1H), 6.68 (d, 1H), 6.61 (m, 1H), 4.00 (m, 2H), 3.86 (s, 3H), 3.82 (m, 2H), 3.74 (s, 3H), 3.66 (m, 4H), 3.33 (m, 2H), 3.15 (m, 5H), 2.64 (m, 2H), 2.15 (m, 2H), 2.07 (s, 6H), 1.71 (m, 2H);<br>MS m/z: 639.72 [M + 1]. |
| HG-9-144-02 | Rt = 2.45 min;<br>$^1$H NMR 600 MHz (DMSO-$d_6$) 9.80 (s, 1H), 9.32 (s, 1H), 8.33 (d, 1H), 7.92 (s, 1H), 7.52 (d, 1H), 7.32 (d, 1H), 7.07 (m, 5H), 6.77 (m, 1H), 6.66 (dd, 1H), 6.58 (d, 1H), 6.05 (m, 1H), 4.00 (m, 2H), 3.85 (s, 3H), 3.78 (s, 3H), 3.75 (m, 2H), 3.66 (m, 4H), 3.34 (m, 4H), 3.15 (m, 2H), 2.90 (m, 1H), 2.68 (m, 2H), 2.15 (m, 2H), 2.06 (s, 6H), 1.70 (m, 2H);<br>MS m/z: 669.71 [M + 1]. |
| HG-9-144-03 | Rt = 2.17 min;<br>MS m/z: 683.76 [M + 1]. |
| HG-9-144-04 | Rt = 2.45 min;<br>MS m/z: 710.73 [M + 1]. |
| HG-9-144-05 | Rt = 2.65 min;<br>MS m/z: 628.82 [M + 1]. |
| HG-9-150-02 | Rt = 2.53 min;<br>MS m/z: 583.65 [M + 1]. |
| HG-11-6-01 | Rt = 3.13 min;<br>MS m/z: 641.55 [M + 1]. |
| HG-11-6-02 | Rt = 2.53 min;<br>MS m/z: 654.72 [M + 1]. |
| WH-4-023 | Rt = 2.48 min;<br>MS m/z: 569.66 [M + 1]. |
| WH-4-025 | MS m/z: 742.71 [M + 1]. |
| WH4-113 | MS m/z: 748.76 [M + 1]. |
| WH4-124-1 | MS m/z: 756.79 [M + 1]. |
| WH4-124-2 | Rt = 2.27 min;<br>MS m/z: 854.66 [M + 1]. |
| WH4-199-1 | MS m/z: 680.70 [M + 1]. |
| WH4-199-2 | MS m/z: 693.71 [M + 1]. |
| WH4-200-1 | MS m/z: 680.76 [M + 1]. |
| WH4-200-2 | MS m/z: 694.73 [M + 1]. |

Example 2. Materials and Methods Involved in Examples 3 to 24

Bone marrow-derived DCs were differentiated from C57BL/6 bone marrow in the presence of GM-CSF-conditioned media. CD11c$^+$ CX$_3$CR1$^{hi}$ myeloid cells and CD11c$^+$ CX$_3$CR1$^-$ DCs were isolated from the small intestine lamina propria of Cx3cr1$^{eGFP/+}$ mice (12). Detection of cell-surface Thy1.1 expression on BMDCs from 10BiT reporter mice was conducted as described previously (24). Cell viability was estimated by change in total cellular ATP levels using CellTiterGlo assays (Promega). Preparation of recombinant SIK proteins and IC$_{50}$ measurements were conducted as described previously (21). Total RNA was extracted using a NucleoSpin 96 RNA isolation kit (Macherey-Nagel) followed by cDNA synthesis and multiplex RT-PCR using a microfluidic dynamic array (Fluidigm). The concentrations of TNF-α, IL-6, IL-10, IL-12p40, IL-1β and RANTES in culture supernatants were detected using a FlexSet Cytometric bead array (BD Biosciences). Alternatively, IL-10 secretion was quantified using ELISA (BD Biosciences) or AlphaLISA (PerkinElmer) assays. NO production was estimated based on nitrate content in culture medium using the Griess reagent.

Example 3. Protein Kinase Assays of the SIK Inhibitors

In another set of experiments, the activities of the SIK inhibitors described herein against SIK were determined according to the methods reported in Hastie et al., *Nature Protocols*, 2006, 1, 968-971.

Materials

Enzyme Dilution Buffer.

This buffer consisted of 50 mM Tris-HCl, pH 7.5, 0.1 mM EGTA, 1 mg ml$^{-1}$ bovine serum albumin and 0.1% (vol/vol) 2-mercaptoethanol.

10× Concentrated Assay Buffer.

An assay buffer of 500 mM Tris-HCl, pH 7.5, 1 mM EGTA, and 100 mM magnesium acetate was used for the protein kinase assay. In some cases, the pH of the buffer was changed (e.g., phosphorylase kinase had an optimum pH of 8.6).

1 mM [γ-$^{32}$P] ATP.

The specific activity of the [γ-$^{32}$P] ATP solution was 1×10$^5$ to 1×10$^6$ c.p.m. per nmol depending on what was needed to produce an optimal signal/noise ratio. Stocks of nonradioactive ("cold") ATP were dissolved in 10 mM HEPES, and the pH of the resulting stock solutions was adjusted to 7.4. To measure the concentration of ATP, a sample of such a stock solution was diluted to 20 μM, and the absorbance of the diluted sample was measured at 259 nm. The absorbance of a 20-μM stock solution of ATP at 259 nm was about 0.31. The 1-mM solution of cold ATP was "spiked" with [γ-$^{32}$P] ATP to produce a radioactivity of 1×10$^5$ to 1×10$^6$ c.p.m. per nmol.

Procedure

1) The number of assay samples needed was determined based on, e.g., the following considerations: (i) each condition was assayed in duplicate; (ii) two controls containing peptide or protein substrate and ATP but no SIK were included to assess contamination by any free ATP not incorporated into substrate, alongside two controls lacking a peptide or protein substrate but containing ATP and SIK to correct for any incorporation of phosphate into the kinase itself (e.g., autophosphorylation); and (iii) a maximum of 40 samples were assayed manually at one time by a single person. Microcentrifuge tubes were label distinctly and were placed on ice.

2) Suspend a wire mesh basket in a beaker containing a magnetic stir bar and not less than 5 ml of 75 mM phosphoric acid per assay sample or a minimum volume of 100 ml. Place this on a magnetic stirrer behind a plexiglass shield.

3) Label 2 cm×2 cm squares of phosphocellulose paper corresponding to the samples to be pipetted into each microcentrifuge tube. Label the phosphocellulose paper using pencil, which was not affected by the solvents used to wash the papers at the end of the assay.

4) Dilute the SIK in enzyme dilution buffer and place on ice.

5) Pipette 5 j±l of 10× concentrated assay buffer, 5 j±l peptide or protein substrate (the two "no-substrate" control tubes had 5 j±l water added instead of peptide or protein substrate), and 30 μl distilled water into each tube. Keep the tubes on ice.

6) Add 5 μl diluted SIK to each tube, except for the two "no-enzyme" control tubes, which had 5 μl enzyme dilution buffer added, and still keeping the tubes on ice. In some cases, premixed "cocktails" of assay components were prepared containing peptide or protein substrate, assay buffer, and distilled water to limit the number of additions to each assay tube. Each of steps 7 to 14 was done behind a plexiglass shield.

7) Insert each tube into the water bath at intervals of 15 s to allow the assay mixture to reach 30° C. Begin the SIK reactions by adding 5 μl of 1 mM [γ-$^{32}$P] ATP to each tube at intervals of 15 s. Close each tube, vortex for 1 s to mix the contents and immediately replace in a rack in the water bath. Incubate for 10 min at 30° C.

8) At 10 min after the addition of ATP, remove each tube from the water bath at intervals of 15 s.

9) "Spot" 40 μl of each reaction mixture onto the center of a 2-cm square of P81 phosphocellulose paper using forceps to handle the paper squares. Immediately immerse the paper into the 75 mM phosphoric acid contained in the wire mesh basket suspended in the beaker that is being stirred continuously with a magnetic stirrer. This was be done within 1 to 2 s, as this step terminated the reaction.

10) After 5 min, remove the wire mesh basket from the beaker, and discard the phosphoric acid in the beaker and replace it with fresh phosphoric acid. Replace the wire mesh basket in the beaker and repeat this washing procedure three times (with 5 min between each wash). This step removes the [γ-$^{32}$P] ATP that has not been incorporated into the peptide or protein substrate.

11) After the final wash in phosphoric acid, rinse the papers briefly with acetone to remove the phosphoric acid and either air-dry or dry with a hair dryer.

12) Transfer each paper to a new, distinctly labeled, 1.5-ml microcentrifuge tube.

13) Measure radioactivity in the samples by Cerenkov counting (e.g., without liquid scintillation fluid) in a liquid scintillation counter using a "$^{32}$P program". Also measure the radioactivity of 1-μl aliquots of the stock of 1 mM [γ-$^{32}$P] ATP in triplicate to determine the specific radioactivity of the ATP in terms of c.p.m. per nanomol ATP (1 μl of 1 mM ATP corresponds to 1 nmol ATP).

14) Calculate the activity of the SIK. One unit (U) of SIK activity is that amount that catalyzes the incorporation of 1 nmol phosphate into the standard peptide or protein substrate in 1 min. In the assay described herein, the activity of the undiluted SIK solution in U ml$^{-1}$ is [(r−b/sa)×d×1.25× 200]/10, where r is the c.p.m. incorporated into the substrate in the SIK reaction, b is the average c.p.m. associated with the phosphocellulose paper in the reaction "blanks", sa is the specific radioactivity of the ATP (c.p.m. nmol$^{-1}$), d is the "fold dilution" of the SIK before assay, 1.25 is a correction for transfer of only 80% of the reaction to the phosphocellulose paper (40 μl of a 50-μl assay volume), 200 corrects for the addition of only 1 of diluted SIK to each assay, and 10 is the incubation time in min. In some cases, if the protein concentration of the assay was known, the activity was converted from U ml$^{-1}$ to U mg$^{-1}$ of protein.

In some experiments of determining the inhibitory activities of a SIK inhibitor described herein against SIK (e.g., experiments yielding the data in Table 3), DMSO was used as a control. The activity of a SIK when treated with DMSO, but not with a SIK inhibitor described herein, was set to 100%. SIK inhibitors resulting in less than 100% activity of a SIK are deemed to be inhibitors of the SIK.

Results

Exemplary results of the protein kinase assays of the SIK inhibitors described herein are shown in Table 3.

TABLE 3

Exemplary inhibitory activities of select SIK inhibitors against SIK.

| SIK inhibitor | IL-10 induction $EC_{50}$ (µM) | Viability loss $EC_{50}$ (µM) | Enzyme Inhibition $IC_{50}$ (µM) | | |
|---|---|---|---|---|---|
| | | | SIK1 | SIK2 | SIK3 |
| I-1 | 5.61531E−06 | 0.00001 | N/A | 0.009725 | 0.0891 |
| I-2 | N/A | 0.00000658 | N/A | 0.087845 | 0.4453 |
| I-3 | 1.23736E−05 | 0.00000361 | N/A | 0.013877 | 0.07891 |
| I-4 | 1.05263E−05 | 0.000005 | N/A | 0.093765 | 0.40875 |
| I-5 | 2.37844E−05 | 0.00000612 | N/A | 0.011964 | 0.07366 |
| I-6 | 2.6E-05 | N/A | N/A | 0.01889 | 0.1764 |
| II-1 | 1.45949E−06 | 1.95E-08 | 0.036185 | 0.06514 | 0.12 |

| SIK inhibitor | Activity of protein kinase treated with 1 µM of I-1 (% control (DMSO)) | | | | Activity of protein kinase treated with 0.1 µM of I-1 (% control (DMSO)) | | | |
|---|---|---|---|---|---|---|---|---|
| | SIK1 | SIK2 | SIK3 | SGK | SIK1 | SIK2 | SIK3 | SGK |
| I-1 | | 5 | 13 | 100 | | 10 | 33 | 96 |
| I-2 | 15.9 | 15 | | | | | | |
| II-1 | | 9 | 16 | | | 37 | 45 | |

N/A: not available.

Example 4. Molecular Biology Methods

The lentiviral luciferase reporter construct for the cAMP-responsive transcription factor CREB was created by combining the pLenti7.3/V5-DEST vector from Life Technologies (Cat # V534-06), the minimal promoter and luc2P open reading frame from Promega's pGL4.29 [luc2P/CRE/Hygro], and an optimized synthetic cAMP-regulated enhancer that contains multiple nonoverlapping binding sites for CREB (Melnikov A, et al. (2012) Systematic dissection and optimization of inducible enhancers in human cells using a massively parallel reporter assay. *Nature biotechnology* 30(3):271-277). The CMV-Gateway-V5 stretch from pLenti7.3/V5-DEST was removed by digestion with BspDI and MluI. The minimal promoter and luc2P open reading frame of pGL4.29 was PCR amplified with Gibson cloning complementary sequence to the digested pLenti7.3/V5-DEST backbone using the primer pair: F_TTCAAAATTT-TATCGATCGCACCAGCGTGTGGATCCGAGAACA-GATCTGGCCTCGG (SEQ ID NO: 1), R_ACTAACCGGTACGCGTTCTAGAGTCGCGGCCT-TAGAC (SEQ ID NO: 2). Clontech's Infusion enzyme mix (Cat #638916) was used to insert the minimal promoter and luc2P into the digested pLenti7.3/V5-DEST. The synthetic cAMP-regulated enhancer ACACCAGACATrGACG-TAAGCTGCCAGATCCCATrCCCGTCATACTCT-GACGTCTTCAGACACCCCATrGACGTCAATGGGA-GAAC (SEQ ID NO: 3) was synthesized as a standard desalted Ultramer from Integrated DNA Technologies and made double stranded with HercII fusion polymerase (Agilent) and Gibson cloning complementary sequence using the primer pair: F_GCACCAGCGTGTGGATC (SEQ ID NO: 4), R_GCCAGATCTGTTCTCGGATC (SEQ ID NO: 5). The pLenti7.3 backbone containing a minimal promoter and luc2P was then digested with BamHI and the synthetic cAMP-regulated enhancer was inserted in front of the minimal promoter using Infusion enzyme mix (Clontech). pLKO shRNAs targeting CRTC3 (TRCN0000241211 or TRCN0000241214), RFP (TRCN0000072206) or LacZ (TRCN0000072256) were obtained from the Broad Institute's Genetic Perturbation Platform. For production of lentiviral particles, 293T cells were transfected with the CREB lentiviral reporter construct or pLKO shRNA plasmids and packaging plasmids dR8.91 and VSV-G using Lipofectamine 2000. The 293T media was changed 24 hr post-transfection to DMEM+30% FBS and Pen/Strep. Media containing lentiviral particles was collected 48 hr post-transfection and stored at −80° C.

Example 5. Mouse Models

C57BL/6 and Balb/c mice were obtained from Jackson Laboratory. CX3CR1GFP/+ and 10BiT mice have been described previously (Jung S, et al. (2000) Analysis of fractalkine receptor CX(3)CR1 function by targeted deletion and green fluorescent protein reporter gene insertion. *Molecular and cellular biology* 20(11):4106-4114; Maynard C L, et al. (2007) Regulatory T cells expressing interleukin 10 develop from Foxp3+ and Foxp3− precursor cells in the absence of interleukin 10. *Nature immunology* 8(9):931-941). Mouse maintenance and cell isolation was performed under protocols approved by the Massachusetts General Hospital Subcommittee on Research Animal Care (SRAC), in conformance with the National Institutes of Health Guide for the Care and Use of Laboratory Animals.

Example 6. Bone Marrow-Derived Cell Culture Methods

C57BL/6 mice were euthanized and bone marrow harvested from femurs and tibias as described previously (Graham D B, et al. (2007) An ITAM-signaling pathway controls cross-presentation of particulate but not soluble antigens in dendritic cells. *The Journal of experimental medicine* 204 (12):2889-2897). BMDCs were differentiated DMEM supplemented with 2 mM GlutaMAX, 10% (vol/vol) FBS, penicillin, streptomycin and 2% mouse GM-CSF conditioned media derived from TOPO cells. Cultures were differentiated for 7 days and routinely analyzed for >90% CD11c (APC anti-CD11c clone HL3; BD Biosciences) positivity by flow cytometry before use in experiments. Lentiviral transduction of bone marrow cultures was conducted by addition of 293T culture supernatants containing lentiviral particles encoding the CREB dependent luciferase reporter construct or CRTC3 targeting or control shRNAs one day post-isolation. Stable integration of lentiviral shRNA constructs was selected by addition of puromycin (3 µg/mL) on day 4 post-transduction. After 2 days, stably transduced BMDCs were released from selection and used in subsequent assays. Unless otherwise indicated, cells were treated for 2 days with PGE2 (5 µM) or HG-9-91-01 (0.5 µM) or an equivalent concentration of DMSO (≤0.5%) and then stimulated for 18 hr with LPS (100 ng/mL), R848 (10 µg/mL) or zymosan (4 µg/mL).

Example 7. Human Myeloid Cell Culture Methods

Heparinized blood from healthy donors was obtained from Research Blood Components. Peripheral blood mononuclear cells (PBMCs) were obtained by density centrifugation of blood diluted 50% (vol/vol) with PBS over Ficoll-Paque (Pharmacia Biotech). PBMCs were further purified by plastic adherence for 1 hr and washed 5× with PBS. Monocytes within the PBMC pool were differentiated towards DCs in X-VIVO media (Lonza) supplemented with IL-4 (50 ng/mL, R&D Systems) and GM-CSF (50 ng/mL, R&D Systems) or macrophages in X-VIVO media supplemented with GM-CSF (5 ng/mL) and IFN-γ (5 ng/mL; PeproTech) for 7 days as described previously (Smeekens S P, et al. (2013) Functional genomics identifies type I interferon pathway as central for host defense against *Candida albicans*. *Nature communications* 4:1342). After third day, half of the culture medium was replaced by fresh DC/macrophages differentiation medium.

Example 8. Methods of High-Throughput Detection of IL-10 Up-Regulation and Cell Viability BMDCs were seeded into black 384-well plates (Corning) at 20,000 cells/well in 40 µL complete DMEM using a Multidrop COMBI (Thermal Scientific) followed by incubation at 37° C. for 2 hr to allow for plate adherence. SIK inhibitors (100 nL/well) were pin-transferred from concentrated DMSO stocks using CyBi-Well Vario (CyBio) into duplicate plates. For each treatment plate, 32 out of 384 wells were pinned with DMSO as negative control and 32 out of 384 wells were pinned with PGE2 (5 µM final concentration). Two days after SIK inhibitor treatment, BMDCs were stimulated with zymosan (4 µg/mL final concentration) dispersed in culture medium (20 µL/well) using a Multidrop COMBI. After 18 hr, 5 µL of resulting supernatant was transferred from the culture plate to white 384-well AlphaLISA plates (Perkin Elmer) using a CyBi-Well Vario. IL-10 abundance in the supernatants was determined using an AlphaLISA assay (PerkinElmer) according to the manufacture's protocol and signal intensity measured using an EnVision multimode plate reader. SIK inhibitor activity was expressed as a % of the differences between the mean abundance of IL-10 in PGE2 versus DMSO wells on a per plate basis. Cell viability assays were conducted on the same tissue culture plates as the IL-10 assay. First media was removed and replaced by solution of 50% (vol/vol) CellTiter-Glo (Promega) in PBS. Luminescence was read using an Envision multimode plate reader, and signal intensity calculated relative to DMSO control wells on a per plate basis.

Example 9. Reporter Gene Assay Methods

Six days post transduction with lentiviral particles encoding the CREB-luciferase reporter construct, BMDCs were seeded into black 384-well plates (Corning) at 20,000 cells/well in 40 µL complete DMEM using a Multidrop COMBI (Thermal Scientific) followed by incubation at 37° C. for 2 hr to allow for plate adherence. SIK inhibitors (100 nL/well) or DMSO (vehicle) were pin-transferred from concentrated DMSO stocks using CyBi-Well Vario (CyBio) into triplicate plates. After incubation with SIK inhibitors for 24 hr, BMDCs were stimulated with zymosan (4 µg/mL) dispersed using a Multidrop COMBI. After 5 hr, media was removed and replaced by solution of 50% (vol/vol) Steadylite Plus (PerkinElmer) in PBS and incubated at room temperature for 10 min. Luminescence was read using an Envision multimode plate reader, and SIK inhibitor activity was expressed fold DMSO treated wells on per plate basis.

Example 10. Methods of Detecting il10-Thy1.1 Reporter Gene

Preparation of BMDCs from 10BiT reporter mice expressing an il10-Thy1.1 transgene, SIK inhibitor treatment and zymosan stimulation was conducted as described above. After 18 hr of stimulation, 10BiT BMDCs were collected by scraping, washed with PBS and stained with LIVE/DEADGreen (Invitrogen) to identify viable cells as well as APC anti-Thy1.1 (clone OX-7; BD Biosciences). Stained cells were then fixed with 4% paraformaldehyde and data acquired on a FACSVerse (BD Biosciences).

Example 11. Multiplex qPCR Methods

Total RNA was extracted using a NucleoSpin 96 RNA isolation kit (Macherey-Nagel). 5 ng of total RNA was used for cDNA synthesis and multiplex RT-PCR using a microfluidic dynamic array (Fluidigm; (Spurgeon S L, Jones R C, & Ramakrishnan R (2008) High throughput gene expression measurement with real time PCR in a microfluidic dynamic array. *PloS one* 3(2):e1662)). Relative gene expression was calculated from Ct values and normalized against ACTB mRNA levels as described previously (Pfaffl MW (2001) A new mathematical model for relative quantification in real-time RT-PCR. *Nucleic acids research* 29(9):e45). The fold-change in gene expression induced by SIK inhibitor treatment is reported relative to DMSO-treated samples exposed to the same microbial stimulus unless otherwise indicated. Genes and corresponding primers used in the multiplex qPCR are available in Table 4. The heat map representing multiplex qPCR data was generated for genes with significantly different expression (p<0.5) between DMSO versus PGE2 or HG-9-91-01-treated samples. One-minus Pearson's based hierarchical clustering of gene expression profiles was conducted using the Gene-E software suite (www.broadinstitute.org/cancer/software/GENE-E/download.html).

TABLE 4

Genes and corresponding primers used in the multiplex qPCR. In the "FP (forward primer)" column, the sequences correspond from top to bottom to SEQ ID NOs: 6 to 96, respectively. In the "RP (reverse primer)" column, the sequences correspond from top to bottom to SEQ ID NOs: 97 to 187, respectively.

| Target | FP (forward primer) | RP (reverse primer) | Design RefSeq (design reference sequence) |
|---|---|---|---|
| Arg1 | GGATTGGCAAGGTGATGGAA | CGACATCAAAGCTCAGGTGAA | NM_007482.3 |
| B2m | CTGGTGCTTGTCTCACTGAC | GGTGGGTGGCGTGAGTATA | NM_009735.3 |
| Batf3 | TCAGCGTGCTGCAGAGAA | TCTCCTTCGAACTTTCCTGTCA | NM_030060.2 |
| Bcl2 | ATTGCCGAGAAGAAGGGAGAA | CGGCGGCAGATGAATTACAA | NM_177410.2 |
| Bcl2l1 | AGCCTTGGATCCAGGAGAAC | GGCTGCTGCATTGTTCCC | NM_009743.4 |
| Bcl2l11 | TCGGAGACGAGTTCAACGAA | ACCATTTGAGGGTGGTCTTCA | NM_207680.2 |
| Ccl17 | CAGGAAGTTGGTGAGCTGGTA | CTTGCCCTGGACAGTCAGAA | NM_011332.3 |
| Ccl19 | CTGTGGCCTGCCTCAGATTA | CAGTCTTCCGCATCATTAGCA | NM_011888.2 |
| Ccl22 | CCTTCTTGCTGTGGCAATTCA | GGCAGCAGATACTGTCTTCCA | NM_009137.2 |
| Cd69 | GTGGTCCTCATCACGTCCTTA | ACAAGCCTGGGCAATTGTAC | NM_001033122.3 |
| Cdkn1b | CAGTGTCCAGGGATGAGGAA | TTCGGGGAACCGTCTGAAA | NM_009875.4 |
| Cebpa | ATGGCAGTGTGCACGTCTA | TGGCAAGAATCAGAGCAAAACC | NM_007678.3 |
| Ciita | GCCATCCGGGACCTTAAGAA | ATCTTTGCCAGTGTGGGGAA | NM_007575.2 |
| Cish | AGCCAAGACGTTCTCCTACC | CCCTCCGGCATCTTCTGTA | NM_009895.3 |
| Cxcl1 | CCTGAAGCTCCCTTGGTTCA | TTCTCCGTTACTTGGGGACAC | NM_008176.3 |
| Cxcl10 | ATCCGGAATCTAAGACCATCAAGAA | GCTCTCTGCTGTCCATCCA | NM_021274.1 |
| Cxcl11 | GAACAGGAAGGTCACAGCCATA | AGCGCCCTGTTTGAACATA | NM_019494.1 |
| Cxcr5 | GGACATGGGCTCCATCACATA | TCCCTCGACTGTAGAGCAGAA | NM_007551.2 |
| Cybb | CCCAACTGGGATAACGAGTTCA | TTCAGGGCCACACAGGAAAA | NM_007807.4 |
| Ebi3 | AAGTACCGACTCCGCTACC | GGTGAAAGTCGTGGCTTCAA | NM_015766.2 |
| Egr2 | GCCCCTTTGACCAGATGAAC | GGAGCGAAGCTACTCGGATA | NM_010118.3 |
| Egr3 | CGACTCGGTAGCCCATTACAA | GTCAGACCGATGTCCATCACA | NM_018781.2 |
| Eomes | GCGGCAAAGCGGACAATAAC | ATCCAGTGGGAGCCAGTGTTA | NM_010136.3 |
| Fas1 | CGAGGAGTGTGGCCCATTTA | AGCGGTTCCATATGTGTCTTCC | NM_010177.3 |
| Fos | ATGGGCTCTCCTGTCAACAC | GCTGTCACCGTGGGGATAA | NM_010234.2 |
| Foxp3 | GACGAGACTTGGAAGACAGTCA | TGGGCATTGGGTTCTTGTCA | NM_054039.1 |
| Gata3 | CCTACCGGGTTCGGATGTAA | CCGCAGTTCACACACTCC | NM_008091.3 |
| Gfi1 | TGAGCCTGGAGCAACACA | AGCGTGGATGACCTCTTGAA | NM_010278.2 |
| Hes1 | TGAAGCACCTCCGGAACC | CGCGGTATTTCCCCAACAC | NM_008235.2 |
| Hif1a | TCGACACAGCCTCGATATGAA | TTCCGGCTCATAACCCATCA | NM_010431.2 |
| Hk2 | AGAACCAGATCTACGCCATTCC | GCATTCGGCAATGTGGTCAA | NM_013820.3 |
| Hmox1 | TCAAGCACAGGGTGACAGAA | ATCACCTGCAGCTCCTCAAA | NM_010442.2 |
| Id2 | GAACACGGACATCAGCATCC | AGCCACAGAGTACTTTGCTATCA | NM_010496.3 |
| Ifit2 | TGCTTTGAGCGCTTTGACA | GCAGATTGCTCTCCAGTGAC | NM_008332.3 |
| Ifnb1 | AGCTCCAAGAAAGGACGAACA | TGGATGGCAAAGGCAGTGTA | NM_010510.1 |
| Ifng | GGCACAGTCATTGAAAGCCTA | GCCAGTTCCTCCAGATATCCA | NM_008337.3 |
| Ikzf1 | GCATAAAGAGCGATGCCACA | TCTGCCATCTCGTTGTGGTA | NM_001025597.1 |
| Il10 | AAAGGACCAGCTGGACAACA | TAAGGCTTGGCAACCCAAGTA | NM_010548.2 |
| Il12a | AAACCAGCACATTGAAGACC | GGAAGAAGTCTCTCTAGTAGCC | NM_001159424.1 |
| Il12b | ATCGTTTTGCTGGTGTCTCC | GGAGTCCAGTCCACCTCTAC | NM_008352.2 |
| Il13 | AGCTTATTGAGGAGCTGAGCAA | CCAGGTCCACACTCCATACC | NM_008355.3 |
| Il15 | CGTGCTCTACCTTGCAAACA | TTTCTCCTCCAGCTCCTCAC | NM_008357.1 |
| Il17a | TGAGTCCAGGGAGAGCTTCA | CGCTGCTGCCTTCACTGTA | NM_010552.3 |
| Il17f | AAGCAGCCATTGGAGAAACC | GGCAAGTCCCAACATCAACA | NM_145856.2 |
| Il18 | CAAAGAAAGCCGCCTCAAAC | GACGCAAGAGTCTTCTGACA | NM_008360.1 |
| Il1b | TGGCAACTGTTCCTGAACTCA | GGGTCCGTCAACTTCAAAGAAC | NM_008361.3 |
| Il2 | CCCAGGATGCTCACCTTCAAA | CCGCAGAGGTCCAAGTTCA | NM_008366.3 |
| Il20 | GTGGGGAAGAAGCAATGGAGAA | CTTTACCACCGCTGCCTGAA | NM_021380.1 |
| Il21 | GATCCTGAACTTCTATCAGCTCCA | GGCCTTCTGAAAACAGGCAAA | NM_021782.2 |
| Il22 | TGGTGCCTTTCCTGACCAAA | TCTGGATGTTCTGGTCGTCAC | NM_016971.2 |
| Il23a | CTGCATGCTAGCCTGGAAC | ACTGGATACGGGGCACATTA | NM_031252.2 |
| Il27 | CCCAATGTTTCCCTGACTTTCC | CGAAGTGTGGTAGCGAGGAA | NM_145636.1 |
| Il2ra | TGCGTTGCTTAGGAAACTCC | CTGGTGTTCAAGTTGAGCTGTA | NM_008367.3 |

TABLE 4-continued

Genes and corresponding primers used in the multiplex qPCR. In the "FP (forward primer)" column, the sequences correspond from top to bottom to SEQ ID NOs: 6 to 96, respectively. In the "RP (reverse primer)" column, the sequences correspond from top to bottom to SEQ ID NOs: 97 to 187, respectively.

| | | | |
|---|---|---|---|
| Il3 | ACTCAAAACTGATGATGAAGGAC | TCTCCTTGGCTTTCCACGAA | NM_010556.4 |
| Il33 | GGTCCCGCCTTGCAAAATA | AGAACGGAGTCTCATGCAGTA | NM_133775.2 |
| Il4 | ACGGAGATGGATGTGCCAAA | GCACCTTGGAAGCCCTACA | NM_021283.2 |
| Il5 | GATGAGGCTTCCTGTCCCTA | TTCAGTATGTCTAGCCCCTGA | NM_010558.1 |
| Il6 | CCAGAAACCGCTATGAAGTTCC | GTTGTCACCAGCATCAGTCC | NM_031168.1 |
| Il9 | CAGCTGCTTGTGTCTCTCC | TGGCATTGGTCAGCTGTAAC | NM_008373.1 |
| Irf4 | TCCCCATTGAGCCAAGCATA | CGAGGATGTCCCGGTAATACA | NM_013674.1 |
| Irf8 | TGCCACTGGTGACCGGATA | AGCTGATGACCATCTGGGAGAA | NM_008320.3 |
| Isg15 | TTCCAGGGGACCTAGAGCTA | GACACCAGGAAATCGTTACCC | NM_015783.3 |
| Ldha16b | AGGAAGACGCATCCAGTTACC | ATACAAGGCACGCTGAGGAA | NM_175349.2 |
| Lef1 | ACACATCCCGTCAGATGTCA | GGGTAGAAGGTGGGGATTTCA | NM_010703.3 |
| MaFB | TGATCCGCCTGAAGCAGAA | CTGCTGGACGCGTTTATACC | NM_010658.3 |
| Mcl1 | AAACGGGACTGGCTTGTCA | CCGCCTTCTAGGTCCTGTAC | NM_008562.3 |
| Myc | AGTGCTGCATGAGGAGACA | TCTCCACAGACACCACATCA | NM_010849.4 |
| Ncf1 | GTGCCCAAAGATGGCAAGAA | AGTCAGCAATGGCCCGATA | NM_010876.3 |
| Nfil3 | TACAGCCGCCCTTTCTTTTCC | GTTGTCCGGCACAGGGTAAA | NM_017373.3 |
| Nos2 | GAGGAGCAGGTGGAAGACTA | GGAAAAGACTGCACCGAAGATA | NM_010927.3 |
| Notch1 | GGACGGCGTGAATACCTACA | GACATTCGTCCACATCCTCTGTA | NM_008714.3 |
| Nqo1 | AAGCTGCAGACCTGGTGATA | ACGAGCACTCTCTCAAACCA | NM_008706.5 |
| Pdia4 | TTGACTATGATGGCTCCAGGAC | CAGGTGGAGGTGTCCAATCA | NM_009787.2 |
| Ptgs2 | CTTCTCCCTGAAGCCGTACA | TGTCACTGTAGAGGGCTTTCA | NM_011198.3 |
| Rorc | TGGAGCTCTGCCAGAATGAC | GGCCCTGCACATTCTGACTA | NM_011281.2 |
| Runx3 | AACCAAGTGGCCAGGTTCAA | ACGGTGATTGTGAGCGTGAA | NM_019732.2 |
| Sfpi1 | AACAGATGCACGTCCTCGATA | CATCCGGGGCATGTAGGAA | NM_011355.1 |
| Slc2a1 | GCTGTGCTGTGCTCATGAC | GATGGCCACGATGCTCAGATA | NM_011400.3 |
| Socs1 | ATCCGCGTGCACTTCCA | AGCTCGAAAAGGCAGTCGAA | NM_009896.2 |
| Socs3 | GCCGGAGATTTCGCTTCG | ACTTGCTGTGGGTGACCAT | NM_007707.3 |
| Sod2 | AAGGAGCAAGGTCGCTTACA | AATCCCCAGCAGCGGAATAA | NM_013671.3 |
| Spib | CTGGATGGCCCACACTTAA | CCCCATCTGAATCTGGGTAAC | NM_019866.1 |
| Sqstm1 | GCTGAAGGAAGCTGCCCTATA | TCTGGGAGAGGGACTCAATCA | NM_011018.2 |
| Tbx21 | CAAGTTCAACCAGCACCAGAC | CCACGGTGAAGGACAGGAA | NM_019507.2 |
| Tcf7 | AAGAGGCGGTCAAGGGAAAA | GGCCTTCTCCGGGTAAGTAC | NM_009331.3 |
| Tcf712 | CAGCTGACGTAGACCCCAAA | GGGCGACAGCGGGTAATA | NM_009333.3 |
| Xbp1 | CAGCAAGTGGTGGATTTGGAA | CAAGGCCGTGAGTTTTCTCC | NM_013842.2 |
| Zbtb10 | CTGAAGCCTGCAGTGGTCA | AAGTGCCAGCACCATCAAACCA | NM_177660.3 |
| Zbtb46 | GCTCTCCAGTACCTTCATTCC | CTCAGTGACCGTCAGGTCTA | NM_028125.3 |
| Zbtb7b | GGACGCGCTTCTTCCTACA | TGGGATTCCAATCAGGTCATCC | NM_009565.4 |
| Zfpm1 | ATTCTACGGGAGCATCCAGAC | CATCCACCATCAGGGTCACA | NM_009569.3 |

| Target | Blast hit | Gene symbol | Gene full name |
|---|---|---|---|
| Arg1 | NM_007482.3 | Arg1 | arginase, liver |
| B2m | NM_009735.3 | B2m | beta-2 microglobulin |
| Batf3 | NM_030060.2 | Batf3 | basic leucine zipper transcription factor, ATF-like 3 |
| Bcl2 | NM_177410.2\|NM_009741.3 | Bcl2 | B-cell leukemia/lymphoma 2 |
| Bcl2l1 | NM_009743.4 | Bcl2l1 | BCL2-like 1 |
| Bcl2l11 | NM_009754.3\|NM_207681.21 NM_207680.2 | Bcl2l11 | BCL2-like 11 (apoptosis facilitator) |
| Ccl17 | NM_011332.3 | Ccl17 | chemokine (C-C motif) ligand 17 |
| Ccl19 | NM_011888.2 | Ccl19 | chemokine (C-C motif) ligand 19 |
| Ccl22 | NM_009137.2 | Ccl22 | chemokine (C-C motif) ligand 22 |
| Cd69 | NM_001033122.3 | Cd69 | CD69 antigen |
| Cdkn1b | NM_009875.4 | Cdkn1b | cyclin-dependent kinase inhibitor 1B |
| Cebpa | NM_007678.3 | Cebpa | CCAAT/enhancer binding protein (C/EBP), alpha |
| Ciita | NM_007575.2 | Ciita | class II transactivator |
| Cish | NM_009895.3 | Cish | cytokine inducible SH2-containing protein |

TABLE 4-continued

Genes and corresponding primers used in the multiplex qPCR. In the "FP (forward primer)" column, the sequences correspond from top to bottom to SEQ ID NOs: 6 to 96, respectively. In the "RP (reverse primer)" column, the sequences correspond from top to bottom to SEQ ID NOs: 97 to 187, respectively.

| | | | |
|---|---|---|---|
| Cxcl1 | NM_008176.3 | Cxcl1 | chemokine (C-X-C motif) ligand 1 |
| Cxcl10 | NM_021274.1 | Cxcl10 | chemokine (C-X-C motif) ligand 10 |
| Cxcl11 | NM_019494.1 | Cxcl11 | chemokine (C-X-C motif) ligand 11 |
| Cxcr5 | NM_007551.2 | Cxcr5 | chemochine (C-X-C motif) receptor 5 |
| Cybb | NM_007807.4 | Cybb | cytochrome b-245, beta polypeptide |
| Ebi3 | NM_015766.2 | Ebi3 | Epstein-Barr virus induced gene 3 |
| Egr2 | NM_010118.3 | Egr2 | early growth response 2 |
| Egr3 | NM_018781.2 | Egr3 | early growth response 3 |
| Eomes | NM_010136.3\|NM_001164789.1 | Eomes | eomesodermin homolog (*Xenopus laevis*) |
| Fasl | NM_010177.3 | Fasl | Fas ligand (TNF superfamily, member 6) |
| Fos | NM_010234.2 | Fos | FBJ osteosarcoma oncogene |
| Foxp3 | NM_054039.1 | Foxp3 | forkhead box P3 |
| Gata3 | NM_008091.3 | Gata3 | GATA binding protein 3 |
| Gfi1 | NM_010278.2 | Gfi1 | growth factor independent 1 |
| Hes1 | NM_008235.2 | Hes1 | hairy and enhancer of split 1 (*Drosophila*) |
| Hif1a | NM_010431.2 | Hif1a | hypoxia inducible factor 1, alpha subunit |
| Hk2 | NM_013820.3 | Hk2 | hexokinase 2 |
| Hmox1 | NM_010442.2 | Hmox1 | heme oxygenase (decycling) 1 |
| Id2 | NM_010496.3 | Id2 | inhibitor of DNA binding 2 |
| Ifit2 | NM_008332.3 | Ifit2 | interferon-induced protein with tetratricopeptide repeats 2 |
| Ifnb1 | NM_010510.1 | Ifnb1 | interferon beta 1, fibroblast |
| Ifng | NM_008337.3 | Ifng | interferon gamma |
| Ikzf1 | NM_001025597.1\|NM_009578.2 | Ikzf1 | IKAROS family zinc finger 1 |
| Il10 | NM_010548.2 | Il10 | interleukin 10 |
| Il12a | NM_001159424.1\|NM_008351.2 | Il12a | interleukin 12a |
| Il12b | NM_008352.2 | Il12b | interleukin 12b |
| Il13 | NM_008355.3 | Il13 | interleukin 13 |
| Il15 | NM_008357.1 | Il15 | interleukin 15 |
| Il17a | NM_010552.3 | Il17a | interleukin 17A |
| Il17f | NM_145856.2 | Il17f | interleukin 17F |
| Il18 | NM_008360.1 | Il18 | interleukin 18 |
| Il1b | NM_008361.3 | Il1b | interleukin 1 beta |
| Il2 | NM_008366.3 | Il2 | interleukin 2 |
| Il20 | NM_021380.1 | Il20 | interleukin 20 |
| Il21 | NM_021782.2 | Il21 | interleukin 21 |
| Il22 | NM_054079.2\|NM_016971.2 | Il22 | interleukin 22 |
| Il23a | NM_031252.2 | Il23a | interleukin 23, alpha subunit p19 |
| Il27 | NM_145636.1 | Il27 | interleukin 27 |
| Il2ra | NM_008367.3 | Il2ra | interleukin 2 receptor, alpha chain |
| Il3 | NM_010556.4 | Il3 | interleukin 3 |
| Il33 | NM_001164724.1\|NM_133775.2 | Il33 | interleukin 33 |
| Il4 | NM_021283.2 | Il4 | interleukin 4 |
| Il5 | NM_010558.1 | Il5 | interleukin 5 |
| Il6 | NM_031168.1 | Il6 | interleukin 6 |
| Il9 | NM_008373.1 | Il9 | interleukin 9 |
| Irf4 | NM_013674.1 | Irf4 | interferon regulatory factor 4 |
| Irf8 | NM_008320.3 | Irf8 | interferon regulatory factor 8 |
| Isg15 | NM_015783.3 | Isg15 | ISG15 ubiquitin-like modifier |
| Ldha16b | NM_175349.2 | Ldha16b | lactate dehydrogenase A-like 6B |
| Lef1 | NM_010703.3 | Lef1 | lymphoid enhancer binding factor 1 |
| Mafb | NM_010658.3 | Mafb | v-maf musculoaponeurotic fibrosarcoma oncogene family, protein B (avian) |
| Mcl1 | NM_008562.3 | Mcl1 | myeloid cell leukemia sequence 1 |
| Myc | NM_001177354.1\|NM_001177353.1\|NM_001177352.1\|NM_010849.4 | Myc | myelocytomatosis oncogene |
| Ncf1 | NM_010876.3 | Ncf1 | neutrophil cytosolic factor 1 |
| Nfil3 | NM_017373.3 | Nfil3 | nuclear factor, interleukin 3, regulated |
| Nos2 | NM_010927.3 | Nos2 | nitric oxide synthase 2, inducible |
| Notch1 | NM_008714.3 | Notch1 | notch 1 |
| Nqo1 | NM_008706.5 | Nqo1 | NAD(P)H dehydrogenase, quinone 1 |
| Pdia4 | NM_009787.2 | Pdia4 | protein disulfide isomerase associated 4 |
| Ptgs2 | NM_011198.3 | Ptgs2 | prostaglandin-endoperoxide synthase 2 |
| Rorc | NM_011281.2 | Rorc | RAR-related orphan receptor gamma |
| Runx3 | NM_019732.2 | Runx3 | runt related transcription factor 3 |
| Sfpi1 | NM_011355.1 | Sfpi1 | SFFV proviral integration 1 |
| Slc2a1 | NM_011400.3 | Slc2a1 | solute carrier family 2 (facilitated glucose transporter), member 1 |

TABLE 4-continued

Genes and corresponding primers used in the multiplex qPCR. In the "FP (forward primer)" column, the sequences correspond from top to bottom to SEQ ID NOs: 6 to 96, respectively. In the "RP (reverse primer)" column, the sequences correspond from top to bottom to SEQ ID NOs: 97 to 187, respectively.

| | | | |
|---|---|---|---|
| Socs1 | NM_009896.2 | Socs1 | suppressor of cytokine signaling 1 |
| Socs3 | NM_007707.3 | Socs3 | suppressor of cytokine signaling 3 |
| Sod2 | NM_013671.3 | Sod2 | superoxide dismutase 2, mitochondrial |
| Spib | NM_019866.1 | Spib | Spi-B transcription factor (Spi-1/PU.1 related) |
| Sqstm1 | NM_011018.2 | Sqstm1 | sequestosome 1 |
| Tbx21 | NM_019507.2 | Tbx21 | T-box 21 |
| Tcf7 | NM_009331.3 | Tcf7 | transcription factor 7, T-cell specific |
| Tcf7l2 | NM_001142924.1\|NM_001142923.1\|NM_001142922.1\|NM_001142921.1\|NM_001142920.1\|NM_001142919.1\|NM_001142918.1\|NM_009333.3 | Tcf7l2 | transcription factor 7-like 2, T-cell specific, HMG-box |
| Xbp1 | NM_013842.2 | Xbp1 | X-box binding protein 1 |
| Zbtb10 | NM_177660.3 | Zbtb10 | zinc finger and BTB domain containing 10 |
| Zbtb46 | NM_028125.3\|NM_027656.2 | Zbtb46 | zinc finger and BTB domain containing 46 |
| Zbtb7b | NM_009565.4 | Zbtb7b | zinc finger and BTB domain containing 7B |
| Zfpm1 | NM_009569.3 | Zfpm1 | zinc finger protein, multitype 1 |

Example 12. Methods for Detecting and NO Production

After stimulation of cells with microbial ligands, the culture medium was removed, clarified by centrifugation for 10 min at 14,000×g, and the concentration of TNF-α, IL-6, IL-10, IL-12p40, IL-1β and RANTES were measured using FlexSet Cytokine Bead Array (BD Biosciences) according to the manufacturer's instructions. Where indicated, ELISAs were used to detect IL-10 and IL-12p70 (BD Biosciences) according to the manufacturer's instructions. NO production was estimated based on nitrate content in culture medium using the Greiss reagent as described previously (Miletic A V, et al. (2007) Vav proteins control MyD88-dependent oxidative burst. *Blood* 109(8):3360-3368).

Example 13. Methods for T Cell Differentiation and FoxP3 Staining

Balb/c mice were euthanized and splenic CD4+CD62L+ T cells were magnetically enriched (Miltenyi Biotec) to >95% purity and cultured in DMEM media on plates pre-coated with anti-CD3 and anti-CD28 antibodies (clones 145-2C11 and 37.51; BioXCell). Culture media was supplemented with 10 μg/mL anti-IL-4 (clone 11B11; BioXCell), anti-IL-12 (clone C17.8; BioXCell), and anti-IFNγ (clone XMG1.2; BioXCell) as well as TGFβ (2 ng/mL; PeproTech). HG-9-91-01 (100 nM) or DMSO were added at day 0. Cultures were fed with DMEM+IL-2 (10 ng/mL, Peprotech) containing small molecules at day 2 and analyzed at day 4. Cells were stained with blue LIVE/DEADAqua stain (Invitrogen) to discriminate live cells, fixed with Foxp3 Permeabilization Buffer (eBioscience), stained with FITC anti-CD4 (clone RM4-5, Biolegend) and PE anti-Foxp3 (clone FJK-16S, eBioscience) and acquired on a FACSVerse (BD Biosciences). For Th0 and Tr1 differentiations, C57BL/6 mice were euthanized and splenic CD4+CD62L+ T cells were magnetically enriched (Miltenyi Biotec) to >95% purity and cultured in DMEM media on plates pre-coated with anti-CD3 and anti-CD28 antibodies (clones 145-2C11 and 37.51; BioXCell) in the absence of neutralizing antibodies. For Tr1 differentiations, the culture media was supplement with TGFβ (2 ng/mL; PeproTech) and rIL-27 (25 ng/mL; R&D Systems) as described previously (Gagliani N, et al. (2013) Coexpression of CD49b and LAG-3 identifies human and mouse T regulatory type 1 cells. *Nature medicine* 19(6):739-746). After 4 days, cells were harvested, washed in PBS and stained with LIVE/DEADGreen to discriminate viable cells and eFluor450 anti-CD4 (BioLegend) and acquired on a FACSVerse (BD Biosciences). Absolute cell numbers were enumerated by adding 5000 10 mm beads (Spherotech) to each well. Analysis was performed using Flowjo (Treestar) excluding samples were significant toxicity was observed. For all differentiation conditions, IL-10 levels were quantified in the culture media at day 4 by ELISA (BD Biosciences).

Example 14. Immunoblotting Methods

Cell lysis and immunoblotting were conducted as described previously (Clark K, et al. (2012) Phosphorylation of CRTC3 by the salt-inducible kinases controls the interconversion of classically activated and regulatory macrophages. *Proceedings of the National Academy of Sciences of the United States of America* 109(42):16986-16991). Briefly, cells were rinsed in ice-cold PBS and extracted in lysis buffer (50 mM Tris.HCl at pH 7.4, 1 mM EDTA, 1 mM EGTA, 50 mM NaF, 10 mM sodium 3-glycerol 1-phosphate, 1 mM DTT, 1 mM sodium orthovanadate, 1% (vol/vol) Triton X-100 and 1× Complete EDTA-free Protease Inhibitor Cocktail (Roche). Cell extracts were clarified by centrifugation at 14,000×g for 10 min at 4° C., and protein concentrations were determined by using the Bradford assay. To detect proteins in cell lysates, 25 gig of protein extract was separated by SDS/PAGE. After transfer to PVDF membranes, proteins were detected by immunoblotting and visualized by treating the blots with SuperSignal West Pico Chemiluminescent Substrate (ThermoScientific) followed by autoradiography. The following antibodies were used for immunoblotting: β-actin (clone 13E5) was from Cell Signaling; CRTC3 (clone EPR3440) was from Abcam; pSer370 (S253D bleed 2) of CRTC3 was a generous gift of P. Cohen (University of Dundee).

Example 15. Methods for Isolation of Lamina Propria Myeloid Cells

CX3CR1GFP/+ mice were euthanized and intestines cut into 3-4 pieces before inversion onto polyethylene tubes (Becton Dickinson). Intestinal fragments were washed with calcium- and magnesium-free PBS (Lonza), and mucus was removed with 1 mM DTT. The intestinal epithelium was eluted with 30 mM EDTA at room temperature, followed by digestion of the tissue with 36 U/ml type IV collagenase (Sigma-Aldrich) in DMEM containing 5% (vol/vol) FBS for 90 min at 37° C. in a 5% CO2 humidified incubator. The digested tissue was gently shaken for 10 min at room temperature and then passed through a 70 μm nylon cell strainer and washed with DMEM. A final OptiPrep density centrifugation at ρ=1.055 g/ml (Axis Shield) yielded lamina propria myeloid cells. To purify CX3CR1-expressing macrophages, cells were stained with PE-conjugated anti-CD11c (HL3; BD Biosciences) and PE/Cy7 conjugated anti-CD45 (30-F11; BioLegend) and enriched with a BD FACSVantage SE-DiVa cell sorter.

Example 16. Methods of Statistical Analysis

Unless otherwise indicated, error bars represent mean±SD for 3 replicates from an independent experiment that is representative of 2 independent experiments. Fisher-Exact tests correlating kinase inhibition with IL-10 up-regulation were conducted using Prism6 (GraphPad). EC50's for IL-10 up-regulation were estimated using the SmartFit Non-linear regression in Genedata Screener software suite (Genedata). Statistical significance of differences between experimental groups was assessed by using unpaired, two-tailed Student t test and differences in means were considered significant if $p<0.05$. Unless otherwise indicated, *$p<0.05$; **$p<0.01$.

Figure 5A:
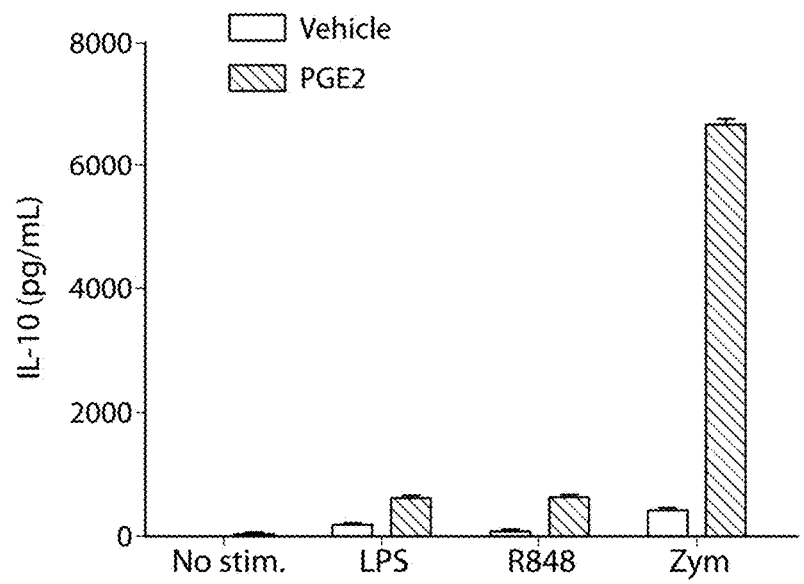
FIG. 5A. Development of high a throughput screen for small molecule enhancers of IL-10 production. Murine bone marrow was differentiated into BMDCs for 7 days in the presence of DMSO or PGE$_2$ (5 μM) followed by either mock stimulation (no stim.), or treatment with LPS (100 ng/mL), R848 (10 μg/mL), or zymosan (Zym) (4 μg/mL). After 18 hr, IL-10 secreted into the culture media was quantified by ELISA. For panels (5A) and (5B), error bars=mean±SD, n=3 from one independent experiment. Data are representative of two independent experiments.
Figure 5B:
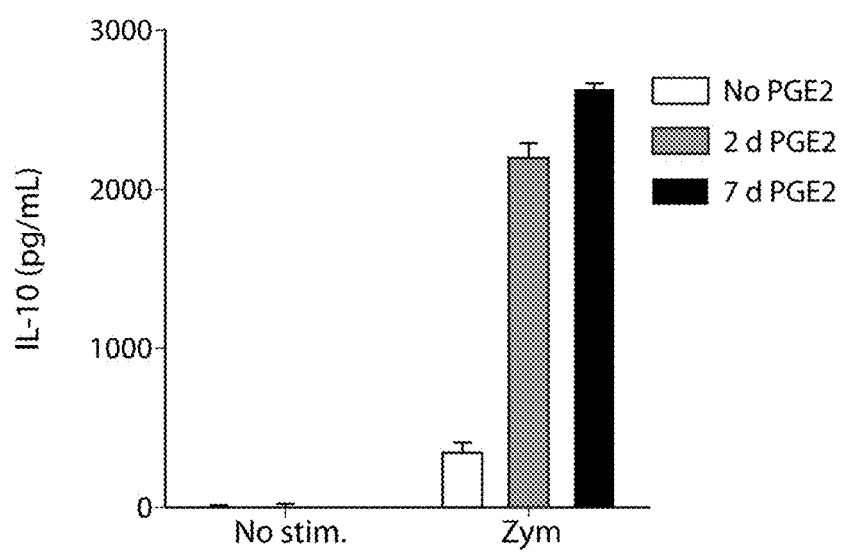
FIG. 5B. BMDCs were differentiated in the presence of DMSO (white bar) or PGE$_2$ (5 μM; black bar) for 7 days. Alternatively, PGE$_2$ (5 μM) was added during the final 2 days of differentiation (grey bar). In all conditions, mock stimulation (no stim.), zymosan (Zym) stimulation and IL-10 detection was conducted as in (5A). For panels (5A) and (5B), error bars=mean±SD, n=3 from one independent experiment. Data are representative of two independent experiments.
Figure 5C:
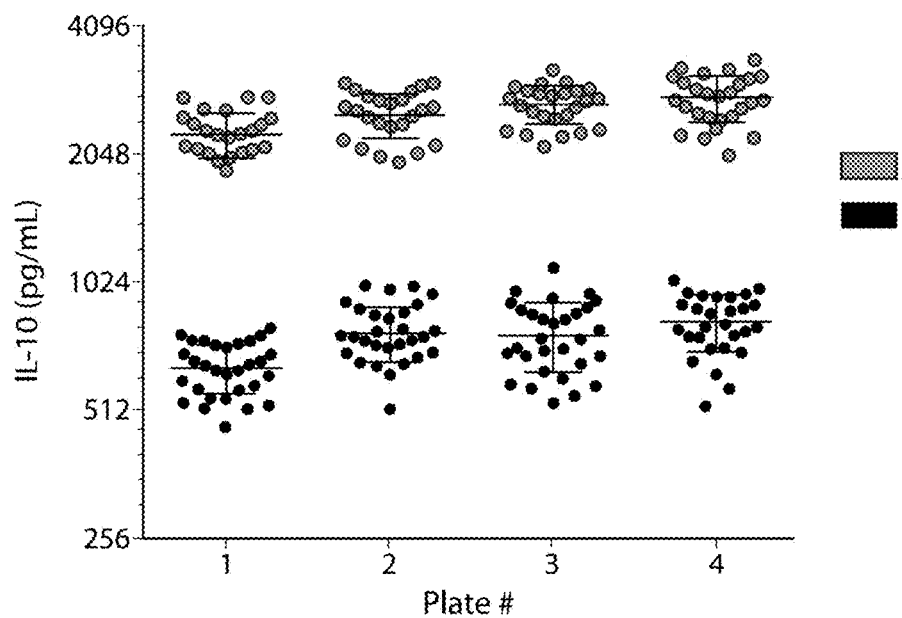
FIG. 5C. After 5 days of differentiation, BMDCs were harvested and cultured in 384-well plates in the presence of DMSO (blue or black circles) or PGE$_2$ (5 μM; red or grey circles) followed by stimulation with zymosan (4 μg/mL). After 18 hr, IL-10 secreted into the culture media was quantified by AlphaLISA. Error bars represent mean±SD, n=32 for one independent experiment that is representative of >5 independent experiments.

Example 17. Focused High-Throughput Screen Identifies Kinase Inhibitors that Enhance IL-10 Production by Activated Dendritic Cells To enable measurement of IL-10 production by myeloid cells in high throughput, we established an AlphaLISA-based assay to detect IL-10 released by BMDCs in 384-well plate format (FIG. 1A). Consistent with established role of EP2/EP4 prostanoid receptor signaling in promoting IL-10 expression in myeloid cells (19), differentiation of BMDCs in the presence $PGE_2$ increased levels of IL-10 detectable in the culture media by ELISA following stimulation with a variety of microbial-derived ligands (FIG. 5A). The robust IL-10-potentiating effect of differentiating BMDCs in the presence of $PGE_2$ was recapitulated in fully differentiated BMDCs treated with $PGE_2$ for 2 days prior to stimulation with the yeast cell wall preparation zymosan (FIG. 5B). Moreover, the stimulatory effects of treatment with $PGE_2$ for 2 days on zymosan-induced IL-10 production were observed with BMDCs cultured in 384-well plates using AlphaLISA-based IL-10 detection (FIG. 5C). Together, these results establish zymosan-stimulated BMDCs as a robust, reproducible assay system to identify small-molecules that enhance IL-10 production by activated myeloid cells.

Figure 5D:
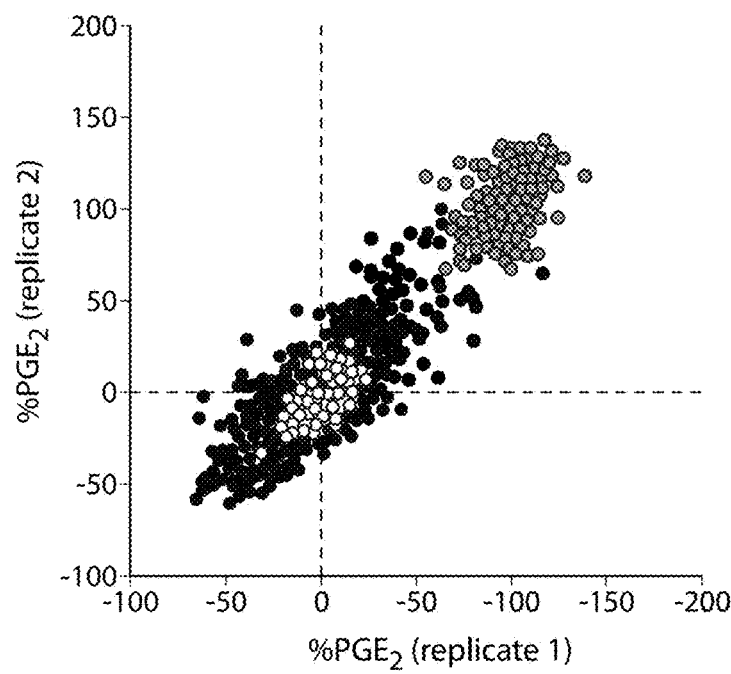
FIG. 5D. After 5 days of differentiation, BMDCs were harvested and cultured in 384-well plates in the presence of DMSO (yellow or white circles), PGE$_2$ (5 μM; red or grey circles) or test compounds (blue or black circles) for 2 d. Zymosan stimulation and IL-10 detection was conducted as in (C). Compound activity is expressed at % of the PGE$_2$ response on per plate basis for 2 replicates.
Figure 6:
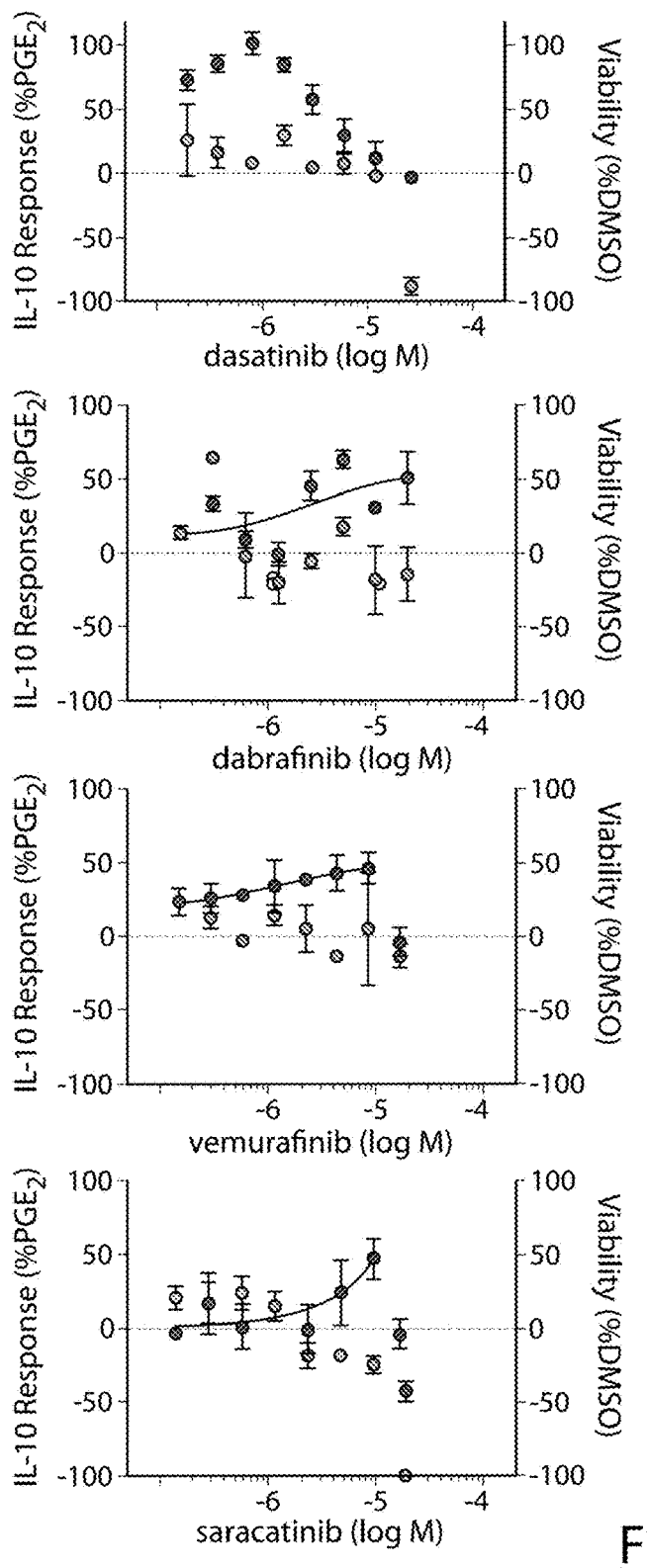
FIG. 6. Concentration response curves for effects of hits compounds on IL-10 production and viability. BMDCs were treated with DMSO, PGE$_2$ (5 μM) or the indicated concentrations of hit compounds for 2 days followed by stimulation with zymosan (4 μg/mL). After 18 hr, secreted IL-10 was measured via AlphaLISA in an aliquot of culture media and is expressed as a percent of the IL-10 potentiation response induced by $PGE_2$. Viability was estimated in terms of change in total cellular ATP levels relative to DMSO-treated cells from the same experiment. Error bars=mean±SD, n=3 from one independent experiment. Data are representative of two independent experiments.
Figure 6:
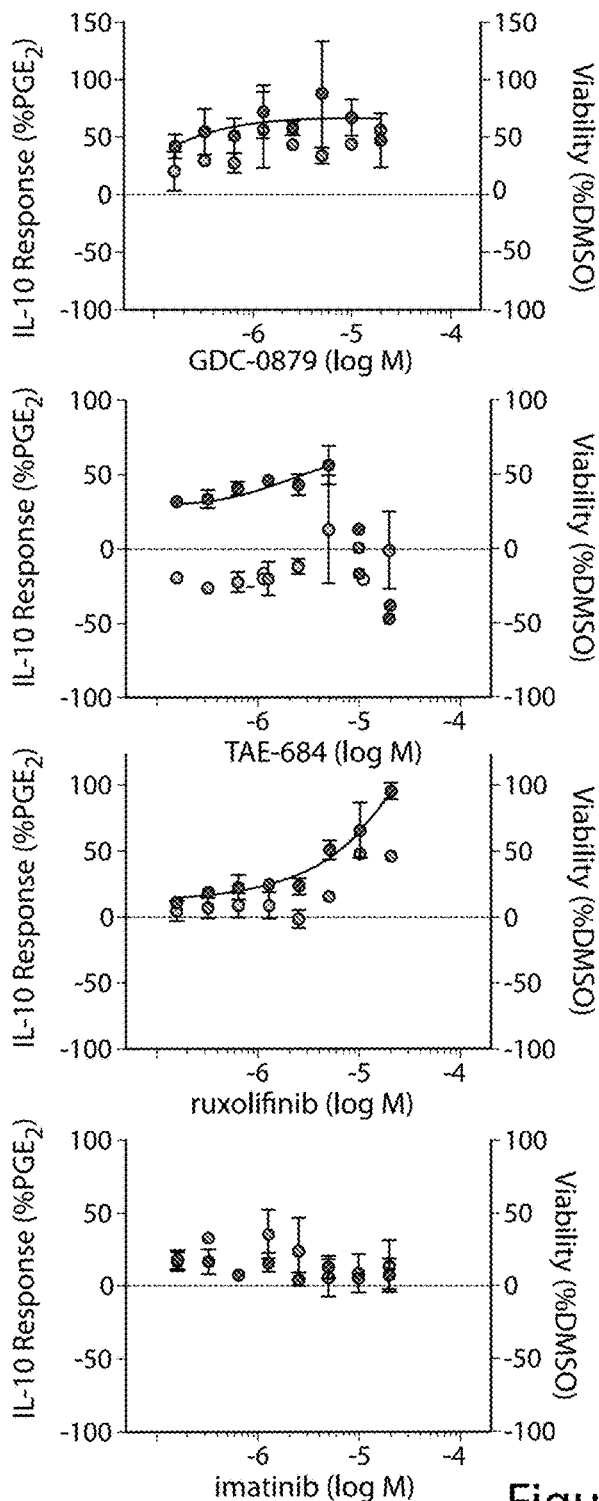
Figure 6:
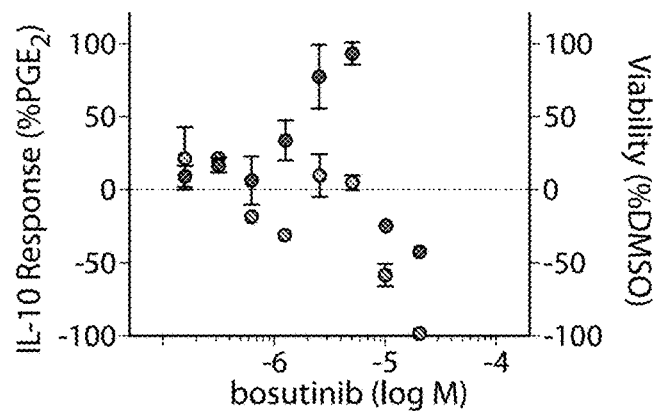
Figure 6:
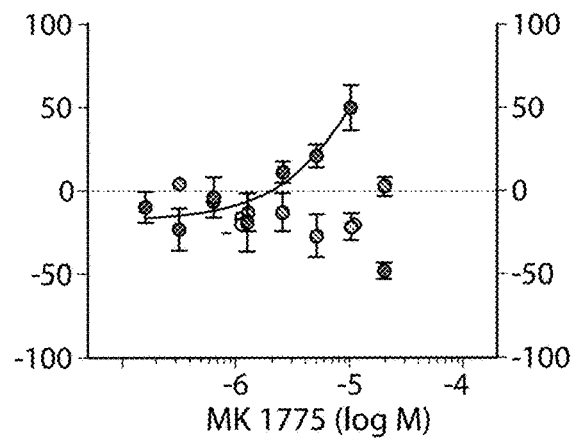
Figure 6:
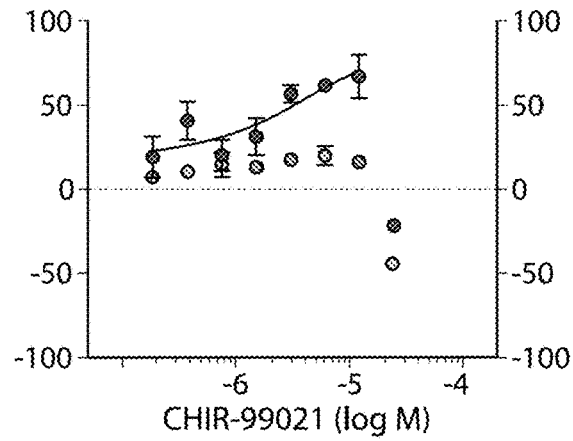

To discover novel small-molecule enhancers of IL-10 production by inflammatory DCs, we screened a collection of >150 kinase inhibitors comprising FDA-approved drugs and well-annotated probe compounds for their effects on zymosan-induced IL-10 production in BMDCs (FIG. 5D). Ten kinase inhibitors were classified as hits based on their ability to dose-dependently potentiate IL-10 production with a maximum effect >30% of the $PGE_2$ response (FIG. 1B and FIG. 6). These hits include the GSK-3β inhibitor CHIR-99021, which further validates the screening strategy because pharmacological or genetic disruption of GSK-3β has been previously reported to enhance IL-10 production by LPS-stimulated MΦs (17). Several of the IL-10-enhancing compounds reduced IL-10 at concentrations greater than 1 μM, an effect that correlates with reduced viability in the case of bosutinib, saracatinib, TAE-684 and CHIR-99021 (FIG. 6). Alternatively, inhibition of kinases (e.g., Src and Syk) that convey proximal signals downstream of the zymosan receptor Dectin-1 may account for the inhibitory effect on IL-10 production at high concentrations of compound. In these cases, $EC_{50}$ values were calculated solely using IL-10-potentiating concentrations for each inhibitor.

Figure 1C:
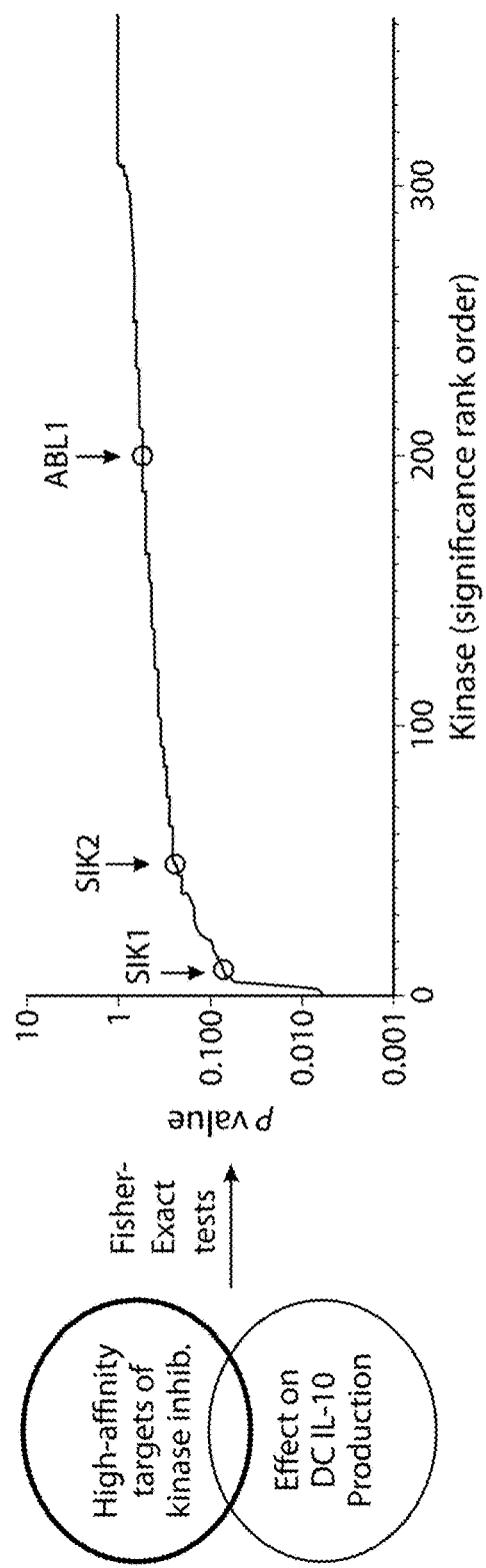
FIG. 1C. Correlation of IL-10-potentiating activity of kinase inhibitors in this screen with their high affinity targets ($K_d$<500 nM) identifies common targets of active compounds potentially accounting for the observed effects on IL-10.

Example 18. Analysis of Shared Targets of Hit SIK Inhibitors Suggests Role for Inhibition Salt-Inducible Kinases in IL-10 Potentiation Dasatinib, bosutinib and saracatinib, which are used clinically to inhibit BCR-Abl, c-Kit and several other kinases for treatment of chronic myeloid leukemia (CML) (22), were among the most potent and active (i.e., large maximum effect) IL-10 enhancers identified in this screen. However, the BCR-Abl-targeting CML drug imatinib was non-toxic in BMDCs, but did not up-regulate IL-10 production (FIG. 6). This contrast suggests that the observed IL-10-potentiating effects of the hit SIK inhibitors might arise from shared 'off-target' inhibition of kinases other than Abl1. This possibility is supported by kinase-profiling data indicating that dasatinib and bosutinib modulate the activity of a large number of kinases (23). To investigate this possibility, we correlated the IL-10-potentiating activity of 38 of the screened kinase inhibitors, including six of the hit SIK inhibitors, with publically available binding affinities ($K_d$'s) for a panel of >400 recombinant kinases (23). Fisher-Exact testing was used to determine whether high affinity ligands of a particular kinase, defined as SIK inhibitors with $K_d<500$ nM, were enriched among the hit SIK inhibitors. This analysis identified statistically significant associations ($p<0.05$) between IL-10 up-regulation and binding to several kinases (FIG. 1C). However, due to the small number of SIK inhibitors with available kinase profiling data and large number of tests, none of the associations remained significant after correction for multiple hypothesis testing.

Figure 1D:
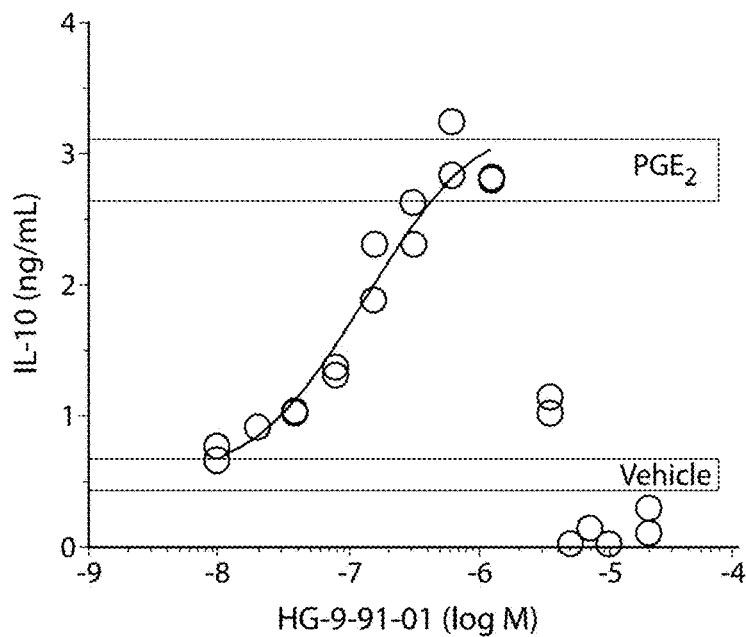
FIG. 1D. Bone marrow derived-dendritic cells (BMDCs) treated with DMSO, prostaglandin E2 (PGE$_2$), (5 μM, gray bars=mean±SD, n=12 from one independent experiment) or the indicated concentrations of the SIK inhibitor HG-9-91-01 in duplicate for 2 days followed by stimulation with zymosan. After 18 hr, secreted IL-10 was detected by ELISA. Data are representative of >5 independent experiments.
Figure 1E:
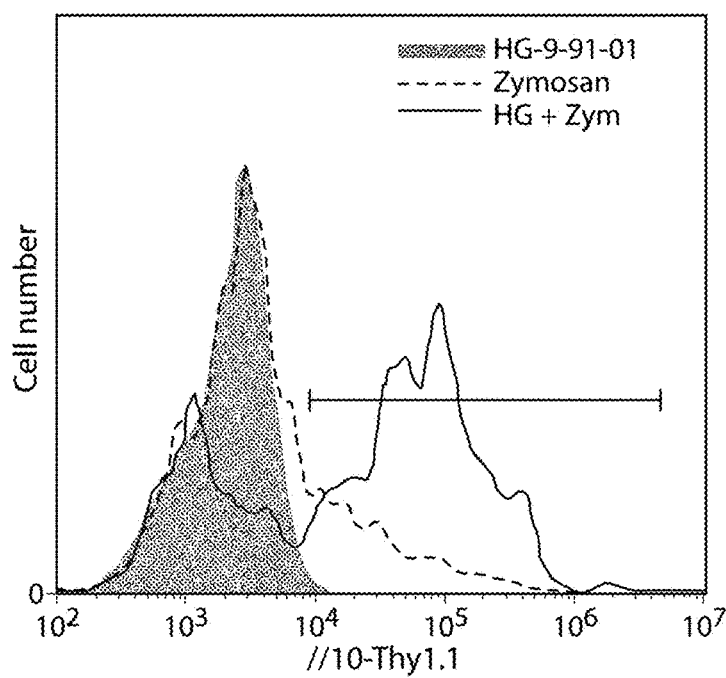
FIG. 1E. Cell surface abundance of Il10-Thy1.1 reporter gene in 10BiT BMDCs treated with DMSO or HG-9-91-01 (HG) (0.5 μM) for 2 days prior to stimulation with zymosan (Zym) for 18 hr.
Figure 1F:
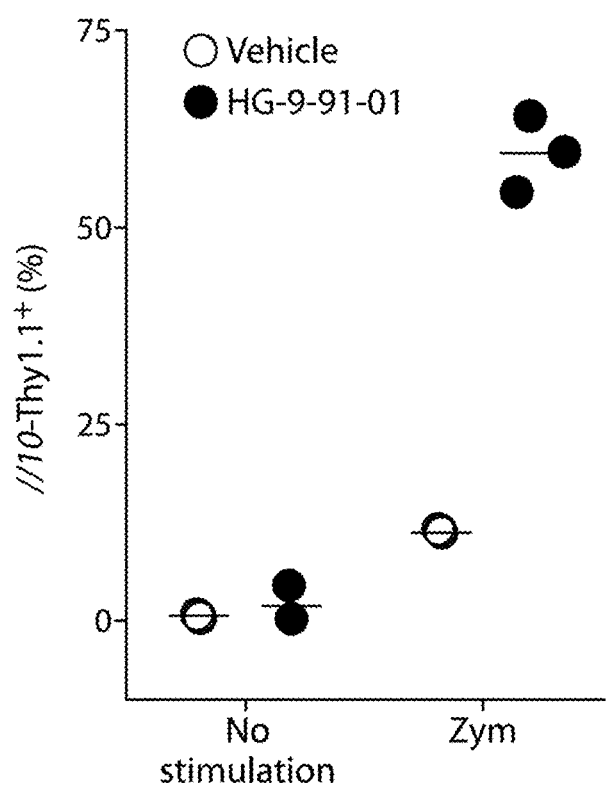
FIG. 1F. Black bars are mean frequency of Il10-Thy1.1$^+$ cells from 10BiT BMDCs from three individual mice treated and analyzed as in (E). Zymosan abbreviated (Zym).
Figure 7A:
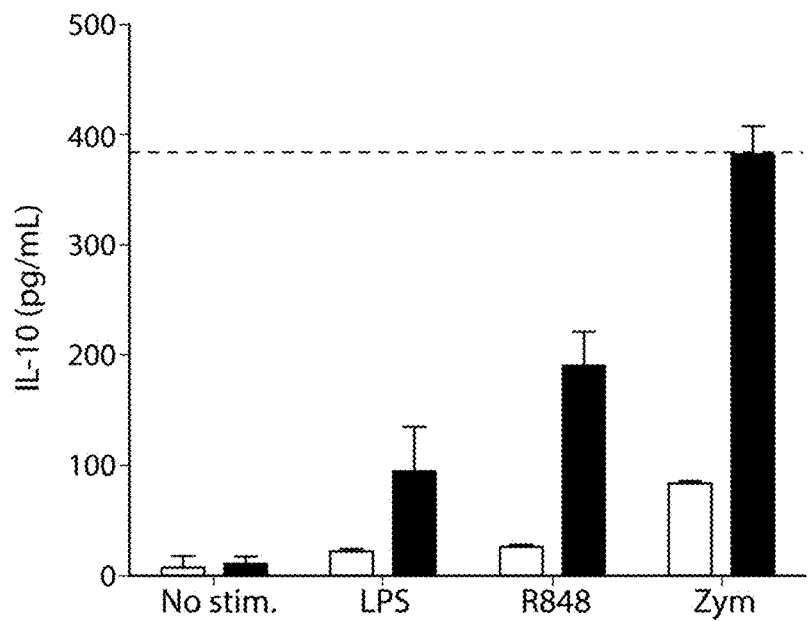
FIG. 7A. Extended pre-treatment enhances the IL-10 potentiating effects of SIK inhibition. BMDCs were treated with DMSO (white bars) or HG-9-91-01 (0.5 µM; black bars) for 2 days followed by either mock stimulation (no stim.) or treatment with LPS (100 ng/mL), R848 (10 µg/mL) or zymosan (Zym) (4 µg/mL). After 18 hr, IL-10 secreted into the culture media was detected by ELISA. Dashed line indicates maximum IL-10 concentration induced 2 days of HG-9-91-01 pre-incubation prior to zymosan stimulation. Error bars=mean±SD, n=3 from one independent experiment. Data are representative of two independent experiments.
Figure 7B:
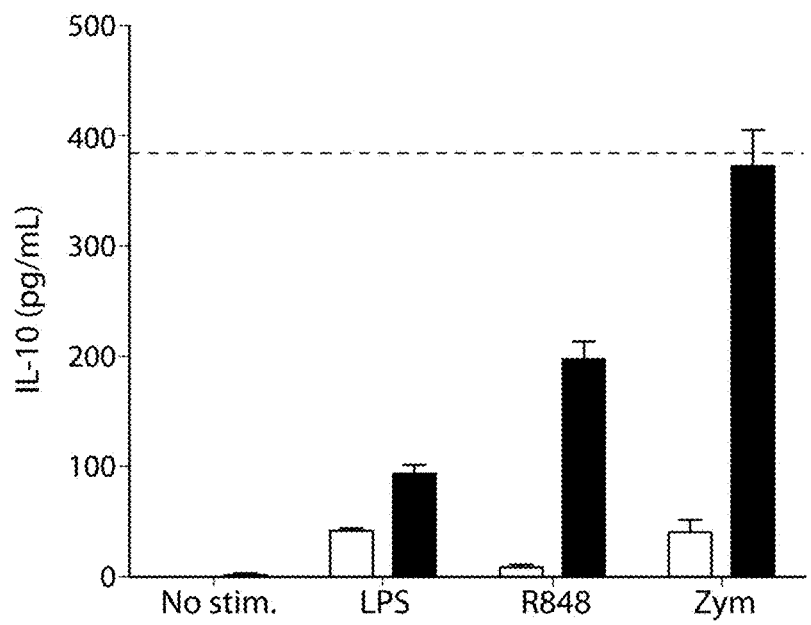
FIG. 7B. BMDCs were treated with DMSO (white bars) or HG-9-91-01 (0.5 µM; black bars) for 1 day followed by either mock stimulation (no stim.) or treatment with LPS (100 ng/mL), R848 (10 µg/mL) or zymosan (Zym) (4 µg/mL). After 18 hr, IL-10 secreted into the culture media was detected by ELISA. Dashed line indicates maximum IL-10 concentration induced 2 days of HG-9-91-01 pre-incubation prior to zymosan stimulation. Error bars=mean±SD, n=3 from 1 independent experiment. Data are representative of 2 independent experiments.
Figure 7C:
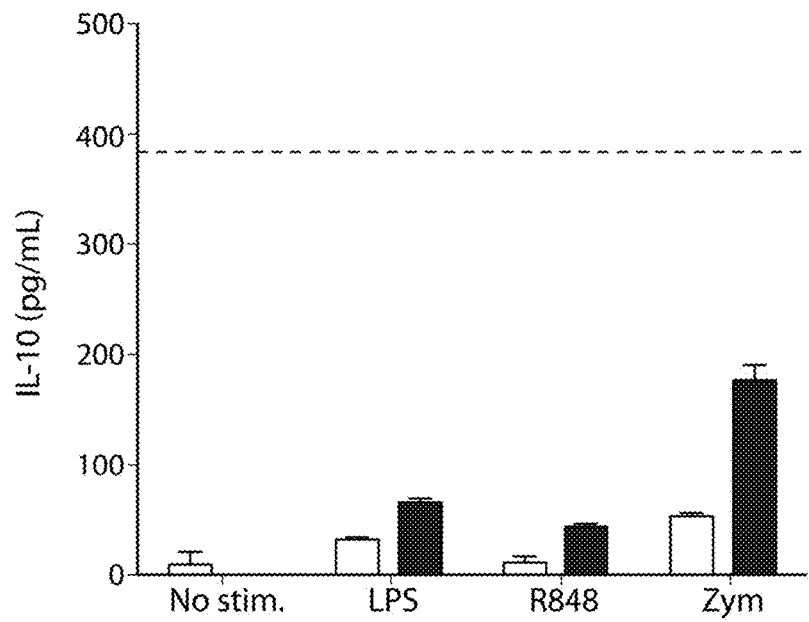
FIG. 7C. BMDCs were treated with DMSO (white bars) or HG-9-91-01 (0.5 µM; black bars) for 2 h. followed by either mock stimulation (No stim.) or treatment with LPS (100 ng/mL), R848 (10 µg/mL) or zymosan (Zym) (4 µg/mL). After 18 hr, IL-10 secreted into the culture media was detected by ELISA. Dashed line indicates maximum IL-10 concentration induced 2 d of HG-9-91-01 pre-incubation prior to zymosan stimulation. Error bars=mean±SD, n=3 from 1 independent experiment. Data are representative of 2 independent experiments.

SIK1 and SIK2 were enriched among the high-affinity targets of the IL-10-potentiating kinase inhibitors (FIG. 1C), which is consistent with the IL-10-potentiating effects of SIK inhibition in activated MΦs (20, 21). In agreement with these reports, pre-treating BMDCs with HG-9-91-01, a recently described inhibitor of SIK1-3, along with several other kinases (21), results in concentration-dependent potentiation of zymosan-induced IL-10 production with an $EC_{50} \approx 200$ nM and a maximum effect similar to that observed with $PGE_2$ (FIG. 1D). Similar to our observations with dasatinib and bosutinib, concentrations of HG-9-91-01 greater than 1 μM suppressed zymosan-induced IL-10 production. This decrease in IL-10 secretion does not correlate with reduced viability (FIG. 2A), suggesting that it may instead result from inhibition of additional kinase targets mediating the effects of zymosan stimulation. For example, HG-9-91-01 potently inhibits Src with less than 4% activity remaining at 1 JAM (21). As with $PGE_2$, extended pre-incubation of BMDCs with HG-9-91-01 was required for robust up-regulation of IL-10 in response to stimulation with zymosan, LPS or the viral RNA mimetic R848 (FIGS. 7A to 7C). To determine if SIK inhibition increases the fraction of cells producing IL-10, BMDCs derived from transgenic mice in which the Il10 promoter drives expression of Thy1.1 ('10BiT' reporter (24)) were treated with HG-9-91-01 for 2 days prior to stimulation with zymosan for 18 hr and immunostaining for cell surface Thy1.1 (FIG. 1E). In this assay system, SIK inhibition enhanced the fraction of BMDCs expressing Il10 following zymosan stimulation more than 5-fold (FIG. 1F). Collectively, these results suggest that SIK inhibition underlies the IL-10-potentiating activity of several of the hit SIK inhibitors identified in this screen by enhancing the fraction of activated dendritic cells that produce IL-10 in response to microbial stimulation.

Figure 8A:
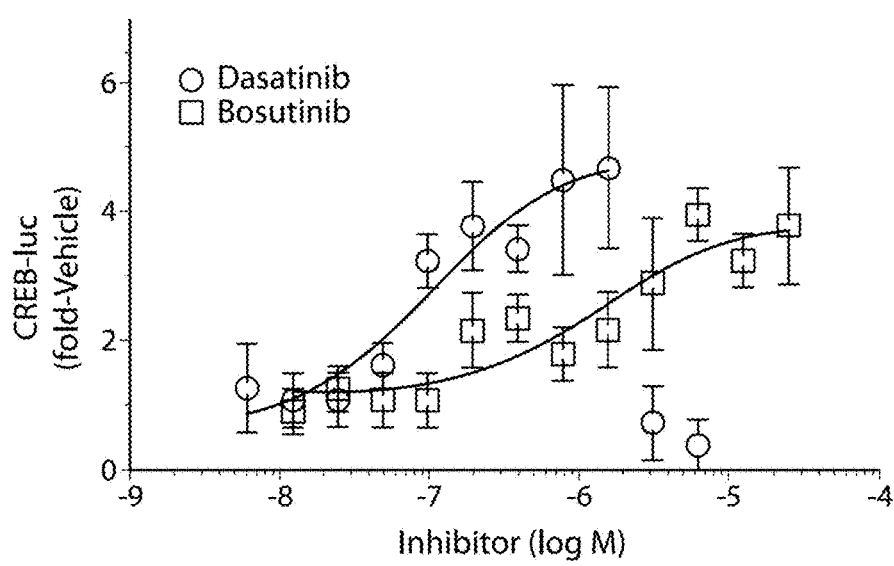
FIG. 8A. Dasatinib and bosutinib up-regulate IL-10 production by a mechanism involving enhanced CREB/CRTC3 signaling. Activity of CREB-dependent luciferase reporter construct was determined in BMDCs treated with DMSO or the indicated concentrations of dasatinib or bosutinib for 24 hr followed by stimulation with zymosan for 5 hr. Error bars=mean±SD, n=4 from 1 independent experiment. Data are representative of 2 independent experiments.
Figure 8B:
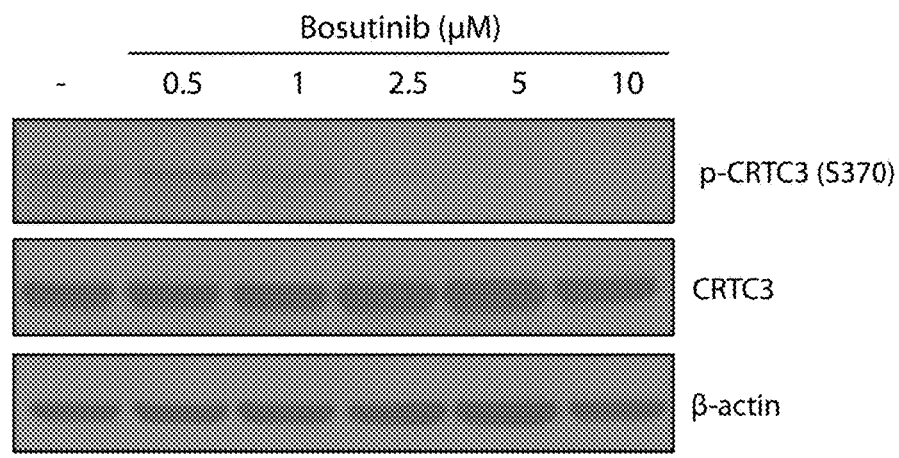
FIG. 8B. Whole cell lysates from BMDCs treated with the indicated concentrations of bosutinib for 24 hr were separated by SDS-PAGE followed by immunoblotting with specific antibodies as indicated.
Figure 8C:
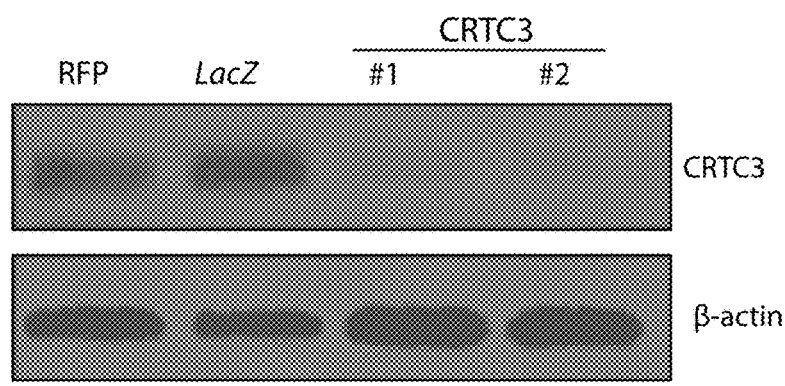
FIG. 8C. CRTC3 levels in whole cell lysates from BMDCs stably transduced with shRNA constructs targeting CRTC3, RFP of LacZ were detected by immunoblotting.
Figure 8D:
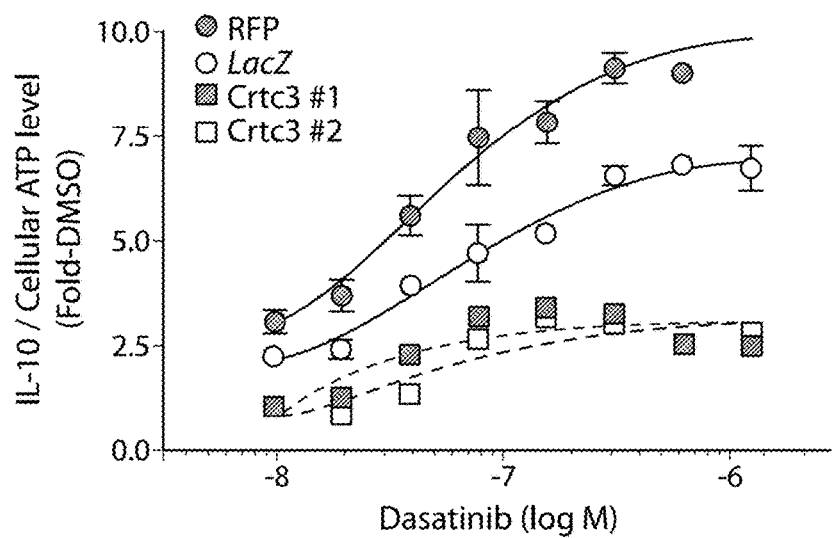
FIG. 8D. BMDCs stably transduced with shRNA constructs targeting RFP, LacZ or CRTC3 were treated with the indicated concentrations of dasatinib for 2 days followed by stimulation with zymosan for 18 hr. IL-10 production in the resulting supernatants was detected by AlphaLISA and is expressed as % of the $PGE_2$ response normalized to cellular ATP levels to account for differences in transduction efficiency of individual lentiviral shRNA preparations. Error bars=mean±SD, n=3 from one independent experiment. Data are representative of two independent experiments.
Figure 8E:
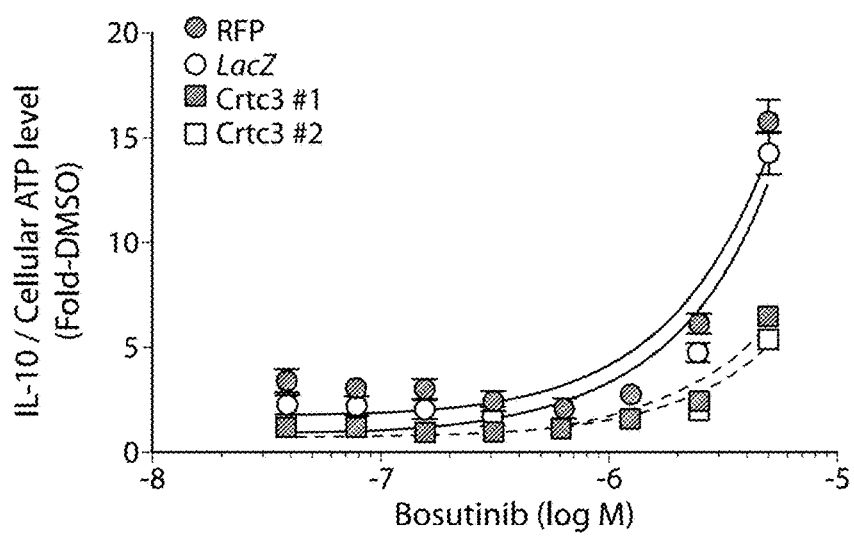
FIG. 8E. BMDCs stably transduced with shRNA constructs targeting RFP, LacZ or CRTC3 were treated with the indicated concentrations of bosutinib for 2 days followed by stimulation with zymosan for 18 hr. IL-10 production in the resulting supernatants was detected by AlphaLISA and is expressed as % of the $PGE_2$ response normalized to cellular ATP levels to account for differences in transduction efficiency of individual lentiviral shRNA preparations. Error bars=mean±SD, n=3 from one independent experiment. Data are representative of 2 independent experiments.

Example 19. FDA-Approved CML Drugs Up-Regulate IL-10 Production by a Mechanism Involving Enhanced CRTC3/CREB Signaling Potent binding to SIK1 and SIK2 by dasatinib, bosutinib and the annotated Alk inhibitor TAE-684 ($K_d$<30 nM in all cases (23)) contributes to the positive correlation between SIK inhibition and IL-10 potentiation. Based on the kinase profiling data, we then studied whether dasatinib and bosutinib, as representative hits, induced cellular effects consistent with up-regulation of IL-10 production via the SIK2/CRTC3/CREB pathway. In support of this hypothesis, pre-incubation of BMDCs with dasatinib or bosutinib resulted in a four-fold induction of a CREB-dependent luciferase reporter construct following zymosan stimulation (FIG. 8A). In addition, as reported for HG-9-91-01 (21), bosutinib treatment is associated with a decrease in SIK-specific phosphorylation of CRTC3 at S370 with an $EC_{50}$ similar to that observed for up-regulation of CREB transcriptional activity and IL-10 production (FIG. 8B). Finally, abundance of CRTC3 protein was reduced to nearly undetectable levels in BMDCs stably transduced with shRNAs targeting its transcript to test whether the IL-10-potentiating effects of dasatinib and bosutinib require functional CREB/CRTC3 complexes (FIG. 8C). In support of this hypothesis, CRTC3 knockdown significantly reduced the maximum IL-10 enhancement induced by both dasatinib and bosutinib relative to control shRNAs targeting RFP or LacZ (FIGS. 8D and 8E). Together, these biochemical and cellular data support a model where enhancement of CREB/CRTC3 signaling following SIK inhibition mediates the IL-10-potentiating activity of dasatinib, bosutinib and potentially other FDA-approved multi-kinase inhibitors.

Figure 2B:
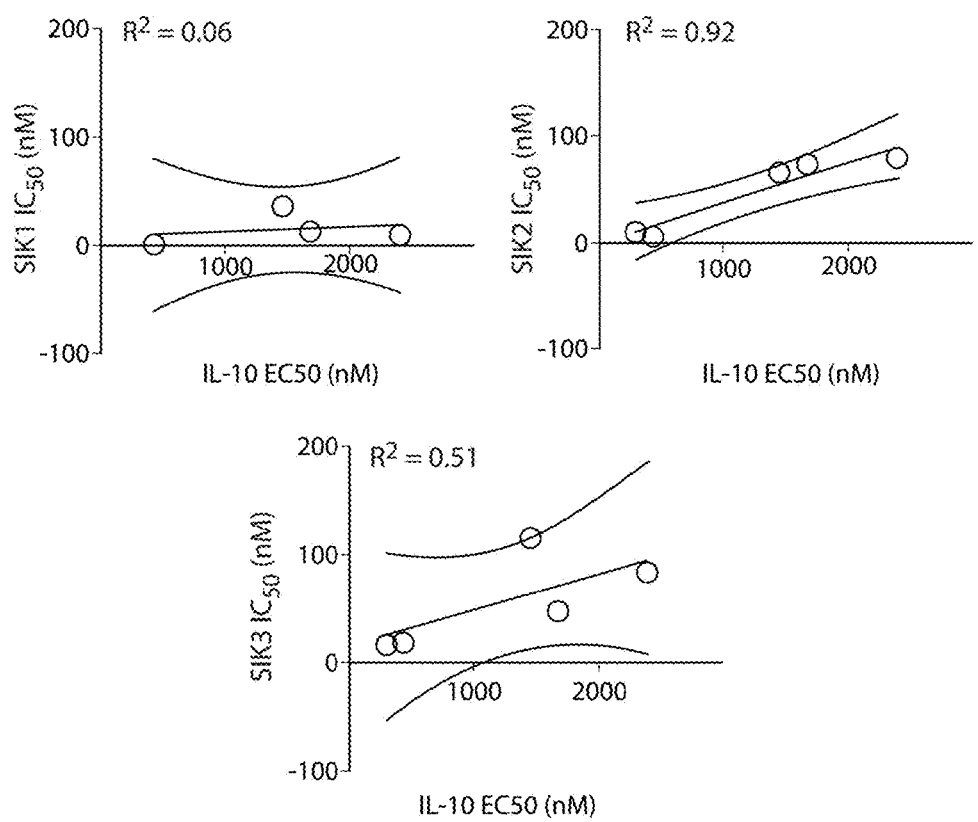
FIG. 2B. Comparison of IL-10-potentiating activity versus SIK inhibitory potencies of HG-9-91-01 analogs retaining the phenyl piperazine moiety. Curved lines indicate 95% confidence intervals for linear regression.
Figure 9A:
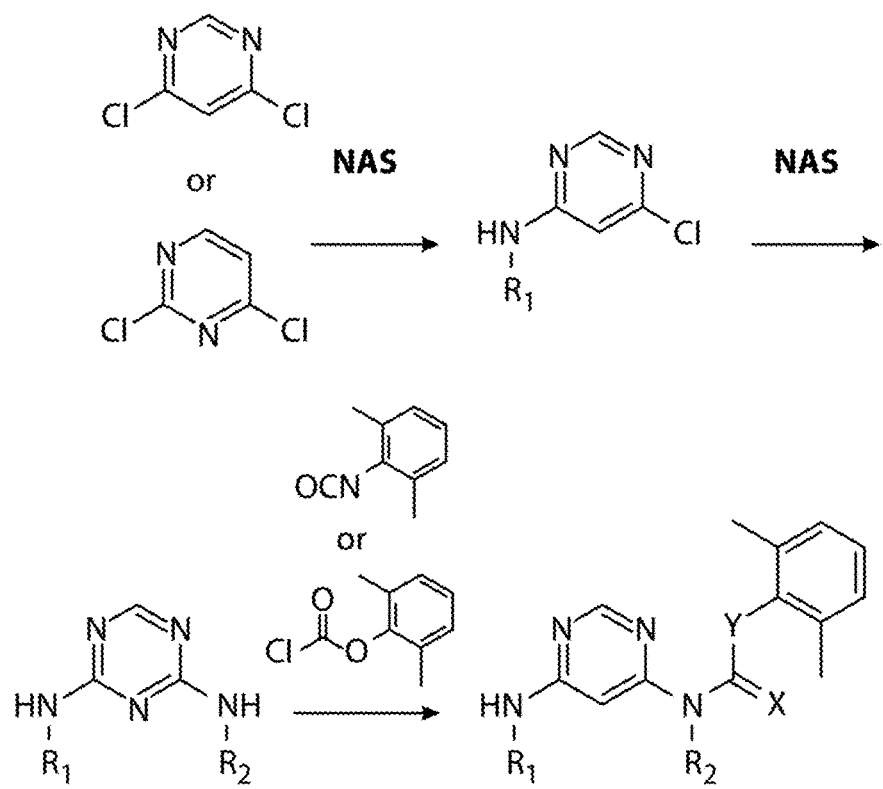
FIG. 9A. Activity of HG-9-91-01 analogs suggests specific role for SIK2 inhibition in IL-10 up-regulation. (A) General synthetic scheme for preparation of HG-9-91-01 and related analogs. NAS, nucleophilic aromatic substitution.

Example 20. Activity of HG-9-91-01 Analogs Suggests Specific Role of SIK2 Inhibition in IL-10 Potentiation HG-9-91-01 potently inhibits SIK1-3 ($IC_{50}$<20 nM (21)) making it challenging to determine how inhibiting particular SIK isoforms contributes to IL-10 up-regulation in activated DCs. This question was addressed by determining how modifying the structure of HG-9-91-01 affects IL-10 potentiation relative to inhibition of SIK1-3. To do so, we first developed a succinct, modular synthesis of HG-9-91-01 and related analogs bearing substitutions of the central heteroaromatic core (FIG. 9A). This series of SIK inhibitors was then tested for their effects on SIK1-3 activity as well as IL-10 production by and viability of zymosan-stimulated DCs (FIG. 2A and FIG. 9B). Despite displaying a range of $EC_{50}$'s for IL-10 up-regulation, these SIK inhibitors were all potent inhibitors of SIK1 such that the two activities appear to be uncorrelated (FIG. 2B). In contrast, SIK inhibitors lacking the 2,4-dimethoxy aniline moieties and/or bearing alterations to the central heteroaromatic core of HG-9-91-01 had differentially reduced potencies of SIK2 and SIK3 inhibition (FIG. 2B). Comparing the $EC_{50}$ values for IL-10 induction versus the $IC_{50}$'s for SIK2 or SIK3 inhibition for the five SIK inhibitors retaining the phenyl piperazine moiety revealed a significant ($R^2$=0.92) positive correlation between the potency of SIK2 inhibition and IL-10 induction, whereas this trend was less pronounced for SIK3 (FIG. 2B). Several SIK inhibitors in this series displayed toxicity at concentrations greater than 1 µM (FIGS. 2A and 9B). However, consistent with data indicating that reduction of Sik2 expression by RNAi is well tolerated in macrophages (21), the toxicity of HG-9-91-01 analogs did not correlate with the $IC_{50}$'s for SIK1-3 inhibition. The close correlation between the potencies of SIK2 inhibition and IL-10 up-regulation suggest that inhibition of this SIK isoform is primarily responsible for the IL-10-potentiating activity of HG-9-91-01 and structurally related SIK inhibitors in activated dendritic cells.

Figure 3A:
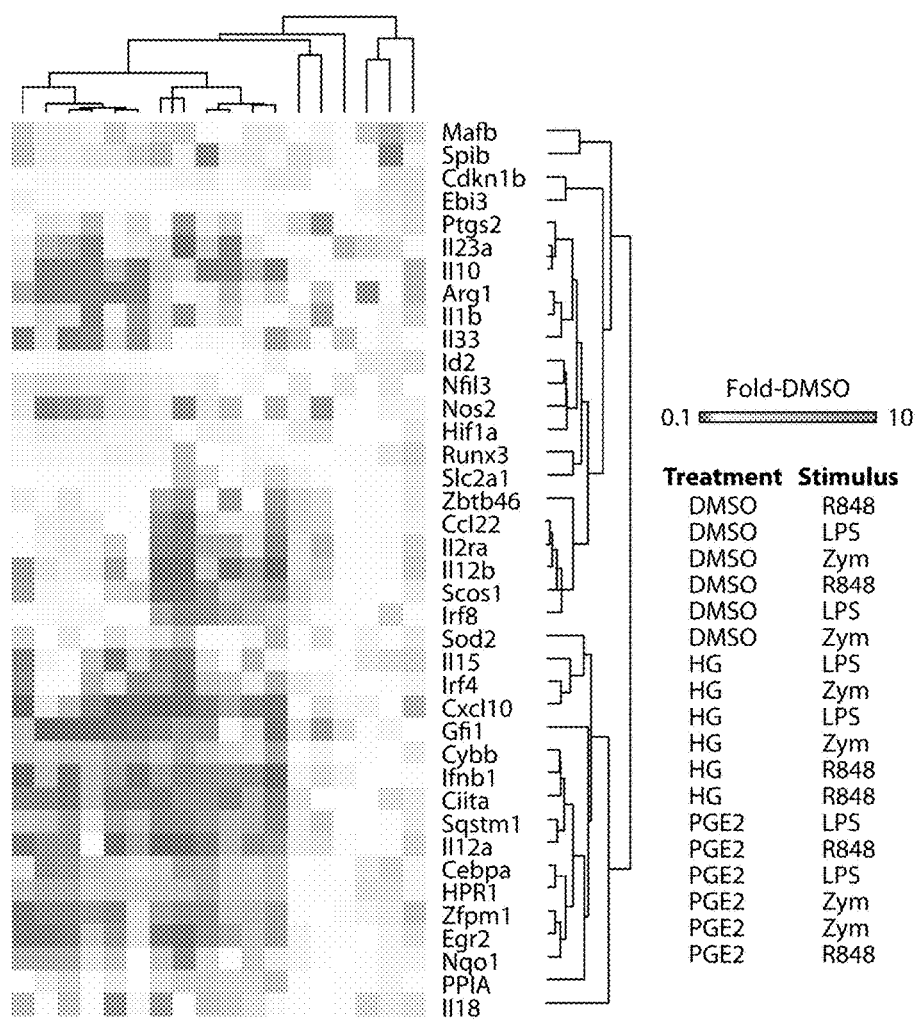
FIG. 3A. SIK inhibition converts activated BMDCs to an anti-inflammatory phenotype distinct from that induced by prostaglandin E2 (PGE$_2$). BMDCs were treated with DMSO, PGE$_2$ (5 μM) or HG-9-91-01 (HG) (0.5 μM) for 2 days followed by stimulation with LPS, R848 or zymosan (Zym) for 4 hr. Abundance of actin-normalized transcripts in PGE$_2$- or HG-9-91-01-treated samples is expressed relative to the mean of the DMSO-treated samples for each microbial stimulus and clustered using One-minus Pearson's correlation. N=2, data are representative of two independent experiments.
Figure 10A:
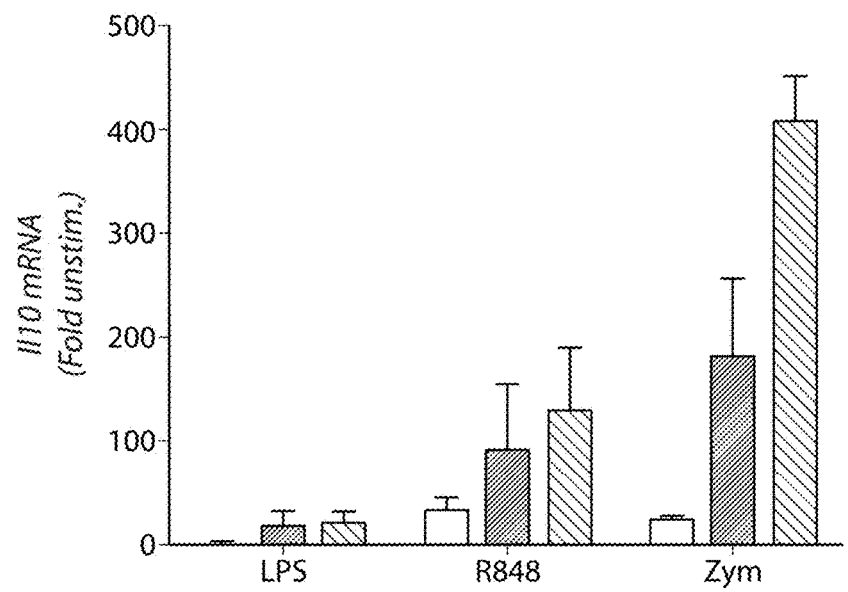
FIG. 10A. $PGE_2$ and SIK inhibition induce differential transcriptional responses. BMDCs were treated with DMSO, $PGE_2$ (5 µM) or HG-9-91-01 (0.5 µM) for 2 days followed by stimulation with LPS (100 ng/mL), R848 (10 µg/mL), or zymosan (Zym) (4 µg/mL) for 4 hours. After cells lysis and total RNA extraction, expression of indicated transcripts was determined by multiplex RT-PCR array. Abundance of actin-normalized Il10 (Fold unstim.=Fold unstimulated).
Figure 10B:
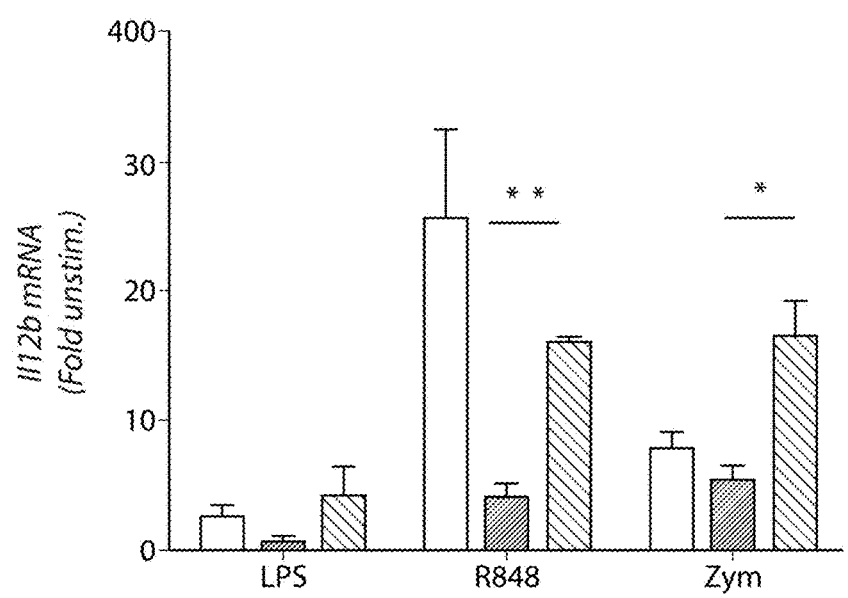
FIG. 10B. BMDCs were treated with DMSO, $PGE_2$ (5 µM) or HG-9-91-01 (0.5 µM) for 2 days followed by stimulation with LPS (100 ng/mL), R848 (10 µg/mL), or zymosan (Zym) (4 µg/mL) for 4 hours. After cells lysis and total RNA extraction, expression of indicated transcripts was determined by multiplex RT-PCR array. Abundance of actin-normalized Il12b (Fold unstim.=Fold unstimulated).
Figure 10C:
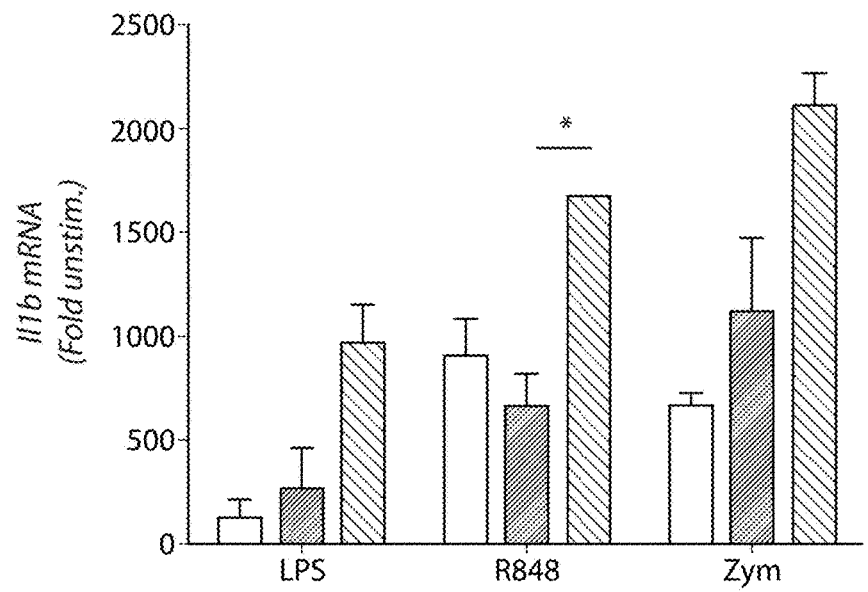
FIG. 10C. BMDCs were treated with DMSO, $PGE_2$ (5 µM) or HG-9-91-01 (0.5 µM) for 2 days followed by stimulation with LPS (100 ng/mL), R848 (10 µg/mL), or zymosan (Zym) (4 µg/mL) for 4 hours. After cells lysis and total RNA extraction, expression of indicated transcripts was determined by multiplex RT-PCR array. Abundance of actin-normalized Il1b (Fold unstim.=Fold unstimulated).
Figure 10D:
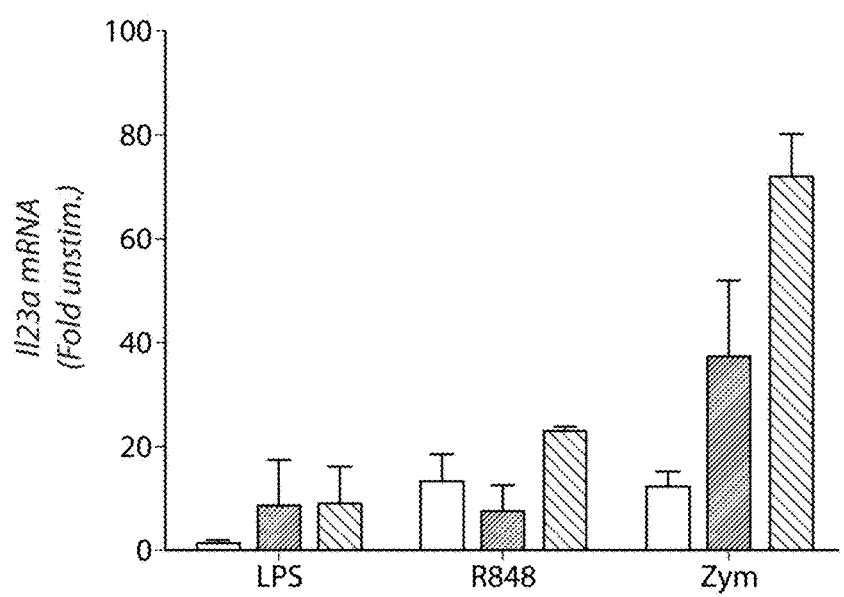
FIG. 10D. BMDCs were treated with DMSO, $PGE_2$ (5 µM) or HG-9-91-01 (0.5 µM) for 2 days followed by stimulation with LPS (100 ng/mL), R848 (10 µg/mL), or zymosan (Zym) (4 µg/mL) for 4 hours. After cells lysis and total RNA extraction, expression of indicated transcripts was determined by multiplex RT-PCR array. Abundance of actin-normalized Il23a (Fold unstim.=Fold unstimulated).
Figure 10E:
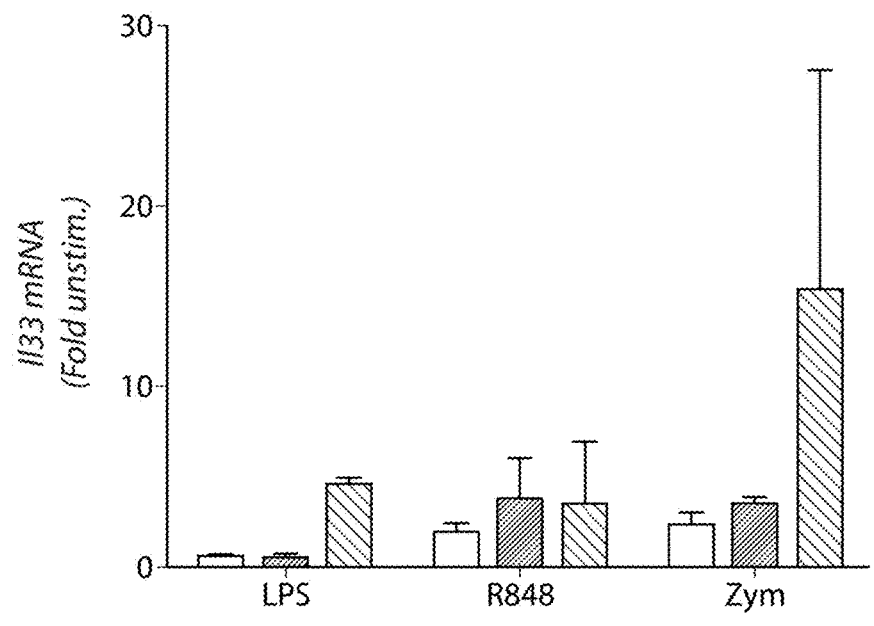
FIG. 10E. BMDCs were treated with DMSO, $PGE_2$ (5 µM), or HG-9-91-01 (0.5 µM) for 2 days followed by stimulation with LPS (100 ng/mL), R848 (10 µg/mL), or zymosan (Zym) (4 µg/mL) for 4 hours. After cells lysis and total RNA extraction, expression of indicated transcripts was determined by multiplex RT-PCR array. Abundance of actin-normalized Il33 (Fold unstim.=Fold unstimulated).
Figure 10F:
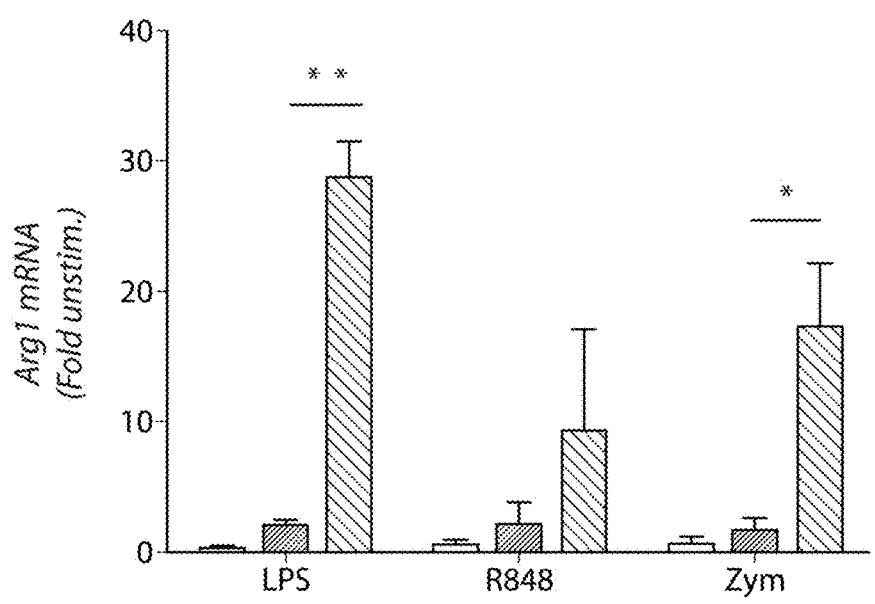
FIG. 10F. BMDCs were treated with DMSO, $PGE_2$ (5 µM), or HG-9-91-01 (0.5 µM) for 2 days followed by stimulation with LPS (100 ng/mL), R848 (10 µg/mL) or zymosan (Zym) (4 µg/mL) for 4 hours. After cells lysis and total RNA extraction, expression of indicated transcripts was determined by multiplex RT-PCR array. Abundance of actin-normalized Arg1 (Fold unstim.=Fold unstimulated).
Figure 10G:
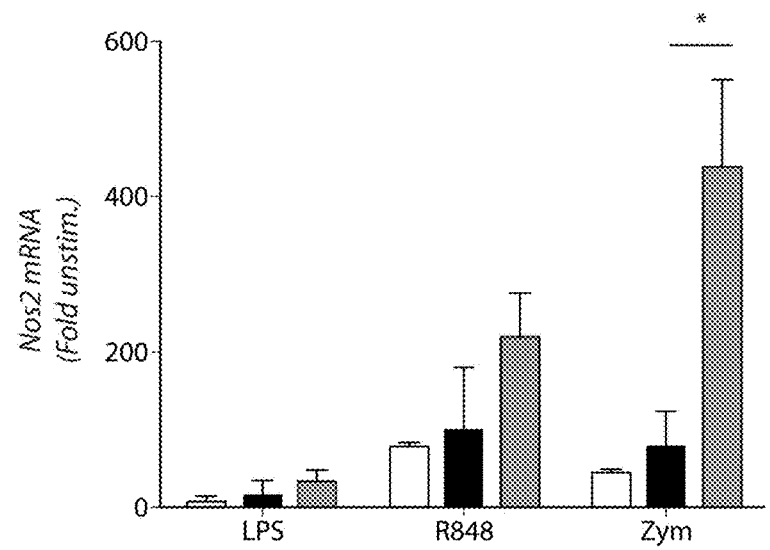
FIG. 10G. Nos2 mRNA in $PGE_2$- or HG-9-91-01-treated samples are expressed as fold-change versus untreated, unstimulated (Fold unstim.) control samples. White bars, DMSO; Black bars, HG-9-91-01; Grey bars, $PGE_2$. Error bars=mean±SD, n=4 pooled from two independent experiments. *, p<0.05, ** p<0.01, unpaired Student's t.

Example 21. SIK Inhibition Converts Activated Myeloid Cells to an Anti-Inflammatory State To test whether SIK inhibition promotes anti-inflammatory phenotypes beyond enhanced IL-10 production, we pre-treated BMDCs with concentrations of HG-9-91-01 or $PGE_2$ that equivalently up-regulate IL-10, and measured the abundance of =100 transcripts encoding key myeloid cytokines and transcriptional regulators after 4 hr stimulation with LPS, R848 or zymosan (FIG. 3A). Transcriptional responses to $PGE_2$ or HG-9-91-01 were normalized to vehicle-treated samples for each activating stimuli, and significantly induced or repressed genes (p<0.05) were clustered using One-minus Pearson's correlations (FIG. 3A). While IL-10 mRNA levels were robustly enhanced by both $PGE_2$ and HG-9-91-01 (FIG. 10A), notable differences are observed in the transcriptional response to these two CREB activating stimuli. Expression of the pro-inflammatory cytokines Il12b and Il1b were significantly elevated in $PGE_2$-versus HG-9-91-01-treated BMDCs (FIGS. 10B and 10C) and similar trends were observed with Il23a and Il33 (FIGS. 10D and 10E). Similarly, abundance of Arg1 and Nos2 transcripts, which encode genes essential arginine catabolism and nitric oxide (NO) production, respectively, were highly induced by $PGE_2$, while these changes were significantly blunted in BMDCs pre-treated with HG-9-91-01 (FIGS. 10F and 10G).

Figure 3B:
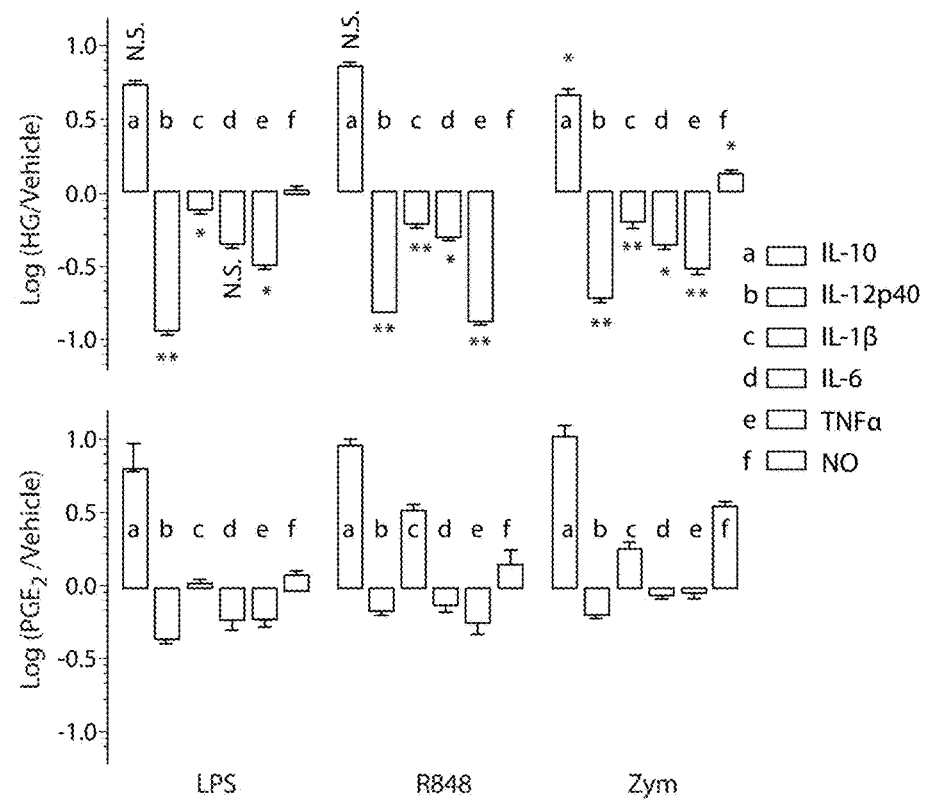
FIG. 3B. BMDCs were treated with DMSO, HG-9-91-01 (0.5 μM), or prostaglandin E2 PGE$_2$) (5 μM) for 2 days followed by stimulation with LPS, R848, or zymosan (Zym) for 18 hr. Effect of HG-9-91-01 (top panel) or PGE$_2$ (bottom panel) on cytokine (CBA assays) and nitric oxide (NO) production (Greiss assay) is expressed relative to DMSO-treated samples for each microbial stimulus. Error bars=mean±SD, n=3 from 1 independent experiment. Data are representative of two independent experiments. *p<0.05, **p<0.01, N.S.=not significant, unpaired Student's t test (HG-9-91-01 versus PGE$_2$).
Figure 11A:
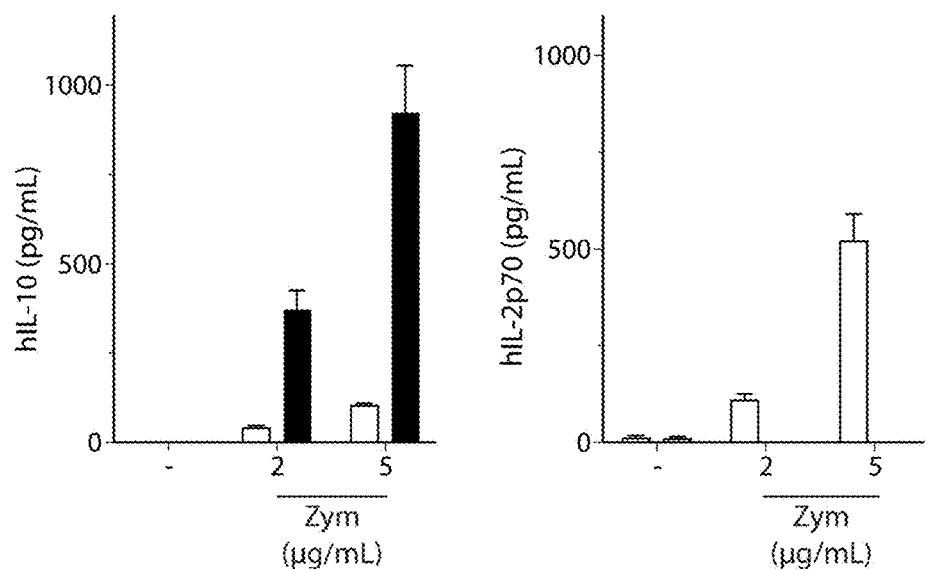
FIG. 11A. SIK inhibition up-regulates IL-10 and suppresses inflammatory cytokine production by human myeloid cells. Macrophages differentiated from PBMCs were treated with DMSO (white bars) or HG-9-91-01 (0.5 µM; black bars) for 24 hr followed by stimulation with the indicated concentrations of zymosan (Zym) for 18 hr. Secreted IL-10 or IL-12p70 was quantified in the resulting culture medium using ELISAs. Error bars=mean±SD, n=3 from one independent experiment. Data are representative of three independent experiments.
Figure 11B:
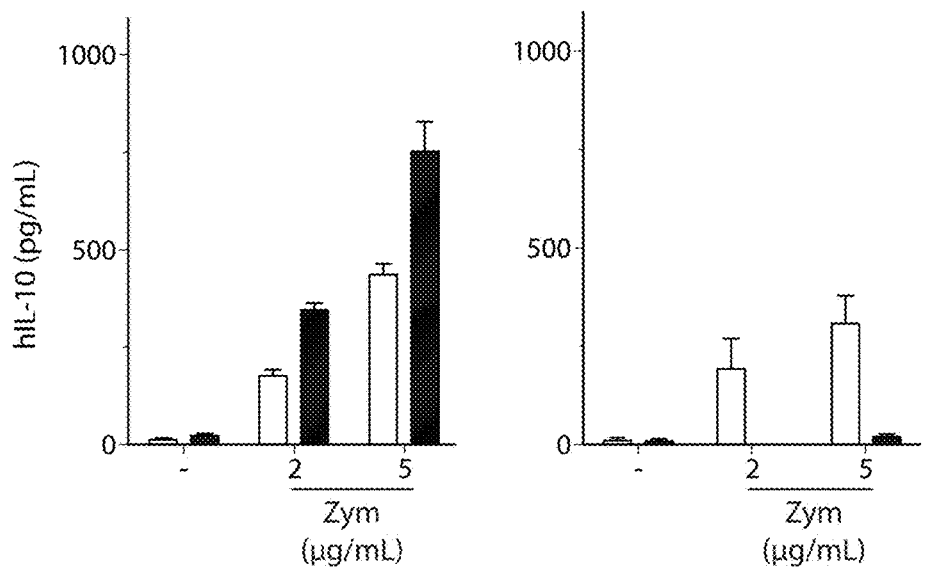
FIG. 11B. Dendritic cells differentiated from PBMCs were treated with DMSO (white bars) or HG-9-91-01 (0.5 µM; black bars) for 24 hr followed by stimulation with the indicated concentrations of zymosan (Zym) for 18 hr. Secreted IL-10 or IL-12p70 was quantified in the resulting culture medium using ELISAs. Error bars=mean±SD, n=3 from one independent experiment. Data are representative of three independent experiments.

Next, we asked how the differential transcriptional responses activated by $PGE_2$ versus SIK inhibition translate into production NO and inflammatory cytokines. While IL-10 secretion was similarly induced in BMDCs pre-treated with $PGE_2$ or HG-9-91-01 before stimulation with LPS, R848 or zymosan, production of several pro-inflammatory mediators was significantly different (FIG. 3B). For instance, production of IL-12p40 and TNF-α was suppressed to a significantly greater extent by treatment with HG-9-91-01 rather than $PGE_2$ regardless of activating stimuli. More strikingly, IL-1β production was enhanced by $PGE_2$ following stimulation with R848 or zymosan, while production of this pro-inflammatory cytokine was suppressed in the presence of the SIK inhibitor. Lastly, elevated expression of Nos2 in PGE2-treated BMDCs relative to HG-9-91-01-treated BMDCs correlated with increased NO production following zymosan stimulation. Consistent with the effects of SIK inhibition in BMDCs, pre-incubating human MΦs or DCs with HG-9-91-01 enhanced IL-10 production while dramatically reducing IL-12p70 secretion in response to zymosan stimulation (FIGS. 11A and 11B). Hence, SIK inhibition converts human and murine myeloid cells to an anti-inflammatory phenotype in which up-regulation of IL-10 is accompanied by reduced secretion of inflammatory cytokines. Moreover, the stimulatory effect of SIK inhibition on several inflammatory mediators is substantially blunted relative to the responses induced by $PGE_2$.

Figure 12A:
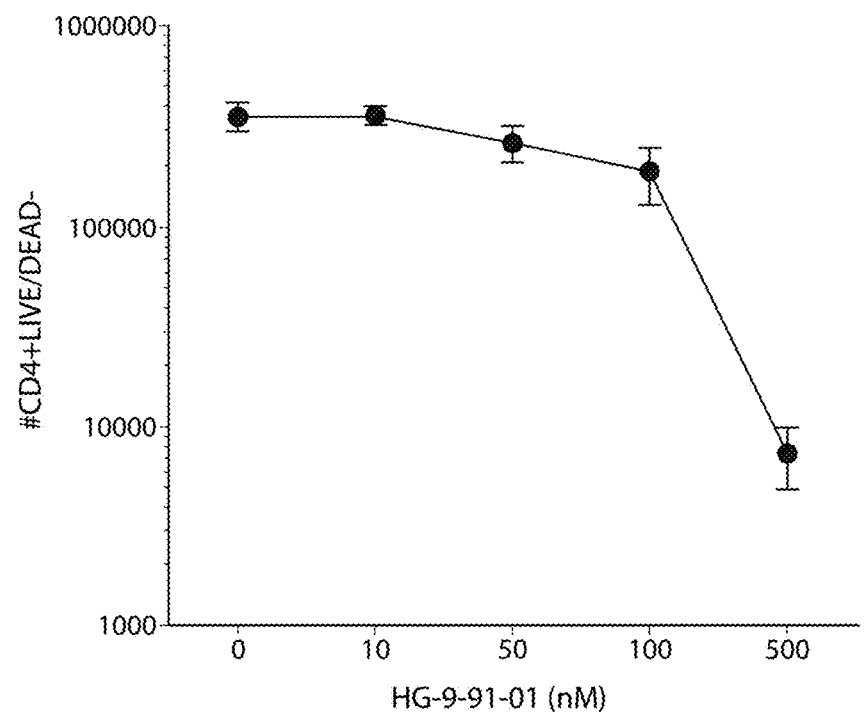
FIG. 12A. SIK inhibition does not promote IL-10 production by regulatory T ($T_{reg}$) cells. Numbers of viable, CD4$^+$ T cells were quantified in cultures of naïve splenic CD4$^+$ T cells differentiated towards the $T_{reg}$ lineage for 4 days in the presence of the concentrations of HG-9-91-01 as indicated.
Figure 12B:
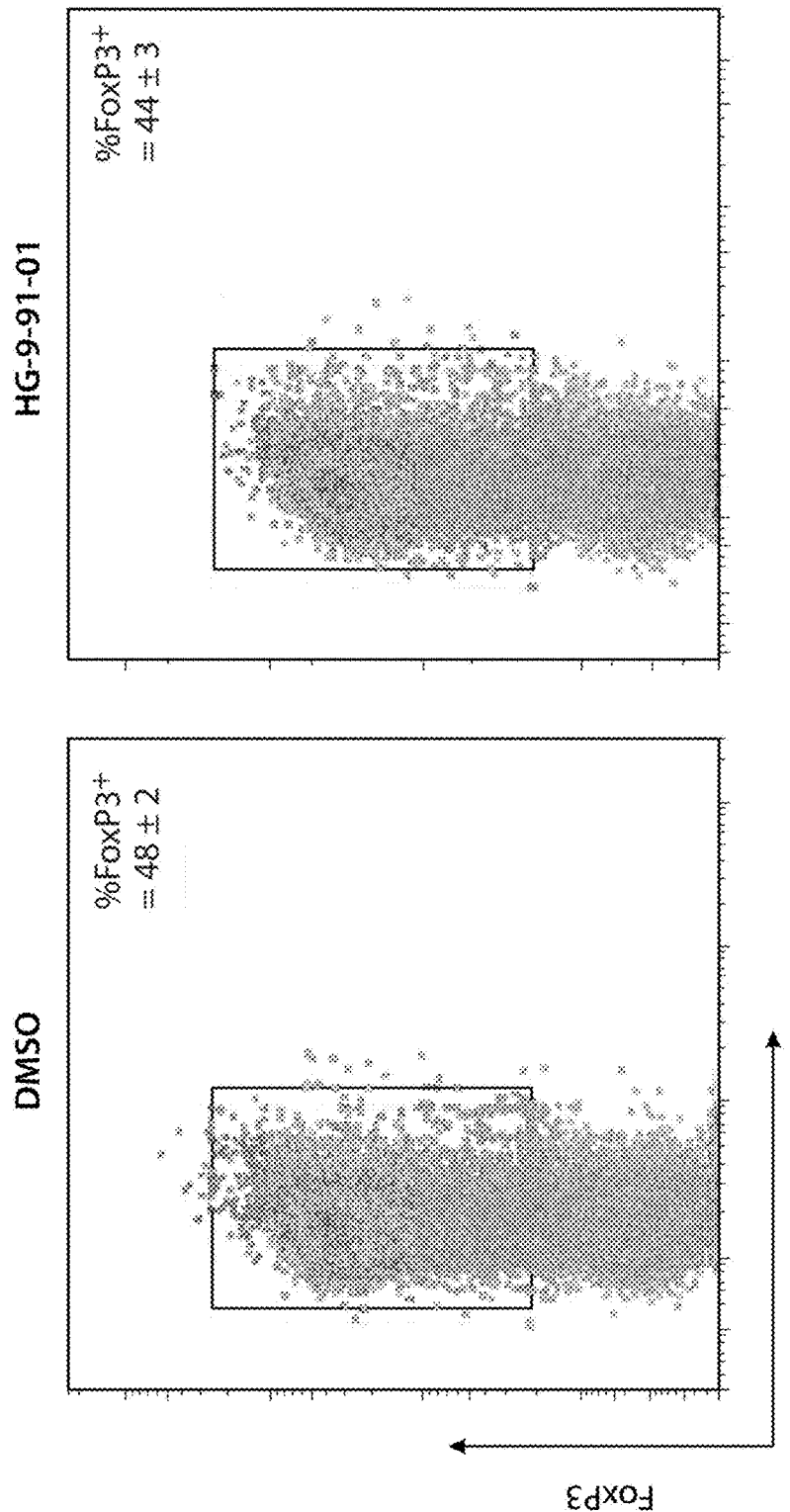
FIG. 12B. After 4 days of culture in the presence of DMSO or HG-9-91-01, levels of FoxP3 protein were determined by intracellular staining and flow cytometric analysis. Data are representative of two independent experiments.
Figure 12C:
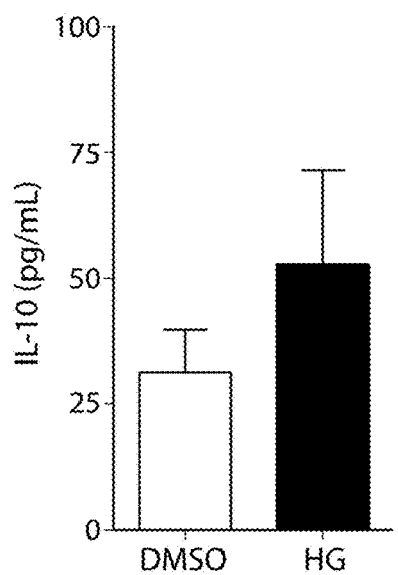
FIG. 12C. After 4 days of culture in the presence of DMSO (white bar) or HG-9-91-01 (HG) (100 nM; black bar), abundance of IL-10 in the culture medium was quantified by ELISA. Error bars=mean±SD, n=3 from one independent experiment. Data are representative of two independent experiments.
Figure 13A:
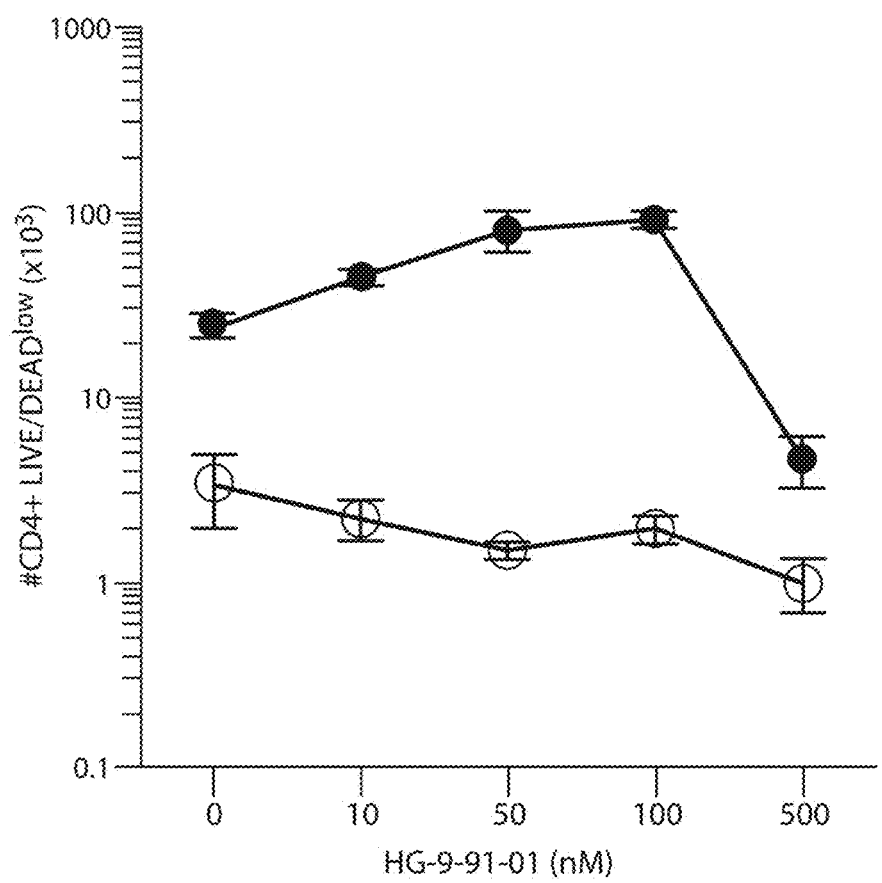
FIG. 13A. SIK inhibition does not promote IL-10 production by Type 1 regulatory (Tr1) cells. Numbers of viable, CD4$^+$ T cells were quantified in cultures of naïve splenic CD4$^+$ T cells differentiated under Th0 (open circles) or Tr1 (closed circles) conditions for 4 days in the presence of the indicated concentrations of HG-9-91-01.
Figure 13B:
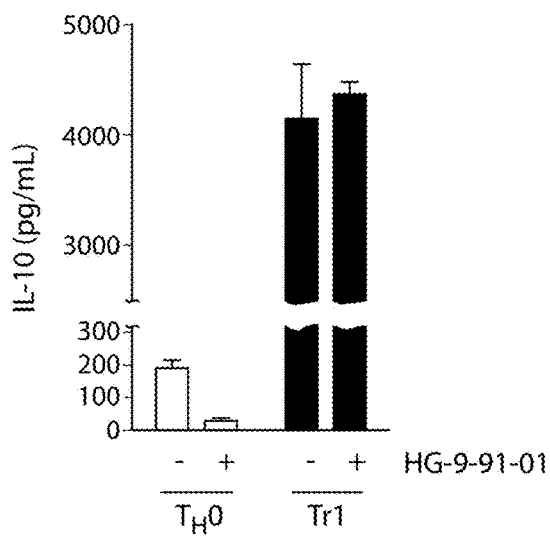
FIG. 13B. Naïve splenic CD4$^+$ T cells were differentiated under Th0 (white bars) or Tr1 (black bars) conditions in the presence of DMSO of HG-9-91-01 (100 nM) and levels of IL-10 in the resulting supernatants was quantified by ELISA. Error bars=mean±SD, n=3 from one independent experiment. Data are representative of two independent experiments.

Example 22. SIK Inhibition does not Enhance IL-10 Production by Regulatory T Cells Subsets Regulatory CD4+ T cells expressing the master transcription factor FoxP3 (i.e., T's) play an essential role in maintaining tolerance to self and commensal antigens (25). In addition, a subset of FoxP3− CD4+ T cells that produce high levels of IL-10, termed type 1 regulatory (Tr1) cells, have been implicated in gut immune homeostasis (26). To determine if SIK inhibition affects differentiation and/or IL-10 production by either regulatory T cell subset, we treated naïve splenic CD4+ T cells with HG-9-91-01 in the presence of culture conditions that promote $T_{reg}$ or Tr1 differentiation for 4 days. In contrast to myeloid cells, concentrations of HG-9-91-01 greater than 0.5 µM were toxic in both $T_{reg}$'s and Tr1 cells (FIGS. 12A and 13A). Differentiation of $T_{reg}$'s in the presence of concentrations of HG-9-91-01 sufficient to potently inhibit SIKs and increase IL-10 in BMDCs did not increase the fraction of Foxp3+ cells or promote IL-10 secretion (FIGS. 12B and 12C). Similarly, although Tr1 cells abundantly secreted IL-10, this activity was not further enhanced by non-toxic concentrations of HG-9-91-01 (FIG. 13B). Together, these data suggest that SIK/CRTC/CREB signaling may play a greater role in regulating Il10 expression in myeloid cells than T lymphocytes.

Figure 4A:
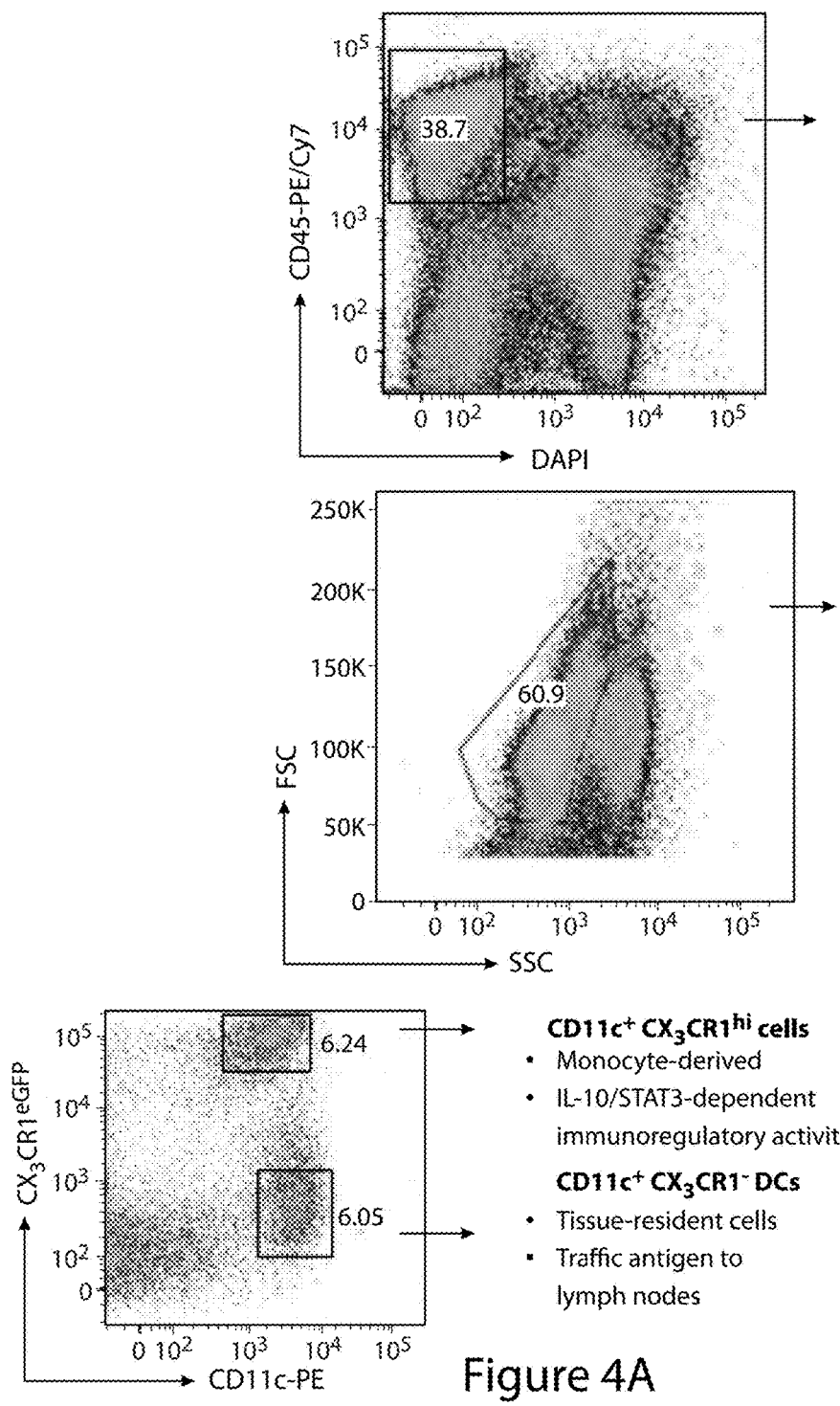
FIG. 4A. SIK inhibition enhances IL-10 production by gut myeloid cells. FACS-based isolation of CD11c$^+$ CX$_3$CR1$^{hi}$ myeloid cells and CD11c$^+$ CX$_3$CR1$^-$ DCs from the small intestine of Cx3cr1$^{eGFP/+}$ mice.
Figure 4B:
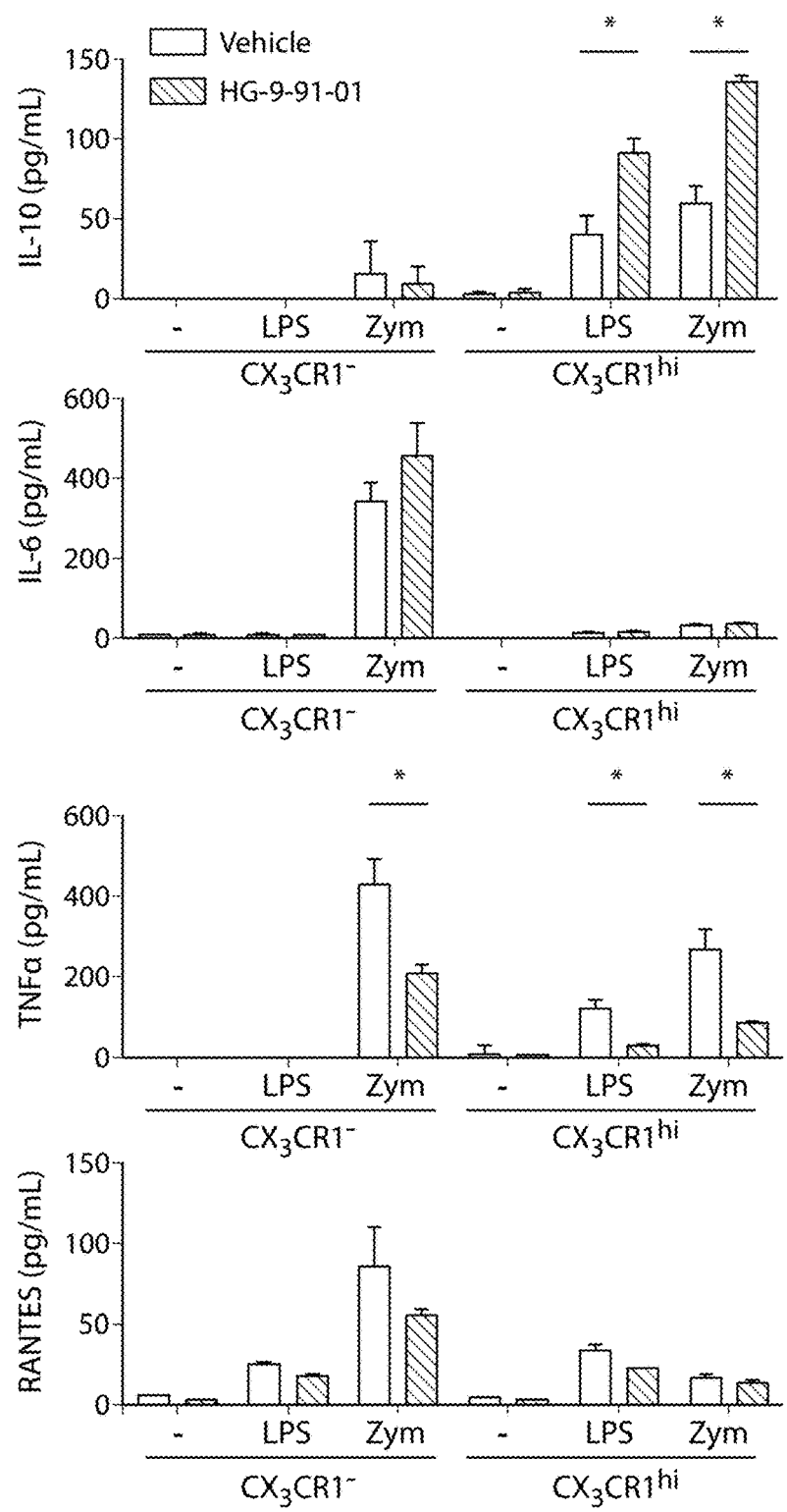
FIG. 4B. CD11c$^+$ CX$_3$CR1$^{hi}$ myeloid cells and CD11c$^+$ CX$_3$CR1$^-$ DCs were treated with vehicle or HG-9-91-01 (0.3 μM) for 30 min prior to stimulation with LPS or zymosan (Zym). After 18 hr, abundance of the indicated cytokines in the resulting supernatants was quantified by cytokine bead array. Error bars=mean±SD, n=3 from one independent experiment. Data are representative of three independent experiments. *p<0.05, unpaired Student's t test.

Example 23. SIK Inhibition Enhances IL-10 Production by Immunoregulatory Gut Myeloid Cells To determine if SIK inhibition enhances IL-10 production by primary myeloid cells from gut tissues, we isolated immunoregulatory CD11c+ $CX_3CR1^{hi}$ cells and a control population of CD11c+ $CX_3CR1^−$ DCs from the small intestine of Cx3cr1$^{eGFP/+}$ mice (FIG. 4A). Because ex vivo survival of primary gut cells is limited, both subsets were pre-treated with HG-9-91-01 for 30 min prior to 18 hr stimulation with LPS or zymosan. Despite the limited pre-treatment, HG-9-91-01 enhanced IL-10 production by CD11c+ $CX_3CR1^{hi}$ cells activated with LPS or zymosan (FIG. 4B). Consistent with our results in BMDCs and human DCs/MΦs, up-regulation of IL-10 was accompanied by reduced secretion of TNF-α in both gut myeloid cell subsets. SIK inhibition does not appear to non-specifically disrupt function of gut DCs/MΦs because production of IL-6 or the IFNγ-responsive chemokine RANTES were not affected by HG-9-91-01 pre-treatment in either subset (FIG. 4B). Thus, the IL-10-potentiating activity of HG-9-91-01 in CD11c+ $CX_3CR1^{hi}$ myeloid cells isolated from the small intestine provides experimental evidence supporting SIKs as novel target to enhance gut IL-10 levels.

Example 24. Discussion of Examples

Described herein, is a small-molecule screen that identified SIK inhibition as a common mechanism by which several multi-kinase inhibitors, including FDA-approved drugs for CML, enhance IL-10 production by activated BMDCs. Evaluation of a series of structural analogs of the selective SIK targeting inhibitor HG-9-91-01 demonstrates a strong correlation between the potency of SIK2 inhibition and enhanced IL-10 production. These results, together with data indicating that expression of a HG-9-91-01-resistant SIK2 allele suppresses the IL-10-potentiating effects of this SIK inhibitor in the RAW264.7 murine macrophages (21), suggests that SIK2 plays a primary role in restraining IL-10 production in activated myeloid cells. Along with enhanced IL-10 secretion, SIK inhibition converted activated BMDCs to an anti-inflammatory phenotype marked by reduced secretion of the inflammatory cytokines IL-1β, IL-6, IL-12 and TNF-α, and these coordinated effects of SIK inhibition were conserved in human DCs/MΦs. In addition, we evaluated whether SIK inhibition enhanced IL-10 production in other immune cell types known to produce IL-10 such as FoxP3+ $T_{reg}$'s or Tr1 cells. In contrast to our observations in myeloid cells, treatment with HG-9-91-01 did not increase IL-10 production during ex vivo differentiation of either regulatory T cell subset, which is consistent with studies indicating that c-MAF and mitogen-activated protein (MAP) kinase signaling play a central role in IL-10 regulation in T lymphocytes (16).

The results indicate that dasatinib and bosutinib induce effects consistent with SIK inhibition in dendritic cells including activation of a CREB-dependent luciferase reporter construct and reduction of SIK-specific phosphorylation of CRTC3 at S370. Significantly, the IL-10-enhancing activity of both dasatinib and bosutinib in activated BMDCs was blunted by knockdown of CRTC3. Together, these results support a model where SIK inhibition underlies the immunomodulatory effects of these FDA-approved CML drugs in myeloid cells and provide new mechanistic insight into the recent report that dasatinib treatment increased serum IL-10 levels, while decreasing TNF-α, following systemic LPS challenge (27). These findings have several potential implications for therapeutic use of dasatinib and related SIK inhibitors. Dasatinib doses administered to CML patients achieve serum concentrations sufficient to potently inhibit SIKs and to up-regulate IL-10 by activated dendritic cells (28), which suggests that SIK inhibition is unlikely to be toxic and that the IL-10-potentiating activity of FDA-approved drugs targeting these kinases might be explored as candidate treatments for IBD. In the context of cancer, it is possible that elevated serum IL-10 levels mediated by 'off-target' SIK inhibition could modulate the chemotherapeutic activity of dasatinib given that T cell-mediated immune responses targeting tumor antigens are a critical component of dasatinib's mode-of-action (29). Therefore, combining dasatinib or related kinase inhibitors with an IL-10 neutralizing strategy might be a rational approach to enhance the chemotherapeutic activity of these SIK inhibitors.

Figure 14:
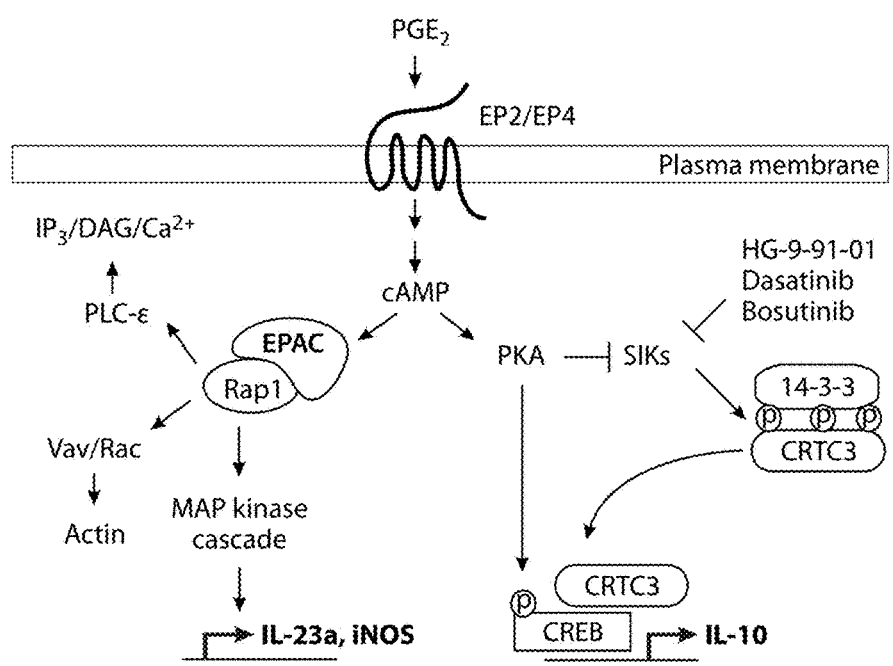
FIG. 14. Model for the differential cellular responses to EP2/EP4 receptor stimulation versus SIK inhibition. Stimulation of EP2/EP4 prostanoid receptors with PGE$_2$ increases intracellular cAMP, which promotes IL-10 transcription via CRTC3/CREB complexes downstream of PKA activation. In addition to activating the PKA/CRTC3/CREB axis, cAMP binding to EPAC scaffolding proteins activates Rap leading to pleiotropic cellular effects. In contract, inhibition of SIKs up-regulates IL-10 expression by reducing inhibitory phosphorylation of CRTC3 in the absence of a cAMP flux.

The results described herein, provide additional mechanistic insight into the ability of SIK inhibitors to selectively enhance IL-10 production by activated myeloid cells. For instance, key differences in the expression of genes encoding inflammatory cytokines (e.g., Il1b, Il12b and Il23a) or NO production (Nos2) were observed in the transcriptional profiles of BMDCs treated with concentrations of $PGE_2$ or HG-9-91-01 that up-regulate IL-10 to a similar extent. Significantly, these differential transcriptional responses were mirrored by greater suppression of IL-12p40 (i.e., the cytokine encoded by Il12b) secretion and a lack of increased NO production in HG-9-91-01-versus PGE2-treated BMDCs. Reduced induction of Il12b and Il23a expression with HG-9-91-01 is significant because these genes encode the two subunits of IL-23, a heterodimeric cytokine that promotes expansion of the inflammatory $T_H17$ T cell lineage (30). Similarly, while NO plays an essential role in the anti-microbial activity of myeloid cells, aberrantly high production of this inflammatory mediator is thought to contribute to IBD pathogenesis (31). Both SIK inhibition and $PGE_2$ enhance IL-10 transcription by via SIK/CRTC/CREB signaling. However, in the case of EP2/EP4 prostanoid receptors agonists like $PGE_2$, these effects are mediated by activation of PKA following an intracellular cAMP flux. In addition to the PKA/CREB cascade, cAMP activates exchange proteins activated by cAMP (Epac's), which are scaffolding proteins that nucleate MAP kinase and cytoskeletal signaling components (32). Of note, the stimulatory effects of $PGE_2$ on IL-23 and NO production have both been linked to the cAMP/ePac pathways in myeloid cells (19). Hence, our findings extend previous studies of SIK inhibitors by suggesting a model in which SIK inhibition promotes selective enhancement of CREB-dependent Il10 expression in the absence of pleiotropic effects of elevated intracellular cAMP (FIG. 14).

In addition to IL-10 and its receptor, SNPs near the genetic loci for PTGER4, which encodes the EP4 prostanoid receptor, and CRTC3 confer increased risk for Crohn's disease and ulcerative colitis (2). In addition, an intronic SNP in the SIK2 confers susceptibility to primary sclerosing cholangitis, a degenerative liver disease that shares significant co-morbidity with IBD (33). These human genetic data potentially implicate EP4/SIK2/CRTC3/CREB signaling as a contributor to IBD (patho)physiology via regulation of gut IL-10 levels, and make it an intriguing target for therapeutic manipulation. This is supported by the efficacy of phosphodiesterase (PDE) inhibitors, which suppress cAMP hydrolysis, and gut restricted delivery of EP4-selective agonists in murine models of colitis (34, 35). Unfortunately, potent emetic effects have hampered therapeutic development of PDE inhibitors (36), while gut-specific activation of prostanoid receptors remains an unproven therapeutic strategy. Specific experimental support for SIK inhibition as a novel IBD treatment comes from our observation that the IL-10-potentiating activity of HG-9-91-01 is maintained in murine $CD11c^+$ $CX_3CR1^{hi}$ cells, a highly abundant subset of myeloid cells that play a key role in maintaining gut immune homeostasis, isolated from the small intestine (13, 14). The anti-inflammatory activity of $CD11c^+$ $CX_3CR1^{hi}$ myeloid cells in the $CD45RB^{hi}$ T cell transfer colitis model requires intact IL-10/STAT3 signaling (15), which suggests that SIK inhibition will enhance the T cell suppressive activity of these cells and, in turn, suppress pathogenic auto-inflammation characteristic of IBD.

The disclosure reveals that SIK inhibition by small molecules converts activated DCs/MΦs to an anti-inflammatory phenotype characterized by enhanced IL-10 production coupled with reduced secretion of inflammatory cytokines. Integrating genetic analysis of IBD susceptibility with the IL-10-potentiating activity of HG-9-91-01 in primary gut myeloid cells supports SIKs as a potential new target for treatment of these disorders. However, because aberrant recruitment/activation of inflammatory myeloid cells also contributes to the pathogenesis of type-1 diabetes, rheumatoid arthritis and systemic lupus erythematosus (10), SIK inhibition may be a more broadly applicable therapeutic strategy for treatment of autoimmune/auto-inflammatory disorders.

REFERENCES

1. Khor B, Gardet A, & Xavier R J (2011) Genetics and pathogenesis of inflammatory bowel disease. *Nature* 474 (7351):307-317.
2. Jostins L, et al. (2012) Host-microbe interactions have shaped the genetic architecture of inflammatory bowel disease. *Nature* 491(7422): 119-124.
3. Shouval D S, et al. (2014) Interleukin 10 receptor signaling: master regulator of intestinal mucosal homeostasis in mice and humans. *Advances in immunology* 122:177-210.
4. Kuhn R, Lohler J, Rennick D, Rajewsky K, & Muller W (1993) Interleukin-10-deficient mice develop chronic enterocolitis. *Cell* 75(2):263-274.
5. Spencer S D, et al. (1998) The orphan receptor CRF2-4 is an essential subunit of the interleukin 10 receptor. *The Journal of experimental medicine* 187(4):571-578.
6. Tomoyose M, Mitsuyama K, Ishida H, Toyonaga A, & Tanikawa K (1998) Role of interleukin-10 in a murine model of dextran sulfate sodium-induced colitis. *Scandinavian journal of gastroenterology* 33(4):435-440.
7. Schreiber S, et al. (2000) Safety and efficacy of recombinant human interleukin 10 in chronic active Crohn's disease. Crohn's Disease IL-10 Cooperative Study Group. *Gastroenterology* 119(6):1461-1472.
8. Marlow G J, van Gent D, & Ferguson L R (2013) Why interleukin-10 supplementation does not work in Crohn's disease patients. *World journal of gastroenterology: WJG* 19(25):3931-3941.
9. Braat H, et al. (2006) A phase I trial with transgenic bacteria expressing interleukin-10 in Crohn's disease. *Clinical gastroenterology and hepatology: the official clinical practice journal of the American Gastroenterological Association* 4(6):754-759.
10. Wynn T A, Chawla A, & Pollard J W (2013) Macrophage biology in development, homeostasis and disease. *Nature* 496(7446):445-455.
11. Grimm M C, et al. (1995) Direct evidence of monocyte recruitment to inflammatory bowel disease mucosa. *Journal of gastroenterology and hepatology* 10(4):387-395.
12. Zigmond E, et al. (2012) Ly6C hi monocytes in the inflamed colon give rise to proinflammatory effector cells and migratory antigen-presenting cells. *Immunity* 37(6): 1076-1090.
13. Zigmond E & Jung S (2013) Intestinal macrophages: well educated exceptions from the rule. *Trends in immunology* 34(4):162-168.
14. Niess J H, et al. (2005) CX3CR1-mediated dendritic cell access to the intestinal lumen and bacterial clearance. *Science* 307(5707):254-258.
15. Kayama H, et al. (2012) Intestinal CX3C chemokine receptor 1(high) (CX3CR1(high)) myeloid cells prevent T-cell-dependent colitis. *Proceedings of the National Academy of Sciences of the United States of America* 109(13):5010-5015.
16. Saraiva M & O'Garra A (2010) The regulation of IL-10 production by immune cells. *Nature reviews. Immunology* 10(3): 170-181.
17. Martin M, Rehani K, Jope R S, & Michalek S M (2005) Toll-like receptor-mediated cytokine production is differentially regulated by glycogen synthase kinase 3. *Nature immunology* 6(8):777-784.
18. Matsumoto T, et al. (2013) Protein kinase C inhibitor generates stable human tolerogenic dendritic cells. *Journal of immunology* 191(5):2247-2257.
19. Rodriguez M, et al. (2014) Polarization of the innate immune response by prostaglandin E2: a puzzle of receptors and signals. *Molecular pharmacology* 85(1):187-197.
20. MacKenzie K F, et al. (2013) PGE(2) induces macrophage IL-10 production and a regulatory-like phenotype via a protein kinase A-SIK-CRTC3 pathway. *Journal of immunology* 190(2):565-577.
21. Clark K, et al. (2012) Phosphorylation of CRTC3 by the salt-inducible kinases controls the interconversion of classically activated and regulatory macrophages. *Proceedings of the National Academy of Sciences of the United States of America* 109(42):16986-16991.
22. Weisberg E, Manley P W, Cowan-Jacob S W, Hochhaus A, & Griffin J D (2007) Second generation inhibitors of BCR-ABL for the treatment of imatinib-resistant chronic myeloid leukaemia. *Nature reviews. Cancer* 7(5):345-356.
23. Davis M L et al. (2011) Comprehensive analysis of kinase inhibitor selectivity. *Nature biotechnology* 29(11): 1046-1051.
24. Maynard C L, et al. (2007) Regulatory T cells expressing interleukin 10 develop from Foxp3+ and Foxp3− precursor cells in the absence of interleukin 10. *Nature immunology* 8(9):931-941.
25. Hori S, Nomura T, & Sakaguchi S (2003) Control of regulatory T cell development by the transcription factor Foxp3. *Science* 299(5609):1057-1061.
26. Pot C, Apetoh L, & Kuchroo V K (2011) Type 1 regulatory T cells (Tr1) in autoimmunity. *Seminars in immunology* 23(3):202-208.
27. Fraser C K, et al. (2009) Dasatinib inhibits the secretion of TNF-alpha following TLR stimulation in vitro and in vivo. *Experimental hematology* 37(12):1435-1444.
28. Kantarjian H, et al. (2010) Dasatinib versus imatinib in newly diagnosed chronic-phase chronic myeloid leukemia. *The New England journal of medicine* 362(24):2260-2270.
29. Yang Y, et al. (2012) Antitumor T-cell responses contribute to the effects of dasatinib on c-KIT mutant murine mastocytoma and are potentiated by anti-OX40. *Blood* 120(23):4533-4543.
30. Ghoreschi K, et al. (2010) Generation of pathogenic T(H)17 cells in the absence of TGF-beta signalling. *Nature* 467(7318):967-971.
31. Cross R K & Wilson K T (2003) Nitric oxide in inflammatory bowel disease. *Inflammatory bowel diseases* 9(3):179-189.
32. Bos J L (2006) Epac proteins: multi-purpose cAMP targets. *Trends in biochemical sciences* 31(12):680-686.
33. Liu J Z, et al. (2013) Dense genotyping of immune-related disease regions identifies nine new risk loci for primary sclerosing cholangitis. *Nature genetics* 45(6): 670-675.
34. Hartmann G, et al. (2000) Specific type IV phosphodiesterase inhibitor rolipram mitigates experimental colitis in mice. *The Journal of pharmacology and experimental therapeutics* 292(1):22-30.
35. Okamoto T, Uemoto S, & Tabata Y (2012) Prevention of trinitrobenzene sulfonic acid-induced experimental colitis by oral administration of a poly(lactic-coglycolic acid) microsphere containing prostaglandin E(2) receptor subtype 4 agonist. The Journal of pharmacology and experimental therapeutics 341(2):340-349.
36. Houslay M D, Schafer P, & Zhang K Y (2005) Keynote review: phosphodiesterase-4 as a therapeutic target. *Drug discovery today* 10(22):1503-1519.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a disease in a subject in need thereof, the method comprising administering to the subject a therapeutically effective amount of a salt-inducible kinase (SIK) inhibitor, wherein:
the disease is inflammatory bowel disease or graft-versus-host disease; and
the SIK inhibitor is a compound of Formula (I):

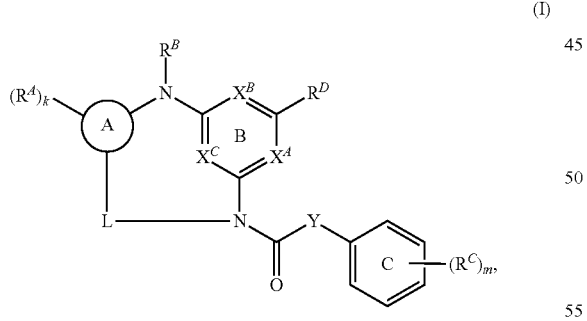

(I)

or a pharmaceutically acceptable salt, solvate, hydrate, polymorph, tautomer, stereoisomer, or isotopically labeled derivative thereof, wherein:
Ring A is a substituted or unsubstituted phenyl ring or a substituted or unsubstituted, monocyclic, 5- to 6-membered heteroaryl ring, wherein one, two, three, or four atoms in the heteroaryl ring system are independently nitrogen, oxygen, or sulfur;
each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;
each instance of $R^a$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^a$ groups are joined to form a substituted or unsubstituted heterocyclic or substituted or unsubstituted heteroaryl ring;
k is 0, 1, 2, 3, or 4;
L is a substituted or unsubstituted, saturated or unsaturated, $C_{3-10}$ hydrocarbon chain, optionally wherein one or more chain atoms of the hydrocarbon chain are independently replaced with —O—, —S—, —$NR^N$—, —N=, or =N—, wherein each instance of $R^N$ is independently hydrogen, substituted or unsubstituted acyl, substituted or unsubstituted $C_{1-6}$ alkyl, or a nitrogen protecting group;
$R^B$ is hydrogen, substituted or unsubstituted acyl, substituted or unsubstituted $C_{1-6}$ alkyl, or a nitrogen protecting group;

each of $X^A$, $X^B$, and $X^C$ is independently N or $CR^X$, wherein $R^X$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

Y is —O— or —$NR^Y$—, wherein $R^Y$ is hydrogen, substituted or unsubstituted acyl, substituted or unsubstituted $C_{1-6}$ alkyl, or a nitrogen protecting group;

or when Y is —$NR^Y$— and $X^A$ is $CR^X$, $R^Y$ and $R^X$ of $X^A$ are joined to form a substituted or unsubstituted, monocyclic, 5- to 7-membered heterocyclic ring that is fused with Ring B;

each instance of $R^C$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$;

m is 0, 1,2,3,4,or 5; and $R^D$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —$C(=NR^a)R^a$, —$C(=NR^a)OR^a$, —$C(=NR^a)N(R^a)_2$, —$C(=O)R^a$, —$C(=O)OR^a$, —$C(=O)N(R^a)_2$, —$NO_2$, —$NR^aC(=O)R^a$, —$NR^aC(=O)OR^a$, —$NR^aC(=O)N(R^a)_2$, —$OC(=O)R^a$, —$OC(=O)OR^a$, or —$OC(=O)N(R^a)_2$.

2. The method of claim 1, wherein the disease is inflammatory bowel disease.

3. The method of claim 1, wherein the disease is graft-versus-host disease.

4. The method of claim 1, wherein:
Y is —O—.

5. The method of claim 1, wherein the SIK inhibitor is of the formula:

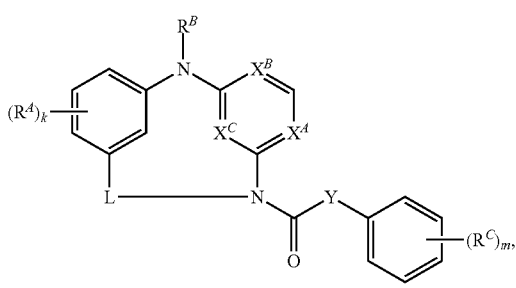

or a pharmaceutically acceptable salt solvate, hydrate, polymorph, tautomer, stereoisomer, or isotopically labeled derivative thereof.

6. The method of claim 1, wherein the SIK inhibitor is of the formula:

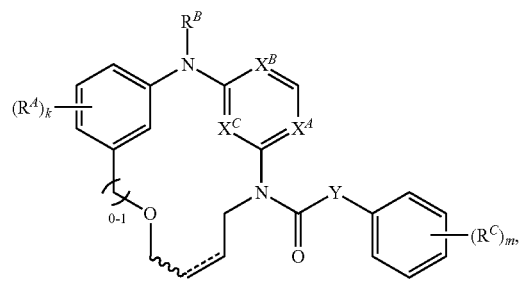

or a pharmaceutically acceptable salt, solvate, hydrate, polymorph, tautomer, stereoisomer, or isotopically labeled derivative thereof.

7. The method of claim 1, wherein the SIK inhibitor is of the formula:

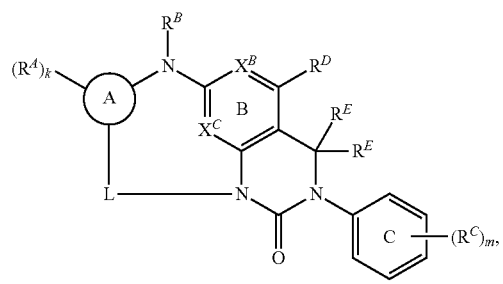

or a pharmaceutically acceptable salt, solvate, hydrate, polymorph, tautomer, stereoisomer, or isotopically labeled derivative thereof wherein each instance of $R^E$ is independently hydrogen, halogen, or substituted or unsubstituted $C_{1-5}$ alkyl.

8. The method of claim 7, Wherein the SIK inhibitor is of the formula:

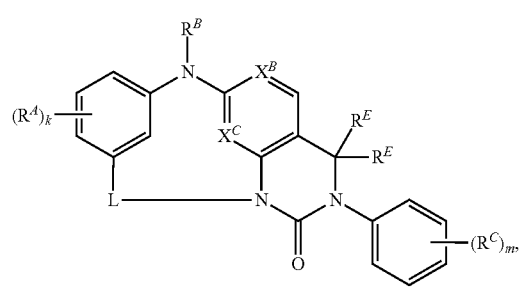

or a pharmaceutically acceptable salt, solvate, hydrate, polymorph, tautomer, stereoisomer, or isotopically labeled derivative thereof.

9. The method of claim 7, wherein the SIK inhibitor is of the formula:

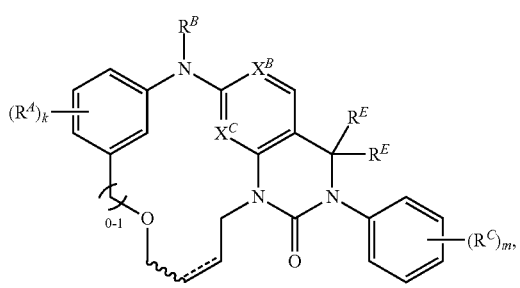

or a pharmaceutically acceptable salt, solvate, hydrate, polymorph, tautomer, stereoisomer, or isotopically labeled derivative thereof.

10. The method of claim 1, wherein L is a substituted or unsubstituted, saturated or unsaturated $C_{5-6}$ hydrocarbon chain, wherein one or two chain atoms of the hydrocarbon chain are independently replaced with —O—, —S—, or —NR$^N$—.

11. The method of claim 1, wherein $X^A$ is $CR^X$ and each of $X^B$ and $X^C$ is N.

12. The method of claim 1, wherein:

the disease is inflammatory bowel disease; and the SIK inhibitor is of the formula

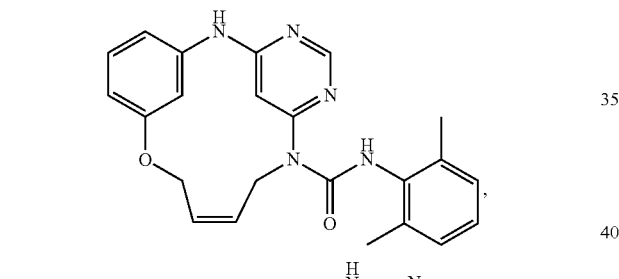

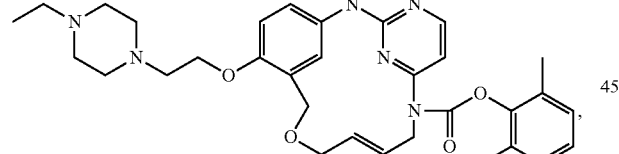

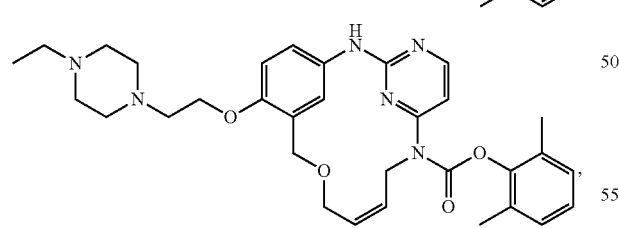

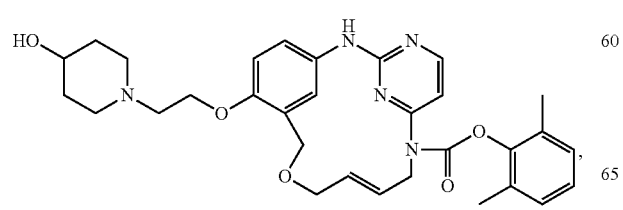

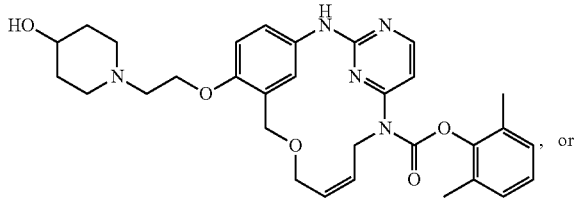

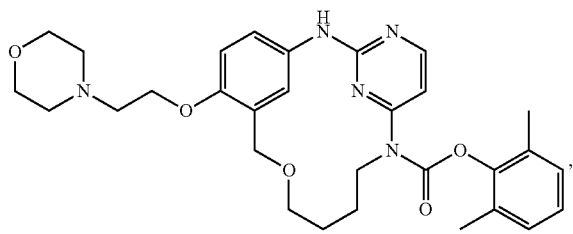

or a pharmaceutically acceptable salt, solvate, hydrate, polymorph, tautomer, stereoisomer, or isotopically labeled derivative thereof.

13. The method of claim 1, wherein:

the disease is inflammatory bowel disease; and the SIK inhibitor is of the formula:

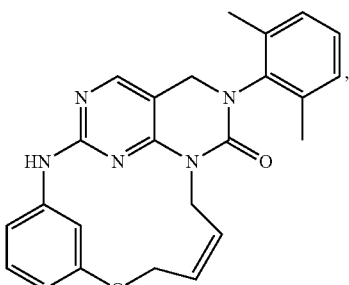

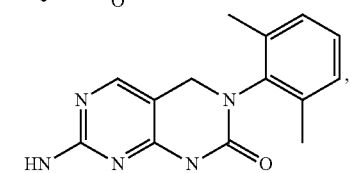

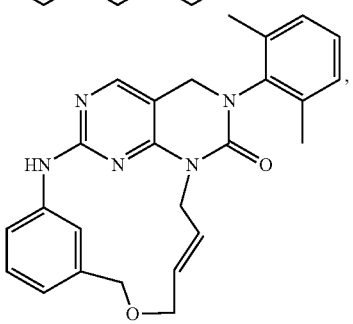

307
-continued
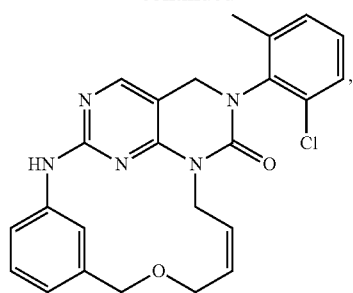
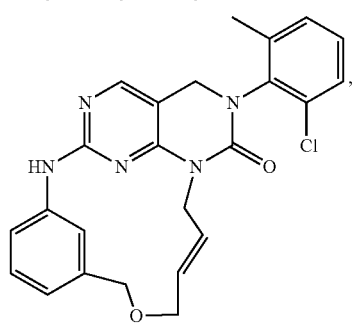
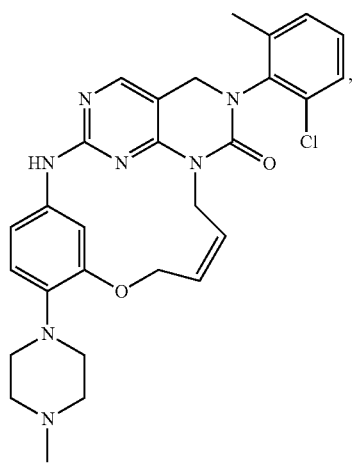
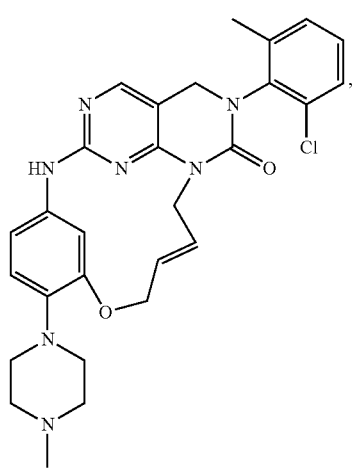
308
-continued
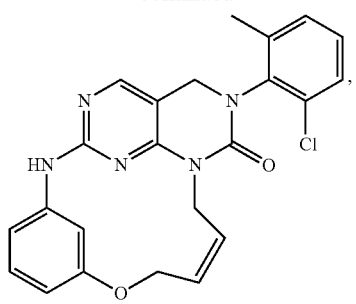
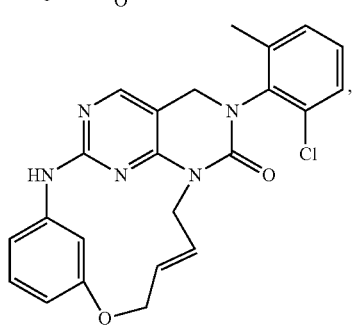
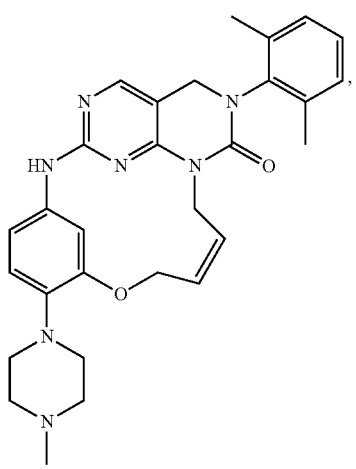
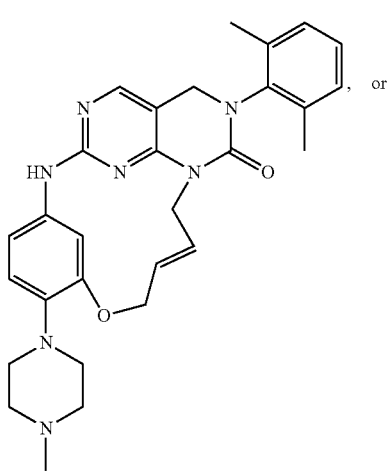, or -continued

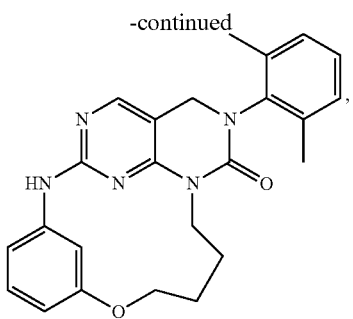

or a pharmaceutically acceptable salt, solvate, hydrate, polymorph, tautomer, stereoisomer, or isotopically labeled derivative thereof.

14. The method of claim 2, wherein the inflammatory bowel disease is Crohn's disease.

15. The method of claim 3, wherein the graft-versus-host disease is chronic graft-versus-host disease.

16. The method of claim 1, wherein
Y is $-NR^Y-$;
$X^A$ is $CR^X$; and
$R^Y$ and $R^X$ of $X^A$ are joined to form a substituted or unsubstituted, monocyclic, 5- to 7-membered heterocyclic ring that is fused with Ring B.

17. The method of claim 1, wherein Ring A is a substituted or unsubstituted phenyl ring.

18. The method of claim 7, wherein L is a substituted or unsubstituted, saturated or unsaturated $C_{5-6}$ hydrocarbon chain, wherein one or two chain atoms of the hydrocarbon chain are independently replaced with $-O-$, $-S-$, or $-NR^N-$.

19. The method of claim 1, wherein L is of the formula:

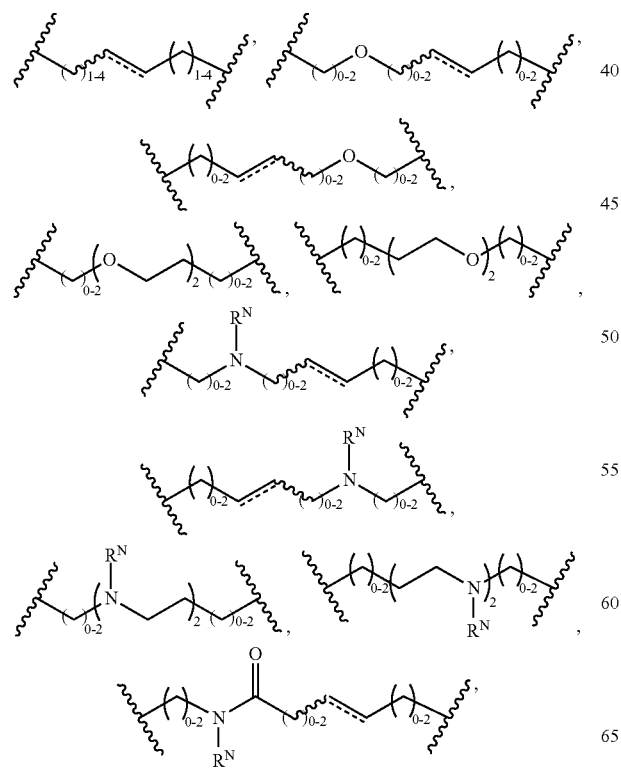

-continued

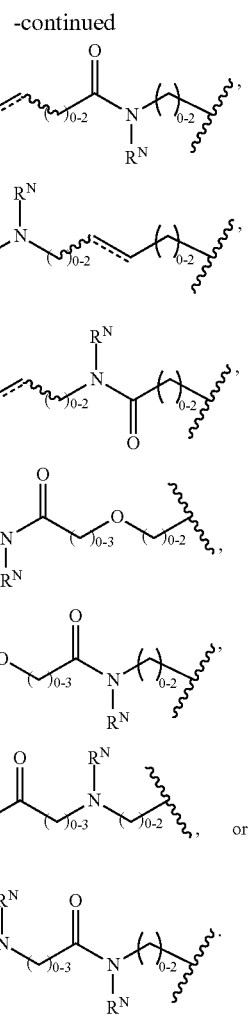

20. The method of claim 1, wherein $X^C$ is $CR^X$, and each of $X^A$ and $X^B$ is N.

21. The method of claim 1, wherein at least one instance of $R^A$ is substituted or unsubstituted, monocyclic, 3- to 7-membered heterocyclyl, wherein one, two, or three atoms in the heterocyclic ring system are independently selected from the group consisting of nitrogen, oxygen, and sulfur.

22. The method of claim 1, wherein $R^B$ is hydrogen.

23. The method of claim 1, wherein $R^D$ is hydrogen.

24. The method of claim 1, wherein Ring C is of the formula:

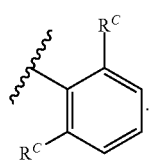

25. The method of claim 1, wherein at least one instance of $R^C$ is halogen or substituted or unsubstituted alkyl.

26. The method of claim 1, wherein:
the disease is inflammatory bowel disease; and
the SIK inhibitor is a compound of the formula:

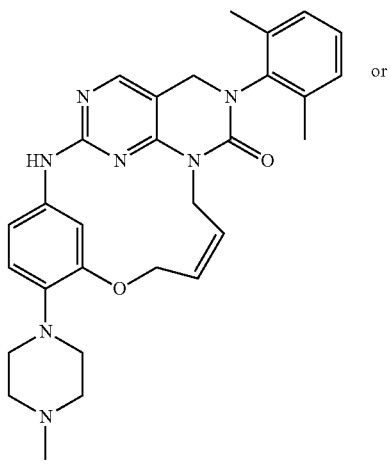

or

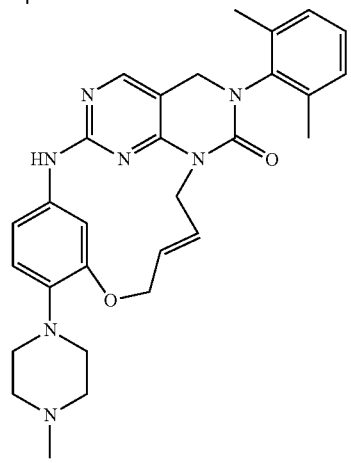

or a pharmaceutically acceptable salt thereof.

27. The method of claim 1, wherein the SIK inhibitor is a compound of Formula (I):

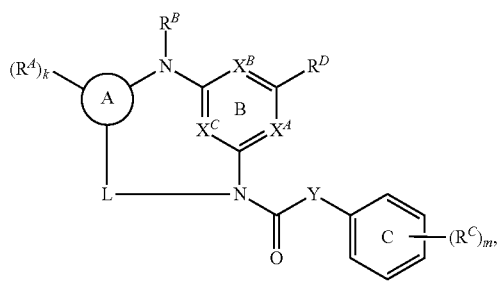

or a pharmaceutically acceptable salt thereof.

28. The method of claim 1, wherein at least one instance of $R^A$ is halogen, substituted or unsubstituted alkyl, or —$OR^a$.

29. The method of claim 1, wherein L is a substituted or unsubstituted, saturated or unsaturated, $C_{3-10}$ hydrocarbon chain, optionally wherein one or more chain atoms of the hydrocarbon chain are replaced with —O—.

30. The method of claim 1, wherein Y is —$NR^Y$—.

31. The method of claim 1, wherein Y is —NH—.

32. The method of claim 1, wherein:
Y is —$NR^Y$—;
$X^A$ is $CR^X$; and
$R^Y$ and $R^X$ of $X^A$ are joined to form a substituted or unsubstituted, monocyclic, 6-membered heterocyclic ring that is fused with Ring B.

33. The method of claim 1, wherein the SIK inhibitor is of the formula

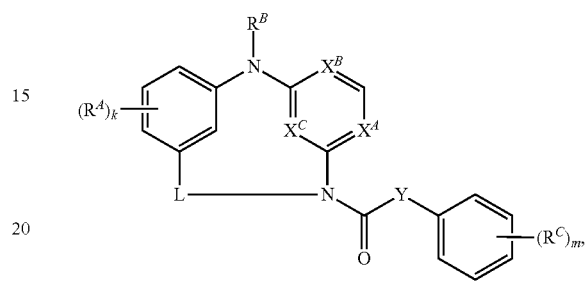

or a pharmaceutically acceptable salt, solvate, hydrate, polymorph, tautomer, stereoisomer, or isotopically labeled derivative thereof.

34. The method of claim 7, wherein the SIK inhibitor is of the formula

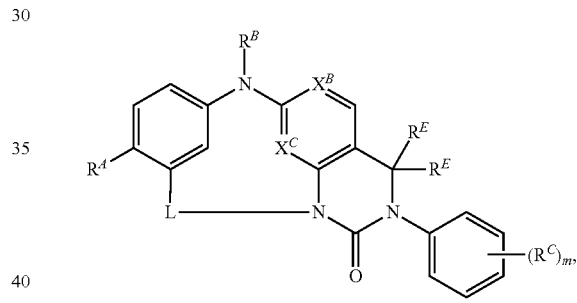

or a pharmaceutically acceptable salt, solvate, hydrate, polymorph, tautomer, stereoisomer, or isotopically labeled derivative thereof.

35. The method of claim 1, wherein:
the disease is graft-versus-host disease; and
the SIK inhibitor is of the formula:

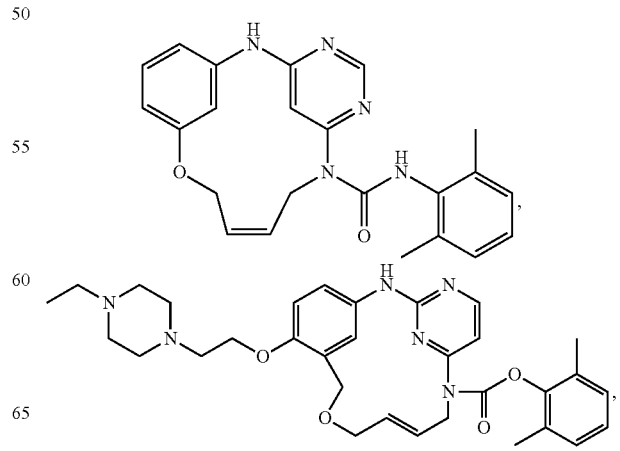

313
-continued
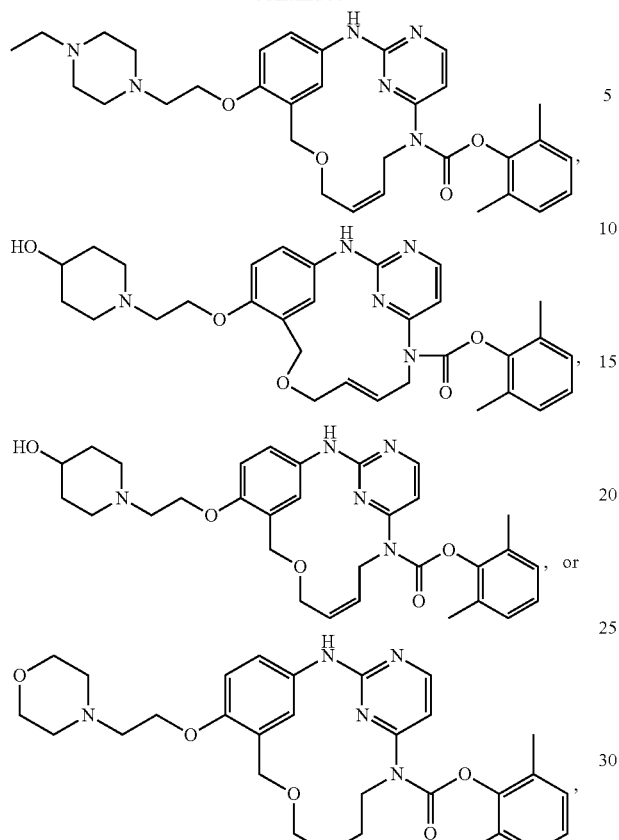
or a pharmaceutically acceptable salt, solvate, hydrate, polymorph, tautomer, stereoisomer, or isotopically labeled derivative thereof.
36. The method of claim 1, wherein:
the disease is graft-versus-host disease; and
the SIK inhibitor is of formula:
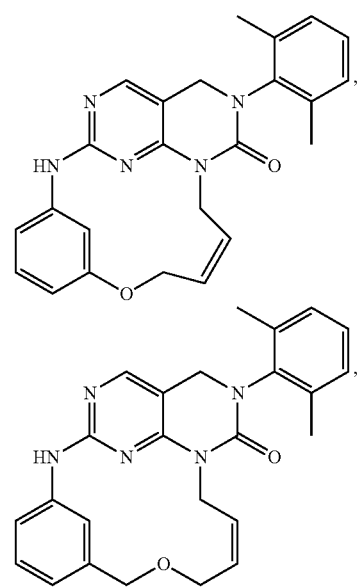
314
-continued
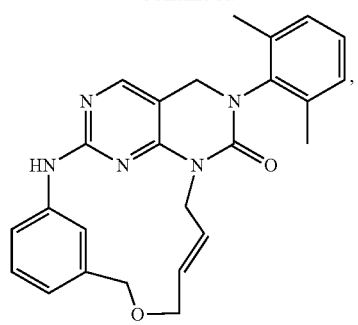
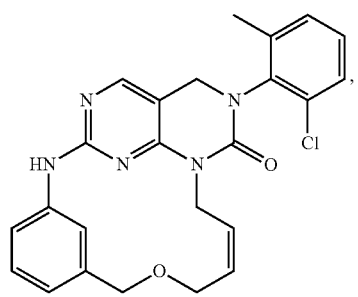
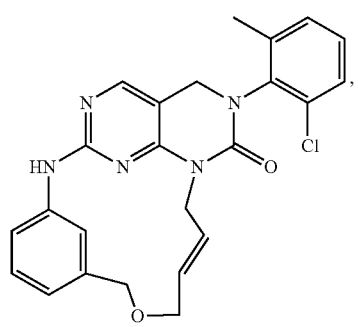
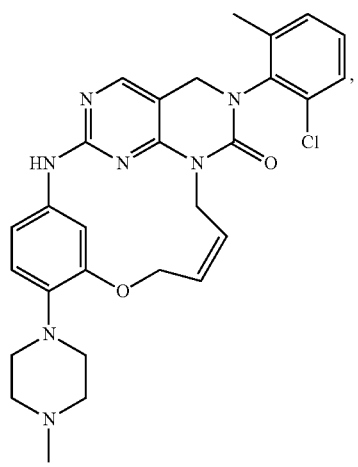

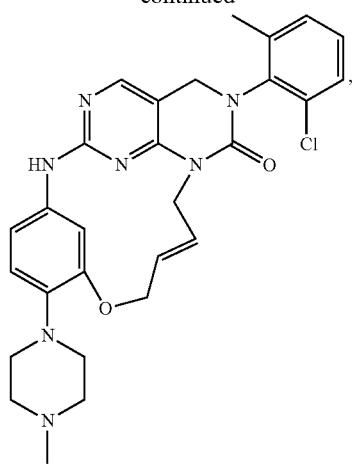
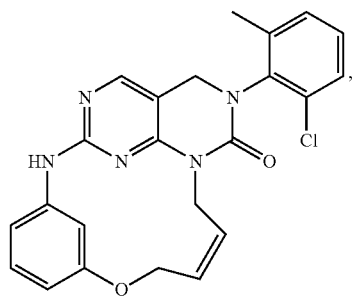
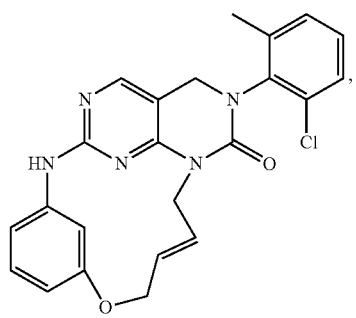
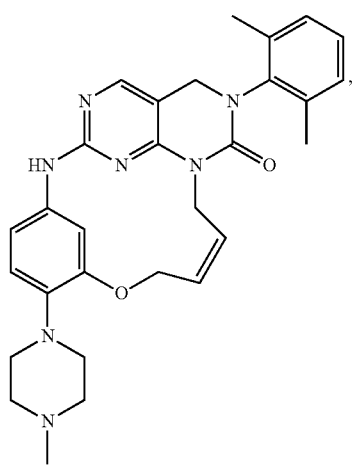
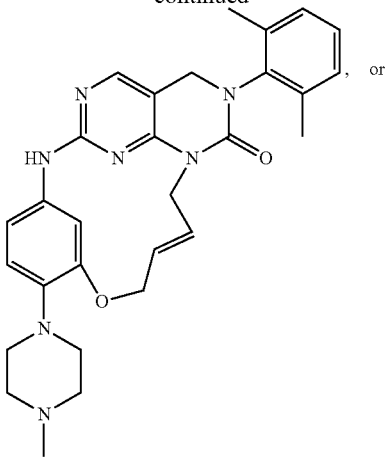
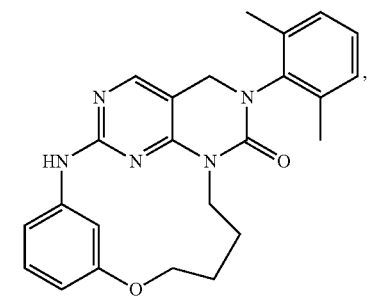
or a pharmaceutically acceptable salt, solvate, hydrate, polymorph, tautomer, stereoisomer, or isotopically labeled derivative thereof.
37. The method of claim 1, wherein
the disease is graft-versus-host disease; and
the SIK inhibitor is a compound of the formula:
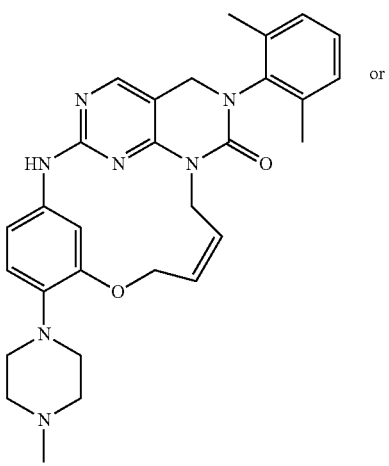

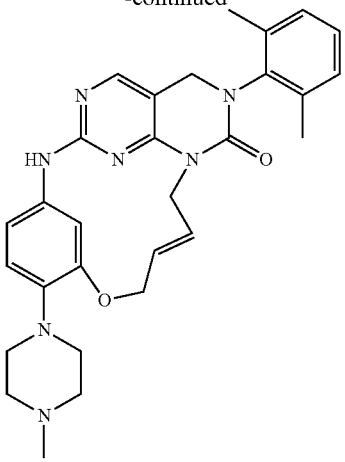
or a pharmaceutically acceptable salt thereof.
38. The method of claim 1, wherein the subject is a human.

UNITED STATES PATENT AND TRADEMARK OFFICE
CERTIFICATE OF CORRECTION

PATENT NO. : 10,265,321 B2
APPLICATION NO. : 15/847856
DATED : April 23, 2019
INVENTOR(S) : Alykhan Shamji et al.

Page 1 of 1

It is certified that error appears in the above-identified patent and that said Letters Patent is hereby corrected as shown below:

In the Claims

In Claim 7, at Column 304, Line 45, the text: "$C_{1-5}$" should be replaced with: --$C_{1-6}$--.

In Claim 33, at Column 312, Lines 10-23, the formula: " 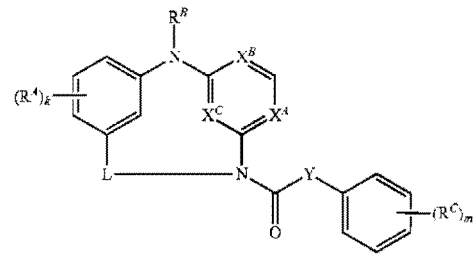 "

should be replaced with the formula: -- 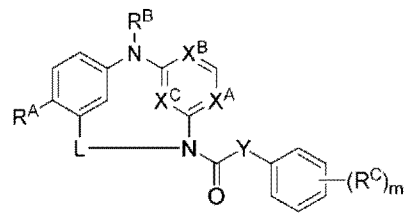 --.

Signed and Sealed this
Eighteenth Day of February, 2020

Andrei Iancu
*Director of the United States Patent and Trademark Office*